US011872273B2

(12) United States Patent
Burkhardt et al.

(10) Patent No.: US 11,872,273 B2
(45) Date of Patent: *Jan. 16, 2024

(54) PROTEINS AND IMMUNIZING COMPOSITIONS CONTAINING *KLEBSIELLA* PROTEINS AND METHODS OF USE

(71) Applicant: EPITOPIX, LLC, Willmar, MN (US)

(72) Inventors: Douglas T. Burkhardt, Dassel, MN (US); Daryll Emery, New London, MN (US); Darren Straub, New London, MN (US)

(73) Assignee: Epitopix, LLC, Willmar, MN (US)

( * ) Notice: Subject to any disclaimer, the term of this patent is extended or adjusted under 35 U.S.C. 154(b) by 131 days.

This patent is subject to a terminal disclaimer.

(21) Appl. No.: 17/226,761

(22) Filed: Apr. 9, 2021

(65) Prior Publication Data
US 2021/0330776 A1 Oct. 28, 2021

Related U.S. Application Data

(63) Continuation of application No. 15/741,574, filed as application No. PCT/US2016/041614 on Jul. 8, 2016, now Pat. No. 11,000,582.

(60) Provisional application No. 62/190,947, filed on Jul. 10, 2015.

(51) Int. Cl.
*A61K 39/108* (2006.01)
*A61K 39/116* (2006.01)
*A61K 39/00* (2006.01)
*C07K 14/26* (2006.01)
*A61K 39/40* (2006.01)

(52) U.S. Cl.
CPC ........ *A61K 39/0266* (2013.01); *A61K 39/116* (2013.01); *A61K 39/40* (2013.01); *C07K 14/26* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 6,027,736 A | 2/2000 | Emery | |
| 6,610,836 B1 | 8/2003 | Breton | |
| 11,000,582 B2 * | 5/2021 | Burkhardt | ............... C07K 14/26 |
| 2005/0186217 A1 | 8/2005 | Emery | |

FOREIGN PATENT DOCUMENTS

| | | |
|---|---|---|
| CA | 2029906 A1 | 9/1990 |
| JP | 03143388 A | 6/1991 |
| WO | WO 90/11349 | 10/1990 |
| WO | WO 95/21627 | 8/1995 |
| WO | WO 96/01620 A1 | 1/1996 |
| WO | WO 01/37810 A2 | 5/2001 |
| WO | WO 02/053180 | 7/2002 |
| WO | WO 2006/088803 | 8/2006 |
| WO | WO 2008/135446 | 11/2008 |
| WO | WO 2010/111273 | 9/2010 |

OTHER PUBLICATIONS

Chu et al., "Siderphore Uptake in Bacteria and the Battle for Iron with the Host; a Bird's Eye View," Biometals (2010) 23:601-611.
Office Action issued in Mexico for Application No. MX/a/2018/000395 dated Aug. 22, 2022 (7 pages).
PCT Patent Application No. US2016/041614, filed Jul. 8, 2016; International Preliminary Report on Patentability dated Jan. 25, 2018; 15 pages.
PCT Patent Application No. US2016/041614, filed Jul. 8, 2016; International Search Report and Written Opinion dated Mar. 6, 2017; 27 pages.
Baghal et al., Production and Immunogenicity of Recombinant Ferric Enterobactin Protein (FepA), *International Journal of Infectious Diseases*, 14S (2010) pp. 166-170.
Biegel Carson et al., "Ferric Enterobactin Binding and Utilization by Neisseria Gonorrhoeae", Journal of Bacteriology, vol. 181, No. 9, May 1, 1999, pp. 2895-2901.
Bouchet et al., "Immunological Variants of the Aerobactin-Cloacin DF13 Outer Membrane Protein Receptor IUTA Among Enteric Bacteria", *Infection and Immunity*, vol. 62, No. 7, Jul. 1, 1994, pp. 3017-3021.
Boulianne, "Production of functional chimaeric mouse/human antibody" 1984 *Nature*, 312(5995):643-6.
Brisse, "The genus *Klebsiella*" in Dworkin, Ed., *The prokaryotes, 3rd ed, vol. 6*, Springer: New York, NY; 2006. Cover page, title page, table of contents, pp. 159-196.
Bruggeman, "Production of human antibody repertoires in transgenic mice" 1997 *Curr. Opin. Biotechnol.*, 8(4):455-8.
Budzikiewicz, "Siderophore from bacteria and from fungi" in *Iron uptake and homeostasis in Microorganisms*. 1st ed., Cornelis , ed., Caister Academic Press: Poole, UK; 2010. Cover page, publisher's page, and Chapter 1.
Chander, "Differentiation of Klebsiella pneumoniae and Klebsiella oxytoca by multiplex poly-merase chain reaction" 2011 *Intern J Appl Res Vet Med.*, 9:138-142.
Cryz, "Experimental Klebsiella pneumoniae burn wound sepsis: role of capsular polysaccharide" Jan. 1984 *J Infect Dis*, 150(1):817-822.
Cryz, "Purification and vaccine potential of Klebsiella capsular polysaccharides" 1985 *Infect Immun*, 50:225-230.
Cryz, "Seroepidemiology of Klebsiella bacteremic isolates and implications for vaccine development" 1986 *J Clin Microbiol*, 23: 687-690.
Daugherty, "Polymerase chain reaction facilitates the cloning, CDR grafting, and rapid expression of a murine monoclonal antibody directed against the CD18 component of leukocyte integrins" 1991 *Nucleic Acids Res.*, 19(9): 2471-6.

(Continued)

*Primary Examiner* — S. Devi
(74) *Attorney, Agent, or Firm* — Mueting Raasch Group

(57) ABSTRACT

Provided herein are isolated proteins isolatable from a *Klebsiella* spp. Also provided are compositions that include one or more of the proteins, and methods for making and methods for using the proteins.

5 Claims, 33 Drawing Sheets

Specification includes a Sequence Listing.

(56) References Cited

OTHER PUBLICATIONS

Goujon, "A new bioinformatics analysis tools framework at EMBL-EBI" 2010 Nucleic acids research Jul. 2010, 38 Suppl: W695-9.
Greenspan et al., Nature Biotechnology 17: 936-937, 1999.
Grohn, "Effect of pathogen-specific clinical mastitis on milk yield in dairy cows" 2004 *J. Dairy Sci.*, 87:3358-3374.
Harlow, Ed., *Antibodies, a Laboratory Manual*, Cold Spring Harbor Laboratory: Cold Spring Harbor, NY; 1988. Cover page, title page, table of contents, and Chapter 5.
Hoblet, "Costs associated with selected preventive practices and with episodes of clinical mastitis in nine herds with low somatic cell counts" Jul. 1991 *J. Am Vet Med. Assoc.*, 199(2):190-196.
Hogan et al., "Iron Uptake and Growth Responses by *Escherichia coli* Cultured with Antibodies from Cows Immunized with High Affinity Ferric Receptors," Mastitis in Dairy Production: Current Knowledge and Future Solutions Wageningen Academic Publishers, Postbus 220, 6700 AE Wageningen, Netherlands, 4$^{th}$ IDF International Mastitis Conference, Maastricht, Netherlands, Jun. 12-15, 2005, pp. 297-301.
Houghten et al., New Approaches to Immunization, Vaccine86, Cold Spring Harbor Laboratory, pp. 21-25, 1986.
Jeannin, "Outer membrane protein A (OmpA): a new pathogen-associated molecular pattern that interacts with antigen presenting cells-impact on vaccine strategies" 2002 Vaccine 20, Suppl. 4: A23-A27.
Jones, "Replacing the complementarity-determining regions in a human antibody with those from a mouse" 1986 *Nature*, 321(6069):522-5.
Jurkevitch, "Differential Siderophore Utilization and Iron Uptake by Soil and Rhizosphere Bacteria" 1992 *Appl Environ Microbiol.*, 58(1):119.
Keler, "Metachromatic Assay for the Quantitative Determination of Bacterial Endotoxins" 1986 *Analyt. Biochem.*, 156, 189.
Kurupati et al., "Identification of Vaccine Candidate Antigens of an ESBL Producing *Klebsiella pneumoniae* Clinical Strain by Immunoproteome Analysis," Proteomics, (2006), 6, pp. 836-844.
Kurupati, "Protective Efficacy of DNA Vaccines Encoding Outer Membrane Protein A and OmpK36 of Klebsiella pneumoniae in Mice" Jan. 2011 *Clinical Vaccine Immunol.*, 18(1):82-88.
Lazar et al., Mol. Cellular Biol. 8: 1247-1252, 1988.
Libon, "*Streptococcus* pneumoniae polysaccharides conjugated to the outer membrane protein A from Klebsiella pneumoniae elicit protective antibodies" May 2002 *Vaccine*, 20:2174-2180.
Lin et al., "Immunization of Cows with Ferric Enterobactin Receptor from Coliform Bacteria," *Journal of Dairy Science*, American Dairy Science Association, U.S., vol. 81, No. 8, (1998), pp. 2151-2158.
Lin et al., "Inhibition of In Vitro Growth of Coliform Bacteria by a Monoclonal Antibody Directed Against Ferric Enterobactin Receptor FepA", *Journal of Dairy Science*, vol. 81, No. 5, May 1, 1998, pp. 1267-1274.
Lobuglio, "Mouse/human chimeric monoclonal antibody in man: Kinetics and immune response" Jun. 1989 *Proc. Natl. Acad. Sci. USA*, 86(11):4220-4.
Lodge, "Influence of Growth Rate and Iron Limitation on the Expression of Outer Membrane Proteins and Enterobactin by Klebsiella pneumoniae Grown in Continuous Culture" Feb. 1986 *Journal of Bacteriology*, 165(2):353-356.
Lonberg, "Antigen-specific human antibodies from mice comprising four distinct genetic modifications" 1994 *Nature*, 368:856-9.
Lonberg, "Human Antibodies from Transgenic Mice" 1995 *Int. Rev. Immunol.*, 13(1):65-93.
Lundberg, "Identification and characterization of antigens as vaccine candidates against Klebsiella pneumoniae" 2013, *Human Vaccines Immunotherapeutics*, 9(3):497-505.
Lyczak, "Lung infections associated with cystic fibrosis" 2002 *Clinical microbiology reviews* 15.2:194-222.

Meno, "The Surface Hydrophobicity and Avirulent Character of an Encapsulated Strain of Klebsiella pneumoniae" 1991 *Microbiol. Immuniol.*, 35(10):841-848.
Miethke, "Siderophore-based iron acquisition and pathogen control" 2007 *Microbiol Mol Rev*, 71(3):413-451.
Morrison, "Chimeric human antibody molecules: Mouse antigen-binding domains with human constant region domains" 1984 *Proc. Natl. Acad. Sci. USA*, 81(21):6851-5.
Murphy et el., "Surface Topology of the *Escherichia coli* K-12 Ferric Enterobactin Receptor", *Journal of Bacteriology*, vol. 172, No. 5, May 1, 1990, pp. 2736-2746.
Nikaido, "Outer Membrane" in: *Escherichia coli* and *Salmonella typhimurium*, Cellular and Molecular Biology, Neidhardt, (ed.); American Society for Microbiology: Washington, D.C .; 1987. Cover page, title page, table of contents, and pp. 7-22.
Parchuri, "Extended spectrum beta-lactamase-producing Klebsiella pneumoniae chronic ambulatory peritoneal dialysis peritonitis treated successfully with polymyxin B" 2005 *Heart lung*, 5:360-363.
Perkins, "Probability-based protein identification by searching sequence databases using mass spectrometry data" 1999 *Electrophoresis* 20, 3551-3567.
Pinzon-Sanchez, "Decision tree analysis of treatment strategies for mild and moderate cases of clinical mastitis occurring in early lactation" 2011 *J. Dairy Sci.*, 94:1873-1892.
Podschun, "*Klebsiella* spp. as nosocomial pathogens: epidemiology, taxonomy, typing methods, and pathogenicity factors" 1998 *Clin. Microbiol. Rev.* 11(4):589-603.
Queen, "A humanized antibody that binds to the interleukin 2 receptor" 1989 *Proc. Natl. Acad. Sci. USA*, 86(24):10029-33.
Rabsch, "Role of Receptor Proteins for Enterobactin and 2,3-Dihydroxybenzoylserine in Virulence of *Salmonella enterica*" Dec. 2003 *Infect Immun.*, 12:6953-6961.
Riechmann, "Reshaping human antibodies for therapy" 1988 *Nature*, 332(6162):323-7.
Roberts et al., "Inhibition of Biological Activities of the Aerobactin Receptor Protein in Rough Strains of *Escherichia coli* by Polyclonal Antiserum Raised Against Native Protein", Journal of General Microbiology, vol. 135, Jan. 1, 1989, pp. 2387-2398.
Rudinger et al., In: Peptide Hormones. (Ed) JA Parsons, University Park Press, pp. 1-7, 1979.
Sanchez, "" Jan. 2013 *Emerg Infect Dis.*, 19(1):133-6.
Shand, "In Vivo Evidence That Bacteria in Urinary Tract Infection Grow Under Iron-Restricted Conditions" Apr. 1985 *Infection and Immunity*, 48(1):35-39.
Sievers, "Fast, scalable generation of high-quality protein multiple sequence alignments using Clustal Omega" *Molecular Systems Biology* 7:539.
Skolnick et al., Trends in Biotechnology, 18: 34-39, 2000.
Stamm, "Comparison of endemic and epidemic nosocomial infections" in Dixon (ed.), *Nosocomial infections*, Yorke Medical Books: Atlanta, GA; 1981. Cover page, title page, table of contents, and pp. 9-13.
Tatusova, "BLAST 2 Sequences, a new tool for comparing protein and nucleotide sequences" 1999 *FEMS Microbiol Lett*, 174, 247-250.
Taylor, "A transgenic mouse that expresses a diversity of human sequence heavy and light chain immunoglobulins" Dec. 1992 *Nucleic Acids Res.*, 20:6287-95.
Toky, "Establishment of a sepsis model following implantation of Klebsiella pneumoniae-infected fibrin clot into the peritoneal cavity of mice" 2003 *Folia Microbiol (Praha)*, 48(5):665-669.
Traxler. "Interspecies modulation of bacterial development through iron competition and siderophore piracy" Nov. 2012 *Mol. Microbiol.*, 86:628-644.
Tuntufye et al., *Escherichia coli* Ghosts or Live *E. coli* Expressing the Ferri-Siderophore Receptors FepA, FhuE, IroN and IutA Do Not Protect Boiler Chickens Against Avian Pathogenic *E. coli* (APEC), *Veterinary Microbiology*, 159 (2012) pp. 470-478.
Ueda, "In Vitro and In Vivo Antibacterial Activities of SM-216601, a New Broad-Spectrum Parenteral Carbapenem" Oct. 2005 *Antimicrob Agents Chemother*, 49:4185-4196.

(56) References Cited

OTHER PUBLICATIONS

Vered, "Susceptibility to klebsiella pneumonaie infection in collaborative cross mice is a complex trait controlled by at least three loci acting at different time points" 2014, *BMC Genomics*, 15:865.
Verhoeyen, "Reshaping human antibodies: grafting an antilysozyme activity" 1988 *Science*, 239(4847):1534-6.
Watson, Ed., *Endotoxins and Their Detection With the Limulus Amebocyte Lystate Test*, Alan R. Liss, Inc.: New York, NY; 1982. Cover page, title page and table of contents.
Williams, "Expression of high affinity iron uptake systems by clinical isolates of Klebsiella" Nov. 1987 *FEMS Microbiol Lett.*, 44:407-412.
Wolf et al., "Iron Uptake by *Escherichia coli* Cultured with Antibodies from Cows Immunized with High-Affinity Ferric Receptors," *Journal of Dairy Science*, 87 (2004) pp. 2103-2107.
Wu, "Identification of a novel cephalosporinase (DHA-3) in Klebsiella pneumoniae isolated in Taiwan" 2005 *Clin Microbiol Infect*, 11: 893-897.
Yadav, "Lipopolysaccharide-mediated protection againstKlebsiella pneumoniae-induced lobar pneumonia: Intranasalvs. intramuscular route of immunization" Jan. 2005 *Folia Microbiologica*, 50:83-86.
Yu, "Virulence characteristics of Klebsiella and clinical manifestations of K. pneumoniae bloodstream infections" 2007 *Emerg. Inf. Dis.* 13:986-993.

\* cited by examiner

SDS-PAGE

Western Blot

Fig. 7

| Klebsiella pneumoniae 1571 FecA (Ferric Citrate Receptor) Gene Sequence. SEQ ID NO:1 |
|---|
| ATGACGCCGTTACGCGTTTTTCGTAAAACAACTCCTTTGGTTAACGCCATTCGCCTGAGCCTGCTGCCGCTGGCC
GGTCTCTCGTTTTCCGCTTTTGCTGCACAGGTTGATATCGCACCGGGATCGCTCGACAAAGCGCTCAATCAGTAT
GCCGCACACAGCGGAATTACCCTCTCGGTTGACGCCAGCCTGACGCGCGGCAAGCAGAGCAACGGCCTGCACGGA
GATTACGACGTCGAGAGCGGCCTGCAACAGCTGCTGGACGGCAGCGGACTGCAGGTAAAACCGCTGGGAAATAAC
AGCTGGACGCTGGAGCCCGCGCCCGCGCCAAAAGAAGATGCCCTGACCGTGGTCGGCGACTGGCTGGGCGATGCG
CGTGAAAACGACGTATTTGAACATGCTGGCGCGCGTGACGTGATCCGCCGTGAGGATTTCGCCAAAACCGGCGCA
ACCACCATGCGTGAGGTGCTTAACCGCATCCCTGGCGTCAGCGCGCCGGAAAACAACGGCACCGGCAGCCACGAC
CTGGCGATGAACTTTGGCATCCGGGGCCTGAACCCACGCCTCGCCAGCCGCTCGACCGTCCTGATGGACGGCATC
CCCGTCCCCTTTGCCCCTTACGGTCAGCCGCAGCTTTCACTGGCTCCCGTTTCGCTCGGCAACATGGATGCCATT
GACGTGGTGCGCGGTGGTGGTGCGGTGCGTTACGGACCGCAGAGCGTGGGCGGCGTGGTGAACTTTGTTACCCGC
GCCATTCCGCAGGACTTTGGTATCGAGGCGGGGGTGGAAGGTCAGCTCAGCCCAACCTCTTCACAAAACAACCCG
AAAGAGACGCACAACCTGATGGTGGGCGGCACAGCGGACAACGGTTTTGGCACCGCGCTGCTCTACTCCGGCACG
CGCGGCAGTGACTGGCGCGAGCACAGCGCCACCCGCATCGACGACCTGATGCTGAAAAGCAAATATGCGCCGAAT
GAGGTGCACACCTTCAACAGCCTGCTGCAATATTACGATGGTGAAGCCGACATGCCCGGCGGCCTGTCCCGCGCG
GATTACGACGCCGATCGCTGGCAATCCACCCGCCCGTATGACGCTTCTGGGGCCGTCGCAAGCTGGCGAGCCTG
GGCTACCAGTTCCAGCCGGACAGCCAGCATAAATTCAACATTCTGGGGTTCTACACCCAAACCCTGCGCAGCGGC
TACCTGGAGCAAGGCAAACGCATCACCCTCTCGCCGCGTAACTACTGGGTGCGCGGTATTGAGCCACGCTACAGC
CAGAGCTTTATGATCGGCCCTTCCGCGCACGAAGTGGGCGTGGGCTATCGCTATGTGAATGAATCAACGCATGAA
ATGCGTTACTACACCGCCACCAGCAGCGGGCAGTTGCCGTCCGGCTCAAGCCCTTACGACGCGCGACACGCGTTCC
GGCACCGAGGCGCACGCCTGGTATCTGGATGACAAAATCGACATCGGCAACTGGACCATCACGCCGGGTATGCGT
TTCGAACATATCGAGTCATACCAGAACAACGCCATCAAAGGCACGCACGAAGAGGTAAGCTATAACGCACCGCTT
CCGGCGTTGAACGTGCTCTATCACCTGACTGACAGCTGGAATCTTTATGCAAACACTGAAGGCTCGTTCGGCACC
GTACAGTACAGCCAGATTGGCAAGGCTGTGCAAAGCGGCAATGTGGAACCGGAAAAAGCGCGAACCTGGGAACTC
GGTACCCGCTACGACGACGGCGCGCTGACGGCGGAAATGGGGCTGTTCCTGATTAACTTTAACAATCAGTACGAC
TCCAACCAGACCAACGACACCGTCACTGCACGTGGCAAAACGCGCCATACCGGGCTGGAAACGCAGGCACGTTAC
GACCTGGGTACGCTAACGCCAACGCTTGATAACGTTTCCGTCTACGCCAGCTATGCGTATGTGAACGCGGAAATC
CGCGAGAAAGGCGACACCTATGGCAATCAGGTGCCATTCTCCCCGAAACATAAAGGCACGCTGGGCGTGGACTAC
AAGCCGGGCAACTGGACGTTCAATCTGAACAGCGATTTCCAGTCCAGCCAGTTTGCGGATAACGCCAATACGGTG
AAAGAGAGCGCCGACGGCAGTACCGGCCGCATTCCCGGCTTCATGCTCTGGGGCGCACGCGTGGCGTATGACTTT
GGCCCGCAGATGGCAGATCTGAACCTGGCGTTCGGTGTGAAAAACATCTTCGACCAGGACTACTTCATCCGCTCT
TATGACGACAACAACAAAGGCATCTACGCAGGCCAGCCGCGCACGCTGTATATGCAGGGTCGTTGAAGTTCTGA |
| Klebsiella pneumoniae 1571 FecA (Ferric Citrate Receptor) AA Sequence, SEQ ID NO:2. Underlined sequence is the signal sequence. Sequence of protein without signal sequence is SEQ ID NO:41, and the calculated molecular weight is 81.6 kDa. |
| <u>MTPLRVFRKTTPLVNAIRLSLLPLAGLSFSAFAA</u>QVDIAPGSLDKALNQYAAHSGITLSVDASLTRGKQSNGLHG
DYDVESGLQQLLDGSGLQVKPLGNNSWTLEPAPAPKEDALTVVGDWLGDARENDVFEHAGARDVIRREDFAKTGA
TTMREVLNRIPGVSAPENNGTGSHDLAMNFGIRGLNPRLASRSTVLMDGIPVPFAPYGQPQLSLAPVSLGNMDAI
DVVRGGAVRYGPQSVGGVVNFVTRAIPQDFGIEAGVEGQLSPTSSQNNPKETHNLMVGGTADNGFGTALLYSGT
RGSDWREHSATRIDDLMLKSKYAPNEVHTFNSLLQYYDGEADMPGGLSRADYDADRWQSTRPYDRFWGRRKLASL
GYQFQPDSQHKFNILGFYTQTLRSGYLEQGKRITLSPRNYWVRGIEPRYSQSFMIGPSAHEVGVGYRYVNESTHE
MRYYTATSSGQLPSGSSPYDRDTRSGTEAHAWYLDDKIDIGNWTITPGMRFEHIESYQNNAIKGTHEEVSYNAPL
PALNVLYHLTDSWNLYANTEGSFGTVQYSQIGKAVQSGNVEPEKARTWELGTRYDDGALTAEMGLFLINFNNQYD
SNQTNDTVTARGKTRHTGLETQARYDLGTLTPTLDNVSVYASYAYVNAEIREKGDTYGNQVPFSPKHKGTLGVDY
KPGNWTFNLNSDFQSSQFADNANTVKESADGSTGRIPGFMLWGARVAYDFGPQMADLNLAFGVKNIFDQDYFIRS
YDDNNKGIYAGQPRTLYMQGSLKF |

Fig. 8

| |
|---|
| Klebsiella pneumoniae 1571 FhuA (Ferrichrome Receptor) Gene Sequence. SEQ ID NO:3. |
| ATGGCGCGTCCAAAAACTGCTCAGCCAAATCACTCGCTGCGTAAAGTCGCAGCTGTAGTAGCCACGGCGGTTAGC GGCATGTCTGTCTACGCACAGGCAGCAGAACAACCGAAGCAAGAAGAAACCATCACCGTCGTTGCCGCCCCGGCC GCCCAGGAAAACGCCTGGGGACCGGCGCCGACTATCGCGGCAAAACGCTCCGCCACGGCGACCAAAACCGATACC CCGATTGAAAAAACGCCGCAGTCTGTGTCGGTGGTGACGCGCCATGAGATGGAGATGCGCCAGCCGACGACGGTA AAAGAGGCGCTCTCCTATACGCCAAGCGTCTTCTCCACTCGCGGCAGTTCGACCACCTATGACGTGGTCACCATT CGCGGCTTCACCACCTCGACGACCGTCAACACCAACCAGTATCTGGACGGCATGAAGCTGCAGGGGAATAACTAC TCTGAAGTCTCCATGGATCCTTACTTCCTCGAGCGTGTGGAAGTGATGCGCGGGCCAACCTCGGTGCTGTACGGC AACAGCAACCCGGGCGGTATCGTCAGCATGGTCAGCAAGCGCCCGACTACCGAGCCGCTGAAAGAAGTGCAGTTT AAGATGGGCACCGACAATCTGTGGCAGACCGGGTTTGACTTTAGCGACGCCATTGATGATGCCGGCGTCTGGTCG TATCGCCTGACCGGCCTTGGCCGCAGTCAGGATGCCCAGCAGCAGATGGCGAAATCGACTCGCTACGCGGTGGCG CCCTCCTTTAGCTGGCGTCCGGACGATAAAACCGACTTCACCTTCCTGAGCAACTTCCAGAATGACCCGGATGCG GGCTACTACGGCTGGCTGCCGCGCGAAGGCACCGTGGTGCCGTATTACGACGCCAACGGTAAGGCGCACAAGCTG CCGACCGATTTCAACGAAGGCGAGTCCGATAATAAAATCTCCCGCCGCCAGAAGATGGTGGGCTACAGCTTCTCC CATCAGTTCGATGACACCTTTACCGTGCGGCAGAACCTGCGCTATGCCGATGTGCATACGCTCTATCGTTCGGTA TACGGCAACGGCTATGTCGCGCCGGGCTACATGAATCGCGCCTACGTGCGCTCCGACGAGCACCTGAACACCTTC ACCGTCGATACCCAGCTGCAGTCTGATTTCGCCACCGGCGCGGTCAGCCATACGCTGCTGACCGGCGTGGACTAC TCGCGGATGCGTAACGATGTGGATGCCGACTACGGGACGGCGGATCCTATCAGCATGAGCAATCCGCAGTACGGC AATCCGAATATTCAGGTCACCTTCCCGTACGCGGTCCTCAACCGGATGGAGCAGACCGGCCTGTACGCGCAGGAT CAGATGGAGTGGGATAAATGGGTGATGACCCTGGGCGGCCGTTACGATTACGCCACGACCTCAACGTTAACCCGC GCCACCAACAGCCTGGCGGAGAATCACGACCAGCAGTTCAGCTGGCGCGGCGGCATCAACTACCTGTTCGATAAC GGCATCTCGCCGTACTTCAGCTACAGCGAATCGTTTGAACCGGTATCGGGTTCCAACAGCCGCGGCCAGCCGTTC GATCCGTCGCGCGGTAAGCAGTATGAAGCCGGCGTGAAATACGTGCCGAAAGATATGCCGGTGGTGGTCACCGCG GCGGTCTATCAGCTGACCAAAGACAAGAACCTGACGGCTGATCCGGCTAACCAGGCGTTCAGCATCCAGACCGGC GAGATCCGCTCCCGCGGCCTTGAGCTGGAGGCGAAGGCGGCGGTGAACGCCAATATTAACGTCACCGCGGCCTAC AGCTACACCGATGCGGAGTACACTCACGATACGGTGTTCAACGGCAAACGTCCGGCGGAAGTGCCGCGTAACATG GCCTCCCTGTGGGCGGATTATACCTTCCACGAAACCGCGCTGAGCGGTCTGACGATTGGGGCCGGGGCGCTAT ATCGGTTCAACGGTCAGCTACTACAAAAATGACACCAGCACCGGTAAGAAAAATGATGCCTTTAGTGTGGCCGGT TATGCGCTGATGGATGCGACGGTGAAATACGATCTGGCGCGCTTTGGCCTGCCGGGATCGTCGGTCGGCGTCAAC GTCAACAACCTGTTCGACCGCGAATATGTCTCCAGTTGCTACAGCGAATACGCCTGCTACTGGGGCGCCGGACGT CAGGTCGTCGCCACCGCCACCTTCCGTTTCTAA |
| Klebsiella pneumoniae 1571 FhuA (Ferrichrome Receptor) AA Sequence, 735 aa, SEQ ID NO:4. Underlined sequence is the signal sequence. Sequence of protein without signal sequence is SEQ ID NO:42, and the calculated molecular weight is 78 kDa. |
| <u>MARPKTAQPNHSLRKVAAVVATAVSGMSVYAQA</u>AEQPKQEETITVVAAPAAQENAWGPAPTIAAKRSATATKTDT PIEKTPQSVSVVTRHEMEMRQPTTVKEALSYTPSVFSTRGSSTTYDVVTIRGFTTSTTVNTNQYLDGMKLQGNNY SEVSMDPYFLERVEVMRGPTSVLYGNSNPGGIVSMVSKRPTTEPLKEVQFKMGTDNLWQTGFDFSDAIDDAGVWS YRLTGLGRSQDAQQQMAKSTRYAVAPSFSWRPDDKTDFTFLSNFQNDPDAGYYGWLPREGTVVPYYDANGKAHKL PTDFNEGESDNKISRRQKMVGYSFSHQFDDTFTVRQNLRYADVHTLYRSVYGNGYVAPGYMNRAYVRSDEHLNTF TVDTQLQSDFATGAVSHTLLTGVDYSRMRNDVDADYGTADPISMSNPQYGNPNIQVTFPYAVLNRMEQTGLYAQD QMEWDKWVMTLGGRYDYATTSTLTRATNSLAENHDQQFSWRGGINYLFDNGISPYFSYSESFEPVSGSNSRGQPF DPSRGKQYEAGVKYVPKDMPVVVTAAVYQLTKDKNLTADPANQAFSIQTGEIRSRGLELEAKAAVNANINVTAAY SYTDAEYTHDTVFNGKRPAEVPRNMASLWADYTFHETALSGLTIGAGARYIGSTVSYYKNDTSTGKKNDAFSVAG YALMDATVKYDLARFGLPGSSVGVNVNNLFDREYVSSCYSEYACYWGAGRQVVATATFRF |

Fig. 9

| |
|---|
| Table 5. Klebsiella pneumoniae 1571 CirA (Colicin I Receptor) Gene Sequence. SEQ ID NO:5. |
| ATGTTCAGGTTAAACCCTTTTATCCGGGCGGGATTGTCTGCGTCCGTCGTATCGTTGGCGTTTCCGGCTCTGGCC<br>GATGTGAATGAAGAAACGCTGGTGGTGACCGCCTCGGCCACTGAACAGAATGTCAAAGACGCGCCGGCGAGCATC<br>AGCGTCATCACCCAACAGGATTTACAACGCAAGCCTGTTCAGAACCTGAAAGACGTGCTGCGCGATGTGCCTGGG<br>GTCCAGCTCACCAACGAAGGGGATAACCGCAAGGGCGTTAGCATCCGCGGTCTGAGCAGCAGCTATACCCTGATC<br>CTGGTCGACGGCAAGCGCGTTAACTCGCGGAACGCCGTCTTCCGCCACAATGACTTCGACCTTAACTGGATCCCG<br>GTGGATGCTATTGAGCGTATCGAAGTGGTGCGCGGCCCGATGTCCTCCCTTTACGGCTCCGATGCGCTCGGTGGG<br>GTGGTCAACATTATTACCAAAAAAATCGGCCAGAAATGGACCGGGACGCTGAGTGCTGATACCACTATTCAGGAG<br>CACCGCGATCGCGGGGATACCTATAACGGCCAGTTCTTCACCAGCGGCCCGCTGATCGACGGCGTACTTGGAATG<br>AAGGCCTACGGCAGCCTGGCAAAACGCGCCAAGGACGATCCGCAGTCATCCAGTAATGCCACCGGCGAGACGCCG<br>CGCATCGAGGGCTTCACCAGCCGCGATGGCAATGTTGAATTCGCCTGGACGCCGAACGAAAACCACGATTTTACC<br>GCAGGCTACGGCTTTGACCGTCAGGATCGCGATTCCGATTCCCTTGACCGCAACCGCCTTGAGCGGGAGAACTAC<br>TCTCTGAGCCATAACGGCCGCTGGGATATTGGCAATAGCGAGCTCAAGTTCTACGGCGAAAAGGTGGATAACAAA<br>AATCCAGGGCAGAGCGGGACTATTACCTCGGAAAGCAATGCCATCGACGGCAAGTATGTCCTGCCGCTGGGCATG<br>ATTAACCAGCTGGTGACCTTCGGCGGCGAATGGCGCCACGACAAACTGAAAGATCCGGTCAACCTGAGCAGCGGC<br>GGCCAGTCAACGTCGGCCAGCCAGTACGCCCTGTTTATCGAAGACGAATGGCGCATCATCGAGCCGCTGGCGCTG<br>ACCACCGGCATTCGTATGGACGACCATCAGACCTATGGCGATCACTGGAGCCCGCGCGCCTATCTGGTGTATAAC<br>GCCACCGATACCGTCACCGTCAAAGGCGGCTGGGCGACGGCGTTTAAAGCCCCGTCGCTGCTGCAGCTTAACCCC<br>GACTGGACCACCAACTCCTGCCGCGGCTCGTGCAGCATCGTCGGTAACCCGGATCTGAAACCGGAAACCAGCGAA<br>AGCTTCGAGCTCGGTCTCTACTACCGCGGGGAAGAGGGCTGGCTTGAAAATGTCGAAGGCAGCATCACCACCTTC<br>CAGAATAATGTCGACGACATGATCGATGTTCTGCGCACCTCCAGCGCCAGCGAAGCGCCGGGCTACCCGAACTTT<br>GTCGGCTGGAAAACCGTCAACGGCAAGCGCGTGCCGATCTTCCGCTATTTCAACGTCAACAAAGCCCGCATCAAA<br>GGGGTGGAGACGGAGGTGAAGATCCCGTTTGGCGATGAGTGGAAGCTGACGGTGAACTACACATACAACGATGGT<br>CGCGATCTGAGCAATGGCGGCGACAAACCGCTGCAGACGCTGCCGTTCCATACCGCCAACGGCACGCTCGACTGG<br>AAACCGCTGGACGATTGGTCCTTCTACGTGACGGCCAACTATACCGGCCAGCAGCGCGCGGTGAGCGCCACCGGC<br>AAAACGCCGGGCGGCTACACCCTGTTTGACGTTGGCGCGGCATGGCAGGTGACCAAAAACGTGAAACTGCGCTCC<br>GGGGTGCAGAACGTGGGTGATAAAGATCTGAGCCGGGACGACTACAGCTATACCGAAGAAGGCCGTCGCTACTTT<br>ATGGCGGTGGATTATCGCTTCTGA |
| Klebsiella pneumoniae 1571 CirA (Colicin I Receptor) AA Sequence, SEQ ID NO:6. Underlined sequence is the signal sequence. Sequence of protein without signal sequence is SEQ ID NO:43, and the calculated molecular weight is 70.4 kDa. |
| MFRLNPFIRAGLSASVVSLAFPALADVNEETLVVTASATEQNVKDAPASISVITQQDLQRKPVQNLKDVLRDVPG<br>VQLTNEGDNRKGVSIRGLSSSYTLILVDGKRVNSRNAVFRHNDFDLNWIPVDAIERIEVVRGPMSSLYGSDALGG<br>VVNIITKKIGQKWTGTLSADTTIQEHRDRGDTYNGQFFTSGPLIDGVLGMKAYGSLAKRAKDDPQSSSNATGETP<br>RIEGFTSRDGNVEFAWTPNENHDFTAGYGFDRQDRDSDSLDRNRLERENYSLSHNGRWDIGNSELKFYGEKVDNK<br>NPGQSGTITSESNAIDGKYVLPLGMINQLVTFGGEWRHDKLKDPVNLSSGGQSTSASQYALFIEDEWRIIEPLAL<br>TTGIRMDDHQTYGDHWSPRAYLVYNATDTVTVKGGWATAFKAPSLLQLNPDWTTNSCRGSCSIVGNPDLKPETSE<br>SFELGLYYRGEEGWLENVEGSITTFQNNVDDMIDVLRTSSASEAPGYPNFVGWKTVNGKRVPIFRYFNVNKARIK<br>GVETEVKIPFGDEWKLTVNYTYNDGRDLSNGGDKPLQTLPFHTANGTLDWKPLDDWSFYVTANYTGQQRAVSATG<br>KTPGGYTLFDVGAAWQVTKNVKLRSGVQNVGDKDLSRDDYSYTEEGRRYFMAVDYRF |

Fig. 10

Klebsiella pneumoniae 1571 FepA (Ferrienterobactin Receptor) Gene Sequence. SEQ ID NO:7. N refers to A, T, G, or C.

ATGAATAACAGGATCAAATCCCTGGCCTTGCTGGTCAATCTGGGAATTTACGGGGTTGCTTTTCCGTTAAGCGCA
GCGGAAACCGCCACCGACGATAAAAACAGCGCCGCTGAAGAGACCATGGTGGTCACCGCCGCCGAGCAGAACCTG
CAGGCGCCGGGCGTCTCCACCATCACCGCCGATGAGATCCGCAAACGCCCCCCGGCGCGCGACGTCTCGGAGATC
ATTCGCACCATGCCGGGAGTCAACCTGACCGGCAACTCCACCAGCGGCCAGCGCGGCAACAACCGCCAGATTGAT
ATCCGCGGCATGGGCCCGGAAAATACCCTGATCCTGATCGACGGCAAGCCGGTCACCAGCCGCAACTCCGTGCGC
CTTGGCTGGCGCGGCGAGCGCGACACCCGCGGCGATACCAGCTGGGTGCCGCCGGAGATAATCGAACGTATCGAA
GTGATTCGCGGCCCGGCCGCCGCCCGCTACGGCAACGGCGCCGCCGGCGGCGTGGTGAATATCATCACCAAAAAA
ACCGGCGATGAGTGGCACGGCTCATGGAACACCTATATGAACGCCCCGGAGCACAAGGATGAAGGCTCCACCAAA
CGCACTAACTTCAGCCTCAGCGGCCCGCTGGGCGGCGATTTTAGCTTCCGCCTGTTCGGTAACCTCGACAAAACG
CAGGCCGACGCCTGGGATATCAACCAGGGCCATCAGTCCGAGCGTACCGGGATCTATGCCGATACTCTGCCGGCC
GGGCGCGAAGGGGTGAAAAACAAAAACATCGATGGTCTGGTGCGCTGGGAATTCGCTCCGATGCAGTCGCTGGAG
TTTGAGGCCGGCTACAGCCGCCAGGGCAACCTCTACGCCGGCGACACCCAGAACACCAACTCCAACGACCTGGTA
AAAGAGAACTACGGCAAAGAGACCAACCGTCTGTATCGCAACACCTACTCGGTTACCTGGAACGGCGCCTGGGAC
AACGGGGTGACCACCAGCAACTGGGCGCAGTACGAACGCACCCGCAACTCGCGCAAAGGCGAAGGCCTGGCCGGC
GGCACCGAGGGGATCTTTAACAGCAACCAGTTCACGGATATCGATCTGGCGGATGTGATGCTGCACAGCGAAGTC
AGCATTCCCTTCGACTATCTGGTTAATCAGAACCTGACGCTGGGCAGCGAGTGGAATCAACAGCGGATGAAGGAT
AACGCGTCCAACACCCAGGCGCTGTCGGGAGGCGGAATTCCGGGCTACGACAGCACCGGCCGCAGCCCGTACTCG
CAGGCGGAAATCTTCTCGCTGTTCGCCGAGAACAACATGGAGCTGACCGACACCACCATGCTGACTCCGGCGCTG
CGTTTCGATCATCACAGCATTGTCGGCAATAACTGGAGCCCGTCCCTCAACCTGTCGCAGGGCCTGTGGGATGAC
TTCACGCTGAAGANNNNNNNNNCCCGCGCCTATAAAGCGCCGAGCCTGTATCAGACCAACCCGAACTACATTCTC
TACAGTAAAGGCCAGGGCTGCTACGCCAGTAAAGACGGCTGCTATCTGCAGGGTAATGACGACTTAAAAGCCGAG
ACCAGCATCAACAAAGAGATTGGCCTCGAGTTTAAACGCGACGGCTGGCTGGCGGGCGTCACCTGGTTCCGCAAC
GACTACCGCAACAAGATTGAAGCGGGCTATGCCCCGGTCTATCAAAACAATAAAGGTACCGATCTCTACCAGTGG
GAAAACGTGCCGAAAGCGGTGGTGGAAGGTCTGGAGGGGACGTTGAACGTTCCGGTGAGCGAGACCGTCAACTGG
ACCAACAACATCACCTATATGCTGCAGAGTAAGAACAAAGAGACCGGCGATCGTCTGTCGATTATCCCGGAATAC
ACGCTGAACTCCACCCTGAGCTGGCAGGTTCGCGATGACGTTTCGCTGCAGTCGACCTTCACCTGGTACGGCAAG
CAGGAGCCGAAGAAGTACAACTACAAGGGTCAACCGGTCACCGGCAGCGAGAAGAACGAGGTTAGCCCCTACAGC
ATCCTCGGCCTGAGCGCGACCTGGGACGTCACCAAATACGTCAGTCTGACCGGCGGCGTGGATAACGTCTTCGAT
AAGCGCCACTGGCGCGCGGGCAACGCCCAGACCACCGGGGCGCCACCGGCACGATGTACGGCGCCGGCGCCGAG
ACCTACAATGAATCGGGCCGCACCTGGTACCTGAGCGTCAACACCCACTTCTGA

Klebsiella pneumoniae 1571 FepA (Ferrienterobactin Receptor) AA Sequence, SEQ ID NO:8. Underlined sequence is the signal sequence. Sequence of protein without signal sequence is SEQ ID NO:44, and the calculated molecular weight is estimated to be 79.7 kDa based on an average of 110 Daltons per amino acid depicted as X. X refers to any amino acid.

<u>MNNRIKSLALLVNLGIYGVAFPLSAAETATDDKNSAAEETMVVTAAEQNLQAPGVSTITADEIRKRPPARDVSEI</u>
IRTMPGVNLTGNSTSGQRGNNRQIDIRGMGPENTLILIDGKPVTSRNSVRLGWRGERDTRGDTSWVPPEIIERIE
VIRGPAAARYGNGAAGGVVNIITKKTGDEWHGSWNTYMNAPEHKDEGSTKRTNFSLSGPLGGDFSFRLFGNLDKT
QADAWDINQGHQSERTGIYADTLPAGREGVKNKNIDGLVRWEFAPMQSLEFEAGYSRQGNLYAGDTQNTNSNDLV
KENYGKETNRLYRNTYSVTWNGAWDNGVTTSNWAQYERTRNSRKGEGLAGGTEGIFNSNQFTDIDLADVMLHSEV
SIPFDYLVNQNLTLGSEWNQQRMKDNASNTQALSGGGIPGYDSTGRSPYSQAEIFSLFAENNMELTDTTMLTPAL
RFDHHSIVGNNWSPSLNLSQGLWDDFTLKXXXXRAYKAPSLYQTNPNYILYSKGQGCYASKDGCYLQGNDDLKAE
TSINKEIGLEFKRDGWLAGVTWFRNDYRNKIEAGYAPVYQNNKGTDLYQWENVPKAVVEGLEGTLNVPVSETVNW
TNNITYMLQSKNKETGDRLSIIPEYTLNSTLSWQVRDDVSLQSTFTWYGKQEPKKYNYKGQPVTGSEKNEVSPYS
ILGLSATWDVTKYVSLTGGVDNVFDKRHWRAGNAQTTGGATGTMYGAGAETYNESGRTWYLSVNTHF

Fig. 11

| Klebsiella pneumoniae 1571 BtuB (Vitamin B12 Transporter) Gene Sequence. SEQ ID NO:9. N refers to A, T, G. or C. |
|---|
| ATGATTAAAAAAGCTTCGCTGATGACGGCCTTATCCGTCACGGCATTTTCCGGCTGGGCGCAGGATAGCAATTCA<br>GATACGTTGGTGGTGACAGCAAACCGTTTTCAACAGCCGGTCAATACCGTGCTGGCGCCGACCGACATTGTGACG<br>CGCGATGACATCGACCGCTGGCAGTCCAAAGATTTAAACGATGTCATGCGTCGTCTTCCCGGGGTCGATATTGCC<br>CGCAACGGCGGCATGGGGCAGAGCGCTTCGCTGTATGTTCGGGGGACGGAGGCTCGTCACGTGCTGGTGCTGATC<br>GACGGTGTGCCGATGGCGCGTCCGGGGATCTCCAACGGCGTAGATATCAGTCAGATCCCTATCTCACTGGTCCAG<br>CGGGTGGAATACATCCGCGGCCCCGCGCTCCGCGGTGTANNNNNNNNNNNNNNNNNNNNNNNNNNNNNNNNNNNN<br>NNNNNNACCGACGCTGAGCGTTCGCAAATCAACGCCGGCGCGGGCACGAACGGCTATCAGTCCTATGACGGCGCC<br>TTTAACAAGCGGTTTGGCAACACGCTGGTTACCGCTGCTGGCGCCTATCAGACCACCAAAGGGTTTAACGTCCAG<br>CCGAATTCCTCTTATAGCGGCGACAGCGATCGCGACGGCTACCGCAATAAAATGCTGTGGGGCGGGGTACAGCAT<br>CAGTTCGATGACAACTTCTCGGGGTTCTTCCGCGGCTATGGTTATTCCGCCAACGCTGACTATGACCAGGGTAAC<br>TGGGGCTACGCAGGTGGAAACGATGAAGATCAATCCTATACCCAATCCTGGGATACCGGTCTGCACTACCACTCC<br>GGAATTTACTCCTCCCAGCTGATTGCTAACTATCAGCGCATCAAAGATTACAACTACAGCAGCGACGCTGGCCGC<br>TATGCCGCGGGCACCACCCTGGATGATATGGAACAGCGCTATATCCAGTGGGGAAATAATGTTGTGGTAGGCCAT<br>GGGGCAGTGAGCGGCGGCGTTGACTGGAAACAAGAGAAGCTGAAATCCAGCGGAACGACCAGTACCGACGTGTAT<br>AAGCGTGACACCACCGGTCTTTATCTGACGGGACAGCAGCAGATTGACAGCGTGACGCTGGAAGCTTCCGGCCGT<br>GAGGATCATGACGAGCAGTTTGGCTGGCACGGTACCTGGCAGACGGCCGCAGGCTGGGAATTTATCGACGGTTAT<br>CGGACAACGCTCTCGTACGGCACAGGATTCCTCGCCCCCTCCCTCGGGCAGCAGTACGGCGCAGAACGCTTTGGC<br>ATCGCCTCTAACCCGAATCTGAAGCCAGAGGAGTCGAAGCAATGGGAAGCGGGCCTTGAAGGGTTAACGGGGCCG<br>GTCGACTGGCGCCTCTCCGCATATCGCTATGAGATTCAAAACCTCATCGATTACGACAACAACGCCTATTACAAC<br>GTCAAGTCGGCGACGATTAAGGGGCTGGAGTGGACGGGGAATATAACCACCGGGCCGGTGGAGCACCATCTGACG<br>CTGCAGTATGTTGACCCTCGCGATGATGAAACCAATAAGATCCTCTATCGCCGGGCGAAGCAGCAGGTGAAATAC<br>GAGCTGAACGGCCAGGTCTACGATCTGGGGTGGGATGTGACGTATCACTACATCGGCAAGCGTTACGATTATGAC<br>TACGACAACTCGCGTACCGTCAATATGGGTGGGTTGAGCCTCTGGGATGTCGGTTTATCGTATCCCGTCACCTCA<br>CACCTGACAGTTCGTGGTAAAATAGCCAACCTGTTCGATAAAGATTACGAGACAGTTTATGGCTACCAATCTGCA<br>GGACGGGAATACACCTTGTCTGGCAGCTACACCTTC |
| Klebsiella pneumoniae 1571 BtuB (Vitamin B12 Transporter) AA Sequence, SEQ ID NO:10 Underlined sequence is the signal sequence. Sequence of protein without signal sequence is SEQ ID NO:45, and the calculated molecular weight is estimated to be 66.2 kDa based on an average of 110 Daltons per amino acid depicted as X. X is any amino acid. |
| <u>MIKKASLMTALSVTAFSGWA</u>QDSNSDTLVVTANRFQQPVNTVLAPTDIVTRDDIDRWQSKDLNDVMRRLPGVDIA<br>RNGGMGQSASLYVRGTEARHVLVLIDGVPMARPGISNGVDISQIPISLVQRVEYIRGPRSAVXXXXXXXXXXXXX<br>XXTDAERSQINAGAGTNGYQSYDGAFNKRFGNTLVTAAGAYQTTKGFNVQPNSSYSGDSDRDGYRNKMLWGGVQH<br>QFDDNFSGFFRGYGYSANADYDQGNWGYAGGNDEDQSYTQSWDTGLHYHSGIYSSQLIANYQRIKDYNYSSDAGR<br>YAAGTTLDDMEQRYIQWGNNVVVGHGAVSGGVDWKQEKLKSSGTTSTDVYKRDTTGLYLTGQQQIDSVTLEASGR<br>EDHDEQFGWHGTWQTAAGWEFIDGYRTTLSYGTGFLAPSLGQQYGAERFGIASNPNLKPEESKQWEAGLEGLTGP<br>VDWRLSAYRYEIQNLIDYDNNAYYNVKSATIKGLEWTGNITTGPVEHHLTLQYVDPRDDETNKILYRRAKQQVKY<br>ELNGQVYDLGWDVTYHYIGKRYDYDYDNSRTVNMGGLSLWDVGLSYPVTSHLTVRGKIANLFDKDYETVYGYQSA<br>GREYTLSGSYTF |

Fig. 12

| Klebsiella pneumoniae 1571 YbiL (catecholate siderophore receptor) NT Sequence. SEQ ID NO:11. |
|---|
| ATGGAAAAAAACGCTTCTCTGCCTTTCGGCAGTTTCAACTCATTGGCATTGTTTACAGGTCTGTGTCTGGGAGCC<br>TCGCCGGCAGCAGGCATCGCAGCGGAAAATTCGGTCAAAAATAGTGAAGAGACGCTGGTAGTGGAAGCCGCTCCG<br>CCTTCACTCTACTCCCCCGGCGCTTCCGCCGATCCCAAGTTCAATAAACCGCTGGTCGATACCACCCGCACCATC<br>ACCGTGATCCCGGAACAGGTGATTAAAGATCAGGGCGTCACCAACCTGACTGACGCCCTCAAAAACGTTCCCGGC<br>GTGGGGGCGTTTTATGCCGGGGAGAATGGCAGCTCAACCACCGGGGATGCCATCTTTATGCGCGGCGTGGATACC<br>TCTAACAGCATCTATGTGGACGGCATTCGCGACATCGGCAGCGTGACGCGCGATACCTTCAATACCCAGCAGGTG<br>GAAGTCATCAAAGGGCCCGCCGGCACGGACTATGGCCGCAGCGCGCCCTCCGGCTCGATCAATATGATCAGCAAG<br>CAGCCGCGCCTTGACTCCGGGATCGACGGCTCGGCCAGCATCGGCAGCGCCTGGTCGCGCCGGGGCACTCTCGAC<br>CTGAACCAGGCGTTTAGCGACAACGCTGCGTTCCGTCTGAACCTGATGGGGGAAAAAACCCATGACGCTGGTCGG<br>GACCGCATTGAAAACGAACGCTATGGCATCGCACCGTCGCTGGCCTTCGGCCTTGATACCCCAACTCGTCTGTAT<br>CTGAACTATCTGCACGTCCGGCAGAACAACACCCCGGATGGCGGGATCCCTACCGTCGGCCTGCCGGGCTATTCG<br>GCGCCTTCGCCGAAGTATGCCGCACTCAACTCCACCGGGAAGGTCGATACCAGCAATTTCTATGGCACCGACTCC<br>GATTACGATAAATCTACTACCGACAGCGGTACCCTGCGCTTCGAACACGATCTGACAGAGAGCACCACCGTGCGC<br>AATACCACCCGCTGGTCGCGAGTGAAACAGGAGTATCTTTTGACCGCGGTGATGGGCGGCGCGAACAATATCACC<br>GCCCCCGATATCAATGACGTCAACACCTGGAGCTGGTCGCGTCTGGTTAATACCAAAGATGTCAGCAACCGCATT<br>CTGACCAACCAGACCAATATCACCTCGACCTTCGATACTGGCTCGATAGGCCATGACGTCAGCGCCGGCGTGGAG<br>TTTACCCGGGAAAACCAGACCAACTATGGCGTTAACGCCAGGACCGCGCCGGCGGTGAATCTCTACCATCCGGTG<br>AGCAACCTGTCGATTGGCGGGCTGGACAGAAACGGGGCGAACGCCAACGGCCAGACCGATACCTTCGGGATTTAT<br>GCCTTTGATACGCTGACGCTGACCGAGCGGATTGAGATCAACGGCGGGCTGCGTCTCGACAATTACCATACCAAA<br>TATGACAGCGCCACCGCCTGCGGCGGCAGCGGACGCGGGGCTATCGCCTGCCCGCCCGGACAGTCGACCGGCAGC<br>CCGGTCACCACTGTCGATACCGCTAAATCCGGCAATCTGGTTAACTGGAAAGCCGGGGCGCTGTACCGCTTAACC<br>GAGCAGGGCAATGTCTACGTCAACTACGCCATCTCACAGCAGCCGCCGGGAGGCAGCAGCTTCGCCCTGGCCGCC<br>AGCGGCAGCGGCAACAGCGCTAACCGAACCGACTTTAAGCCGCAGAAGGCAAAATCCAGCGAGCTGGGCACCAAG<br>TGGCAAATCTTCGACAACCGTCTGCTGCTCAGCGCGGCGTTATTCCGCACCGATATTGAAAACGAAGTGGCCGCC<br>AACGATGACGGAACCTGGTCGCAGTACGGCAAAAAGCGCGTGGAGGGGTATGAACTCTCCGCGACCGGAAACCTG<br>ACCCCGGACTGGACGATTATCGCCGGCTACACTCAGCAGCATGCGACAGTGACGGAGGGACAGAACGTTGCACAG<br>GATGGATCTTCCGCCCTGGCCTACACCCCGAAACATGCCTTTACGCTGTGGACGCAGTATCAGGCCACCAGCGAT<br>CTGTCCGTCGGCGGCGGTGTGCGCTATGTCGGAAGCCTGCGCCGGGGCAGCGATGGTGCAGTCGGTACCCCGGAT<br>CACACCGAGGGCTACTGGGTTGCCGACGCCAAACTGGGCTATCGGGTCAACAGCAACCTCGATCTGCAGCTCAAT<br>ATGTATAACCTGTTTGATACCGATTACGTGGCCTCCATCAACAAGAGCGGCTATCGCTATCATCCGGGCGAACCC<br>CGGACCTTTATGCTGACGGCGAACGTCCATTTC |
| Klebsiella pneumoniae 1571 YbiL (catecholate siderophore receptor) AA Sequence, SEQ ID NO:12. Underlined sequence is the signal sequence. Sequence of protein without signal sequence is SEQ ID NO:46, and the calculated molecular weight is 78.4 kDa. |
| MEKNASLPFGSFNSLALFTGLCLGASPAAGIAAENSVKNSEETLVVEAAPPSLYSPGASADPKFNKPLVDTTRTI<br>TVIPEQVIKDQGVTNLTDALKNVPGVGAFYAGENGSSTTGDAIFMRGVDTSNSIYVDGIRDIGSVTRDTFNTQQV<br>EVIKGPAGTDYGRSAPSGSINMISKQPRLDSGIDGSASIGSAWSRRGTLDLNQAFSDNAAFRLNLMGEKTHDAGR<br>DRIENERYGIAPSLAFGLDTPTRLYLNYLHVRQNNTPDGGIPTVGLPGYSAPSPKYAALNSTGKVDTSNFYGTDS<br>DYDKSTTDSGTLRFEHDLTESTTVRNTTRWSRVKQEYLLTAVMGGANNITAPDINDVNTWSWSRLVNTKDVSNRI<br>LTNQTNITSTFDTGSIGHDVSAGVEFTRENQTNYGVNARTAPAVNLYHPVSNLSIGGLDRNGANANGQTDTFGIY<br>AFDTLTLTERIEINGGLRLDNYHTKYDSATACGGSGRGAIACPPGQSTGSPVTTVDTAKSGNLVNWKAGALYRLT<br>EQGNVYVNYAISQQPPGGSSFALAASGSGNSANRTDFKPQKAKSSELGTKWQIFDNRLLLSAALFRTDIENEVAA<br>NDDGTWSQYGKKRVEGYELSATGNLTPDWTIIAGYTQQHATVTEGQNVAQDGSSALAYTPKHAFTLWTQYQATSD<br>LSVGGGVRYVGSLRRGSDGAVGTPDHTEGYWVADAKLGYRVNSNLDLQLNMYNLFDTDYVASINKSGYRYHPGEP<br>RTFMLTANVHF |

Fig. 13

| |
|---|
| Klebsiella pneumoniae 1571 YncD (Probable TonB Dependent Receptor) Gene Sequence. SEQ ID NO:13. |
| ATGAAAATCCTGTCCGTGCGTCACGCCGCCCTCCCGGCCCTGCTCTTGCCGCTCATTGCCGCAGCCCAGGCCGCT<br>GATGAACAAACCATGGTGGTGACCGCCGCGCCAACCACGGTTTCTGAACTGGATACCCCCGCCGCCGTCAGCGTG<br>GTGAATGGGGATGAGATGCGCCAGGCCGCGCCGCGCGTCAATCTCTCTGAATCGCTGGGCGCCGTGCCGGGCCTG<br>CAGGTGCAGAACCGGCAAAACTATGCCCAGGATCTGCAGCTGTCGATTCGCGGCTTTGGCTCGCGCTCAACCTAT<br>GGCGTGCGCGGACTACGCATCTATGTGGATGGCATTCCGGCCACCATGCCCGACGGCCAGGGGCAGACCTCAAAT<br>ATTGATATCGGCAGCGTTGACACCATTGAGGTGCTGCGCGGCCCCTTCTCTGCCCTGTACGGTAACTCGTCCGGC<br>GGGGTGATCAACGTCACCAGCCAGACCGGCACCCAGCCGCCCACCGTGGAAGCCAGCAGCTACTATGGCAGCTTC<br>GGCACCTGGCACTACGGGATGAAAGCCACTGGCGCCGTTGGCGACGGCAGCCACGCAGGCGATGTGGATTACACG<br>GTCTCAACCAATCGCTTCACCACCCATGGCTATCGCGATCACAGCGGCGCGCGCAAAAATCTGGCGAACGCCCGG<br>CTGGGGGTGCGCATCAACGACGTCAGTAAGCTGACTCTGCTGCTGAATAGCGTGGATATCAAAGCCAATGACGCC<br>GGTGGCCTGACCGCCGATGAATGGCGCGATAACCCGCGCCAGTCGCCGCGCGGCGACCAGTATAATACCCGCAAG<br>AATACCCGACAGACCCAGGCCGGCCTGCGCTATGAGCGCCAGCTCAGTGCCCAGGACGATCTCAGCGTATG |
| Klebsiella pneumoniae 1571 YncD (Probable TonB Dependent Receptor) AA Sequence, SEQ ID NO:14. Underlined sequence is predicted to be the signal sequence. |
| <u>MKILSVRHAALPALLLPLIAAAQA</u>ADEQTMVVTAAPTTVSELDTPAAVSVVNGDEMRQAAPRVNLSESLGAVPGL<br>QVQNRQNYAQDLQLSIRGFGSRSTYGVRGLRIYVDGIPATMPDGQGQTSNIDIGSVDTIEVLRGPFSALYGNSSG<br>GVINVTSQTGTQPPTVEASSYYGSFGTWHYGMKATGAVGDGSHAGDVDYTVSTNRFTTHGYRDHSGARKNLANAR<br>LGVRINDVSKLTLLLNSVDIKANDAGGLTADEWRDNPRQSPRGDQYNTRKNTRQTQAGLRYERQLSAQDDLSV |

Fig. 14

| Klebsiella pneumoniae 1571 IroN Gene Sequence. SEQ ID NO:15. N is A, T, G, or C. |
|---|
| GTCGATTATCACGGCTGAGGATATTGCTAAGCAGCCGCCGGTCAACGATCTCTCAGACATCATCCGTAAAATGCC CGGGGGTGAACTTGACCGGCAACAGCGCCAGCGGCAGTCGGGGCAACAACCGCCAGATTGATATCCGCGGCATGGG GCCGGAGAACACCCTGATCCTGATAGATGGGGTACCGGTCACGTCACGTAACGCGGTTCGCTATAGCTGGCGCGG CGAACGCGATACCCGGGGCGACAGCAACTGGGTACCTGCCGAAATGGTCGAACGGATTGAAGTTCTNNNNNNNNN NNNNNNNNNNNNNNNNNNNNNNNNNNNNNNNNNNNNNNGGAGTGGTCAATATCATTACCAAACGTCCGACCAACACCTG GCACGGTTCGCTGTCTTTCTTCACCAACCAGCCGGAAAACAACAAAGAAGGCACGACCAATCGCGCTAACTTCAA TCTCAGCGGCCCACTGGCCGGCGAGGCGCTGACGATGCGCCTGTATGGCAATATCAATAAAACGGAACCCGACGC CTGGGATATTAACCATGCGCAAAACGGCTCTTACGCTGCGGGGCGCGAAGGGGTCCGCAATAAAGACATTAACGC GCTACTGTCATGGAAAATGACCCCGCAACAAATTCTCGATTTCAGCTACGCCTATAGCCGTCAGGGGAATATCTA TGCTGGCGATACCCAGTACAGCAACGGCAATCTTAGCCCGAACGGGCTGGTGGACTCCCTGTACGGCCACGAAAC AAATCGCCTCTATCGCCAGTCCTGGGGACTCACCTACAACGGTCTATGGGATTGGGGTCAGTCCAAAGCCGGTGT TTACTACGAGAAAACCAACAATACCCGCCTGCAGGAAGGCTCTACCGGCCGCGTCGAAGGCATGATCAACAGTGA AGATTATGCCACCAGCCGTCTGGAATCCTGGCGTACTACCTCGGAATTCAATGTGCCTTTCTTCTGGCTGGCGGA CCAGACGCTGACGCTGGGAATGGAATGGAACCATGATCAGCTTGACGACCCGGCATCAATGCAGGCCACTAACAG CAACGGCGAGACTATCCCTGGGACCTCGGGCGACCCTACGCAACGCAGTACCAAAAACAGCGCCACCCTCACCGG TATCTATCTGGAAGATAATATCGAAGCCGTGCCCGGCACCAACCTGATCCCCGGCATTCGCTTCGATTATCATAA TCAGTTTGGCAGTAACTGGAGCCCCAGCCTCAATCTGTCCCAGGAGCTCGGCGATATGTTCACGCTGAAGGCCGG TATCGCGCGCGTGTTTAAAGCGCCAAACCTCTATCAATCCAGTAAAGGCTATTTGCTCTCCACCCGCGGCAACGG TTGTCCAAACACGATCGCTGAAGGCAGCTGCTACCTGCTGGGTAACCCTGACCTCGACCCGGAGATCAGTATCAA CAAAGAGATCGGTATCGAATTTAACCTTAATGGTTACGCTGCCGGAGTCACCTGGTTTCGCAACGATTACAAAAA CAAAATCGTCTCCGGAACAGAGGTACTGGGCTATACCTCCAGCGGCAATAATATTTTGCAATGGCAGAACGGCGG CAAAGCCGTGGTCGAGGGGCTGGAAGGAAATCTGCTGATCCCGGTGCTGAGAGATGTCCTCAGCTGGCGGACCAA TGCCACCTGGATGCTCAAATCTGAAAGTAAAGAGACTGGCAACCCGCTGTCGGTTATCCCGAAATATACCGTTAA CACGATGCTTGACTGGCAGGTAAACGACGCCCTGTCTGCGAATGTGAACTGGACGCTTTATGGCCGTCAGAAGCC GCGTCAGTATGCGGAGATCCGCAACGAAACCGGGACCCTTGCCACCACCGAGGTTGGCGCCTATTCCATCGTGGG TATTGGTACTCAGTATCAGCTAAACCGGGATATTCGCCTGAATGCCGGAATAAGTAATCTATTTGATAAGCAACT GTATCGCGAAAATGCCGGCGCCTCGACCTACAATGAGCCTGGCCGCGCGTATTACGCCGGCGTTACCCTCTCCTT CTGA |
| Klebsiella pneumoniae 1571 IroN AA Sequence, 675 aa, SEQ ID NO:16    X is any amino acid. |
| SIITAEDIAKQPPVNDLSDIIRKMPGVNLTGNSASGSRGNNRQIDIRGMGPENTLILIDGVPVTSRNAVRYSWRG ERDTRGDSNWVPAEMVERIEVLXXXXXXXXXXXXXXGVVNIITKRPTNTWHGSLSFFTNQPENNKEGTTNRANFN LSGPLAGEALTMRLYGNINKTEPDAWDINHAQNGSYAAGREGVRNKDINALLSWKMTPQQILDFSYAYSRQGNIY AGDTQYSNGNLSPNGLVDSLYGHETNRLYRQSWGLTYNGLWDWGQSKAGVYYEKTNNTRLQEGSTGRVEGMINSE DYATSRLESWRTTSEFNVPFFWLADQTLTLGMEWNHDQLDDPASMQATNSNGETIPGTSGDPTQRSTKNSATLTG IYLEDNIEAVPGTNLIPGIRFDYHNQFGSNWSPSLNLSQELGDMFTLKAGIARVFKAPNLYQSSKGYLLSTRGNG CPNTIAEGSCYLLGNPDLDPEISINKEIGIEFNLNGYAAGVTWFRNDYKNKIVSGTEVLGYTSSGNNILQWQNGG KAVVEGLEGNLLIPVLRDVLSWRTNATWMLKSESKETGNPLSVIPKYTVNTMLDWQVNDALSANVNWTLYGRQKP RQYAEIRNETGTLATTEVGAYSIVGIGTQYQLNRDIRLNAGISNLFDKQLYRENAGASTYNEPGRAYYAGVTLSF |

Fig. 15

| |
|---|
| Klebsiella pneumoniae 1571 IutA (Ferric Aerobactin). Gene Sequence. SEQ ID NO:17. |
| ATGAAAAAGCGCCTCTGGGTGCTCCACCCTCTGCTGCTGGCCAGCACGCTGCCTGCGCTGGCGGCTCAGTCTGAT
GAAGACAGCATCATCGTTAGCGCAAACCGCACCCATCGCACCGTGGCCGAAATGGCCCAAACCACCTGGGTCATT
GAGGGCCAGGAGATTGAGCAGCAGGTCCAGGGCGGGAAAGAGTTCAAAGACGTGCTGGCGCAGCTGATCCCCGGC
ATCGACGTCAGCAGCCAGGGGCGGACCAACTATGGGATGAACATGCGCGGGCGCGCGATCGTCGTGCTGATTGAC
GGCGTCCGGCTCAACTCCTCACGCACCGACAGCCGCCAGCTCGACGCCATCGATCCATTCAACATCGAACATATC
GAAGTGATCTCCGGAGCGACCTCGCTGTACGGCGGGGGCAGTACCGGCGGGCTTATCAACATCGTTACCAAAAAG
GGGCAGCAGGATCGTCAGGTCGATCTTGAGGTGGGCAGCAAGAGCGGTTTTGCGAACAGCAACGATCATGATGAG
CGCGTCGCGGCGGCCGTCAGCGGCGGAACAGACCACGCATCCGGCCGCTTGTCGGTAGCCTATCAGCGTTTCGGC
GGCTGGTACGACGGCAATACCGATGCGCTGATCCTCGATAATACCCAAACGGGGCTCCAGCATTCTGACCGCCTC
GACGTGATGGGGACGGGGACGATTGAGATCGATAATAACCGCCAGCTGCAGTTGGTCACCCAGTATTATAAAAGC
CAGGGCGATGATGACTACGGTCTGTGGCTCGGGAAGAACATGTCCGCGGTCACCAGCGGCGGCAAAGCGTATACC
ACCGACGGGCTCAATTCCGACCGTATCCCCGGCACCGAACGCCATCTGATCAGCCTCCAGTACTCTGATGCCGAC
TTTTTCGGCCAGAATCTGGTGAGCCAGGTGTACTATCGCGATGAGTCCCTCACCTTCTATCCGTTCCCGACGCTC
ACGAAAGGTCAGGTCAGTAGCTTCTCCTCGTCGCAGCAGGATACCGATCAGTATGGGGCCAAGCTGACCCTCAAC
AGCCAACCGCTGGCGGGGTGGGATCTCACCTGGGGTCTCGACGCCGATCATGAGACCTTTAATGCCAACCAAATG
TTCTTCGATCTGCCACAATCGATGGCCTCCGGCGGGTTGCACAACGAATCGATCTACACAACCGGCCGCTACCCG
GGATACAGTATTTCCAATGTCGCGCCATTCCTGCAGTCCAGCTACGATCTGAACGATATCTTTACCGTCAGCGGC
GGGGTACGCTACCAGTGGACCGAAAACCGGGTCGACGACTTTGTCGGCTACGCCCAGCAGCAGGATATCGCCAAC
GGCAAAGCGCGCTCCGCCGACGCCATCAAAGGCGGCAAAACCGATTACGATAACTTCCTGTTTAACGCCGGGATC
GTGGCCCACCTGACCGAGCGTCAACAAACCTGGTTTAACTTCTCGCAGGGCGTCGAGCTACCGGACCCTGGTAAA
TACTATGGCATCGGTAAATATGGCGCTGCGGTGAATGGTCATCTGCCGCTGATCTCCAGCGTCAACGTCGATGAC
TCGCCGCTGCAGGGGATCAAAGTTAACTCGTACGAGCTGGGCTGGCGCTACACCGGCGATAACCTGCGCACCCAG
CTGGCGGCGTACTACTCGACCTCAGATAAGACCATTGTCGTCAACCGCACCGACATGACCATCGACGTTCAGTCC
GACAAACGGCGTATTTACGGCGTTGAGGGGCGGTCGACTACTTTATTCCGGATAGCGACTGGAGCGTCGGCGGT
AACTTCAACGTGCTGAAATCCCAGGTGCAGACCGACGGCCGCTGGCAAAAATGGGACGTCACCCTCGCCTCGCCG
TCTAAAGCCACCGCCTGGGTGGGCTGGGCGCCGGATCCGTGGAGCCTGCGCGTGCAGAGTCAGCAGGTATTTGAC
CTCAGCGATGCCGCCGGCAACAAGCTGGAAGGCTATAACACCGTCGATTTTATCGGTAGTTACGCGCTGCCGGTG
GGGAAACTGACCTTCAGTATCGAAAACCTGCTTAACGAAGACTATGTGACTATATGGGGCCAGCGCGCGCCGCTG
CTCTACAGCCCAACCTACGGCAGTTCATCGCTGTATGAGTACAAAGGTCGTGGCCGCACCTTTGGTCTGAACTAC
GCCTTAACCT |
| Klebsiella pneumoniae 1571 IutA (Ferric Aerobactin) AA Sequence, SEQ ID NO:18 Underlined sequence is the signal sequence. Sequence of protein without signal sequence is SEQ ID NO:49, and the calculated molecular weight is 78 kDa. |
| <u>MKKRLWVLHPLLLASTLPALAAQS</u>DEDSIIVSANRTHRTVAEMAQTTWVIEGQEIEQQVQGGKEFKDVLAQLIPG
IDVSSQGRTNYGMNMRGRAIVVLIDGVRLNSSRTDSRQLDAIDPFNIEHIEVISGATSLYGGGSTGGLINIVTKK
GQQDRQVDLEVGSKSGFANSNDHDERVAAAVSGGTDHASGRLSVAYQRFGGWYDGNTDALILDNTQTGLQHSDRL
DVMGTGTIEIDNNRQLQLVTQYYKSQGDDDYGLWLGKNMSAVTSGGKAYTTDGLNSDRIPGTERHLISLQYSDAD
FFGQNLVSQVYYRDESLTFYPFPTLTKGQVSSFSSSQQDTDQYGAKLTLNSQPLAGWDLTWGLDADHETFNANQM
FFDLPQSMASGGLHNESIYTTGRYPGYSISNVAPFLQSSYDLNDIFTVSGGVRYQWTENRVDDFVGYAQQQDIAN
GKARSADAIKGGKTDYDNFLFNAGIVAHLTERQQTWFNFSQGVELPDPGKYYGIGKYGAAVNGHLPLISSVNVDD
SPLQGIKVNSYELGWRYTGDNLRTQLAAYYSTSDKTIVVNRTDMTIDVQSDKRRIYGVEGAVDYFIPDSDWSVGG
NFNVLKSQVQTDGRWQKWDVTLASPSKATAWVGWAPDPWSLRVQSQQVFDLSDAAGNKLEGYNTVDFIGSYALPV
GKLTFSIENLLNEDYVTIWGQRAPLLYSPTYGSSSLYEYKGRGRTFGLNYALT |

Fig. 16

```
Klebsiella pneumoniae 1571 FitA (ferric coprogen receptor). SEQ ID NO:19.

CCCGCCGCGGCTTCGGCGCCAACCGCGACGGCTCGATCATGACCAACGGCCTGCGCACCGTGCTGCCGCGCAGCT
TTAACGCCGCCACCGAACGGGTGGAAGTCCTGAAGGGGCCCGCCTCGACGCTGTACGGTATCCTCGACCCCGGCG
GGCTGATCAACGTCATCACTAAACGGCCGGAGCGGCAGTTCTCCGGTTCGGTTTCCGGGACCTCCACCAGCTTTG
GCGGCGGCACCGGCAGCGTCGACATCACCGGCCCCATCGAAGGCACAAATCTGGCGTACCGACTGATCGGCGAAT
ATCAGAATGAGGATTACTGGCGCAATTTCGGTAAAAACAAAAGCAGCTTTATCGCCCCTTCCCTGACCTGGTTTG
GCGAGCGGGCAACGGTGACCGCGTCCTATTCGCACCGCGACTACAGCGCCCCCTTTGATCGCGGAACTATCTTCG
ATCTGAATACCGGCCATGCGGTTAACGTCGATCGCAAAACCCGCTTCGATGAAGCGTTTAATATTACCGATGGCT
ATTCCGATCTCGCTCAGCTCAACGCCGAGTATCGCCTTAACGACGCCTGGACCGCGCGCTTCGACTACAGCTACA
GCCAGGATCATTACAACGATAACCAGGCGCGGGTAATGGCCTATGATTCGGCGACCGGCAACCTCCCCGCCGGG
TCGATGGTACCCACGGTTCAACGCAGAAGATGCACTCCACCCGCGCCGACCTGCAGGGCAACGTGGTAGTGGGCG
GCTTTTATAACGAGCTGCTGACCGGCGTCGCCTATGAGAATTACGATCTGCTGCGCACCGATATGCTGCGCTGTA
AGAACGTTAAAGGCTTTAACATCTATCATCCGGTCTACGGCACTCTCGACACCTGTAATACCGTCTCCGCCTCCG
ACAGCGACCAGCGCATTCAGCAGGAGAGCTATGCCGCATACGTGCAGGACGCGCTGTACCTGACCGACAACTGGA
TCGCCGTCGCCGGCGTGCGCTACCAGTACTACACCCAGTACGCCGGTAAAGGCCGACCGTTTAACGTCAATACCG
ACAGCCGCGATGAGAAATGGACGCCGAAAGCCGGCCTGGTCTACAAGGTCACGCCGAACGTCTCCCTGTTCGCCA
ACGTCGCCCAGTCGTTTATGCCGCAGTCGTCGATCGCCAGCTATATCGGCGAGCTGCCGCCGGAAGAGTCCACCT
CTTACGAAGTGGGCGCCAAATTCGACCTGTTAAACGGCATTACCGCCAATATCGCGTTGTTTGATATTCATAAGC
GTAACGTGCTGTACACCGAGAGCATTGGCGATGAGACGGTGGCCAAAACGGCGGGCAAAGTGCGTTCCCAGGGCG
TGGAAGTGGATCTGGCGGGGTCCATCACCGATAACCTCAGCGTGATCGCCAGCTACGGCTACACCGACGCCAAAG
TGCTGGAAGATCCGGATTACGCCGGGAAACCGCTGCCAAACGTACCGAAACATACCGGTTCGCTGTTCCTGACCT
ATGACATTCATAACGTCTATAACAGCAACACCCTGACCGTCGGCGGCGGCGGCCACGCGGTCAGCAAGCGTTCCG
GCACCAACGGCGCGGATTATTATTTGCAGGGGTATGCGGTGGCGGATGTGTTTGCTGCCTATAAGATGAAGCTGC
AGTATCCGGTGACGCTGCAGGTGAATGTGAAGAACCTGTTTGATAAGACCTATTACACTTCCTCGATCGGCACCA
ATAATCTCGGCAACCAGATTGGCGACCCGCGCGAAGTGCAGTTCACGGTGAAGATGGATTTTTAA
```

```
Klebsiella pneumoniae 1571 FitA AA Sequence, SEQ ID NO:20.

RRGFGANRDGSIMTNGLRTVLPRSFNAATERVEVLKGPASTLYGILDPGGLINVITKRPERQFSGSVSGTSTSFG
GGTGSVDITGPIEGTNLAYRLIGEYQNEDYWRNFGKNKSSFIALSLTWFGERATVTASYSHRDYSAPFDRGTIFD
LNTGHAVNVDRKTRFDEAFNITDGYSDLAQLNAEYRLNDAWTARFDYSYSQDHYNDNQARVMAYDSATGNLPRRV
DGTHGSTQKMHSTRADLQGNVVVGGFYNELLTGVAYENYDLLRTDMLRCKNVKGFNIYHPVYGTLDTCNTVSASD
SDQRIQQESYAAYVQDALYLTDNWIAVAGVRYQYYTQYAGKGRPFNVNTDSRDEKWTPKAGLVYKVTPNVSLFAN
VAQSFMPQSSIASYIGELPPEESTSYEVGAKFDLLNGITANIALFDIHKRNVLYTESIGDETVAKTAGKVRSQGV
EVDLAGSITDNLSVIASYGYTDAKVLEDPDYAGKPLPNVPKHTGSLFLTYDIHNVYNSNTLTVGGGGHAVSKRSG
TNGADYYLQGYAVADVFAAYKMKLQYPVTLQVNVKNLFDKTYYTSSIGTNNLGNQIGDPREVQFTVKMDF
```

Fig. 17

```
Klebsiella pneumoniae 1571 FcuA (Ferrichrome receptor) SEQ ID NO:21

ATGGGGCAAATTATGCACACCACGCACTATTCATCCTTCCCGCTGCGTAAAACGCTGCTGGCCTTAGCCATCGGC
GCCGCCAGTCAAACGGCGATGGCCGCGGACGCTGCCGCCGCGAAGCAGCCTGGCGAAGAGACCCTCATCGTCGAG
GCTAACGAAACCAGCGATTTTAAATCCGGCGGTGACCTGGTGGTTCCGGCATTCCTCGATGGCCAGATCGCCCAC
GGCGGCCGTCTGGGGATGCTTGGCGAACAAAAAGCGATGGACGTCCCGTTTAACGTCATCGGCTATACCTCGAAG
CTGATTCAGGATCAGCAGGCGAAAACTATCGCCGATGTCGTCAGTAACGACGCTGGCGTGCAGGCCGTACAGGGC
TACGGCAACTTCGCCGAGACCTATCGAATCCGCGGGTTTAAGCTCGATGGCGATGACATGACGATGGGCGGCCTG
GCGGGCGTGGTGCCGCGTCAGGTGATGGACACCCAGATGCTGGAGCGCGTTGAAATTTTCAAAGGGGCTAACAGC
CTGCTTAACGGCGCGGCCAGCAGCGGTGTCGGCGGGGTGATTTACCTCGAGCCGAAGCGGGCGGAAGATCTGCCG
ACCGCACGCGTTGGCGTCGACTATACCTCTGATTCTCAGGTGGGCGGCACCCTCGACCTGGGGCGCCGTTTCGGC
GACAACAACCAGTTCGGCGCCCGGGTCAACCTGGTGCACCGCGAGGGTGAAGGCGCTATCGATAATGATAAACGC
CGTACCACGCTGGCTTCGCTGGGGCTTGATTACCGCGGCGACCGTTTCCGCTCCTCGCTCGATTTCGGCTATCAG
AAGAAAACGTTCCACGGCGGTACGATGGGCGTCAATATCAGCGGCGTGGATTTCGTTCCGGCGCTGCCGGACAAC
AGCAAAAACTACAGCCAGAAGTGGGGCTATAGCGATATTGAAAGCGAGTTTGGCATGGCGAAGGCAGAATATGAC
CTGACCGATAGCTGGACGGTATACAGCGCCCTCGGCGGCCAGCATTCGCATGAAATTGGTACCTACAGCGCGCCG
AAGCTTCTGAATAAAAACGGCGATGCGACGGTGGGCCGCCTGGATACTAACCGCATTATCGACGCGATCAGCGGC
ATGGGCGGGGTACGCGGCGATTTCAATACCGGCGCGATTTCGCATACGGTGAACCTCGGCTATGCGGCGCAGGTG
CATACCGATGCGACCGCCTGGCGGATGTCGGCCAGGAACCCGACCACTAATATCTATGACAACCATGATGTGGCG
ATGCCGGATAACGCCTATTTTGGCGGCAACTACCACGATCCGCTGGTCACCTCGCGCAGCCGTACGCAGGGCTGG
CTGTTGAGTGATACCCTCGGCTTCTTTAACGATAAAGTGCTGTTTACCGCCGCTGCTCGTCATCAGAAAGTGGTT
GTGCGCAACTACAGCAACGCCACCGGGCTGGAAGATACCTCTTCGCGTTATACCCAAAGCCGCTGGATGCCGACG
TTTGGCCTGGTGTACAAGCCGTGGGAGCAGCTGTCGCTGTATGCTAACCATACCGAAGCGCTGCAGCCGGGCTCT
GTGGCGCCGACGACGGCGGCCAATGCCGGGCAGAGTACCGGGATCGCGCACTCGAAGCAGGACGAAGTGGGCGTC
AAGATCGACTACGGTACGATCGGAGGATCGCTGGCGCTGTTTGAAATCAAAAAACCGAACGCCATTTCCGATACC
GCTGGCAATTACGGCCTCGACGGCGAGCAGCGTAACCGCGGCGTAGAGATGAACGTCTTTGGCGAGCCGATGCTG
GGACTGCGTCTTAACGCCAGTACCGTCTGGCTGGATGCCAAACAGACTAAAACCGCTGAAGGCGCAACCGACGGT
AAAGATGCCATCGGGGTGGCTAACTTCTACGCGGTACTCGGCGCCGAATATGACATCAAGCCGGTGGAAGGCCTG
ACCGCCACCGCGCGCGTCAATCATAGCGGCTCGCAGTATGCCGATGCGGCCAATACCAAGAAGCTGGATAGCTAC
ACCACCCTGGATTTAGGCCTGCGCTATCGTATGCGTCTGAACGCCGACCAGAACGAAATGATCTGGCGCGTCGGG
GTGACCAACGTGACCAACGAGAAGTACTGGTCTGGCATTGACGATACCGGTACTTACCTGTTCGAAGGCGATCCG
CGTACCGTCCGCGTCTCAATGAGCTACGACTTCTGA
```

Klebsiella pneumoniae 1571 FcuA AA sequence, SEQ ID NO:22. Underlined sequence is the signal sequence. Sequence of protein without signal sequence is SEQ ID NO:51, and the calculated molecular weight is 76.2 kDa.

MGQIMHTTHYSSFPLRKTLLALAIGAASQTAMAADAAAAKQPGEETLIVEANETSDFKSGGDLVVPAFLDGQIAH
GGRLGMLGEQKAMDVPFNVIGYTSKLIQDQQAKTIADVVSNDAGVQAVQGYGNFAETYRIRGFKLDGDDMTMGGL
AGVVPRQVMDTQMLERVEIFKGANSLLNGAASSGVGGVIYLEPKRAEDLPTARVGVDYTSDSQVGGTLDLGRRFG
DNNQFGARVNLVHREGEGAIDNDKRRTTLASLGLDYRGDRFRSSLDFGYQKKTFHGGTMGVNISGVDFVPALPDN
SKNYSQKWGYSDIESEFGMAKAEYDLTDSWTVYSALGGQHSHEIGTYSAPKLLNKNGDATVGRLDTNRIIDAISG
MGGVRGDFNTGAISHTVNLGYAAQVHTDATAWRMSARNPTTNIYDNHDVAMPDNAYFGGNYHDPLVTSRSRTQGW
LLSDTLGFFNDKVLFTAAARHQKVVVRNYSNATGLEDTSSRYTQSRWMPTFGLVYKPWEQLSLYANHTEALQPGS
VAPTTAANAGQSTGIAHSKQDEVGVKIDYGTIGGSLALFEIKKPNAISDTAGNYGLDGEQRNRGVEMNVFGEPML
GLRLNASTVWLDAKQTKTAEGATDGKDAIGVANFYAVLGAEYDIKPVEGLTATARVNHSGSQYADAANTKKLDSY
TTLDLGLRYRMRLNADQNEMIWRVGVTNVTNEKYWSGIDDTGTYLFEGDPRTVRVSMSYDF*

Fig. 18

```
Klebsiella pneumoniae 1571 Ferric Enterbactin Colicin B/D receptor. SEQ ID
NO:23

ATGTACAAATCGACTCCGTCAGCAGCATGGTGTAAAAAACGCCTGCTGGTGACCTCTTTGTTTGCAGCAATTTAT
CAGACTTCTGCCATCGCAGCAGATACTTCCGCCGTTAGCGGCGAGGCGGTGGATGACACCTCGGAACAAATGACC
GTCACCGCCCCCGCGCCGGTGCAGAAAGCCGGTAGCGAACATAGCATCAGCGCCCGGGAGCTGGAGAATAAAGGC
GCTAACGATTTCGGCTCAATCATGCGCTATGAGCCGCTCATCAGCGCCACCGGGGCCAGCGGCGGCTCCGGCAAC
GGCAAAAGCGGCTTCGACCGCGGAGGTTACACCGGCTACAACATTCGCGGTATGGAGAGCAACCGCGTCGGCATC
GACGTGGACGGTATCGCGCAACCCAACGCCACCGGCCGCGGCTACGTCGGCCGCGCCGGGCTCAACACCTTCGGC
ATCGGCCGCGATTATATCGACCCGTATATGTACGGCAGCGTGGATATCCAGTCCGGCGCCACCTCGACGGAAACG
GCCAACAGCGCTATCGGGGGAATGTCTCCTTCCGCCCGAAATCAGCGGATGATTACCTGCGCCCGGGCAAGACC
AGCGCCTTCGGCTACCGCAGCGGTTACGACTCTGCGGATCGCAGCTGGCACAACGGGGTGACCGTCGCCGGCGGC
GATGAGTTCCTGCGCGGGATTTTGGTCTATAGCCGCCGTGACGGCCAGGAAACCGAAAACAACAGCGGCACCGTC
GACGCCTACCCGGCGAACTGGCACTCCGATGCTTTTCTGGCCTCCGGGATCTGGCAGCCTAACGATGAGCACAAG
CTGACCAGCACCTTCGACTATTACCATAAAACCAACCACACCCACTACGATACCTGGGACTCCAGCGGCAACAGC
ACCATCGGCACCGCCAACCAGACCAGCCAGACCCGGCGCTGGGGCCTGAGCCTGAAGGATGACTGGACGCCGATG
AACGACTACCTCGACAGCGTCTCCACAAAAATCTACTACCAGCATACCGAAGCCCATGACTGGACTTATATGCCG
GACAGCGTCACCCGCAGAATGCAGACGGTGAACTCTAACTACGATACCGACACCTGGGGCCTGCAGACCGCGCTG
GCGAAAACCCTGGGCCGCCACGATCTGAGCGCCGGTTTCAACGCCAGCACCAGCAAAACCCAGCGGCCGTTCAGC
CAGTCGCCGATCCCCAGCGTTTACAGCGAGATCATGCAGCCGGAGGCAGACAGCCGCAGCTACACCCTCGGCGGC
TTTGTCCAGGATAAGATCAACTTCGACCTTGATAGCCACAACTTCGCCGTTATTCCCGGCGTGCGCGTGGTGCAT
CAATCGACTAAGCCGGAAAATCTGTCCGATCTCGCCGCCAACAGCAGCGTGCTGAGCGAATCGTCGGTGGCGAAT
CTGTACGGCAAAAACAGCGATACCCAGGTTCTGCCGTCGTTGACCTTCCAGTACGACCTCACCCCGCGCCTGATG
ACCTACCTGCAGTACCAGCGCGGGGCGCAGTTCCCCAACGCCAGCCAGCTGTATGGCTCCTGGAACCTCGGCTCC
AGCTACGCCGGCAGCCAGCAGTATGCCCTGATCGGCAATACCGATCTGAAGACGGAAACCAGCGATAATCTCGAG
TGGGGGCTGAAGGGGGAAGTTACCGAAGGCATCACCCTGCGCACGGCGCTGTTCTACAACAGCTATAAGAACTTT
ATCGCCTATACCCGCTATACCCGCGCCAACAATCCGGGCCAGTTCACGAATGTGCCGTCGAACATCTACACCATT
TATCAGGCGGAAAACCGCGATAAAGCCTATATCTACGGCGGTGAGATTAGCACCAAATTTAACTTTGGCACCTGG
TTTGAGCAGGTGGACGGCCTGAGCGCCACCCTCGCCCTCGGCTATAGCGAAGGGAAATCGAAATCCAGCTACAGC
GGCGATAAATACGTCGACCTCGACAGCGTGGCGCCAATGAAAGCCATCGTCGGCGTGGCGTGGGACGATCCGGCG
AAACGCTACGGCACCGCCCTGACGGCGACCTTTGTCAAAGGGAAACAGGCGACCGCCACCAACCGCGAAAGCTAC
AGCAACAGCGGATCCGCCATCACCGATGCCAGTAGCGACTATATGCGCGTGCCGGGCTACGGCATGCTGGACTGG
ACCGCGTACTGGCAGGTGGCGAAAAACGTGCGCCTCAATGGCGGGGTCTACAACCTCACCGATCGTAAATACTGG
GATTACCTGAGCAGCCGCAATATCGAGACCGGCACCAACCAGGACGCCAACGATAAAGCGCTGGCGGTGATGCCG
GGCCGCACCTGGCAGCTGGGCGTCAACGTCGACTTCTGA
```

```
Klebsiella pneumoniae 1571 Ferric Enterbactin Colicin B/D receptor AA
sequence.  SEQ ID NO:24.  Underlined sequence is the signal sequence.
Sequence of protein without signal sequence is SEQ ID NO:52, and the
calculated molecular weight is 83 kDa.

MYKSTPSAAWCKKRLLVTSLFAAIYQTSAIAADTSAVSGEAVDDTSEQMTVTAPAPVQKAGSEHSISARELENKG
ANDFGSIMRYEPLISATGASGGSGNGKSGFDRGGYTGYNIRGMESNRVGIDVDGIAQPNATGRGYVGRAGLNTFG
IGRDYIDPYMYGSVDIQSGATSTETANSAIGGNVSFRPKSADDYLRPGKTSAFGYRSGYDSADRSWHNGVTVAGG
DEFLRGILVYSRRDGQETENNSGTVDAYPANWHSDAFLASGIWQPNDEHKLTSTFDYYHKTNHTHYDTWDSSGNS
TIGTANQTSQTRRWGLSLKDDWTPMNDYLDSVSTKIYYQHTEAHDWTYMPDSVTRRMQTVNSNYDTDTWGLQTAL
AKTLGRHDLSAGFNASTSKTQRPFSQSPIPSVYSEIMQPEADSRSYTLGGFVQDKINFDLDSHNFAVIPGVRVVH
QSTKPENLSDLAANSSVLSESSVANLYGKNSDTQVLPSLTFQYDLTPRLMTYLQYQRGAQFPNASQLYGSWNLGS
SYAGSQQYALIGNTDLKTETSDNLEWGLKGEVTEGITLRTALFYNSYKNFIAYTRYTRANNPGQFTNVPSNIYTI
YQAENRDKAYIYGGEISTKFNFGTWFEQVDGLSATLALGYSEGKSKSSYSGDKYVDLDSVAPMKAIVGVAWDDPA
KRYGTALTATFVKGKQATATNRESYSNSGSAITDASSDYMRVPGYGMLDWTAYWQVAKNVRLNGGVYNLTDRKYW
DYLSSRNIETGTNQDANDKALAVMPGRTWQLGVNVDF*
```

Fig. 19

```
Klebsiella pneumoniae 1571 FoxA SEQ ID NO:25

TTGGTTCAGGATGATCTTATGAACGTGGCTATTTCTCGAAAACGCCCGGGGCTGCTGTATGCCCTTGCGGTCACA
CTCCCCTTCACCGCGCAAGCCGAAGAGACGGTGGTGGTCACTGCCACCCCGCCGGCGTCCGCCAGCGCGCCGACG
GAGGGCTACAGCGCCAGCACCTCGCTCGGGGCGACGAAAACCGACCAGCCGTTAATCACTACCGCCCAGTCGGTG
TCGGTGGTCACCCGCCAGCAGATGGCGGATCAGGGGGCGAATACCATCAGCCAGGCGCTGGAATATACCCCGGGG
GTCTACTCCAGCTTCGGCGGCGGCGCCACCCGGTTCGACGCCATCTCCCTGCGCGGCTACCACGGCGGCGACGTC
GATAACCTGTTCCTCGACGGCATGCGCCTGATGAGCGACGGCGGCAGCCATAACGTACTGCAAATCGACCCGTGG
TTTATCGAACGCGTGGATGTGATCCGCGGCCCCTCCTCCGCGCTCTACGGGCAGAGCGTGCCGGGCGGCGTGGTC
AACCTGACTTCCAAACGTCCGCAGTTCAGCCAGCAGGGCCACATCCGCCTGACCGGCGGCACGCAAAATACCAAA
GGCGCGGCCTTCGATTACACCGACGCCATCAATGACCAGTGGGCATGGCGGCTGATCGGGATGACCCGCAGCAGC
GACACGCAGTATGACCATACCCGCGAAGAGCGCTACGCGATTTCGCCTTCCCTGCTGTGGCAGCCGGACAGCGAC
ACCTCGCTGCTGCTGCGCGCCTATCTGCAAAAAGATCCTTCCGGCGGCTACCACGGCTCTTTGCCGCTGGACGGC
ACCCGCTACGCGCACAATGGCCGTAAGCTCTCCCCCAGCACCAACGAAGGCGATCCGGGAGATGGCTATCAGCGC
CGCCAGCAGATCTACAGCTATGAGTTTGACCACCAGTTCACCGACGTCTGGTCGGTCTATTCCGCCGGGAGCTAC
ACCCATACCAACGTCTCCCTCGATCAGGTCTACCAGGTCGGCTGGATAGATGAAAGCGACATGCTGGCCCGCGGC
TACAGCGGTTCGCGCGGTTCGCTGGACGGCTGGTCAACCGATAACCGCCTGCGCGCCGATTTCAATACAGGCGAC
CTGGCGCACACCCTGATCCTCGGCGCCGAATATCATCGCTTCCGTAACGACCTGTGGACCGGCGCCGGCGGCGCG
GCGCCCCTTAACCCGTTTAGCGGCTATACCGAGCAGACCGGACATACCGTTACCTACAGCGACGACAATAATCGC
CGCTATTACCAGACCGGGCTGTATCTGCAGGATGAGATGGTCTGGAACCGCTGGCATGTGGATGTTTCCGCCCGC
TACGACCGCATCGTTTCCCAGCAGGTCAGCGATACCCAGGGGACCTCAAACCGCCGTTCAGACGACCATATCAGC
GGCCGCGCCTCGCTGTTGTACGCCCTGGACAACGGTCTGTCGCCCTACCTGAGCTACAGCCAGGCGATCACTCCG
GCGATGCTGCCGGGCGCGGACGGCAAACCGTTGAAACCGACCACCGCCGAACAGGTTGAAGCCGGCCTGAAGTTC
CAGCCGCCGGGCAGCAGCGATCTCTATAGCATCGCGATTTACGACCTGACGCAAAAGGATGTCGCCACTCGCGAC
CCGAACATCGCCACCGCCACCTATATTCCGGCGGGTAAGGTCCATTCCCAGGGCGTTGAGCTGGAAGCGCACCAC
CAGATCACCCCGCAGCTGAGTACTATCGCCTCGTATACCTGGAATCGTCTGCGTTTCCAGGACACCCAAGACGGG
ACCGACAATAACACGCCGCAGCTGACCCCGGATCAGATGGCCTCCTTCTGGGCGCGCTATCAGTTCCCGGCGGGG
ATCTCCGTTGGCGCCGGCGTCCGCTACATCGGTAAACAGTGGGCGGATGATGCCAACACCGCGCGGCTGCCGTCG
GTCACGTTGATGGACGCCATGATGCGGGCCGACCTCGGCGTCTGGTCGCCAACGCTGAAAGGCGCTTATGTGCAG
GTTAACGCCAACAATATCGGCGACCGCGAGTATATTTCCGGCTGCTATGGCACCGGCAACTGTTACTGGGGAGCA
GAGCGCAGCGTTATAGCCACCGTGGGCTACGATTTCTGA
```

Klebsiella pneumoniae 1571 FoxA AA sequence, SEQ ID NO:26. Underlined sequence is the signal sequence. Sequence of protein without signal sequence is SEQ ID NO:53, and the calculated molecular weight is 74.7 kDa.

<u>MVQDDLMNVAISRKRPGLLYALAVTLPFTAQAEET</u>VVVTATPPASASAPTEGYSASTSLGATKTDQPLITTAQSV
SVVTRQQMADQGANTISQALEYTPGVYSSFGGGATRFDAISLRGYHGGDVDNLFLDGMRLMSDGGSHNVLQIDPW
FIERVDVIRGPSSALYGQSVPGGVVNLTSKRPQFSQQGHIRLTGGTQNTKGAAFDYTDAINDQWAWRLIGMTRSS
DTQYDHTREERYAISPSLLWQPDSDTSLLLRAYLQKDPSGGYHGSLPLDGTRYAHNGRKLSPSTNEGDPGDGYQR
RQQIYSYEFDHQFTDVWSVYSAGSYTHTNVSLDQVYQVGWIDESDMLARGYSGSRGSLDGWSTDNRLRADFNTGD
LAHTLILGAEYHRFRNDLWTGAGGAAPLNPFSGYTEQTGHTVTYSDDNNRRYYQTGLYLQDEMVWNRWHVDVSAR
YDRIVSQQVSDTQGTSNRRSDDHISGRASLLYALDNGLSPYLSYSQAITPAMLPGADGKPLKPTTAEQVEAGLKF
QPPGSSDLYSIAIYDLTQKDVATRDPNIATATYIPAGKVHSQGVELEAHHQITPQLSTIASYTWNRLRFQDTQDG
TDNNTPQLTPDQMASFWARYQFPAGISVGAGVRYIGKQWADDANTARLPSVTLMDAMMRADLGVWSPTLKGAYVQ
VNANNIGDREYISGCYGTGNCYWGAERSVIATVGYDF*

Fig. 20

| Klebsiella pneumoniae 1571 OmpC gene sequence. SEQ ID NO:27 |
|---|
| ATGAAAGTTAAAGTACTGTCCCTCCTGGTACCGGCTCTGCTGGTAGCAGGCGCAGCAAATGCGGCTGAAATTTAT<br>AACAAAGACGGCAACAAATTAGACCTGTACGGTAAAATTGACGGTCTGCACTACTTCTCTGACGACAAGAGCGTC<br>GACGGCGACCAGACCTACATGCGTGTAGGCGTGAAAGGCGAAACCCAGATCAACGACCAGCTGACCGGTTACGGC<br>CAGTGGGAATACAACGTTCAGGCGAACAACACTGAAAGCTCCAGCGATCAGGCATGGACTCGTCTGGCATTCGCA<br>GGCCTGAAATTTGGCGACGCGGGCTCTTTCGACTACGGTCGTAACTACGGCGTAGTATACGACGTAACGTCCTGG<br>ACCGACGTTCTGCCGGAATTCGGCGGCGACACCTACGGTTCTGACAACTTCCTGCAGTCCCGTGCTAACGGCGTT<br>GCAACCTACCGTAACTCTGATTTCTTCGGTCTGGTTGACGGCCTGAACTTTGCTCTGCAGTATCAGGGTAAAAAC<br>GGCAGCGTCAGCGGCGAAGGCGCTCTGTCTCCTACCAACAACGGTCGTACCGCCTTGAAACAGAACGGCGACGGT<br>TACGGTACTTCTCTGACCTATGACATCTATGATGGCATCAGCGCTGGTTTCGCATACTCTAACTCCAAACGTCTT<br>GGCGACCAGAACAGCAAGCTGGCACTGGGTCGTGGCGACAACGCTGAAACCTACACCGGCGGTCTGAAATACGAT<br>GCGAACAACATCTACCTGGCCACTCAGTACACCCAGACCTACAACGCGACCCGCGCCGGTTCCCTGGGCTTTGCT<br>AACAAAGCGCAGAACTTCGAAGTGGTTGCTCAGTACCAGTTCGACTTCGGTCTGCGTCCGTCCGTGGCTTACCTG<br>CAGTCTAAAGGTAAGGATCTGGAAGGCTACGGCGACCAGGACATCCTGAAATATGTTGACGTTGGCGCGACCTAC<br>TACTTCAACAAAAACATGTCCACCTATGTTGACTACAAAATCAACCTGCTGGACGACAACAGCTTCACCCACAAC<br>GCCGGTATCTCTACCGACGACGTGGTTGCACTGGGCCTGGTTTACCAGTTCTAA |
| Klebsiella pneumoniae 1571 OmpC amino acid sequence. SEQ ID NO:28.<br>Underlined sequence is the signal sequence. Sequence of protein without<br>signal sequence is SEQ ID NO:54. |
| MKVKVLSLLVPALLVAGAANAAEIYNKDGNKLDLYGKIDGLHYFSDDKSVDGDQTYMRVGVKGETQINDQLTGYG<br>QWEYNVQANNTESSSDQAWTRLAFAGLKFGDAGSFDYGRNYGVVYDVTSWTDVLPEFGGDTYGSDNFLQSRANGV<br>ATYRNSDFFGLVDGLNFALQYQGKNGSVSGEGALSPTNNGRTALKQNGDGYGTSLTYDIYDGISAGFAYSNSKRL<br>GDQNSKLALGRGDNAETYTGGLKYDANNIYLATQYTQTYNATRAGSLGFANKAQNFEVVAQYQFDFGLRPSVAYL<br>QSKGKDLEGYGDQDILKYVDVGATYYFNKNMSTYVDYKINLLDDNSFTHNAGISTDDVVALGLVYQF |

Fig. 21

| Klebsiella pneumoniae 1571 OmpA gene sequence. SEQ ID NO:29 |
|---|
| ATGAAAAAGACAGCTATCGCGATTGCAGTGGCACTGGCTGGCTTCGCTACCGTAGCGCAGGCCGCTCCGAAAGAT<br>AACACCTGGTATGCAGGTGGTAAACTGGGTTGGTCCCAGTATCACGACACCGGTTTCTACGGTAACGGTTTCCAG<br>AACAACAACGGTCCGACCCGTAACGATCAGCTTGGTGCTGGTGCGTTCGGTGGTTACCAGGTTAACCCGTACCTC<br>GGTTTCGAAATGGGTTATGACTGGCTGGGCCGTATGGCATATAAAGGCAGCGTTGACAACGGTGCTTTCAAAGCT<br>CAGGGCGTTCAGCTGACCGCTAAACTGGGTTACCCGATCACTGACGATCTGGACATCTACACCCGTCTGGGCGGC<br>ATGGTTTGGCGCGCTGACTCCAAAGGCAACTACGCTTCTACCGGCGTTTCCCGTAGCGAACACGACACTGGCGTT<br>TCCCCAGTATTTGCTGGCGGCGTAGAGTGGGCTGTTACTCGTGACATCGCTACCCGTCTGGAATACCAGTGGGTT<br>AACAACATCGGCGACGCGGGCACTGTGGGTACCCGTCCTGATAACGGCATGCTGAGCCTGGGCGTTTCCTACCGC<br>TTCGGTCAGGAAGATGCTGCACCGGTTGTTGCTCCGGCTCCGGCTCCGGCTCCGGAAGTGGCTACCAAGCACTTC<br>ACCCTGAAGTCTGACGTTCTGTTCAACTTCAACAAAGCTACCCTGAAACCGGAAGGTCAGCAGGCTCTGGATCAG<br>CTGTACACTCAGCTGAGCAACATGGATCCGAAAGACGGTTCCGCTGTTGTTCTGGGCTACACCGACCGCATCGGT<br>TCCGAAGCTTACAACCAGCAGCTGTCTGAGAAACGTGCTCAGTCCGTTGTTGACTACCTGGTTGCTAAAGGCATC<br>CCGGCTGGCAAAATCTCCGCTCGCGGCATGGGTGAATCCAACCCGGTTACTGGCAACACCTGTGACAACGTGAAA<br>GCTCGCGCTGCCCTGATCGATTGCCTGGCTCCGGATCGTCGTGTAGAGATCGAAGTTAAAGGCTACAAAGAAGTT<br>GTAACTCAGCCGGCGGCTTAA |
| Klebsiella pneumoniae 1571 OmpA amino acid sequence. SEQ ID NO:30.<br>Underlined sequence is the signal sequence. Sequence of protein without<br>signal sequence is SEQ ID NO:55. |
| MKKTAIAIAVALAGFATVAQAAPKDNTWYAGGKLGWSQYHDTGFYGNGFQNNNGPTRNDQLGAGAFGGYQVNPYL<br>GFEMGYDWLGRMAYKGSVDNGAFKAQGVQLTAKLGYPITDDLDIYTRLGGMVWRADSKGNYASTGVSRSEHDTGV<br>SPVFAGGVEWAVTRDIATRLEYQWVNNIGDAGTVGTRPDNGMLSLGVSYRFGQEDAAPVVAPAPAPAPEVATKHF<br>TLKSDVLFNFNKATLKPEGQQALDQLYTQLSNMDPKDGSAVVLGYTDRIGSEAYNQQLSEKRAQSVVDYLVAKGI<br>PAGKISARGMGESNPVTGNTCDNVKARAALIDCLAPDRRVEIEVKGYKEVVTQPAA |

Fig. 36

| E. coli CFT073 CirA Gene Sequence, SEQ ID NO:56 |
|---|
| ATGAGAGGATCGCATCACCATCACCATCACGGATCTGGCTCTGGATCTGGTATCGAGGGAAGGCCTGTCGAT
GATGATGGCGAAACGATGGTTGTCACTGCATCTTCCGTTGAACAAAACCTTAAAGATGCTCCCGCCAGTATCA
GCGTCATTACCCAGGAAGACCTGCAGCGAAAACCGGTACAGAATCTGAAGGATGTCCTCAAAGAAGTGCCTG
GCGTACAACTGACGAACGAAGGGGATAACCGTAAGGGCGTAAGTATTCGTGGTCTGGACAGCAGCTACACCC
TGATTCTTGTCGACGGTAAACGCGTTAACTCCCGCAATGCCGTCTTCCGCCACAATGATTTCGATCTGAACTGG
ATCCCGGTCGATTCCATCGAACGTATTGAAGTGGTTCGTGGCCCGATGTCGTCGCTGTACGGTTCCGATGCGC
TCGGCGGTGTAGTGAATATCATCACCAAAAAAATCGGTCAGAAATGGTCGGGCACCGTTACCGTCGATACCAC
CGTTCAGGAACATCGCGATCGCGGTGATACCTATAACGGTCAATTCTTTACCAGCGGACCATTAATTGACGGC
GTGCTGGGAATGAAAGCTTACGGCAGCCTGGCAAAACGTGAAAAGGATGACCCGCAAAACTCAACGACCACC
GATACCGGAGAAACGCCGCGTATTGAAGGATTCTCCAGCCGCGACGGCAATGTCGAATTTGCCTGGACACCG
AATCAAAATCACGATTTTACTGCCGGATACGGTTTCGACCGTCAGGATCGTGATTCCGACTCGCTGGACAAAA
ACCGCCTGGAACGCCAGAACTACTCCGTCAGCCATAATGGGCGTTGGGATTACGGCACCAGCGAACTGAAAT
ACTACGGTGAGAAAGTCGAGAACAAAAACCCTGGCAACAGCAGCCCGATAACTTCCGAAAGCAATACGGTCG
ACGGCAAATACACGTTGCCGCTGACGGCGATTAATCAGTTTCTCACGGTTGGCGGTGAATGGCGTCACGACA
AACTTAGCGATGCGGTGAACCTGACCGGGGGAACCAGCTCCAAAACGTCTGCCAGCCAGTACGCGCTGTTTG
TGGAAGATGAATGGCGGATCTTCGAGCCGCTGGCGCTGACGACCGGCGTGCGTATGGACGATCACGAAACCT
ACGGTGAACACTGGAGTCCGCGTGCCTACCTGGTTTATAACGCCACCGACACCGTAACGGTGAAAGGGGCT
GGGCGACGGCATTTAAAGCCCCTTCTCTGTTGCAACTTAGCCCTGACTGGACGAGCAATTCCTGCCGTGGCGC
ATGTAAGATTGTGGGTAGCCCGGATCTGAAACCAGAAACCAGCGAAAGTTGGGAGCTGGGGCTTTACTACAT
GGGTGAAGAAGGCTGGCTGGAAGGGGTTGAATCCAGCGTTACCGTTTTCCGTAACGATGTGAAAGATCGTAT
CAGCATTAGCCGTACGTCTGACGTCAATGCTGCACCGGGCTACCAAAACTTTGTCGGTTTTGAGACGGGCGCT
AACGGACGGCGCATACCGGTATTTAGCTACTACAACGTTAACAAAGCTCGTATTCAGGGCGTGGAAACCGAA
CTGAAAATTCCGTTCAACGATGAATGGAAACTGTCGATCAACTACACCTACAACGATGGTCGTGATGTCAGCA
ACGGCGAAAACAAACCGCTATCCGATCTGCCGTTCCATACTGCTAACGGTACGCTGGACTGGAAACCGCTGGC
GCTGGAAGACTGGTCATTCTATGTTTCTGGTCACTATACCGGGCAGAAACGCGCCGACAGCGCGACGGCTAA
AACACCGGGCGGTTATACCATCTGGAATACCGGCGCGGCCTGGCAGGTGACTAAAGACGTCAAACTGCGCGC
AGGCGTGCTGAACCTTGGCGACAAGGATCTCAGTCGTGACGACTACAGCTATAACGAAGACGGACGTCGTTA
CTTTATGGCAGTGGATTATCGCTTCTGA |
| E. coli CFT073 CirA amino acid sequence. SEQ ID NO:57. Amino acids 1-22 are a His tag and Xa protease cleavage site. Sequence of protein without His tag and Xa protease cleavage site is SEQ ID NO:58. |
| MRGSHHHHHHGSGSGSGIEGRPVDDDGETMVVTASSVEQNLKDAPASISVITQEDLQRKPVQNLKDVLKEVPGV
QLTNEGDNRKGVSIRGLDSSYTLILVDGKRVNSRNAVFRHNDFDLNWIPVDSIERIEVVRGPMSSLYGSDALGGVV
NIITKKIGQKWSGTVTVDTTVQEHRDRGDTYNGQFFTSGPLIDGVLGMKAYGSLAKREKDDPQNSTTTDTGETPRI
EGFSSRDGNVEFAWTPNQNHDFTAGYGFDRQDRDSDSLDKNRLERQNYSVSHNGRWDYGTSELKYYGEKVENK
NPGNSSPITSESNTVDGKYTLPLTAINQFLTVGGEWRHDKLSDAVNLTGGTSSKTSASQYALFVEDEWRIFEPLALTT
GVRMDDHETYGEHWSPRAYLVYNATDTVTVKGGWATAFKAPSLLQLSPDWTSNSCRGACKIVGSPDLKPETSES
WELGLYYMGEEGWLEGVESSVTVFRNDVKDRISISRTSDVNAAPGYQNFVGFETGANGRRIPVFSYYNVNKARIQ
GVETELKIPFNDEWKLSINYTYNDGRDVSNGENKPLSDLPFHTANGTLDWKPLALEDWSFYVSGHYTGQKRADSA
TAKTPGGYTIWNTGAAWQVTKDVKLRAGVLNLGDKDLSRDDYSYNEDGRRYFMAVDYRF |

Fig. 37

| E. coli CFT073 FepA Gene Sequence, SEQ ID NO:59. |
|---|
| ATGAGAGGATCGCATCACCATCACCATCACGGATCTGGCTCTGGATCTGGTATCGAGGGAAGGCCTCAAGAGCCGACCGATACTCCTGTTTCACATGACGATACCATTGTCGTTACCGCCGCCGAGCAGAACTTGCAGGCGCCTGGCGTTTCGACCATTACCGCAGATGAAATCCGCAAAAACCCGGTTGCCCGCGATGTATCGGAGATCATTCGTACCATGCCTGGCGTTAACCTGACCGGTAACTCCACCAGTGGTCAGCGTGGTAATAACCGCCAGATTGATATTCGCGGCATGGGTCCGGAAAACACGCTGATTTTGATTGACGGCAAGCCGGTAAGCAGCCGTAACTCTGTGCGTCAGGGCTGGCGTGGCGAGCGCGATACCCGTGGTGATACCTCCTGGGTGCCGCCTGAAATGATTGAACGTATTGAAGTTCTGCGTGGTCCGGCAGCTGCGCGTTATGGCAACGGCGCGGCGGGCGGCGTGGTTAACATCATTACCAAAAAAGGCAGCGGTGAGTGGCACGGCTCCTGGGATGCTTATTTCAATGCGCCAGAACATAAAGAGGAAGGTGCCACCAAACGCACCAACTTCAGCCTGACCGGTCCGCTGGGCGACGAATTCAGCTTCCGCTTGTATGGCAACCTCGACAAAACCCAGGCTGACGCGTGGGATATCAACCAGGGCCATCAGTCCGCGCGTGCCGGAACGTATGCCACGACGTTACCAGCCGGGCGCGAAGGGGTGATCAACAAAGATATTAATGGCGTGGTGCGCTGGGACTTCGCGCCTCTGCAGTCACTCGAACTGGAAGCGGGCTACAGCCGCCAGGGTAACCTGTATGCGGGTGATACGCAGAACACCAACTCTGACGCTTACACTCGATCGAAATATGGCGATGAAACCAACCGCCTGTATCGCCAGAACTACTCGCTGACCTGGAACGGTGGCTGGGATAACGGCGTGACCACCAGCAACTGGGTGCAGTACGAACACACCCGTAACTCGCGTATTCCGGAAGGTCTGGCGGGCGGTACCGAAGGGAAATTTAACGAAAAGCGGCACAGGATTTTGTAGATATCGATCTTGATGACGTGATGCTGCACAGCGAAGTTAACCTGCCGATTGATTTCCTCGTAAACCAAACGCTGACGCTGGGTACAGAGTGGAATCAGCAACGGATGAAGGACTTAAGTTCCAACACCCAGGCGCTGACCGGGACGAATACCGGCGGTGCTATTGATGGTGTGAGTGCCACCGACCGTAGCCCGTATTCAAAAGCAGAAATTTTCTCGCTGTTTGCCGAAAACAATATGGAGCTGACTGACAGCACCATCGTAACGCCGGGGCTGCGTTTCGATCATCACAGTATTGTCGGCAATAACTGGAGCCCGGCGCTGAACATATCGCAAGGTTTAGGCGATGACTTCACGCTGAAAATGGGCATCGCCCGCGCCTATAAAGCGCCGAGCCTGTACCAGACTAACCCAAACTACATTCTCTACAGTAAAGGTCAGGGCTGCTATGCCAGCGCGGGCGGCTGCTATCTGCAAGGTAATGATGACCTGAAAGCAGAAACCAGCATCAACAAGGAGATTGGTCTGGAGTTCAAACGCGACGGTTGGCTGGCGGGCGTGACCTGGTTCCGTAACGATTATCGCAATAAGATTGAAGCGGGCTATGTGGCTGTAGGGCAAAACGCAGTCGGCACCGATCTCTATCAGTGGGATAACGTACCGAAAGCGGTGGTTGAAGGTCTGGAAGGATCGTTAAACGTACCGGTTAGCGAAACGGTGATGTGGACCAATAACATCACTTATATGCTGAAGAGTGAAAACAAAACCACGGGCGACCGTTTGTCGATCATCCCGGAGTATACGTTGAACTCAACGCTGAGCTGGCAGGCACGGGAAGATTTGTCGATGCAAACGACCTTCACCTGGTACGGCAAACAGCAGCCGAAGAAGTACAACTATAAAGGTCAGCCAGCGGTTGGACCGGAAACCAAAGAAATCAGTCCGTACAGCATTGTTGGCCTGAGCGCGACCTGGGATGTGACGAAGAATGTCAGTCTGACCGGCGGCGTGGACAACCTGTTCGACAAACGTTTGTGGCGTGCGGGTAATGCCCAGACCACGGGCGATCTGGCAGGGGCCAACTATATCGCCGGTGCCGGTGCGTATACCTATAACGAGCCGGGACGTACGTGGTATATGAGCATTAATACTCACTTCTGA |
| E. coli CFT073 FepA amino acid sequence. SEQ ID NO:60. Amino acids 1-22 are a His tag and Xa protease cleavage site. Sequence of protein without His tag and Xa protease cleavage site is SEQ ID NO:61. |
| MRGSHHHHHHGSGSGSGIEGRPQEPTDTPVSHDDTIVVTAAEQNLQAPGVSTITADEIRKNPVARDVSEIIRTMPGVNLTGNSTSGQRGNNRQIDIRGMGPENTLILIDGKPVSSRNSVRQGWRGERDTRGDTSWVPPEMIERIEVLRGPAAARYGNGAAGGVVNIITKKGSGEWHGSWDAYFNAPEHKEEGATKRTNFSLTGPLGDEFSFRLYGNLDKTQADAWDINQGHQSARAGTYATTLPAGREGVINKDINGVVRWDFAPLQSLELEAGYSRQGNLYAGDTQNTNSDAYTRSKYGDETNRLYRQNYSLTWNGGWDNGVTTSNWVQYEHTRNSRIPEGLAGGTEGKFNEKAAQDFVDIDLDDVMLHSEVNLPIDFLVNQTLTLGTEWNQQRMKDLSSNTQALTGTNTGGAIDGVSATDRSPYSKAEIFSLFAENNMELTDSTIVTPGLRFDHHSIVGNNWSPALNISQGLGDDFTLKMGIARAYKAPSLYQTNPNYILYSKGQGCYASAGGCYLQGNDDLKAETSINKEIGLEFKRDGWLAGVTWFRNDYRNKIEAGYVAVGQNAVGTDLYQWDNVPKAVVEGLEGSLNVPVSETVMWTNNITYMLKSENKTTGDRLSIIPEYTLNSTLSWQAREDLSMQTTFTWYGKQQPKKYNYKGQPAVGPETKEISPYSIVGLSATWDVTKNVSLTGGVDNLFDKRLWRAGNAQTTGDLAGANYIAGAGAYTYNEPGRTWYMSINTHF |

Fig. 38

| E. coli CFT073 IutA Gene Sequence, SEQ ID NO:62. |
|---|
| ATGAGAGGATCGCATCACCATCACCATCACGGATCTGGCTCTGGATCTGGTATCGAGGGAAGGCCTCAGCAA
AACGATGATAATGAGATCATAGTGTCTGCCAGCCGCAGCAATCGAACTGTAGCGGAGATGGCGCAAACCACC
TGGGTTATCGAAAATGCCGAACTGGAGCAGCAGATTCAGGGCGGTAAAGAGCTGAAAGACGCACTGGCTCA
GTTAATCCCCGGCCTTGATGTCAGCAGCCAGAGCCGAACCAACTACGGTATGAACATGCGTGGCCGCCCGCTG
GTTGTCCTGATTGACGGTGTGCGCCTCAACTCTTCACGTTCCGACAGCCGACAACTGGACTCTGTCGATCCTTT
TAATATCGACCATATTGAAGTGATCTCCGGCGCGACGGCCCTGTACGGTGGCGGGAGTACCGGAGGGTTGAT
CAACATCGTGACCAAAAAGGCCAGCCGGAAACCATGATGGAGTTTGAGGCTGGCACAAAAGTGGCTTTAA
CAGCAGTAAAGATCACGATGAGCGCATTGCCGGTGCTGTCTCCGGCGGAAATGACCATATCTCCGGACGTCTT
TCCGTGGCATATCAGAAATTTGGCGGCTGGTTTGACGGTAACGGCGATGCCACCCTGCTTGATAACACCCAGA
CCGGCCTGCAGCACTCCAATCGGCTGGACATCATGGGAACCGGTACGCTGAACATCGATGAATCCCGGCAGC
TTCAACTGATAACGCAGTACTATAAAAGTCAGGGGACGACAATTACGGGCTTAATCTCGGGAAAGGCTTTTC
CGCCATCAGCGGGAGCAGCACACCATACGTCAGTAAGGGGCTGAATTCTGACCGCATTCCCGGCACTGAGCG
GCATTTGATCAGCCTGCAGTACTCTGACAGTGATTTCCTGAGACAGGAACTGGTCGGTCAGGTTTACTACCGC
GATGAGTCGTTGCGGTTCTACCCGTTCCCGACGGTAAATGCGAATAAACAGGCGACGGCTTTCTCCTCGTCAC
AGCAGGATACCGACCAGTACGGCATGAAACTGACTCTGAACAGCCAACTTATGGACGGCTGGCAAATCACCT
GGGGGCTGGATGCTGAGCATGAGCGCTTTACCTCCAACCAGATGTTCTTCGATCTGGCTCAGGCAAGTGCTTC
CGGAGGGCTGAACAACCATAAGATTTACACCACCGGGCGCTATCCGTCATATGACATCACCAATCTGGCGGCC
TTCCTGCAATCCAGCTATGACATTAATGATATTTTTACCGTTAGCGGTGGCGTACGCTATCAGTATACTGAGAA
CAGGGTAGATGATTTCATCGACTACACGCAGCAACAGAAGATTGCTGCCGGGAAGGCGATATCTGCCGACGC
CATTCCTGGTGGTTCGGTAGATTACGATAACTTTCTGTTCAATGCTGGTCTGCTGATGCACATCACCGAACGTC
AGCAGGCATGGTTCAATTTTTCCCAGGGGGTGGCATTGCCGGATCCGGGGAAATATTATGGTCGCGGCATCT
ATGGTGCAGCAGTGAACGGCCATCTTCCCCTGACAAAGAGCGTGAACGTCAGCGACAGTAAGCTGGAAGGC
GTGAAAGTCGATTCTTATGAACTGGGCTGGCGCTTTACCGGTGACAACCTGCGGACTCAAATCGCGGCATATT
ACTCGCTTTCCAATAAGAGCGTGGAAAGGAATAAAGATCTGACCATCAGTGTGAAGGACGACAGGCGCCGTA
TTTACGGCGTGGAAGGTGCGGTGGACTACCTGATCCCGGATACTGACTGGAGTACCGGTGTGAACTTCAATG
TGCTGAAAACCGAGTCGAAAGTGAACGGTCAATGGCAAAAATATGACGTGAAGGAATCAAGTCCATCGAAAG
CGACAGCTTACATTAACTGGGCGCCGGAACCGTGGAGTCTGCGTGTACAGAGCACCACTTCTTTCGACGTAAG
CGATGCAGAGGGTAACGATATTAATGGTTACACTACCGTCGATTTTATCAGTAGTTGGCAGCTTCCGGTGGGA
ACACTCAGCTTCAGCGTTGAGAACCTCTTCGACCGTGACTATACCACTGTCTGGGGACAGCGTGCACCTCTGTA
CTACAGCCCGGGTTACGGCCCTGCTTCACTGTACGACTACAAAGGCCGGGCCGAACCTTTGGTCTGAACTAC
TCAGTGCTGTTCTGA |
| E. coli CFT073 IutA amino acid sequence. SEQ ID NO:63. Amino acids 1-22 are a His tag and Xa protease cleavage site. Sequence of protein without His tag and Xa protease cleavage site is SEQ ID NO:64. |
| MRGSHHHHHHGSGSGSGIEGRPQQNDDNEIIVSASRSNRTVAEMAQTTWVIENAELEQQIQGGKELKDALAQLI
PGLDVSSQSRTNYGMNMRGRPLVVLIDGVRLNSSRSDSRQLDSVDPFNIDHIEVISGATALYGGGSTGGLINIVTKK
GQPETMMEFEAGTKSGFNSSKDHDERIAGAVSGGNDHISGRLSVAYQKFGGWFDGNGDATLLDNTQTGLQHSN
RLDIMGTGTLNIDESRQLQLITQYYKSQGDDNYGLNLGKGFSAISGSSTPYVSKGLNSDRIPGTERHLISLQYSDSDFL
RQELVGQVYYRDESLRFYPFPTVNANKQATAFSSSQQDTDQYGMKLTLNSQLMDGWQITWGLDAEHERFTSNQ
MFFDLAQASASGGLNNHKIYTTGRYPSYDITNLAAFLQSSYDINDIFTVSGGVRYQYTENRVDDFIDYTQQQKIAAG
KAISADAIPGGSVDYDNFLFNAGLLMHITERQQAWFNFSQGVALPDPGKYYGRGIYGAAVNGHLPLTKSVNVSDS
KLEGVKVDSYELGWRFTGDNLRTQIAAYYSLSNKSVERNKDLTISVKDDRRRIYGVEGAVDYLIPDTDWSTGVNFN
VLKTESKVNGQWQKYDVKESSPSKATAYINWAPEPWSLRVQSTTSFDVSDAEGNDINGYTTVDFISSWQLPVGTL
SFSVENLFDRDYTTVWGQRAPLYYSPGYGPASLYDYKGRGRTFGLNYSVLF |

SEQUENCE LISTING

```
<160> NUMBER OF SEQ ID NOS: 64

<210> SEQ ID NO 1
<211> LENGTH: 2325
<212> TYPE: DNA
<213> ORGANISM: Klebsiella pneumoniae

<400> SEQUENCE: 1
atgacgccgt tacgcgtttt tcgtaaaaca actcctttgg ttaacgccat tcgcctgagc        60
ctgctgccgc tggccggtct ctcgttttcc gcttttgctg cacaggttga tatcgcaccg       120
ggatcgctcg acaaagcgct caatcagtat gccgcacaca gcggaattac cctctcggtt       180
gacgccagcc tgacgcgcgg caagcagagc aacggcctgc acggagatta cgacgtcgag       240
agcggcctgc aacagctgct ggacggcagc ggactgcagg taaaaccgct gggaaataac       300
```

```
agctggacgc tggagcccgc gcccgcgcca aagaagatg ccctgaccgt ggtcggcgac    360
tggctgggcg atgcgcgtga aaacgacgta tttgaacatg ctggcgcgcg tgacgtgatc    420
cgccgtgagg atttcgccaa aaccggcgca accaccatgc gtgaggtgct taaccgcatc    480
cctggcgtca gcgcgccgga aaacaacggc accggcagcc acgacctggc gatgaacttt    540
ggcatccggg gcctgaaccc acgcctcgcc agcgctcga ccgtcctgat ggacggcatc    600
cccgtcccct tgcccctta cggtcagccg cagctttcac tggctcccgt ttcgctcggc    660
aacatggatg ccattgacgt ggtgcgcggt ggtggtgcgg tgcgttacgg accgcagagc    720 gtgggcggc tggtgaactt tgttacccgc gccattccgc aggactttgg tatcgaggcg    780
ggggtggaag gtcagctcag cccaacctct tcacaaaaca cccgaaaga gacgcacaac    840 ctgatggtgg gcggcacagc ggacaacggt tttggcaccg cgctgctcta ctccggcacg    900
cgcggcagtg actggcgcga gcacagcgcc acccgcatcg acgacctgat gctgaaaagc    960
aaatatgcgc cgaatgaggt gcacaccttc aacagcctgc tgcaatatta cgatggtgaa   1020
gccgacatgc ccgccggcct gtcccgcgcg gattacgacg ccgatcgctg gcaatccacc   1080
cgcccgtatg accgcttctg gggccgtcgc aagctggcga gcctgggcta ccagttccag   1140
ccggacagcc agcataaatt caacattctg gggttctaca cccaaacct gcgcagcggc   1200 tacctggagc aaggcaaacg catcaccctc tcgccgcgta actactgggt gcgcggtatt   1260
gagccacgct acagccagag ctttatgatc ggcccttccg cgcacgaagt gggcgtgggc   1320
tatcgctatg tgaatgaatc aacgcatgaa atgcgttact acaccgccac cagcagcggg   1380
cagttgccgt ccggctcaag cccttacgac cgcgacacgc gttccggcac cgaggcgcac   1440
gcctggtatc tggatgacaa aatcgacatc ggcaactgga ccatcacgcc gggtatgcgt   1500
ttcgaacata tcgagtcata ccagaacaac gccatcaaag gcacgcacga agaggtaagc   1560
tataacgcac cgcttccggc gttgaacgtg ctctatcacc tgactgacag ctggaatctt   1620
tatgcaaaca ctgaaggctc gttcggcacc gtacagtaca gccagattgg caaggctgtg   1680
caaagcggca atgtggaacc ggaaaaagcg cgaacctggg aactcggtac ccgctacgac   1740 gacgcgcgc tgacgcggga aatggggctg ttcctgatta actttaacaa tcagtacgac   1800
tccaaccaga ccaacgacac cgtcactgca cgtggcaaaa cgcgccatac cgggctggaa   1860
acgcaggcac gttacgacct gggtacgcta acgccaacgc ttgataacgt ttccgtctac   1920
gccagctatg cgtatgtgaa cgcggaaatc cgcgagaaag cgacaccta tggcaatcag   1980 gtgccattct ccccgaaaca taaaggcacg ctgggcgtgg actacaagcc gggcaactgg   2040
acgttcaatc tgaacagcga tttccagtcc agccagtttg cggataacgc caatacggtg   2100
aaagagagcg ccgacggcag taccggccgc attcccggct tcatgctctg gggcgcacgc   2160
gtggcgtatg actttggccc gcagatggca gatctgaacc tggcgttcgg tgtgaaaaac   2220
atcttcgacc aggactactt catccgctct tatgacgaca caacaaagg catctacgca   2280 ggccagccgc gcacgctgta tatgcagggg tcgttgaagt tctga                   2325
```

<210> SEQ ID NO 2
<211> LENGTH: 774
<212> TYPE: PRT
<213> ORGANISM: Klebsiella pneumoniae

```
<400> SEQUENCE: 2

Met Thr Pro Leu Arg Val Phe Arg Lys Thr Pro Leu Val Asn Ala
1               5                   10                  15

Ile Arg Leu Ser Leu Leu Pro Leu Ala Gly Leu Ser Phe Ser Ala Phe
                20                  25                  30

Ala Ala Gln Val Asp Ile Ala Pro Gly Ser Leu Asp Lys Ala Leu Asn
            35                  40                  45

Gln Tyr Ala Ala His Ser Gly Ile Thr Leu Ser Val Asp Ala Ser Leu
50                  55                  60

Thr Arg Gly Lys Gln Ser Asn Gly Leu His Gly Asp Tyr Asp Val Glu
65                  70                  75                  80

Ser Gly Leu Gln Gln Leu Leu Asp Gly Ser Gly Leu Gln Val Lys Pro
                85                  90                  95

Leu Gly Asn Asn Ser Trp Thr Leu Glu Pro Ala Pro Ala Pro Lys Glu
            100                 105                 110

Asp Ala Leu Thr Val Val Gly Asp Trp Leu Gly Asp Ala Arg Glu Asn
            115                 120                 125

Asp Val Phe Glu His Ala Gly Ala Arg Asp Val Ile Arg Arg Glu Asp
130                 135                 140

Phe Ala Lys Thr Gly Ala Thr Thr Met Arg Glu Val Leu Asn Arg Ile
145                 150                 155                 160

Pro Gly Val Ser Ala Pro Glu Asn Asn Gly Thr Gly Ser His Asp Leu
                165                 170                 175

Ala Met Asn Phe Gly Ile Arg Gly Leu Asn Pro Arg Leu Ala Ser Arg
            180                 185                 190

Ser Thr Val Leu Met Asp Gly Ile Pro Val Pro Phe Ala Pro Tyr Gly
            195                 200                 205

Gln Pro Gln Leu Ser Leu Ala Pro Val Ser Leu Gly Asn Met Asp Ala
210                 215                 220

Ile Asp Val Val Arg Gly Gly Ala Val Arg Tyr Gly Pro Gln Ser
225                 230                 235                 240

Val Gly Gly Val Val Asn Phe Val Thr Arg Ala Ile Pro Gln Asp Phe
                245                 250                 255

Gly Ile Glu Ala Gly Val Glu Gly Gln Leu Ser Pro Thr Ser Ser Gln
            260                 265                 270

Asn Asn Pro Lys Glu Thr His Asn Leu Met Val Gly Thr Ala Asp
            275                 280                 285

Asn Gly Phe Gly Thr Ala Leu Leu Tyr Ser Gly Thr Arg Gly Ser Asp
            290                 295                 300

Trp Arg Glu His Ser Ala Thr Arg Ile Asp Asp Leu Met Leu Lys Ser
305                 310                 315                 320

Lys Tyr Ala Pro Asn Glu Val His Thr Phe Asn Ser Leu Leu Gln Tyr
                325                 330                 335

Tyr Asp Gly Glu Ala Asp Met Pro Gly Gly Leu Ser Arg Ala Asp Tyr
            340                 345                 350

Asp Ala Asp Arg Trp Gln Ser Thr Arg Pro Tyr Asp Arg Phe Trp Gly
            355                 360                 365

Arg Arg Lys Leu Ala Ser Leu Gly Tyr Gln Phe Gln Pro Asp Ser Gln
370                 375                 380

His Lys Phe Asn Ile Leu Gly Phe Tyr Thr Gln Thr Leu Arg Ser Gly
385                 390                 395                 400

Tyr Leu Glu Gln Gly Lys Arg Ile Thr Leu Ser Pro Arg Asn Tyr Trp
                405                 410                 415
```

```
Val Arg Gly Ile Glu Pro Arg Tyr Ser Gln Ser Phe Met Ile Gly Pro
                420                 425                 430

Ser Ala His Glu Val Gly Val Gly Tyr Arg Tyr Val Asn Glu Ser Thr
            435                 440                 445

His Glu Met Arg Tyr Tyr Thr Ala Thr Ser Ser Gly Gln Leu Pro Ser
        450                 455                 460

Gly Ser Ser Pro Tyr Asp Arg Asp Thr Arg Ser Gly Thr Glu Ala His
465                 470                 475                 480

Ala Trp Tyr Leu Asp Asp Lys Ile Asp Ile Gly Asn Trp Thr Ile Thr
                485                 490                 495

Pro Gly Met Arg Phe Glu His Ile Glu Ser Tyr Gln Asn Asn Ala Ile
            500                 505                 510

Lys Gly Thr His Glu Glu Val Ser Tyr Asn Ala Pro Leu Pro Ala Leu
        515                 520                 525

Asn Val Leu Tyr His Leu Thr Asp Ser Trp Asn Leu Tyr Ala Asn Thr
530                 535                 540

Glu Gly Ser Phe Gly Thr Val Gln Tyr Ser Gln Ile Gly Lys Ala Val
545                 550                 555                 560

Gln Ser Gly Asn Val Glu Pro Glu Lys Ala Arg Thr Trp Glu Leu Gly
                565                 570                 575

Thr Arg Tyr Asp Asp Gly Ala Leu Thr Ala Glu Met Gly Leu Phe Leu
            580                 585                 590

Ile Asn Phe Asn Asn Gln Tyr Asp Ser Asn Gln Thr Asn Asp Thr Val
        595                 600                 605

Thr Ala Arg Gly Lys Thr Arg His Thr Gly Leu Glu Thr Gln Ala Arg
        610                 615                 620

Tyr Asp Leu Gly Thr Leu Thr Pro Thr Leu Asp Asn Val Ser Val Tyr
625                 630                 635                 640

Ala Ser Tyr Ala Tyr Val Asn Ala Glu Ile Arg Glu Lys Gly Asp Thr
                645                 650                 655

Tyr Gly Asn Gln Val Pro Phe Ser Pro Lys His Lys Gly Thr Leu Gly
            660                 665                 670

Val Asp Tyr Lys Pro Gly Asn Trp Thr Phe Asn Leu Asn Ser Asp Phe
        675                 680                 685

Gln Ser Ser Gln Phe Ala Asp Asn Ala Asn Thr Val Lys Glu Ser Ala
        690                 695                 700

Asp Gly Ser Thr Gly Arg Ile Pro Gly Phe Met Leu Trp Gly Ala Arg
705                 710                 715                 720

Val Ala Tyr Asp Phe Gly Pro Gln Met Ala Asp Leu Asn Leu Ala Phe
                725                 730                 735

Gly Val Lys Asn Ile Phe Asp Gln Asp Tyr Phe Ile Arg Ser Tyr Asp
            740                 745                 750

Asp Asn Asn Lys Gly Ile Tyr Ala Gly Gln Pro Arg Thr Leu Tyr Met
        755                 760                 765

Gln Gly Ser Leu Lys Phe
    770

<210> SEQ ID NO 3
<211> LENGTH: 2208
<212> TYPE: DNA
<213> ORGANISM: Klebsiella pneumoniae
```

<400> SEQUENCE: 3

```
atggcgcgtc caaaaactgc tcagccaaat cactcgctgc gtaaagtcgc agctgtagta      60
gccacggcgg ttagcggcat gtctgtctac gcacaggcag cagaacaacc gaagcaagaa     120
gaaaccatca ccgtcgttgc cgccccggcc gcccaggaaa acgcctgggg accggcgccg     180
actatcgcgg caaaacgctc cgccacggcg accaaaaccg ataccccgat tgaaaaaacg     240
ccgcagtctg tgtcggtggt gacgcgccat gagatggaga tgcgccagcc gacgacggta     300
aaagaggcgc tctcctatac gccaagcgtc ttctccactc gcggcagttc gaccacctat     360
gacgtggtca ccattcgcgg cttcaccacc tcgacgaccg tcaacaccaa ccagtatctg     420
gacggcatga agctgcaggg gaataactac tctgaagtct ccatggatcc ttacttcctc     480
gagcgtgtgg aagtgatgcg cgggccaacc tcggtgctgt acggcaacag caacccgggc     540
ggtatcgtca gcatggtcag caagcgcccg actaccgagc cgctgaaaga agtgcagttt     600
aagatgggca ccgacaatct gtggcagacc gggtttgact ttagcgacgc cattgatgat     660
gccgcgtct ggtcgtatcg cctgaccggc cttggccgca gtcaggatgc ccagcagcag     720
atggcgaaat cgactcgcta cgcggtggcg ccctccttta gctggcgtcc ggacgataaa     780
accgacttca ccttcctgag caacttccag aatgacccgg atgcgggcta ctacggctgg     840
ctgccgcgcg aaggcaccgt ggtgccgtat tacgacgcca acgtaaggc gcacaagctg     900
ccgaccgatt tcaacgaagg cgagtccgat aataaaatct cccgccgcca agagatggtg     960
ggctacagct tctcccatca gttcgatgac accttttaccg tgcggcagaa cctgcgctat    1020
gccgatgtgc atacgctcta tcgttcggta tacggcaacg gctatgtcgc gccgggctac    1080
atgaatcgcg cctacgtgcg ctccgacgag cacctgaaca ccttcaccgt cgatacccag    1140
ctgcagtctg atttcgccac cggcgcggtc agccatacgc tgctgaccgg cgtggactac    1200
tcgcggatgc gtaacgatgt ggatgccgac tacgggacgg cggatcctat cagcatgagc    1260
aatccgcagt acggcaatcc gaatattcag gtcaccttcc cgtacgcggt cctcaaccgg    1320
atggagcaga ccggcctgta cgcgcaggat cagatggagt gggataaatg ggtgatgacc    1380
ctgggcggcc gttacgatta cgccacgacc tcaacgttaa cccgcgccac caacagcctg    1440
gcggagaatc acgaccagca gttcagctgg cgcggcggca tcaactacct gttcgataac    1500
ggcatctcgc cgtacttcag ctacagcgaa tcgtttgaac cggtatcggg ttccaacagc    1560
cgcggccagc cgttcgatcc gtcgcgcggt aagcagtatg aagccggcgt gaaatacgtg    1620
ccgaaagata tgccggtggt ggtcaccgcg gcggtctatc agctgaccaa agacaagaac    1680
ctgacggctg atccggctaa ccaggcgttc agcatccaga ccggcgagat ccgctcccgc    1740
ggccttgagc tggaggcgaa ggcggcggtg aacgccaata ttaacgtcac cgcggcctac    1800
agctacaccg atgcggagta cactcacgat acggtgttca acggcaaacg tccggcggaa    1860
gtgccgcgta acatggcctc cctgtgggcg gattatacct tccacgaaac cgcgctgagc    1920
ggtctgacga ttggggccgg ggcgcgctat atcggttcaa cggtcagcta ctacaaaaat    1980
gacaccagca ccggtaagaa aaatgatgcc tttagtgtgg ccggttatgc gctgatggat    2040
gcgacggtga aatacgatct ggcgcgcttt ggcctgccgg atcgtcggt cggcgtcaac    2100
gtcaacaacc tgttcgaccg cgaatatgtc tccagttgct acagcgaata cgcctgctac    2160
tggggcgccg gacgtcaggt cgtcgccacc gccaccttcc gtttctaa              2208
```

<210> SEQ ID NO 4
<211> LENGTH: 735
<212> TYPE: PRT
<213> ORGANISM: Klebsiella pneumoniae

<400> SEQUENCE: 4

Met Ala Arg Pro Lys Thr Ala Gln Pro Asn His Ser Leu Arg Lys Val
1               5                   10                  15

Ala Ala Val Val Ala Thr Ala Val Ser Gly Met Ser Val Tyr Ala Gln
            20                  25                  30

Ala Ala Glu Gln Pro Lys Gln Glu Glu Thr Ile Thr Val Val Ala Ala
        35                  40                  45

Pro Ala Ala Gln Glu Asn Ala Trp Gly Pro Ala Pro Thr Ile Ala Ala
    50                  55                  60

Lys Arg Ser Ala Thr Ala Thr Lys Thr Asp Thr Pro Ile Glu Lys Thr
65                  70                  75                  80

Pro Gln Ser Val Ser Val Val Thr Arg His Glu Met Glu Met Arg Gln
                85                  90                  95

Pro Thr Thr Val Lys Glu Ala Leu Ser Tyr Thr Pro Ser Val Phe Ser
            100                 105                 110

Thr Arg Gly Ser Ser Thr Thr Tyr Asp Val Val Thr Ile Arg Gly Phe
        115                 120                 125

Thr Thr Ser Thr Thr Val Asn Thr Asn Gln Tyr Leu Asp Gly Met Lys
    130                 135                 140

Leu Gln Gly Asn Asn Tyr Ser Glu Val Ser Met Asp Pro Tyr Phe Leu
145                 150                 155                 160

Glu Arg Val Glu Val Met Arg Gly Pro Thr Ser Val Leu Tyr Gly Asn
                165                 170                 175

Ser Asn Pro Gly Gly Ile Val Ser Met Val Ser Lys Arg Pro Thr Thr
            180                 185                 190

Glu Pro Leu Lys Glu Val Gln Phe Lys Met Gly Thr Asp Asn Leu Trp
        195                 200                 205

Gln Thr Gly Phe Asp Phe Ser Asp Ala Ile Asp Ala Gly Val Trp
    210                 215                 220

Ser Tyr Arg Leu Thr Gly Leu Gly Arg Ser Gln Asp Ala Gln Gln Gln
225                 230                 235                 240

Met Ala Lys Ser Thr Arg Tyr Ala Val Ala Pro Ser Phe Ser Trp Arg
                245                 250                 255

Pro Asp Asp Lys Thr Asp Phe Thr Phe Leu Ser Asn Phe Gln Asn Asp
            260                 265                 270

Pro Asp Ala Gly Tyr Tyr Gly Trp Leu Pro Arg Glu Gly Thr Val Val
        275                 280                 285

Pro Tyr Tyr Asp Ala Asn Gly Lys Ala His Lys Leu Pro Thr Asp Phe
    290                 295                 300

Asn Glu Gly Glu Ser Asp Asn Lys Ile Ser Arg Arg Gln Lys Met Val
305                 310                 315                 320

Gly Tyr Ser Phe Ser His Gln Phe Asp Asp Thr Phe Thr Val Arg Gln
                325                 330                 335

Asn Leu Arg Tyr Ala Asp Val His Thr Leu Tyr Arg Ser Val Tyr Gly
            340                 345                 350

Asn Gly Tyr Val Ala Pro Gly Tyr Met Asn Arg Ala Tyr Val Arg Ser
        355                 360                 365

Asp Glu His Leu Asn Thr Phe Thr Val Asp Thr Gln Leu Gln Ser Asp
    370                 375                 380

| Phe | Ala | Thr | Gly | Ala | Val | Ser | His | Thr | Leu | Leu | Thr | Gly | Val | Asp | Tyr |
| 385 | | | | 390 | | | | | 395 | | | | | 400 | |

| Ser | Arg | Met | Arg | Asn | Asp | Val | Asp | Ala | Asp | Tyr | Gly | Thr | Ala | Asp | Pro |
| | | | 405 | | | | | 410 | | | | | 415 | | |

| Ile | Ser | Met | Ser | Asn | Pro | Gln | Tyr | Gly | Asn | Pro | Asn | Ile | Gln | Val | Thr |
| | | | 420 | | | | | 425 | | | | | 430 | | |

| Phe | Pro | Tyr | Ala | Val | Leu | Asn | Arg | Met | Glu | Gln | Thr | Gly | Leu | Tyr | Ala |
| | | 435 | | | | | 440 | | | | | 445 | | | |

| Gln | Asp | Gln | Met | Glu | Trp | Asp | Lys | Trp | Val | Met | Thr | Leu | Gly | Gly | Arg |
| | | 450 | | | | | 455 | | | | | 460 | | | |

| Tyr | Asp | Tyr | Ala | Thr | Thr | Ser | Thr | Leu | Thr | Arg | Ala | Thr | Asn | Ser | Leu |
| 465 | | | | 470 | | | | | 475 | | | | | 480 | |

| Ala | Glu | Asn | His | Asp | Gln | Gln | Phe | Ser | Trp | Arg | Gly | Gly | Ile | Asn | Tyr |
| | | | 485 | | | | | 490 | | | | | 495 | | |

| Leu | Phe | Asp | Asn | Gly | Ile | Ser | Pro | Tyr | Phe | Ser | Tyr | Ser | Glu | Ser | Phe |
| | | | 500 | | | | | 505 | | | | | 510 | | |

| Glu | Pro | Val | Ser | Gly | Ser | Asn | Ser | Arg | Gly | Gln | Pro | Phe | Asp | Pro | Ser |
| | | | | 515 | | | | | 520 | | | | | 525 | |

| Arg | Gly | Lys | Gln | Tyr | Glu | Ala | Gly | Val | Lys | Tyr | Val | Pro | Lys | Asp | Met |
| | 530 | | | | | 535 | | | | | 540 | | | | |

| Pro | Val | Val | Thr | Ala | Ala | Val | Tyr | Gln | Leu | Thr | Lys | Asp | Lys | Asn |
| 545 | | | | 550 | | | | | 555 | | | | | 560 |

| Leu | Thr | Ala | Asp | Pro | Ala | Asn | Gln | Ala | Phe | Ser | Ile | Gln | Thr | Gly | Glu |
| | | | | 565 | | | | | 570 | | | | | 575 | |

| Ile | Arg | Ser | Arg | Gly | Leu | Glu | Leu | Glu | Ala | Lys | Ala | Ala | Val | Asn | Ala |
| | | | 580 | | | | | 585 | | | | | 590 | | |

| Asn | Ile | Asn | Val | Thr | Ala | Ala | Tyr | Ser | Tyr | Thr | Asp | Ala | Glu | Tyr | Thr |
| | | | 595 | | | | | 600 | | | | | 605 | | |

| His | Asp | Thr | Val | Phe | Asn | Gly | Lys | Arg | Pro | Ala | Glu | Val | Pro | Arg | Asn |
| | 610 | | | | | 615 | | | | | 620 | | | | |

| Met | Ala | Ser | Leu | Trp | Ala | Asp | Tyr | Thr | Phe | His | Glu | Thr | Ala | Leu | Ser |
| 625 | | | | 630 | | | | | 635 | | | | | 640 | |

| Gly | Leu | Thr | Ile | Gly | Ala | Gly | Ala | Arg | Tyr | Ile | Gly | Ser | Thr | Val | Ser |
| | | | 645 | | | | | 650 | | | | | 655 | | |

| Tyr | Tyr | Lys | Asn | Asp | Thr | Ser | Thr | Gly | Lys | Lys | Asn | Asp | Ala | Phe | Ser |
| | | | 660 | | | | | 665 | | | | | 670 | | |

| Val | Ala | Gly | Tyr | Ala | Leu | Met | Asp | Ala | Thr | Val | Lys | Tyr | Asp | Leu | Ala |
| | | | 675 | | | | | 680 | | | | | 685 | | |

| Arg | Phe | Gly | Leu | Pro | Gly | Ser | Ser | Val | Gly | Val | Asn | Val | Asn | Asn | Leu |
| | 690 | | | | | 695 | | | | | 700 | | | | |

| Phe | Asp | Arg | Glu | Tyr | Val | Ser | Ser | Cys | Tyr | Ser | Glu | Tyr | Ala | Cys | Tyr |
| 705 | | | | 710 | | | | | 715 | | | | | 720 | |

| Trp | Gly | Ala | Gly | Arg | Gln | Val | Val | Ala | Thr | Ala | Thr | Phe | Arg | Phe |
| | | | 725 | | | | | 730 | | | | | 735 |

<210> SEQ ID NO 5
<211> LENGTH: 1974
<212> TYPE: DNA
<213> ORGANISM: Klebsiella pneumoniae

<400> SEQUENCE: 5

```
atgttcaggt taaacccttt tatccgggcg ggattgtctg cgtccgtcgt atcgttggcg      60
tttccggctc tggccgatgt gaatgaagaa acgctggtgg tgaccgcctc ggccactgaa     120
cagaatgtca agacgcgcc ggcgagcatc agcgtcatca cccaacagga tttacaacgc     180
```

```
aagcctgttc agaacctgaa agacgtgctg cgcgatgtgc ctggggtcca gctcaccaac    240 gaagggata accgcaaggg cgttagcatc cgcggtctga gcagcagcta cccctgatc     300 ctggtcgacg gcaagcgcgt taactcgcgg aacgccgtct ccgccacaa tgacttcgac    360 cttaactgga tcccggtgga tgctattgag cgtatcgaag tggtgcgcgg cccgatgtcc   420 tcccttacg gctccgatgc gctcggtggg gtggtcaaca ttattaccaa aaaaatcggc    480
cagaaatgga ccgggacgct gagtgctgat accactattc aggagcaccg cgatcgcggg   540 gataccata acggccagtt cttcaccagc ggcccgctga tcgacggcgt acttggaatg    600
aaggcctacg gcagcctggc aaaacgcgcc aaggacgatc gcagtcatc cagtaatgcc    660 accggcgaga cgccgcgcat cgagggcttc accagccgcg atggcaatgt tgaattcgcc   720
tggacgccga acgaaaacca cgattttacc gcaggctacg gctttgaccg tcaggatcgc   780
gattccgatt cccttgaccg caaccgcctt gagcgggaga actactctct gagccataac   840
ggccgctggg atattggcaa tagcgagctc aagttctacg gcgaaaaggt ggataacaaa   900
aatccagggc agagcgggac tattacctcg gaaagcaatg ccatcgacgg caagtatgtc   960
ctgccgctgg gcatgattaa ccagctggtg accttcggcg gcgaatggcg ccacgacaaa  1020
ctgaaagatc cggtcaacct gagcagcggc ggccagtcaa cgtcggccag ccagtacgcc  1080
ctgtttatcg aagacgaatg gcgcatcatc gagccgctgg cgctgaccac cggcattcgt  1140
atggacgacc atcagaccta tggcgatcac tggagcccgc gcgcctatct ggtgtataac  1200
gccaccgata ccgtcaccgt caaaggcggc tgggcgacgg cgtttaaagc cccgtcgctg  1260
ctgcagctta accccgactg gaccaccaac tcctgccgcg gctcgtgcag catcgtcggt  1320 aacccgatc tgaaaccgga aaccagcgaa agcttcgagc tcggtctcta ctaccgcggg  1380
gaagagggct ggcttgaaaa tgtcgaaggc agcatcacca ccttccagaa taatgtcgac  1440
gacatgatcg atgttctgcg cacctccagc gccagcgaag cgccgggcta cccgaacttt  1500
gtcggctgga aaaccgtcaa cggcaagcgc gtgccgatct ccgctatttt caacgtcaac  1560
aaagcccgca tcaaagggt ggagacggag gtgaagatcc cgtttggcga tgagtggaag  1620
ctgacggtga actacacata caacgatggt cgcgatctga gcaatggcgg cgacaaaccg  1680
ctgcagacgc tgccgttcca taccgccaac ggcacgctcg actggaaacc gctggacgat  1740
tggtccttct acgtgacggc caactatacc ggccagcagc gcgcggtgag cgccaccggc  1800
aaaacgccgg cggctacac cctgtttgac gttggcgcgg catggcaggt gaccaaaaac  1860
gtgaaactgc gctccggggt gcagaacgtg ggtgataaag atctgagccg ggacgactac  1920
agctataccg aagaaggccg tcgctacttt atggcggtgg attatcgctt ctga         1974
```

<210> SEQ ID NO 6
<211> LENGTH: 657
<212> TYPE: PRT
<213> ORGANISM: Klebsiella pneumoniae

<400> SEQUENCE: 6

```
Met Phe Arg Leu Asn Pro Phe Ile Arg Ala Gly Leu Ser Ala Ser Val
1               5                   10                  15

Val Ser Leu Ala Phe Pro Ala Leu Ala Asp Val Asn Glu Glu Thr Leu
            20                  25                  30

Val Val Thr Ala Ser Ala Thr Glu Gln Asn Val Lys Asp Ala Pro Ala
        35                  40                  45

Ser Ile Ser Val Ile Thr Gln Gln Asp Leu Gln Arg Lys Pro Val Gln
```

```
                50                  55                  60
Asn Leu Lys Asp Val Leu Arg Asp Val Pro Gly Val Gln Leu Thr Asn
 65                  70                  75                  80

Glu Gly Asp Asn Arg Lys Gly Val Ser Ile Arg Gly Leu Ser Ser Ser
                    85                  90                  95

Tyr Thr Leu Ile Leu Val Asp Gly Lys Arg Val Asn Ser Arg Asn Ala
                100                 105                 110

Val Phe Arg His Asn Asp Phe Asp Leu Asn Trp Ile Pro Val Asp Ala
                115                 120                 125

Ile Glu Arg Ile Glu Val Val Arg Gly Pro Met Ser Ser Leu Tyr Gly
130                 135                 140

Ser Asp Ala Leu Gly Gly Val Val Asn Ile Ile Thr Lys Lys Ile Gly
145                 150                 155                 160

Gln Lys Trp Thr Gly Thr Leu Ser Ala Asp Thr Thr Ile Gln Glu His
                165                 170                 175

Arg Asp Arg Gly Asp Thr Tyr Asn Gly Gln Phe Phe Thr Ser Gly Pro
                180                 185                 190

Leu Ile Asp Gly Val Leu Gly Met Lys Ala Tyr Gly Ser Leu Ala Lys
                195                 200                 205

Arg Ala Lys Asp Asp Pro Gln Ser Ser Ser Asn Ala Thr Gly Glu Thr
210                 215                 220

Pro Arg Ile Glu Gly Phe Thr Ser Arg Asp Gly Asn Val Glu Phe Ala
225                 230                 235                 240

Trp Thr Pro Asn Glu Asn His Asp Phe Thr Ala Gly Tyr Gly Phe Asp
                245                 250                 255

Arg Gln Asp Arg Asp Ser Asp Ser Leu Asp Arg Asn Arg Leu Glu Arg
                260                 265                 270

Glu Asn Tyr Ser Leu Ser His Asn Gly Arg Trp Asp Ile Gly Asn Ser
                275                 280                 285

Glu Leu Lys Phe Tyr Gly Glu Lys Val Asp Asn Lys Asn Pro Gly Gln
                290                 295                 300

Ser Gly Thr Ile Thr Ser Glu Ser Asn Ala Ile Asp Gly Lys Tyr Val
305                 310                 315                 320

Leu Pro Leu Gly Met Ile Asn Gln Leu Val Thr Phe Gly Gly Glu Trp
                325                 330                 335

Arg His Asp Lys Leu Lys Asp Pro Val Asn Leu Ser Ser Gly Gly Gln
                340                 345                 350

Ser Thr Ser Ala Ser Gln Tyr Ala Leu Phe Ile Glu Asp Glu Trp Arg
                355                 360                 365

Ile Ile Glu Pro Leu Ala Leu Thr Thr Gly Ile Arg Met Asp Asp His
370                 375                 380

Gln Thr Tyr Gly Asp His Trp Ser Pro Arg Ala Tyr Leu Val Tyr Asn
385                 390                 395                 400

Ala Thr Asp Thr Val Thr Val Lys Gly Gly Trp Ala Thr Ala Phe Lys
                405                 410                 415

Ala Pro Ser Leu Leu Gln Leu Asn Pro Asp Trp Thr Thr Asn Ser Cys
                420                 425                 430

Arg Gly Ser Cys Ser Ile Val Gly Asn Pro Asp Leu Lys Pro Glu Thr
                435                 440                 445

Ser Glu Ser Phe Glu Leu Gly Leu Tyr Tyr Arg Gly Glu Glu Gly Trp
                450                 455                 460

Leu Glu Asn Val Glu Gly Ser Ile Thr Thr Phe Gln Asn Asn Val Asp
465                 470                 475                 480
```

```
Asp Met Ile Asp Val Leu Arg Thr Ser Ser Ala Ser Glu Ala Pro Gly
                485                 490                 495

Tyr Pro Asn Phe Val Gly Trp Lys Thr Val Asn Gly Lys Arg Val Pro
            500                 505                 510

Ile Phe Arg Tyr Phe Asn Val Asn Lys Ala Arg Ile Lys Gly Val Glu
        515                 520                 525

Thr Glu Val Lys Ile Pro Phe Gly Asp Glu Trp Lys Leu Thr Val Asn
    530                 535                 540

Tyr Thr Tyr Asn Asp Gly Arg Asp Leu Ser Asn Gly Gly Asp Lys Pro
545                 550                 555                 560

Leu Gln Thr Leu Pro Phe His Thr Ala Asn Gly Thr Leu Asp Trp Lys
                565                 570                 575

Pro Leu Asp Asp Trp Ser Phe Tyr Val Thr Ala Asn Tyr Thr Gly Gln
            580                 585                 590

Gln Arg Ala Val Ser Ala Thr Gly Lys Thr Pro Gly Gly Tyr Thr Leu
        595                 600                 605

Phe Asp Val Gly Ala Ala Trp Gln Val Thr Lys Asn Val Lys Leu Arg
    610                 615                 620

Ser Gly Val Gln Asn Val Gly Asp Lys Asp Leu Ser Arg Asp Asp Tyr
625                 630                 635                 640

Ser Tyr Thr Glu Glu Gly Arg Arg Tyr Phe Met Ala Val Asp Tyr Arg
                645                 650                 655

Phe
```

```
<210> SEQ ID NO 7
<211> LENGTH: 2229
<212> TYPE: DNA
<213> ORGANISM: Klebsiella pneumoniae
<220> FEATURE:
<221> NAME/KEY: modified_base
<222> LOCATION: (1439)..(1447)
<223> OTHER INFORMATION: a, c, t or g

<400> SEQUENCE: 7
atgaataaca ggatcaaatc cctggccttg ctggtcaatc tgggaattta cggggttgct      60
tttccgttaa gcgcagcgga aaccgccacc gacgataaaa acagcgccgc tgaagagacc     120
atggtggtca ccgccgccga gcagaacctg caggcgccgg gcgtctccac catcaccgcc     180
gatgagatcc gcaaacgccc cccggcgcgc gacgtctcgg agatcattcg caccatgccg     240
ggagtcaacc tgaccggcaa ctccaccagc ggccagcgcg gcaacaaccg ccagattgat     300
atccgcggca tgggcccgga aaatacccctg atcctgatcg acggcaagcc ggtcaccagc     360
cgcaactccg tgcgccttgg ctggcgcggc gagcgcgaca cccgcggcga taccagctgg     420
gtgccgccgg agataatcga acgtatcgaa gtgattcgcg gcccggccgc cgcccgctac     480
ggcaacggcg ccgccggcgg cgtggtgaat atcatcacca aaaaaaccgg cgatgagtgg     540
cacggctcat ggaacaccta tatgaacgcc ccggagcaca aggatgaagg ctccaccaaa     600
cgcactaact tcagcctcag cggcccgctg gcgcggatt ttagcttccg cctgttcggt     660
aacctcgaca aaacgcaggc cgacgcctgg gatatcaacc agggccatca gtccgagcgt     720
accgggatct atgccgatac tctgccggcc gggcgcgaag gggtgaaaaa caaaaacatc     780
gatggtctgg tgcgctggga attcgctccg atgcagtcgc tggagtttga ggccggctac     840
agccgccagg gcaacctcta cgccggcgac acccagaaca ccaactccaa cgacctggta     900
aaagagaact acggcaaaga gaccaaccgt ctgtatcgca acacctactc ggttacctgg     960
```

```
aacggcgcct gggacaacgg ggtgaccacc agcaactggg cgcagtacga acgcacccgc      1020
aactcgcgca aaggcgaagg cctggccggc ggcaccgagg ggatctttaa cagcaaccag      1080
ttcacggata tcgatctggc ggatgtgatg ctgcacagcg aagtcagcat tcccttcgac      1140
tatctggtta atcagaacct gacgctgggc agcgagtgga atcaacagcg gatgaaggat      1200
aacgcgtcca cacccaggc gctgtcggga ggcggaattc cgggctacga cagcaccggc       1260
cgcagcccgt actcgcaggc ggaaatcttc tcgctgttcg ccgagaacaa catggagctg      1320
accgacacca ccatgctgac tccggcgctg cgtttcgatc atcacagcat tgtcggcaat      1380
aactggagcc cgtccctcaa cctgtcgcag ggcctgtggg atgacttcac gctgaagann      1440
nnnnnnnccc gcgcctataa agcgccgagc ctgtatcaga ccaacccgaa ctacattctc      1500
tacagtaaag gccagggctg ctacgccagt aaagacggct gctatctgca gggtaatgac      1560
gacttaaaag ccgagaccag catcaacaaa gagattggcc tcgagtttaa acgcgacggc      1620
tggctggcgg gcgtcacctg gttccgcaac gactaccgca acaagattga agcgggctat      1680
gccccggtct atcaaaacaa taaggtacc gatctctacc agtgggaaaa cgtgccgaaa       1740
gcggtggtgg aaggtctgga ggggacgttg aacgttccgg tgagcgagac cgtcaactgg      1800
accaacaaca tcacctatat gctgcagagt aagaacaaag agaccggcga tcgtctgtcg      1860
attatcccgg aatacacgct gaactccacc ctgagctggc aggttcgcga tgacgtttcg      1920
ctgcagtcga ccttcacctg gtacggcaag caggagccga agaagtacaa ctacaagggt      1980
caaccggtca ccggcagcga gaagaacgag gttagccccct acagcatcct cggcctgagc      2040
gcgacctggg acgtcaccaa atacgtcagt ctgaccggcg gcgtggataa cgtcttcgat      2100
aagcgccact ggcgcgcggg caacgcccag accaccgggg gcgccaccgg cacgatgtac      2160
ggcgccggcg ccgagaccta caatgaatcg ggccgcacct ggtacctgag cgtcaacacc      2220
cacttctga                                                             2229
```

<210> SEQ ID NO 8
<211> LENGTH: 742
<212> TYPE: PRT
<213> ORGANISM: Klebsiella pneumoniae
<220> FEATURE:
<221> NAME/KEY: MOD_RES
<222> LOCATION: (480)..(483)
<223> OTHER INFORMATION: Any amino acid

<400> SEQUENCE: 8

Met Asn Asn Arg Ile Lys Ser Leu Ala Leu Leu Val Asn Leu Gly Ile
1               5                   10                  15

Tyr Gly Val Ala Phe Pro Leu Ser Ala Ala Glu Thr Ala Thr Asp Asp
            20                  25                  30

Lys Asn Ser Ala Ala Glu Glu Thr Met Val Val Thr Ala Ala Glu Gln
        35                  40                  45

Asn Leu Gln Ala Pro Gly Val Ser Thr Ile Thr Ala Asp Glu Ile Arg
    50                  55                  60

Lys Arg Pro Pro Ala Arg Asp Val Ser Glu Ile Ile Arg Thr Met Pro
65                  70                  75                  80

Gly Val Asn Leu Thr Gly Asn Ser Thr Ser Gly Gln Arg Gly Asn Asn
                85                  90                  95

Arg Gln Ile Asp Ile Arg Gly Met Gly Pro Glu Asn Thr Leu Ile Leu
            100                 105                 110

Ile Asp Gly Lys Pro Val Thr Ser Arg Asn Ser Val Arg Leu Gly Trp

-continued

```
            115                 120                 125
Arg Gly Glu Arg Asp Thr Arg Gly Asp Thr Ser Trp Val Pro Pro Glu
    130                 135                 140
Ile Ile Glu Arg Ile Glu Val Ile Arg Gly Pro Ala Ala Ala Arg Tyr
145                 150                 155                 160
Gly Asn Gly Ala Ala Gly Gly Val Val Asn Ile Ile Thr Lys Lys Thr
                165                 170                 175
Gly Asp Glu Trp His Gly Ser Trp Asn Thr Tyr Met Asn Ala Pro Glu
                180                 185                 190
His Lys Asp Glu Gly Ser Thr Lys Arg Thr Asn Phe Ser Leu Ser Gly
                195                 200                 205
Pro Leu Gly Gly Asp Phe Ser Phe Arg Leu Phe Gly Asn Leu Asp Lys
    210                 215                 220
Thr Gln Ala Asp Ala Trp Asp Ile Asn Gln Gly His Gln Ser Glu Arg
225                 230                 235                 240
Thr Gly Ile Tyr Ala Asp Thr Leu Pro Ala Gly Arg Glu Gly Val Lys
                245                 250                 255
Asn Lys Asn Ile Asp Gly Leu Val Arg Trp Glu Phe Ala Pro Met Gln
                260                 265                 270
Ser Leu Glu Phe Glu Ala Gly Tyr Ser Arg Gln Gly Asn Leu Tyr Ala
    275                 280                 285
Gly Asp Thr Gln Asn Thr Asn Ser Asn Asp Leu Val Lys Glu Asn Tyr
    290                 295                 300
Gly Lys Glu Thr Asn Arg Leu Tyr Arg Asn Thr Tyr Ser Val Thr Trp
305                 310                 315                 320
Asn Gly Ala Trp Asp Asn Gly Val Thr Thr Ser Asn Trp Ala Gln Tyr
                325                 330                 335
Glu Arg Thr Arg Asn Ser Arg Lys Gly Glu Gly Leu Ala Gly Gly Thr
                340                 345                 350
Glu Gly Ile Phe Asn Ser Asn Gln Phe Thr Asp Ile Asp Leu Ala Asp
                355                 360                 365
Val Met Leu His Ser Glu Val Ser Ile Pro Phe Asp Tyr Leu Val Asn
    370                 375                 380
Gln Asn Leu Thr Leu Gly Ser Glu Trp Asn Gln Gln Arg Met Lys Asp
385                 390                 395                 400
Asn Ala Ser Asn Thr Gln Ala Leu Ser Gly Gly Ile Pro Gly Tyr
                405                 410                 415
Asp Ser Thr Gly Arg Ser Pro Tyr Ser Gln Ala Glu Ile Phe Ser Leu
                420                 425                 430
Phe Ala Glu Asn Asn Met Glu Leu Thr Asp Thr Thr Met Leu Thr Pro
                435                 440                 445
Ala Leu Arg Phe Asp His His Ser Ile Val Gly Asn Asn Trp Ser Pro
    450                 455                 460
Ser Leu Asn Leu Ser Gln Gly Leu Trp Asp Asp Phe Thr Leu Lys Xaa
465                 470                 475                 480
Xaa Xaa Xaa Arg Ala Tyr Lys Ala Pro Ser Leu Tyr Gln Thr Asn Pro
                485                 490                 495
Asn Tyr Ile Leu Tyr Ser Lys Gly Gln Gly Cys Tyr Ala Ser Lys Asp
                500                 505                 510
Gly Cys Tyr Leu Gln Gly Asn Asp Asp Leu Lys Ala Glu Thr Ser Ile
                515                 520                 525
Asn Lys Glu Ile Gly Leu Glu Phe Lys Arg Asp Gly Trp Leu Ala Gly
    530                 535                 540
```

```
Val Thr Trp Phe Arg Asn Asp Tyr Arg Asn Lys Ile Glu Ala Gly Tyr
545                 550                 555                 560

Ala Pro Val Tyr Gln Asn Asn Lys Gly Thr Asp Leu Tyr Gln Trp Glu
                565                 570                 575

Asn Val Pro Lys Ala Val Val Glu Gly Leu Glu Gly Thr Leu Asn Val
            580                 585                 590

Pro Val Ser Glu Thr Val Asn Trp Thr Asn Asn Ile Thr Tyr Met Leu
        595                 600                 605

Gln Ser Lys Asn Lys Glu Thr Gly Asp Arg Leu Ser Ile Ile Pro Glu
    610                 615                 620

Tyr Thr Leu Asn Ser Thr Leu Ser Trp Gln Val Arg Asp Asp Val Ser
625                 630                 635                 640

Leu Gln Ser Thr Phe Thr Trp Tyr Gly Lys Gln Glu Pro Lys Lys Tyr
                645                 650                 655

Asn Tyr Lys Gly Gln Pro Val Thr Gly Ser Glu Lys Asn Glu Val Ser
            660                 665                 670

Pro Tyr Ser Ile Leu Gly Leu Ser Ala Thr Trp Asp Val Thr Lys Tyr
        675                 680                 685

Val Ser Leu Thr Gly Gly Val Asp Asn Val Phe Asp Lys Arg His Trp
    690                 695                 700

Arg Ala Gly Asn Ala Gln Thr Thr Gly Gly Ala Thr Gly Thr Met Tyr
705                 710                 715                 720

Gly Ala Gly Ala Glu Thr Tyr Asn Glu Ser Gly Arg Thr Trp Tyr Leu
                725                 730                 735

Ser Val Asn Thr His Phe
            740

<210> SEQ ID NO 9
<211> LENGTH: 1836
<212> TYPE: DNA
<213> ORGANISM: Klebsiella pneumoniae
<220> FEATURE:
<221> NAME/KEY: modified_base
<222> LOCATION: (414)..(456)
<223> OTHER INFORMATION: a, c, t or g

<400> SEQUENCE: 9
atgattaaaa aagcttcgct gatgacggcc ttatccgtca cggcattttc cggctgggcg      60
caggatagca attcagatac gttggtggtg acagcaaacc gttttcaaca gccggtcaat     120
accgtgctgg cgccgaccga cattgtgacg cgcgatgaca tcgaccgctg gcagtccaaa     180
gatttaaacg atgtcatgcg tcgtcttccc ggggtcgata ttgcccgcaa cggcggcatg     240
gggcagagcg cttcgctgta tgttcggggg acggaggctc gtcacgtgct ggtgctgatc     300
gacggtgtgc cgatggcgcg tccggggatc tccaacggcg tagatatcag tcagatccct     360
atctcactgg tccagcgggt ggaatacatc cgcggcccgc gctccgcggt gtannnnnnn     420
nnnnnnnnnn nnnnnnnnnn nnnnnnnnnn nnnnnaccg acgctgagcg ttcgcaaatc     480
aacgccggcg cgggcacgaa cggctatcag tcctatgacg gcgcctttaa caagcggttt     540
ggcaacacgc tggttaccgc tgctggcgcc tatcagacca ccaaagggtt taacgtccag     600
ccgaattcct cttatagcgg cgacagcgat cgcgacggct accgcaataa aatgctgtgg     660
ggcggggtac agcatcagtt cgatgacaac ttctcggggt tcttccgcgg ctatggttat     720
tccgccaacg ctgactatga ccagggtaac tggggctacg caggtggaaa cgatgaagat     780
caatcctata cccaatcctg ggataccggt ctgcactacc actccggaat ttactcctcc     840
```

```
cagctgattg ctaactatca gcgcatcaaa gattacaact acagcagcga cgctggccgc      900
tatgccgcgg gcaccaccct ggatgatatg aacagcgct atatccagtg gggaaataat       960
gttgtggtag ccatggggc agtgagcggc ggcgttgact ggaaacaaga gaagctgaaa      1020
tccagcggaa cgaccagtac cgacgtgtat aagcgtgaca ccaccggtct ttatctgacg     1080
ggacagcagc agattgacag cgtgacgctg gaagcttccg gccgtgagga tcatgacgag     1140
cagtttggct ggcacggtac ctggcagacg gccgcaggct gggaatttat cgacggttat    1200
cggacaacgc tctcgtacgg cacaggattc ctcgccccct ccctcgggca gcagtacggc     1260
gcagaacgct ttggcatcgc ctctaacccg aatctgaagc cagaggagtc gaagcaatgg     1320
gaagcgggcc ttgaagggtt aacggggccg gtcgactggc gcctctccgc atatcgctat    1380
gagattcaaa acctcatcga ttacgacaac aacgcctatt acaacgtcaa gtcggcgacg    1440
attaaggggc tggagtggac ggggaatata accaccgggc cggtggagca ccatctgacg    1500
ctgcagtatg ttgacccctcg cgatgatgaa accaataaga tcctctatcg ccgggcgaag   1560
cagcaggtga aatacgagct gaacggccag gtctacgatc tggggtggga tgtgacgtat   1620
cactacatcg gcaagcgtta cgattatgac tacgacaact cgcgtaccgt caatatgggt    1680
gggttgagcc tctgggatgt cggtttatcg tatcccgtca cctcacacct gacagttcgt    1740
ggtaaaatag ccaacctgtt cgataaagat tacgagacag tttatggcta ccaatctgca   1800
ggacgggaat acaccttgtc tggcagctac accttc                              1836
```

<210> SEQ ID NO 10
<211> LENGTH: 612
<212> TYPE: PRT
<213> ORGANISM: Klebsiella pneumoniae
<220> FEATURE:
<221> NAME/KEY: MOD_RES
<222> LOCATION: (138)..(152)
<223> OTHER INFORMATION: Any amino acid

<400> SEQUENCE: 10

```
Met Ile Lys Lys Ala Ser Leu Met Thr Ala Leu Ser Val Thr Ala Phe
1               5                   10                  15

Ser Gly Trp Ala Gln Asp Ser Asn Ser Asp Thr Leu Val Val Thr Ala
            20                  25                  30

Asn Arg Phe Gln Gln Pro Val Asn Thr Val Leu Ala Pro Thr Asp Ile
        35                  40                  45

Val Thr Arg Asp Asp Ile Asp Arg Trp Gln Ser Lys Asp Leu Asn Asp
    50                  55                  60

Val Met Arg Arg Leu Pro Gly Val Asp Ile Ala Arg Asn Gly Gly Met
65                  70                  75                  80

Gly Gln Ser Ala Ser Leu Tyr Val Arg Gly Thr Glu Ala Arg His Val
                85                  90                  95

Leu Val Leu Ile Asp Gly Val Pro Met Ala Arg Pro Gly Ile Ser Asn
            100                 105                 110

Gly Val Asp Ile Ser Gln Ile Pro Ile Ser Leu Val Gln Arg Val Glu
        115                 120                 125

Tyr Ile Arg Gly Pro Arg Ser Ala Val Xaa Xaa Xaa Xaa Xaa Xaa
    130                 135                 140

Xaa Xaa Xaa Xaa Xaa Xaa Xaa Thr Asp Ala Glu Arg Ser Gln Ile
145                 150                 155                 160

Asn Ala Gly Ala Gly Thr Asn Gly Tyr Gln Ser Tyr Asp Gly Ala Phe
                165                 170                 175
```

```
Asn Lys Arg Phe Gly Asn Thr Leu Val Thr Ala Ala Gly Ala Tyr Gln
            180                 185                 190
Thr Thr Lys Gly Phe Asn Val Gln Pro Asn Ser Ser Tyr Ser Gly Asp
            195                 200                 205
Ser Asp Arg Asp Gly Tyr Arg Asn Lys Met Leu Trp Gly Gly Val Gln
210                 215                 220
His Gln Phe Asp Asp Asn Phe Ser Gly Phe Phe Arg Gly Tyr Gly Tyr
225                 230                 235                 240
Ser Ala Asn Ala Asp Tyr Asp Gln Gly Asn Trp Gly Tyr Ala Gly Gly
            245                 250                 255
Asn Asp Glu Asp Gln Ser Tyr Thr Gln Ser Trp Asp Thr Gly Leu His
            260                 265                 270
Tyr His Ser Gly Ile Tyr Ser Ser Gln Leu Ile Ala Asn Tyr Gln Arg
            275                 280                 285
Ile Lys Asp Tyr Asn Tyr Ser Ser Asp Ala Gly Arg Tyr Ala Ala Gly
            290                 295                 300
Thr Thr Leu Asp Asp Met Glu Gln Arg Tyr Ile Gln Trp Gly Asn Asn
305                 310                 315                 320
Val Val Val Gly His Gly Ala Val Ser Gly Gly Val Asp Trp Lys Gln
            325                 330                 335
Glu Lys Leu Lys Ser Ser Gly Thr Thr Ser Thr Asp Val Tyr Lys Arg
            340                 345                 350
Asp Thr Thr Gly Leu Tyr Leu Thr Gly Gln Gln Gln Ile Asp Ser Val
            355                 360                 365
Thr Leu Glu Ala Ser Gly Arg Glu Asp His Asp Glu Gln Phe Gly Trp
            370                 375                 380
His Gly Thr Trp Gln Thr Ala Ala Gly Trp Glu Phe Ile Asp Gly Tyr
385                 390                 395                 400
Arg Thr Thr Leu Ser Tyr Gly Thr Gly Phe Leu Ala Pro Ser Leu Gly
            405                 410                 415
Gln Gln Tyr Gly Ala Glu Arg Phe Gly Ile Ala Ser Asn Pro Asn Leu
            420                 425                 430
Lys Pro Glu Glu Ser Lys Gln Trp Glu Ala Gly Leu Glu Gly Leu Thr
            435                 440                 445
Gly Pro Val Asp Trp Arg Leu Ser Ala Tyr Arg Tyr Glu Ile Gln Asn
            450                 455                 460
Leu Ile Asp Tyr Asp Asn Asn Ala Tyr Tyr Asn Val Lys Ser Ala Thr
465                 470                 475                 480
Ile Lys Gly Leu Glu Trp Thr Gly Asn Ile Thr Thr Gly Pro Val Glu
            485                 490                 495
His His Leu Thr Leu Gln Tyr Val Asp Pro Arg Asp Asp Glu Thr Asn
            500                 505                 510
Lys Ile Leu Tyr Arg Arg Ala Lys Gln Gln Val Lys Tyr Glu Leu Asn
            515                 520                 525
Gly Gln Val Tyr Asp Leu Gly Trp Asp Val Thr Tyr His Tyr Ile Gly
            530                 535                 540
Lys Arg Tyr Asp Tyr Asp Tyr Asp Asn Ser Arg Thr Val Asn Met Gly
545                 550                 555                 560
Gly Leu Ser Leu Trp Asp Val Gly Leu Ser Tyr Pro Val Thr Ser His
            565                 570                 575
Leu Thr Val Arg Gly Lys Ile Ala Asn Leu Phe Asp Lys Asp Tyr Glu
            580                 585                 590
```

```
Thr Val Tyr Gly Tyr Gln Ser Ala Gly Arg Glu Tyr Thr Leu Ser Gly
    595                 600                 605

Ser Tyr Thr Phe
    610

<210> SEQ ID NO 11
<211> LENGTH: 2283
<212> TYPE: DNA
<213> ORGANISM: Klebsiella pneumoniae

<400> SEQUENCE: 11
atggaaaaaa acgcttctct gcctttcggc agtttcaact cattggcatt gtttacaggt      60
ctgtgtctgg gagcctcgcc ggcagcaggc atcgcagcgg aaaattcggt caaaaatagt     120
gaagagacgc tggtagtgga agccgctccg ccttcactct actccccgg cgcttccgcc      180 gatcccaagt tcaataaacc gctggtcgat accacccgca ccatcaccgt gatcccggaa     240
caggtgatta agatcagggg cgtcaccaac ctgactgacg ccctcaaaaa cgttcccggc     300 gtggggcgt tttatgccgg ggagaatggc agctcaacca ccgggatgc catctttatg      360 cgcggcgtgg atacctctaa cagcatctat gtggacggca ttcgcgacat cggcagcgtg     420
acgcgcgata ccttcaatac ccagcaggtg aagtcatca aagggcccgc cggcacggac      480
tatggccgca gcgcgccctc cggctcgatc aatatgatca gcaagcagcc gcgccttgac     540
tccgggatcg acggctcggc cagcatcggc agcgcctggt cgcgccgggg cactctcgac     600
ctgaaccagg cgtttagcga caacgctgcg ttccgtctga acctgatggg ggaaaaaacc     660
catgacgctg gtcgggaccg cattgaaaac gaacgctatg catcgcacc gtcgctggcc      720 ttcggccttg atacccccaac tcgtctgtat ctgaactatc tgcacgtccg gcagaacaac     780
accccggatg gcgggatccc taccgtcggc ctgccgggct attcggcgcc ttcgccgaag     840
tatgccgcac tcaactccac cgggaaggtc gataccagca atttctatgg caccgactcc     900
gattacgata aatctactac cgacagcggt accctgcgct tcgaacacga tctgacagag     960
agcaccaccg tgcgcaatac caccgctgg tcgcgagtga acaggagta tcttttgacc     1020 gcggtgatgg gcgcgcgaa caatatcacc gcccccgata tcaatgacgt caacacctgg     1080
agctggtcgc gtctggttaa taccaaagat gtcagcaacc gcattctgac caaccagacc     1140
aatatcacct cgaccttcga tactggctcg ataggccatg acgtcagcgc cggcgtggag     1200
tttacccggg aaaaccagac caactatggc gttaacgcca ggaccgcgcc ggcggtgaat     1260
ctctaccatc cggtgagcaa cctgtcgatt ggcgggctgg acagaaacgg ggcgaacgcc     1320
aacggccaga ccgatacctt cgggatttat gcctttgata cgctgacgct gaccgagcgg     1380
attgagatca acggcgggct gcgtctcgac aattaccata ccaaatatga cagcgccacc     1440
gcctgcggcg gcagcggacg cggggctatc gcctgcccgc ccggacagtc gaccggcagc     1500
ccggtcacca ctgtcgatac cgctaaatcc ggcaatctgg ttaactggaa agccggggcg     1560
ctgtaccgct taaccgagca gggcaatgtc tacgtcaact acgccatctc acagcagccg     1620
ccgggaggca gcagcttcgc cctggccgcc agcggcagcg gcaacagcgc taaccgaacc     1680
gactttaagc cgcagaaggc aaaatccagc gagctgggca ccaagtggca atcttcgac     1740 aaccgtctgc tgctcagcgc ggcgttattc cgcaccgata ttgaaaacga agtggccgcc     1800
aacgatgacg gaacctggtc gcagtacggc aaaagcgcg tggagggta tgaactctcc     1860 gcgaccggaa acctgacccc ggactggacg attatcgccg gctacactca gcagcatgcg     1920
acagtgacgg agggacagaa cgttgcacag gatggatctt ccgccctggc ctacaccccg     1980
```

```
aaacatgcct ttacgctgtg gacgcagtat caggccacca gcgatctgtc cgtcggcggc    2040
ggtgtgcgct atgtcggaag cctgcgccgg ggcagcgatg gtgcagtcgg taccccggat    2100
cacaccgagg gctactgggt tgccgacgcc aaactgggct atcgggtcaa cagcaacctc    2160
gatctgcagc tcaatatgta taacctgttt gataccgatt acgtggcctc catcaacaag    2220
agcggctatc gctatcatcc gggcgaaccc cggacctta tgctgacggc gaacgtccat    2280
ttc                                                                 2283
```

<210> SEQ ID NO 12
<211> LENGTH: 761
<212> TYPE: PRT
<213> ORGANISM: Klebsiella pneumoniae

<400> SEQUENCE: 12

```
Met Glu Lys Asn Ala Ser Leu Pro Phe Gly Ser Phe Asn Ser Leu Ala
1               5                   10                  15

Leu Phe Thr Gly Leu Cys Leu Gly Ala Ser Pro Ala Ala Gly Ile Ala
            20                  25                  30

Ala Glu Asn Ser Val Lys Asn Ser Glu Glu Thr Leu Val Val Glu Ala
        35                  40                  45

Ala Pro Pro Ser Leu Tyr Ser Pro Gly Ala Ser Ala Asp Pro Lys Phe
    50                  55                  60

Asn Lys Pro Leu Val Asp Thr Thr Arg Thr Ile Thr Val Ile Pro Glu
65                  70                  75                  80

Gln Val Ile Lys Asp Gln Gly Val Thr Asn Leu Thr Asp Ala Leu Lys
                85                  90                  95

Asn Val Pro Gly Val Gly Ala Phe Tyr Ala Gly Glu Asn Gly Ser Ser
            100                 105                 110

Thr Thr Gly Asp Ala Ile Phe Met Arg Gly Val Asp Thr Ser Asn Ser
        115                 120                 125

Ile Tyr Val Asp Gly Ile Arg Asp Ile Gly Ser Val Thr Arg Asp Thr
    130                 135                 140

Phe Asn Thr Gln Gln Val Glu Val Ile Lys Gly Pro Ala Gly Thr Asp
145                 150                 155                 160

Tyr Gly Arg Ser Ala Pro Ser Gly Ser Ile Asn Met Ile Ser Lys Gln
                165                 170                 175

Pro Arg Leu Asp Ser Gly Ile Asp Gly Ser Ala Ser Ile Gly Ser Ala
            180                 185                 190

Trp Ser Arg Arg Gly Thr Leu Asp Leu Asn Gln Ala Phe Ser Asp Asn
        195                 200                 205

Ala Ala Phe Arg Leu Asn Leu Met Gly Glu Lys Thr His Asp Ala Gly
    210                 215                 220

Arg Asp Arg Ile Glu Asn Glu Arg Tyr Gly Ile Ala Pro Ser Leu Ala
225                 230                 235                 240

Phe Gly Leu Asp Thr Pro Thr Arg Leu Tyr Leu Asn Tyr Leu His Val
                245                 250                 255

Arg Gln Asn Asn Thr Pro Asp Gly Gly Ile Pro Thr Val Gly Leu Pro
            260                 265                 270

Gly Tyr Ser Ala Pro Ser Pro Lys Tyr Ala Ala Leu Asn Ser Thr Gly
        275                 280                 285

Lys Val Asp Thr Ser Asn Phe Tyr Gly Thr Asp Ser Asp Tyr Asp Lys
    290                 295                 300

Ser Thr Thr Asp Ser Gly Thr Leu Arg Phe Glu His Asp Leu Thr Glu
```

```
           305                 310                 315                 320
Ser Thr Thr Val Arg Asn Thr Thr Arg Trp Ser Arg Val Lys Gln Glu
                    325                 330                 335

Tyr Leu Leu Thr Ala Val Met Gly Gly Ala Asn Asn Ile Thr Ala Pro
                    340                 345                 350

Asp Ile Asn Asp Val Asn Thr Trp Ser Trp Ser Arg Leu Val Asn Thr
                    355                 360                 365

Lys Asp Val Ser Asn Arg Ile Leu Thr Asn Gln Thr Asn Ile Thr Ser
370                 375                 380

Thr Phe Asp Thr Gly Ser Ile Gly His Asp Val Ser Ala Gly Val Glu
385                 390                 395                 400

Phe Thr Arg Glu Asn Gln Thr Asn Tyr Gly Val Asn Ala Arg Thr Ala
                    405                 410                 415

Pro Ala Val Asn Leu Tyr His Pro Val Ser Asn Leu Ser Ile Gly Gly
                    420                 425                 430

Leu Asp Arg Asn Gly Ala Asn Ala Asn Gly Gln Thr Asp Thr Phe Gly
                    435                 440                 445

Ile Tyr Ala Phe Asp Thr Leu Thr Leu Thr Glu Arg Ile Glu Ile Asn
                    450                 455                 460

Gly Gly Leu Arg Leu Asp Asn Tyr His Thr Lys Tyr Asp Ser Ala Thr
465                 470                 475                 480

Ala Cys Gly Gly Ser Gly Arg Gly Ala Ile Ala Cys Pro Pro Gly Gln
                    485                 490                 495

Ser Thr Gly Ser Pro Val Thr Thr Val Asp Thr Ala Lys Ser Gly Asn
                    500                 505                 510

Leu Val Asn Trp Lys Ala Gly Ala Leu Tyr Arg Leu Thr Glu Gln Gly
                    515                 520                 525

Asn Val Tyr Val Asn Tyr Ala Ile Ser Gln Gln Pro Pro Gly Gly Ser
                    530                 535                 540

Ser Phe Ala Leu Ala Ala Ser Gly Ser Gly Asn Ser Ala Asn Arg Thr
545                 550                 555                 560

Asp Phe Lys Pro Gln Lys Ala Lys Ser Ser Glu Leu Gly Thr Lys Trp
                    565                 570                 575

Gln Ile Phe Asp Asn Arg Leu Leu Leu Ser Ala Ala Leu Phe Arg Thr
                    580                 585                 590

Asp Ile Glu Asn Glu Val Ala Ala Asn Asp Gly Thr Trp Ser Gln
                    595                 600                 605

Tyr Gly Lys Lys Arg Val Glu Gly Tyr Glu Leu Ser Ala Thr Gly Asn
                    610                 615                 620

Leu Thr Pro Asp Trp Thr Ile Ile Ala Gly Tyr Thr Gln His Ala
625                 630                 635                 640

Thr Val Thr Glu Gly Gln Asn Val Ala Gln Asp Gly Ser Ser Ala Leu
                    645                 650                 655

Ala Tyr Thr Pro Lys His Ala Phe Thr Leu Trp Thr Gln Tyr Gln Ala
                    660                 665                 670

Thr Ser Asp Leu Ser Val Gly Gly Val Arg Tyr Val Gly Ser Leu
                    675                 680                 685

Arg Arg Gly Ser Asp Gly Ala Val Gly Thr Pro Asp His Thr Glu Gly
                    690                 695                 700

Tyr Trp Val Ala Asp Ala Lys Leu Gly Tyr Arg Val Asn Ser Asn Leu
705                 710                 715                 720

Asp Leu Gln Leu Asn Met Tyr Asn Leu Phe Asp Thr Asp Tyr Val Ala
                    725                 730                 735
```

Ser Ile Asn Lys Ser Gly Tyr Arg Tyr His Pro Gly Glu Pro Arg Thr
            740                 745                 750

Phe Met Leu Thr Ala Asn Val His Phe
            755                 760

<210> SEQ ID NO 13
<211> LENGTH: 896
<212> TYPE: DNA
<213> ORGANISM: Klebsiella pneumoniae

<400> SEQUENCE: 13

| | | | | | |
|---|---|---|---|---|---|
| atgaaaatcc | tgtccgtgcg | tcacgccgcc | ctcccggccc | tgctcttgcc | gctcattgcc | 60 |
| gcagcccagg | ccgctgatga | acaaaccatg | gtggtgaccg | ccgcgccaac | cacggttcct | 120 |
| gaactggata | cccccgccgc | cgtcagcgtg | gtgaatgggg | atgagatgcg | ccaggccgcg | 180 |
| ccgcgcgtca | atctctctga | atcgctgggc | gccgtgccgg | gcctgcaggt | gcagaaccgg | 240 |
| caaaactatg | cccaggatct | gcagctgtcg | attcgcggct | ttggctcgcg | ctcaacctat | 300 |
| ggcgtgcgcg | gactacgcat | ctatgtggat | ggcattccgg | ccaccatgcc | cgacggccag | 360 |
| gggcagacct | caaatattga | tatcggcagc | gttgacacca | ttgaggtgct | gcgcggcccc | 420 |
| ttctctgccc | tgtacggtaa | ctcgtccggc | ggggtgatca | acgtcaccag | ccagaccggc | 480 |
| acccagccgc | ccaccgtgga | agccagcagc | tactatggca | gcttcggcac | ctggcactac | 540 |
| gggatgaaag | ccactggcgc | cgttggcgac | ggcagccacg | caggcgatgt | ggattacacg | 600 |
| gtctcaacca | atcgcttcac | cacccatggc | tatcgcgatc | acagcggcgc | gcgcaaaaat | 660 |
| ctggcgaacg | cccggctggg | ggtgcgcatc | aacgacgtca | gtaagctgac | tctgctgctg | 720 |
| aatagcgtgg | atatcaaagc | caatgacgcc | ggtggcctga | ccgccgatga | atggcgcgat | 780 |
| aacccgcgcc | agtcgccgcg | cggcgaccag | tataatcccc | gcaagaatac | ccgacagacc | 840 |
| caggccggcc | tgcgctatga | gcgccagctc | agtgcccagg | acgatctcag | cgtatg | 896 |

<210> SEQ ID NO 14
<211> LENGTH: 298
<212> TYPE: PRT
<213> ORGANISM: Klebsiella pneumoniae

<400> SEQUENCE: 14

Met Lys Ile Leu Ser Val Arg His Ala Ala Leu Pro Ala Leu Leu
1               5                   10                  15

Pro Leu Ile Ala Ala Ala Gln Ala Ala Asp Glu Gln Thr Met Val Val
            20                  25                  30

Thr Ala Ala Pro Thr Thr Val Ser Glu Leu Asp Thr Pro Ala Ala Val
            35                  40                  45

Ser Val Val Asn Gly Asp Glu Met Arg Gln Ala Pro Arg Val Asn
        50                  55                  60

Leu Ser Glu Ser Leu Gly Ala Val Pro Gly Leu Gln Val Gln Asn Arg
65                  70                  75                  80

Gln Asn Tyr Ala Gln Asp Leu Gln Leu Ser Ile Arg Gly Phe Gly Ser
            85                  90                  95

Arg Ser Thr Tyr Gly Val Arg Gly Leu Arg Ile Tyr Val Asp Gly Ile
            100                 105                 110

Pro Ala Thr Met Pro Asp Gly Gln Gly Gln Thr Ser Asn Ile Asp Ile
            115                 120                 125

Gly Ser Val Asp Thr Ile Glu Val Leu Arg Gly Pro Phe Ser Ala Leu
            130                 135                 140

```
Tyr Gly Asn Ser Ser Gly Gly Val Ile Asn Val Thr Ser Gln Thr Gly
145                 150                 155                 160

Thr Gln Pro Pro Thr Val Glu Ala Ser Ser Tyr Tyr Gly Ser Phe Gly
            165                 170                 175

Thr Trp His Tyr Gly Met Lys Ala Thr Gly Ala Val Gly Asp Gly Ser
        180                 185                 190

His Ala Gly Asp Val Asp Tyr Thr Val Ser Thr Asn Arg Phe Thr Thr
        195                 200                 205

His Gly Tyr Arg Asp His Ser Gly Ala Arg Lys Asn Leu Ala Asn Ala
        210                 215                 220

Arg Leu Gly Val Arg Ile Asn Asp Val Ser Lys Leu Thr Leu Leu Leu
225                 230                 235                 240

Asn Ser Val Asp Ile Lys Ala Asn Asp Ala Gly Gly Leu Thr Ala Asp
                245                 250                 255

Glu Trp Arg Asp Asn Pro Arg Gln Ser Pro Arg Gly Asp Gln Tyr Asn
                260                 265                 270

Thr Arg Lys Asn Thr Arg Gln Thr Gln Ala Gly Leu Arg Tyr Glu Arg
        275                 280                 285

Gln Leu Ser Ala Gln Asp Asp Leu Ser Val
        290                 295
```

<210> SEQ ID NO 15
<211> LENGTH: 2029
<212> TYPE: DNA
<213> ORGANISM: Klebsiella pneumoniae
<220> FEATURE:
<221> NAME/KEY: modified_base
<222> LOCATION: (292)..(334)
<223> OTHER INFORMATION: a, c, t or g

<400> SEQUENCE: 15

```
gtcgattatc acggctgagg atattgctaa gcagccgccg gtcaacgatc tctcagacat    60
catccgtaaa atgcccgggg tgaacttgac cggcaacagc gccagcggca gtcggggcaa   120
caaccgccag attgatatcc gcggcatggg gccggagaac accctgatcc tgatagatgg   180
ggtaccggtc acgtcacgta acgcggttcg ctatagctgg cgcggcgaac gcgatacccg   240
gggcgacagc aactgggtac ctgccgaaat ggtcgaacgg attgaagttc tnnnnnnnnn   300
nnnnnnnnnn nnnnnnnnnn nnnnnnnnnn nnnnggagtg gtcaatatca ttaccaaacg   360
tccgaccaac acctggcacg gttcgctgtc tttcttcacc aaccagccgg aaaacaacaa   420
agaaggcacg accaatcgcg ctaacttcaa tctcagcggc ccactggccg gcgaggcgct   480
gacgatgcgc ctgtatggca atatcaataa aacggaaccc gacgcctggg atattaacca   540
tgcgcaaaac ggctcttacg ctgcggggcg cgaaggggtc cgcaataaag acattaacgc   600
gctactgtca tggaaaatga ccccgcaaca aattctcgat ttcagctacg cctatagccg   660
tcagggggaat atctatgctg gcgatacccca gtacagcaac ggcaatctta gcccgaacgg   720
gctggtggac tccctgtacg gccacgaaac aaatcgcctc tatcgccagt cctggggact   780
cacctacaac ggtctatggg attggggtca gtccaaagcc ggtgtttact acgagaaaac   840
caacaatacc cgcctgcagg aaggctctac cggccgcgtc gaaggcatga tcaacagtga   900
agattatgcc accagccgtc tggaatcctg gcgtactacc tcggaattca atgtgccttt   960
cttctggctg gcggaccaga cgctgacgct gggaatggaa tggaaccatg atcagcttga  1020
cgacccggca tcaatgcagg ccactaacag caacggcgag actatccctg ggacctcggg  1080
```

```
cgaccctacg caacgcagta ccaaaaacag cgccaccctc accggtatct atctggaaga  1140
taatatcgaa gccgtgcccg gcaccaacct gatccccggc attcgcttcg attatcataa  1200
tcagtttggc agtaactgga gccccagcct caatctgtcc caggagctcg gcgatatgtt  1260
cacgctgaag gccggtatcg cgcgcgtgtt taaagcgcca aacctctatc aatccagtaa  1320
aggctatttg ctctccaccc gcggcaacgg ttgtccaaac acgatcgctg aaggcagctg  1380
ctacctgctg gtaaccctg acctcgaccc ggagatcagt atcaacaaag agatcggtat  1440
cgaatttaac cttaatggtt acgctgccgg agtcacctgg tttcgcaacg attacaaaaa  1500
caaaatcgtc tccggaacag aggtactggg ctatacctcc agcggcaata atattttgca  1560
atggcagaac ggcggcaaag ccgtggtcga ggggctggaa ggaaatctgc tgatcccggt  1620
gctgagagat gtcctcagct ggcggaccaa tgccacctgg atgctcaaat ctgaaagtaa  1680
agagactggc aacccgctgt cggttatccc gaaatatacc gttaacacga tgcttgactg  1740
gcaggtaaac gacgccctgt ctgcgaatgt gaactggacg ctttatggcc gtcagaagcc  1800
gcgtcagtat gcggagatcc gcaacgaaac cgggacccctt gccaccaccg aggttggcgc  1860
ctattccatc gtgggtattg gtactcagta tcagctaaac cgggatattc gcctgaatgc  1920
cggaataagt aatctatttg ataagcaact gtatcgcgaa aatgccggcg cctcgaccta  1980
caatgagcct ggccgcgcgt attacgccgg cgttaccctc tccttctga              2029
```

<210> SEQ ID NO 16
<211> LENGTH: 675
<212> TYPE: PRT
<213> ORGANISM: Klebsiella pneumoniae
<220> FEATURE:
<221> NAME/KEY: MOD_RES
<222> LOCATION: (98)..(111)
<223> OTHER INFORMATION: Any amino acid

<400> SEQUENCE: 16

```
Ser Ile Ile Thr Ala Glu Asp Ile Ala Lys Gln Pro Pro Val Asn Asp
1               5                   10                  15

Leu Ser Asp Ile Ile Arg Lys Met Pro Gly Val Asn Leu Thr Gly Asn
            20                  25                  30

Ser Ala Ser Gly Ser Arg Gly Asn Asn Arg Gln Ile Asp Ile Arg Gly
        35                  40                  45

Met Gly Pro Glu Asn Thr Leu Ile Leu Ile Asp Gly Val Pro Val Thr
    50                  55                  60

Ser Arg Asn Ala Val Arg Tyr Ser Trp Arg Gly Glu Arg Asp Thr Arg
65                  70                  75                  80

Gly Asp Ser Asn Trp Val Pro Ala Glu Met Val Glu Arg Ile Glu Val
                85                  90                  95

Leu Xaa Xaa Xaa Xaa Xaa Xaa Xaa Xaa Xaa Xaa Xaa Xaa Gly
            100                 105                 110

Val Val Asn Ile Ile Thr Lys Arg Pro Thr Asn Thr Trp His Gly Ser
        115                 120                 125

Leu Ser Phe Phe Thr Asn Gln Pro Glu Asn Asn Lys Glu Gly Thr Thr
    130                 135                 140

Asn Arg Ala Asn Phe Asn Leu Ser Gly Pro Leu Ala Gly Glu Ala Leu
145                 150                 155                 160

Thr Met Arg Leu Tyr Gly Asn Ile Asn Lys Thr Glu Pro Asp Ala Trp
                165                 170                 175

Asp Ile Asn His Ala Gln Asn Gly Ser Tyr Ala Ala Gly Arg Glu Gly
            180                 185                 190
```

```
Val Arg Asn Lys Asp Ile Asn Ala Leu Leu Ser Trp Lys Met Thr Pro
    195                 200                 205

Gln Gln Ile Leu Asp Phe Ser Tyr Ala Tyr Ser Arg Gln Gly Asn Ile
    210                 215                 220

Tyr Ala Gly Asp Thr Gln Tyr Ser Asn Gly Asn Leu Ser Pro Asn Gly
225                 230                 235                 240

Leu Val Asp Ser Leu Tyr Gly His Glu Thr Asn Arg Leu Tyr Arg Gln
            245                 250                 255

Ser Trp Gly Leu Thr Tyr Asn Gly Leu Trp Asp Trp Gly Gln Ser Lys
            260                 265                 270

Ala Gly Val Tyr Tyr Glu Lys Thr Asn Asn Thr Arg Leu Gln Glu Gly
        275                 280                 285

Ser Thr Gly Arg Val Glu Gly Met Ile Asn Ser Glu Asp Tyr Ala Thr
    290                 295                 300

Ser Arg Leu Glu Ser Trp Arg Thr Thr Ser Glu Phe Asn Val Pro Phe
305                 310                 315                 320

Phe Trp Leu Ala Asp Gln Thr Leu Thr Leu Gly Met Glu Trp Asn His
                325                 330                 335

Asp Gln Leu Asp Asp Pro Ala Ser Met Gln Ala Thr Asn Ser Asn Gly
            340                 345                 350

Glu Thr Ile Pro Gly Thr Ser Gly Asp Pro Thr Gln Arg Ser Thr Lys
            355                 360                 365

Asn Ser Ala Thr Leu Thr Gly Ile Tyr Leu Glu Asp Asn Ile Glu Ala
    370                 375                 380

Val Pro Gly Thr Asn Leu Ile Pro Gly Ile Arg Phe Asp Tyr His Asn
385                 390                 395                 400

Gln Phe Gly Ser Asn Trp Ser Pro Ser Leu Asn Leu Ser Gln Glu Leu
                405                 410                 415

Gly Asp Met Phe Thr Leu Lys Ala Gly Ile Ala Arg Val Phe Lys Ala
                420                 425                 430

Pro Asn Leu Tyr Gln Ser Ser Lys Gly Tyr Leu Leu Ser Thr Arg Gly
            435                 440                 445

Asn Gly Cys Pro Asn Thr Ile Ala Glu Gly Ser Cys Tyr Leu Leu Gly
    450                 455                 460

Asn Pro Asp Leu Asp Pro Glu Ile Ser Ile Asn Lys Glu Ile Gly Ile
465                 470                 475                 480

Glu Phe Asn Leu Asn Gly Tyr Ala Ala Gly Val Thr Trp Phe Arg Asn
                485                 490                 495

Asp Tyr Lys Asn Lys Ile Val Ser Gly Thr Glu Val Leu Gly Tyr Thr
            500                 505                 510

Ser Ser Gly Asn Asn Ile Leu Gln Trp Gln Asn Gly Gly Lys Ala Val
            515                 520                 525

Val Glu Gly Leu Glu Gly Asn Leu Leu Ile Pro Val Leu Arg Asp Val
    530                 535                 540

Leu Ser Trp Arg Thr Asn Ala Thr Trp Met Leu Lys Ser Glu Ser Lys
545                 550                 555                 560

Glu Thr Gly Asn Pro Leu Ser Val Ile Pro Lys Tyr Thr Val Asn Thr
                565                 570                 575

Met Leu Asp Trp Gln Val Asn Asp Ala Leu Ser Ala Asn Val Asn Trp
            580                 585                 590

Thr Leu Tyr Gly Arg Gln Lys Pro Arg Gln Tyr Ala Glu Ile Arg Asn
            595                 600                 605
```

| | | | | | | | | | |
|---|---|---|---|---|---|---|---|---|---|
|Glu|Thr|Gly|Thr|Leu|Ala|Thr|Thr|Glu|Val|Gly|Ala|Tyr|Ser|Ile|Val|
| |610| | | |615| | | |620| | | | | | |
|Gly|Ile|Gly|Thr|Gln|Tyr|Gln|Leu|Asn|Arg|Asp|Ile|Arg|Leu|Asn|Ala|
|625| | | | |630| | | | |635| | | | |640|
|Gly|Ile|Ser|Asn|Leu|Phe|Asp|Lys|Gln|Leu|Tyr|Arg|Glu|Asn|Ala|Gly|
| | | | |645| | | | |650| | | | |655| |
|Ala|Ser|Thr|Tyr|Asn|Glu|Pro|Gly|Arg|Ala|Tyr|Tyr|Ala|Gly|Val|Thr|
| | | |660| | | |665| | | | |670| | | |
|Leu|Ser|Phe| | | | | | | | | | | | | |
| | |675| | | | | | | | | | | | | |

<210> SEQ ID NO 17
<211> LENGTH: 2185
<212> TYPE: DNA
<213> ORGANISM: Klebsiella pneumoniae

<400> SEQUENCE: 17

```
atgaaaaagc gcctctgggt gctccaccct ctgctgctgg ccagcacgct gcctgcgctg      60
gcggctcagt ctgatgaaga cagcatcatc gttagcgcaa accgcaccca tcgcaccgtg     120
gccgaaatgg cccaaaccac ctgggtcatt gagggccagg agattgagca gcaggtccag     180
ggcgggaaag agttcaaaga cgtgctggcg cagctgatcc ccggcatcga cgtcagcagc     240
caggggcgga ccaactatgg gatgaacatg cgcgggcgcg cgatcgtcgt gctgattgac     300
ggcgtccggc tcaactcctc acgcaccgac agccgccagc tcgacgccat cgatccattc     360
aacatcgaac atatcgaagt gatctccgga gcgacctcgc tgtacggcgg gggcagtacc     420
ggcgggctta tcaacatcgt taccaaaaag gggcagcagg atcgtcaggt cgatcttgag     480
gtgggcagca agagcggttt tgcgaacagc aacgatcatg atgagcgcgt cgcggcggcc     540
gtcagcggcg aacagacca cgcatccggc cgcttgtcgg tagcctatca gcgtttcggc     600
ggctggtacg acggcaatac cgatgcgctg atcctcgata taccaaac ggggctccag     660
cattctgacc gcctcgacgt gatggggacg gggacgattg agatcgataa taaccgccag     720
ctgcagttgg tcacccagta ttataaaagc cagggcgatg atgactacgg tctgtggctc     780
gggaagaaca tgtccgcggt caccagcggc ggcaaagcgt ataccaccga cgggctcaat     840
tccgaccgta tccccggcac cgaacgccat ctgatcagcc tccagtactc tgatgccgac     900
tttttcggcc agaatctggt gagccaggtg tactatcgcg atgagtccct caccttctat     960
ccgttcccga cgctcacgaa aggtcaggtc agtagcttct cctcgtcgca gcaggatacc    1020
gatcagtatg gggccaagct gaccctcaac agccaaccgc tggcggggtg ggatctcacc    1080
tggggtctcg acgccgatca tgagaccttt aatgccaacc aaatgttctt cgatctgcca    1140
caatcgatgg cctccggcgg gttgcacaac gaatcgatct acacaaccgg ccgctacccg    1200
ggatacagta tttccaatgt cgcgccattc ctgcagtcca gctacgatct gaacgatatc    1260
tttaccgtca gcggcgggt acgctaccag tggaccgaaa accgggtcga cgactttgtc    1320
ggctacgccc agcagcagga tatcgccaac ggcaaagcgc gctccgccga cgccatcaaa    1380
ggcggcaaaa ccgattacga taacttcctg tttaacgccg ggatcgtggc ccacctgacc    1440
gagcgtcaac aaacctggtt taacttctcg cagggcgtcg agctaccgga ccctggtaaa    1500
tactatggca tcggtaaata tggcgctgcg gtgaatggtc atctgccgct gatctccagc    1560
gtcaacgtcg atgactcgcc gctgcagggg atcaaagtta actcgtacga gctgggctgg    1620
cgctacaccg gcgataacct gcgcacccag ctggcggcgt actactcgac ctcagataag    1680
```

-continued

```
accattgtcg tcaaccgcac cgacatgacc atcgacgttc agtccgacaa acggcgtatt   1740
tacggcgttg agggggcggt cgactacttt attccggata gcgactggag cgtcggcggt   1800
aacttcaacg tgctgaaatc ccaggtgcag accgacggcc gctggcaaaa atgggacgtc   1860
accctcgcct cgccgtctaa agccaccgcc tgggtgggct gggcgccgga tccgtggagc   1920
ctgcgcgtgc agagtcagca ggtatttgac ctcagcgatg ccgccggcaa caagctggaa   1980
ggctataaca ccgtcgattt tatcggtagt tacgcgctgc cggtggggaa actgaccttc   2040
agtatcgaaa acctgcttaa cgaagactat gtgactatat ggggccagcg cgcgccgctg   2100
ctctacagcc caacctacgg cagttcatcg ctgtatgagt acaaaggtcg tggccgcacc   2160
tttggtctga actacgcctt aacct                                         2185
```

<210> SEQ ID NO 18
<211> LENGTH: 728
<212> TYPE: PRT
<213> ORGANISM: Klebsiella pneumoniae

<400> SEQUENCE: 18

```
Met Lys Lys Arg Leu Trp Val Leu His Pro Leu Leu Ala Ser Thr
1               5                   10                  15

Leu Pro Ala Leu Ala Ala Gln Ser Asp Glu Asp Ser Ile Ile Val Ser
            20                  25                  30

Ala Asn Arg Thr His Arg Thr Val Ala Glu Met Ala Gln Thr Thr Trp
        35                  40                  45

Val Ile Glu Gly Gln Glu Ile Glu Gln Val Gln Gly Gly Lys Glu
    50                  55                  60

Phe Lys Asp Val Leu Ala Gln Leu Ile Pro Gly Ile Asp Val Ser Ser
65                  70                  75                  80

Gln Gly Arg Thr Asn Tyr Gly Met Asn Met Arg Gly Arg Ala Ile Val
                85                  90                  95

Val Leu Ile Asp Gly Val Arg Leu Asn Ser Ser Arg Thr Asp Ser Arg
            100                 105                 110

Gln Leu Asp Ala Ile Asp Pro Phe Asn Ile Glu His Ile Glu Val Ile
        115                 120                 125

Ser Gly Ala Thr Ser Leu Tyr Gly Gly Ser Thr Gly Gly Leu Ile
    130                 135                 140

Asn Ile Val Thr Lys Lys Gly Gln Gln Asp Arg Gln Val Asp Leu Glu
145                 150                 155                 160

Val Gly Ser Lys Ser Gly Phe Ala Asn Ser Asn Asp His Asp Glu Arg
                165                 170                 175

Val Ala Ala Val Ser Gly Gly Thr Asp His Ala Ser Gly Arg Leu
            180                 185                 190

Ser Val Ala Tyr Gln Arg Phe Gly Gly Trp Tyr Asp Gly Asn Thr Asp
        195                 200                 205

Ala Leu Ile Leu Asp Asn Thr Gln Thr Gly Leu Gln His Ser Asp Arg
    210                 215                 220

Leu Asp Val Met Gly Thr Gly Thr Ile Glu Ile Asp Asn Asn Arg Gln
225                 230                 235                 240

Leu Gln Leu Val Thr Gln Tyr Tyr Lys Ser Gln Gly Asp Asp Tyr
                245                 250                 255

Gly Leu Trp Leu Gly Lys Asn Met Ser Ala Val Thr Ser Gly Gly Lys
            260                 265                 270

Ala Tyr Thr Thr Asp Gly Leu Asn Ser Asp Arg Ile Pro Gly Thr Glu
        275                 280                 285
```

```
Arg His Leu Ile Ser Leu Gln Tyr Ser Asp Ala Asp Phe Phe Gly Gln
    290                 295                 300

Asn Leu Val Ser Gln Val Tyr Tyr Arg Asp Glu Ser Leu Thr Phe Tyr
305                 310                 315                 320

Pro Phe Pro Thr Leu Thr Lys Gly Gln Val Ser Ser Phe Ser Ser Ser
                325                 330                 335

Gln Gln Asp Thr Asp Gln Tyr Gly Ala Lys Leu Thr Leu Asn Ser Gln
                340                 345                 350

Pro Leu Ala Gly Trp Asp Leu Thr Trp Gly Leu Asp Ala Asp His Glu
            355                 360                 365

Thr Phe Asn Ala Asn Gln Met Phe Phe Asp Leu Pro Gln Ser Met Ala
    370                 375                 380

Ser Gly Gly Leu His Asn Glu Ser Ile Tyr Thr Thr Gly Arg Tyr Pro
385                 390                 395                 400

Gly Tyr Ser Ile Ser Asn Val Ala Pro Phe Leu Gln Ser Ser Tyr Asp
                405                 410                 415

Leu Asn Asp Ile Phe Thr Val Ser Gly Gly Val Arg Tyr Gln Trp Thr
                420                 425                 430

Glu Asn Arg Val Asp Asp Phe Val Gly Tyr Ala Gln Gln Gln Asp Ile
            435                 440                 445

Ala Asn Gly Lys Ala Arg Ser Ala Asp Ala Ile Lys Gly Gly Lys Thr
    450                 455                 460

Asp Tyr Asp Asn Phe Leu Phe Asn Ala Gly Ile Val Ala His Leu Thr
465                 470                 475                 480

Glu Arg Gln Gln Thr Trp Phe Asn Phe Ser Gln Gly Val Glu Leu Pro
                485                 490                 495

Asp Pro Gly Lys Tyr Tyr Gly Ile Gly Lys Tyr Gly Ala Ala Val Asn
                500                 505                 510

Gly His Leu Pro Leu Ile Ser Ser Val Asn Val Asp Asp Ser Pro Leu
            515                 520                 525

Gln Gly Ile Lys Val Asn Ser Tyr Glu Leu Gly Trp Arg Tyr Thr Gly
    530                 535                 540

Asp Asn Leu Arg Thr Gln Leu Ala Ala Tyr Tyr Ser Thr Ser Asp Lys
545                 550                 555                 560

Thr Ile Val Val Asn Arg Thr Asp Met Thr Ile Asp Val Gln Ser Asp
                565                 570                 575

Lys Arg Arg Ile Tyr Gly Val Glu Gly Ala Val Asp Tyr Phe Ile Pro
                580                 585                 590

Asp Ser Asp Trp Ser Val Gly Gly Asn Phe Asn Val Leu Lys Ser Gln
            595                 600                 605

Val Gln Thr Asp Gly Arg Trp Gln Lys Trp Asp Val Thr Leu Ala Ser
    610                 615                 620

Pro Ser Lys Ala Thr Ala Trp Val Gly Trp Ala Pro Asp Pro Trp Ser
625                 630                 635                 640

Leu Arg Val Gln Ser Gln Gln Val Phe Asp Leu Ser Asp Ala Ala Gly
                645                 650                 655

Asn Lys Leu Glu Gly Tyr Asn Thr Val Asp Phe Ile Gly Ser Tyr Ala
                660                 665                 670

Leu Pro Val Gly Lys Leu Thr Phe Ser Ile Glu Asn Leu Leu Asn Glu
            675                 680                 685

Asp Tyr Val Thr Ile Trp Gly Gln Arg Ala Pro Leu Leu Tyr Ser Pro
    690                 695                 700
```

Thr Tyr Gly Ser Ser Ser Leu Tyr Glu Tyr Lys Gly Arg Gly Arg Thr
705                 710                 715                 720

Phe Gly Leu Asn Tyr Ala Leu Thr
                725

<210> SEQ ID NO 19
<211> LENGTH: 1790
<212> TYPE: DNA
<213> ORGANISM: Klebsiella pneumoniae

<400> SEQUENCE: 19

| | | | | | |
|---|---|---|---|---|---|
| cccgccgcgg | cttcggcgcc | aaccgcgacg | gctcgatcat | gaccaacggc | ctgcgcaccg | 60 |
| tgctgccgcg | cagctttaac | gccgccaccg | aacgggtgga | agtcctgaag | gggcccgcct | 120 |
| cgacgctgta | cggtatcctc | gaccccggcg | ggctgatcaa | cgtcatcact | aaacggccgg | 180 |
| agcggcagtt | ctccggttcg | gtttccggga | cctccaccag | ctttggcggc | ggcaccggca | 240 |
| gcgtcgacat | caccgccccc | atcgaaggca | caaatctggc | gtaccgactg | atcggcgaat | 300 |
| atcagaatga | ggattactgg | cgcaatttcg | gtaaaaacaa | aagcagcttt | atcgcccctt | 360 |
| ccctgacctg | gtttggcgag | cgggcaacgg | tgaccgcgtc | ctattcgcac | gcgactaca | 420 |
| gcgccccctt | tgatcgcgga | actatcttcg | atctgaatac | cggccatgcg | gttaacgtcg | 480 |
| atcgcaaaac | ccgcttcgat | gaagcgttta | atattaccga | tggctattcc | gatctcgctc | 540 |
| agctcaacgc | cgagtatcgc | cttaacgacg | cctggaccgc | gcgcttcgac | tacagctaca | 600 |
| gccaggatca | ttacaacgat | aaccaggcgc | gggtaatggc | ctatgattcg | gcgaccggca | 660 |
| acctcccccg | ccgggtcgat | ggtacccacg | gttcaacgca | gaagatgcac | tccacccgcg | 720 |
| ccgacctgca | gggcaacgtg | gtagtgggcg | gcttttataa | cgagctgctg | accggcgtcg | 780 |
| cctatgagaa | ttacgatctg | ctgcgcaccg | atatgctgcg | ctgtaagaac | gttaaaggct | 840 |
| ttaacatcta | tcatccggtc | tacggcactc | tcgacacctg | taataccgtc | tccgcctccg | 900 |
| acagcgacca | gcgcattcag | caggagagct | atgccgcata | cgtgcaggac | gcgctgtacc | 960 |
| tgaccgacaa | ctggatcgcc | gtcgccggcg | tgcgctacca | gtactacacc | cagtacgccg | 1020 |
| gtaaaggccg | accgtttaac | gtcaataccg | acagccgcga | tgagaaatgg | acgccgaaag | 1080 |
| ccggcctggt | ctacaaggtc | acgccgaacg | tctccctgtt | cgccaacgtc | gcccagtcgt | 1140 |
| ttatgccgca | gtcgtcgatc | gccagctata | tcggcgagct | gccgccggaa | gagtccacct | 1200 |
| cttacgaagt | gggcgccaaa | ttcgacctgt | taaacggcat | taccgccaat | atcgcgttgt | 1260 |
| ttgatattca | taagcgtaac | gtgctgtaca | ccgagagcat | tggcgatgag | acggtggcca | 1320 |
| aaacggcggg | caaagtgcgt | tcccagggcg | tggaagtgga | tctggcgggg | tccatcaccg | 1380 |
| ataacctcag | cgtgatcgcc | agctacggct | acaccgacgc | caaagtgctg | aagatccgg | 1440 |
| attacgccgg | gaaaccgctg | ccaaacgtac | cgaaacatac | cggttcgctg | ttcctgacct | 1500 |
| atgacattca | taacgtctat | aacagcaaca | ccctgaccgt | cggcggcggc | ggccacgcgg | 1560 |
| tcagcaagcg | ttccggcacc | aacggcgcgg | attattattt | gcaggggtat | gcggtggcgg | 1620 |
| atgtgtttgc | tgcctataag | atgaagctgc | agtatccggt | gacgctgcag | gtgaatgtga | 1680 |
| agaacctgtt | tgataagacc | tattacactt | cctcgatcgg | caccaataat | ctcggcaacc | 1740 |
| agattggcga | cccgcgcgaa | gtgcagttca | cggtgaagat | ggattttaa | | 1790 |

<210> SEQ ID NO 20
<211> LENGTH: 595
<212> TYPE: PRT
<213> ORGANISM: Klebsiella pneumoniae

<400> SEQUENCE: 20

```
Arg Arg Gly Phe Gly Ala Asn Arg Asp Gly Ser Ile Met Thr Asn Gly
1               5                   10                  15

Leu Arg Thr Val Leu Pro Arg Ser Phe Asn Ala Ala Thr Glu Arg Val
            20                  25                  30

Glu Val Leu Lys Gly Pro Ala Ser Thr Leu Tyr Gly Ile Leu Asp Pro
        35                  40                  45

Gly Gly Leu Ile Asn Val Ile Thr Lys Arg Pro Glu Arg Gln Phe Ser
50                  55                  60

Gly Ser Val Ser Gly Thr Ser Thr Ser Phe Gly Gly Thr Gly Ser
65                  70                  75                  80

Val Asp Ile Thr Gly Pro Ile Glu Gly Thr Asn Leu Ala Tyr Arg Leu
                85                  90                  95

Ile Gly Glu Tyr Gln Asn Glu Asp Tyr Trp Arg Asn Phe Gly Lys Asn
                100                 105                 110

Lys Ser Ser Phe Ile Ala Leu Ser Leu Thr Trp Phe Gly Glu Arg Ala
            115                 120                 125

Thr Val Thr Ala Ser Tyr Ser His Arg Asp Tyr Ser Ala Pro Phe Asp
130                 135                 140

Arg Gly Thr Ile Phe Asp Leu Asn Thr Gly His Ala Val Asn Val Asp
145                 150                 155                 160

Arg Lys Thr Arg Phe Asp Glu Ala Phe Asn Ile Thr Asp Gly Tyr Ser
                165                 170                 175

Asp Leu Ala Gln Leu Asn Ala Glu Tyr Arg Leu Asn Asp Ala Trp Thr
            180                 185                 190

Ala Arg Phe Asp Tyr Ser Tyr Ser Gln Asp His Tyr Asn Asp Asn Gln
        195                 200                 205

Ala Arg Val Met Ala Tyr Asp Ser Ala Thr Gly Asn Leu Pro Arg Arg
210                 215                 220

Val Asp Gly Thr His Gly Ser Thr Gln Lys Met His Ser Thr Arg Ala
225                 230                 235                 240

Asp Leu Gln Gly Asn Val Val Gly Gly Phe Tyr Asn Glu Leu Leu
                245                 250                 255

Thr Gly Val Ala Tyr Glu Asn Tyr Asp Leu Leu Arg Thr Asp Met Leu
            260                 265                 270

Arg Cys Lys Asn Val Lys Gly Phe Asn Ile Tyr His Pro Val Tyr Gly
        275                 280                 285

Thr Leu Asp Thr Cys Asn Thr Val Ser Ala Ser Asp Ser Asp Gln Arg
        290                 295                 300

Ile Gln Gln Glu Ser Tyr Ala Ala Tyr Val Gln Asp Ala Leu Tyr Leu
305                 310                 315                 320

Thr Asp Asn Trp Ile Ala Val Ala Gly Val Arg Tyr Gln Tyr Tyr Thr
                325                 330                 335

Gln Tyr Ala Gly Lys Gly Arg Pro Phe Asn Val Asn Thr Asp Ser Arg
            340                 345                 350

Asp Glu Lys Trp Thr Pro Lys Ala Gly Leu Val Tyr Lys Val Thr Pro
        355                 360                 365

Asn Val Ser Leu Phe Ala Asn Val Ala Gln Ser Phe Met Pro Gln Ser
        370                 375                 380

Ser Ile Ala Ser Tyr Ile Gly Glu Leu Pro Pro Glu Ser Thr Ser
385                 390                 395                 400

Tyr Glu Val Gly Ala Lys Phe Asp Leu Leu Asn Gly Ile Thr Ala Asn
```

```
                    405                 410                 415
Ile Ala Leu Phe Asp Ile His Lys Arg Asn Val Leu Tyr Thr Glu Ser
            420                 425                 430

Ile Gly Asp Glu Thr Val Ala Lys Thr Ala Gly Lys Val Arg Ser Gln
            435                 440                 445

Gly Val Glu Val Asp Leu Ala Gly Ser Ile Thr Asp Asn Leu Ser Val
        450                 455                 460

Ile Ala Ser Tyr Gly Tyr Thr Asp Ala Lys Val Leu Glu Asp Pro Asp
465                 470                 475                 480

Tyr Ala Gly Lys Pro Leu Pro Asn Val Pro Lys His Thr Gly Ser Leu
                485                 490                 495

Phe Leu Thr Tyr Asp Ile His Asn Val Tyr Asn Ser Asn Thr Leu Thr
            500                 505                 510

Val Gly Gly Gly Gly His Ala Val Ser Lys Arg Ser Gly Thr Asn Gly
            515                 520                 525

Ala Asp Tyr Tyr Leu Gln Gly Tyr Ala Val Ala Asp Val Phe Ala Ala
        530                 535                 540

Tyr Lys Met Lys Leu Gln Tyr Pro Val Thr Leu Gln Val Asn Val Lys
545                 550                 555                 560

Asn Leu Phe Asp Lys Thr Tyr Tyr Thr Ser Ser Ile Gly Thr Asn Asn
                565                 570                 575

Leu Gly Asn Gln Ile Gly Asp Pro Arg Glu Val Gln Phe Thr Val Lys
            580                 585                 590

Met Asp Phe
        595

<210> SEQ ID NO 21
<211> LENGTH: 2211
<212> TYPE: DNA
<213> ORGANISM: Klebsiella pneumoniae

<400> SEQUENCE: 21
atggggcaaa ttatgcacac cacgcactat tcatccttcc cgctgcgtaa aacgctgctg      60
gccttagcca tcggcgccgc cagtcaaacg gcgatggccg cggacgctgc cgccgcgaag     120
cagcctggcg aagagaccct catcgtcgag gctaacgaaa ccagcgattt taaatccggc     180
ggtgacctgg tggttccggc attcctcgat ggccagatcg cccacggcgg ccgtctgggg     240
atgcttggcg aacaaaaagc gatggacgtc ccgtttaacg tcatcggcta ccctcgaag      300 ctgattcagg atcagcaggc gaaaactatc gccgatgtcg tcagtaacga cgctggcgtg     360
caggccgtac agggctacgg caacttcgcc gagacctatc gaatccgcgg gtttaagctc     420
gatggcgatg acatgacgat gggcggcctg cgggcgtgg tgccgcgtca ggtgatggac      480
acccagatgc tggagcgcgt tgaaattttc aaagggcta acagcctgct taacggcgcg      540
gccagcagcg gtgtcggcgg ggtgatttac ctcgagccga agcgggcgga agatctgccg     600
accgcacgcg ttggcgtcga ctataccct gattctcagg tgggcggcac cctcgacctg      660
gggcgccgtt cggcgacaa caaccagttc ggcgcccggg tcaacctggt gcaccgcgag     720
ggtgaaggcg ctatcgataa tgataaacgc cgtaccacgc tggcttcgct ggggcttgat     780
taccgcggcg accgtttccg ctcctcgctc gatttcggct atcagaagaa aacgttccac     840
ggcggtacga tgggcgtcaa tatcagcggc gtgatttcg ttccggcgct gccggacaac      900
agcaaaaact acagccagaa gtggggctat agcgatattg aaagcgagtt tggcatggcg     960
aaggcagaat atgacctgac cgatagctgg acggtataca gcgccctcgg cggccagcat    1020
```

-continued

```
tcgcatgaaa ttggtaccta cagcgcgccg aagcttctga ataaaaacgg cgatgcgacg      1080
gtgggccgcc tggatactaa ccgcattatc gacgcgatca gcggcatggg cggggtacgc      1140
ggcgatttca ataccggcgc gatttcgcat acggtgaacc tcggctatgc ggcgcaggtg      1200
cataccgatg cgaccgcctg gcggatgtcg gccaggaacc cgaccactaa tatctatgac      1260
aaccatgatg tggcgatgcc ggataacgcc tattttggcg gcaactacca cgatccgctg      1320
gtcacctcgc gcagccgtac gcagggctgg ctgttgagtg atacccctcgg cttctttaac      1380 gataaagtgc tgtttaccgc cgctgctcgt catcagaaag tggttgtgcg caactacagc      1440
aacgccaccg ggctggaaga tacctcttcg cgttataccc aaagccgctg gatgccgacg      1500
tttggcctgg tgtacaagcc gtgggagcag ctgtcgctgt atgctaacca taccgaagcg      1560
ctgcagccgg gctctgtggc gccgacgacg gcggccaatg ccgggcagag taccgggatc      1620
gcgcactcga agcaggacga agtgggcgtc aagatcgact acggtacgat cggaggatcg      1680
ctggcgctgt ttgaaatcaa aaaccgaac gccatttccg ataccgctgg caattacggc      1740
ctcgacggcg agcagcgtaa ccgcggcgta gagatgaacg tctttggcga gccgatgctg      1800
ggactgcgtc ttaacgccag taccgtctgg ctggatgcca aacagactaa aaccgctgaa      1860
ggcgcaaccg acggtaaaga tgccatcggg gtggctaact tctacgcggt actcggcgcc      1920
gaatatgaca tcaagccggt ggaaggcctg accgccaccg cgcgcgtcaa tcatagcggc      1980
tcgcagtatg ccgatgcggc caataccaag aagctggata gctacaccac cctggattta      2040
ggcctgcgct atcgtatgcg tctgaacgcc gaccagaacg aaatgatctg gcgcgtcggg      2100
gtgaccaacg tgaccaacga gaagtactgg tctggcattg acgataccgg tacttacctg      2160
ttcgaaggcg atccgcgtac cgtccgcgtc tcaatgagct acgacttctg a              2211
```

<210> SEQ ID NO 22
<211> LENGTH: 736
<212> TYPE: PRT
<213> ORGANISM: Klebsiella pneumoniae

<400> SEQUENCE: 22

```
Met Gly Gln Ile Met His Thr Thr His Tyr Ser Ser Phe Pro Leu Arg
1               5                   10                  15

Lys Thr Leu Leu Ala Leu Ala Ile Gly Ala Ala Ser Gln Thr Ala Met
            20                  25                  30

Ala Ala Asp Ala Ala Ala Lys Gln Pro Gly Glu Glu Thr Leu Ile
        35                  40                  45

Val Glu Ala Asn Glu Thr Ser Asp Phe Lys Ser Gly Gly Asp Leu Val
    50                  55                  60

Val Pro Ala Phe Leu Asp Gly Gln Ile Ala His Gly Gly Arg Leu Gly
65                  70                  75                  80

Met Leu Gly Glu Gln Lys Ala Met Asp Val Pro Phe Asn Val Ile Gly
                85                  90                  95

Tyr Thr Ser Lys Leu Ile Gln Asp Gln Ala Lys Thr Ile Ala Asp
            100                 105                 110

Val Val Ser Asn Asp Ala Gly Val Gln Ala Val Gln Gly Tyr Gly Asn
        115                 120                 125

Phe Ala Glu Thr Tyr Arg Ile Arg Gly Phe Lys Leu Asp Gly Asp Asp
    130                 135                 140

Met Thr Met Gly Gly Leu Ala Gly Val Val Pro Arg Gln Val Met Asp
145                 150                 155                 160
```

```
Thr Gln Met Leu Glu Arg Val Glu Ile Phe Lys Gly Ala Asn Ser Leu
                165                 170                 175
Leu Asn Gly Ala Ala Ser Ser Gly Val Gly Gly Val Ile Tyr Leu Glu
            180                 185                 190
Pro Lys Arg Ala Glu Asp Leu Pro Thr Ala Arg Val Gly Val Asp Tyr
        195                 200                 205
Thr Ser Asp Ser Gln Val Gly Gly Thr Leu Asp Leu Gly Arg Arg Phe
210                 215                 220
Gly Asp Asn Asn Gln Phe Gly Ala Arg Val Asn Leu Val His Arg Glu
225                 230                 235                 240
Gly Glu Gly Ala Ile Asp Asn Asp Lys Arg Arg Thr Thr Leu Ala Ser
                245                 250                 255
Leu Gly Leu Asp Tyr Arg Gly Asp Arg Phe Arg Ser Ser Leu Asp Phe
            260                 265                 270
Gly Tyr Gln Lys Lys Thr Phe His Gly Gly Thr Met Gly Val Asn Ile
        275                 280                 285
Ser Gly Val Asp Phe Val Pro Ala Leu Pro Asp Asn Ser Lys Asn Tyr
290                 295                 300
Ser Gln Lys Trp Gly Tyr Ser Asp Ile Glu Ser Glu Phe Gly Met Ala
305                 310                 315                 320
Lys Ala Glu Tyr Asp Leu Thr Asp Ser Trp Thr Val Tyr Ser Ala Leu
                325                 330                 335
Gly Gly Gln His Ser His Glu Ile Gly Thr Tyr Ser Ala Pro Lys Leu
            340                 345                 350
Leu Asn Lys Asn Gly Asp Ala Thr Val Gly Arg Leu Asp Thr Asn Arg
        355                 360                 365
Ile Ile Asp Ala Ile Ser Gly Met Gly Gly Val Arg Gly Asp Phe Asn
370                 375                 380
Thr Gly Ala Ile Ser His Thr Val Asn Leu Gly Tyr Ala Ala Gln Val
385                 390                 395                 400
His Thr Asp Ala Thr Ala Trp Arg Met Ser Ala Arg Asn Pro Thr Thr
                405                 410                 415
Asn Ile Tyr Asp Asn His Asp Val Ala Met Pro Asp Asn Ala Tyr Phe
            420                 425                 430
Gly Gly Asn Tyr His Asp Pro Leu Val Thr Ser Arg Ser Arg Thr Gln
        435                 440                 445
Gly Trp Leu Leu Ser Asp Thr Leu Gly Phe Phe Asn Asp Lys Val Leu
450                 455                 460
Phe Thr Ala Ala Ala Arg His Gln Lys Val Val Arg Asn Tyr Ser
465                 470                 475                 480
Asn Ala Thr Gly Leu Glu Asp Thr Ser Ser Arg Tyr Thr Gln Ser Arg
                485                 490                 495
Trp Met Pro Thr Phe Gly Leu Val Tyr Lys Pro Trp Glu Gln Leu Ser
            500                 505                 510
Leu Tyr Ala Asn His Thr Glu Ala Leu Gln Pro Gly Ser Val Ala Pro
        515                 520                 525
Thr Thr Ala Ala Asn Ala Gly Gln Ser Thr Gly Ile Ala His Ser Lys
530                 535                 540
Gln Asp Glu Val Gly Val Lys Ile Asp Tyr Gly Thr Ile Gly Gly Ser
545                 550                 555                 560
Leu Ala Leu Phe Glu Ile Lys Lys Pro Asn Ala Ile Ser Asp Thr Ala
                565                 570                 575
Gly Asn Tyr Gly Leu Asp Gly Glu Gln Arg Asn Arg Gly Val Glu Met
```

|  |  |  |  |  |  |  |  |  |  |  |
|---|---|---|---|---|---|---|---|---|---|---|
|  |  |  | 580 |  |  | 585 |  |  | 590 |  |
| Asn | Val | Phe | Gly | Glu | Pro | Met | Leu | Gly | Leu | Arg | Leu | Asn | Ala | Ser | Thr |
|  |  |  | 595 |  |  | 600 |  |  | 605 |  |

Asn Val Phe Gly Glu Pro Met Leu Gly Leu Arg Leu Asn Ala Ser Thr
                595                     600                 605

Val Trp Leu Asp Ala Lys Gln Thr Lys Thr Ala Glu Gly Ala Thr Asp
            610                 615                 620

Gly Lys Asp Ala Ile Gly Val Ala Asn Phe Tyr Ala Val Leu Gly Ala
625                 630                 635                 640

Glu Tyr Asp Ile Lys Pro Val Glu Gly Leu Thr Ala Thr Ala Arg Val
                645                 650                 655

Asn His Ser Gly Ser Gln Tyr Ala Asp Ala Ala Asn Thr Lys Lys Leu
            660                 665                 670

Asp Ser Tyr Thr Thr Leu Asp Leu Gly Leu Arg Tyr Arg Met Arg Leu
        675                 680                 685

Asn Ala Asp Gln Asn Glu Met Ile Trp Arg Val Gly Val Thr Asn Val
            690                 695                 700

Thr Asn Glu Lys Tyr Trp Ser Gly Ile Asp Asp Thr Gly Thr Tyr Leu
705                 710                 715                 720

Phe Glu Gly Asp Pro Arg Thr Val Arg Val Ser Met Ser Tyr Asp Phe
                725                 730                 735

<210> SEQ ID NO 23
<211> LENGTH: 2364
<212> TYPE: DNA
<213> ORGANISM: Klebsiella pneumoniae

<400> SEQUENCE: 23

```
atgtacaaat cgactccgtc agcagcatgg tgtaaaaaac gcctgctggt gacctctttg      60
tttgcagcaa tttatcagac ttctgccatc gcagcagata cttccgccgt tagcggcgag     120
gcggtggatg acacctcgga acaaatgacc gtcaccgccc ccgcgccggt gcagaaagcc     180
ggtagcgaac atagcatcag cgcccgggag ctggagaata aggcgctaa cgatttcggc      240
tcaatcatgc gctatgagcc gctcatcagc gccaccgggg ccagcggcgg ctccggcaac     300
ggcaaaagcg gcttcgaccg cggaggttac accggctaca acattcgcgg tatggagagc     360
aaccgcgtcg gcatcgacgt ggacggtatc gcgcaaccca cgccaccgg ccgcggctac      420
gtcggccgcg ccgggctcaa caccttcggc atcggccgcg attatatcga cccgtatatg     480
tacggcagcg tggatatcca gtccggcgcc acctcgacgg aaacgccaa cagcgctatc      540
gggggaatg tctccttccg cccgaaatca gcggatgatt acctgcgccc gggcaagacc      600
agcgccttcg gctaccgcag cggttacgac tctgcggatc gcagctggca acggggtg       660
accgtcgccg gcggcgatga gttcctgcgc gggattttgg tctatagccg ccgtgacggc     720
caggaaaccg aaaacaacag cggcaccgtc gacgcctacc ggcgaactg gcactccgat      780
gcttttctgg cctccgggat ctggcagcct aacgatgagc acaagctgac cagcaccttc     840
gactattacc ataaaaccaa ccacacccac tacgataccc tggactccag cggcaacagc     900
accatcggca ccgccaacca gaccagccag acccggcgct ggggcctgag cctgaaggat     960
gactggacgc cgatgaacga ctacctcgac agcgtctcca caaaaatcta ctaccagcat    1020
accgaagccc atgactggac ttatatgccg gacagcgtca cccgcagaat gcagacggtg    1080
aactctaact acgataccga cacctggggc ctgcagaccg cgctggcgaa accctgggc     1140
cgccacgatc tgagcgccgg tttcaacgcc agcaccagca aaaccagcg gccgttcagc    1200
cagtcgccga tccccagcgt ttacagcgag atcatgcagc cggaggcaga cagccgcagc    1260
```

-continued

```
tacaccctcg gcggctttgt ccaggataag atcaacttcg accttgatag ccacaacttc    1320
gccgttattc ccggcgtgcg cgtggtgcat caatcgacta agccggaaaa tctgtccgat    1380
ctcgccgcca acagcagcgt gctgagcgaa tcgtcggtgg cgaatctgta cggcaaaaac    1440
agcgataccc aggttctgcc gtcgttgacc ttccagtacg acctcacccc gcgcctgatg    1500
acctacctgc agtaccagcg cggggcgcag ttccccaacg ccagccagct gtatggctcc    1560
tggaacctcg gctccagcta cgccggcagc cagcagtatg ccctgatcgg caataccgat    1620
ctgaagacgg aaaccagcga taatctcgag tgggggctga aggggaagt taccgaaggc    1680 atcaccctgc gcacggcgct gttctacaac agctataaga actttatcgc ctataccgc    1740 tatacccgcg ccaacaatcc gggccagttc acgaatgtgc cgtcgaacat ctacaccatt    1800
tatcaggcgg aaaaccgcga taagcctat atctacggcg gtgagattag caccaaattt    1860
aactttggca cctggtttga gcaggtggac ggcctgagcg ccaccctcgc cctcggctat    1920
agcgaaggga aatcgaaatc cagctacagc ggcgataaat acgtcgacct cgacagcgtg    1980
gcgccaatga aagccatcgt cggcgtggcg tgggacgatc cggcgaaacg ctacggcacc    2040
gccctgacgg cgacctttgt caagggaaa caggcgaccg ccaccaaccg cgaaagctac    2100
agcaacagcg gatccgccat caccgatgcc agtagcgact atatgcgcgt gccgggctac    2160
ggcatgctgg actggaccgc gtactggcag gtggcgaaaa acgtgcgcct caatggcggg    2220
gtctacaacc tcaccgatcg taaatactgg gattacctga gcagccgcaa tatcgagacc    2280
ggcaccaacc aggacgccaa cgataaagcg ctggcggtga tgccgggccg cacctggcag    2340
ctgggcgtca acgtcgactt ctga                                           2364
```

<210> SEQ ID NO 24
<211> LENGTH: 787
<212> TYPE: PRT
<213> ORGANISM: Klebsiella pneumoniae

<400> SEQUENCE: 24

```
Met Tyr Lys Ser Thr Pro Ser Ala Ala Trp Cys Lys Lys Arg Leu Leu
1               5                   10                  15

Val Thr Ser Leu Phe Ala Ala Ile Tyr Gln Thr Ser Ala Ile Ala Ala
            20                  25                  30

Asp Thr Ser Ala Val Ser Gly Glu Ala Val Asp Thr Ser Glu Gln
        35                  40                  45

Met Thr Val Thr Ala Pro Ala Pro Val Gln Lys Ala Gly Ser Glu His
    50                  55                  60

Ser Ile Ser Ala Arg Glu Leu Glu Asn Lys Gly Ala Asn Asp Phe Gly
65                  70                  75                  80

Ser Ile Met Arg Tyr Glu Pro Leu Ile Ser Ala Thr Gly Ala Ser Gly
                85                  90                  95

Gly Ser Gly Asn Gly Lys Ser Gly Phe Asp Arg Gly Gly Tyr Thr Gly
            100                 105                 110

Tyr Asn Ile Arg Gly Met Glu Ser Asn Arg Val Gly Ile Asp Val Asp
        115                 120                 125

Gly Ile Ala Gln Pro Asn Ala Thr Gly Arg Gly Tyr Val Gly Arg Ala
    130                 135                 140

Gly Leu Asn Thr Phe Gly Ile Gly Arg Asp Tyr Ile Asp Pro Tyr Met
145                 150                 155                 160

Tyr Gly Ser Val Asp Ile Gln Ser Gly Ala Thr Ser Thr Glu Thr Ala
                165                 170                 175
```

Asn Ser Ala Ile Gly Gly Asn Val Ser Phe Arg Pro Lys Ser Ala Asp
            180                 185                 190

Asp Tyr Leu Arg Pro Gly Lys Thr Ser Ala Phe Gly Tyr Arg Ser Gly
        195                 200                 205

Tyr Asp Ser Ala Asp Arg Ser Trp His Asn Gly Val Thr Val Ala Gly
    210                 215                 220

Gly Asp Glu Phe Leu Arg Gly Ile Leu Val Tyr Ser Arg Arg Asp Gly
225                 230                 235                 240

Gln Glu Thr Glu Asn Asn Ser Gly Thr Val Asp Ala Tyr Pro Ala Asn
            245                 250                 255

Trp His Ser Asp Ala Phe Leu Ala Ser Gly Ile Trp Gln Pro Asn Asp
        260                 265                 270

Glu His Lys Leu Thr Ser Thr Phe Asp Tyr Tyr His Lys Thr Asn His
    275                 280                 285

Thr His Tyr Asp Thr Trp Asp Ser Ser Gly Asn Ser Thr Ile Gly Thr
290                 295                 300

Ala Asn Gln Thr Ser Gln Thr Arg Arg Trp Gly Leu Ser Leu Lys Asp
305                 310                 315                 320

Asp Trp Thr Pro Met Asn Asp Tyr Leu Asp Ser Val Ser Thr Lys Ile
            325                 330                 335

Tyr Tyr Gln His Thr Glu Ala His Asp Trp Thr Tyr Met Pro Asp Ser
        340                 345                 350

Val Thr Arg Arg Met Gln Thr Val Asn Ser Asn Tyr Asp Thr Asp Thr
    355                 360                 365

Trp Gly Leu Gln Thr Ala Leu Ala Lys Thr Leu Gly Arg His Asp Leu
370                 375                 380

Ser Ala Gly Phe Asn Ala Ser Thr Ser Lys Thr Gln Arg Pro Phe Ser
385                 390                 395                 400

Gln Ser Pro Ile Pro Ser Val Tyr Ser Glu Ile Met Gln Pro Glu Ala
            405                 410                 415

Asp Ser Arg Ser Tyr Thr Leu Gly Gly Phe Val Gln Asp Lys Ile Asn
        420                 425                 430

Phe Asp Leu Asp Ser His Asn Phe Ala Val Ile Pro Gly Val Arg Val
    435                 440                 445

Val His Gln Ser Thr Lys Pro Glu Asn Leu Ser Asp Leu Ala Ala Asn
450                 455                 460

Ser Ser Val Leu Ser Glu Ser Ser Val Ala Asn Leu Tyr Gly Lys Asn
465                 470                 475                 480

Ser Asp Thr Gln Val Leu Pro Ser Leu Thr Phe Gln Tyr Asp Leu Thr
            485                 490                 495

Pro Arg Leu Met Thr Tyr Leu Gln Tyr Gln Arg Gly Ala Gln Phe Pro
        500                 505                 510

Asn Ala Ser Gln Leu Tyr Gly Ser Trp Asn Leu Gly Ser Ser Tyr Ala
    515                 520                 525

Gly Ser Gln Gln Tyr Ala Leu Ile Gly Asn Thr Asp Leu Lys Thr Glu
530                 535                 540

Thr Ser Asp Asn Leu Glu Trp Gly Leu Lys Gly Glu Val Thr Glu Gly
545                 550                 555                 560

Ile Thr Leu Arg Thr Ala Leu Phe Tyr Asn Ser Tyr Lys Asn Phe Ile
            565                 570                 575

Ala Tyr Thr Arg Tyr Thr Arg Ala Asn Asn Pro Gly Gln Phe Thr Asn
        580                 585                 590

Val Pro Ser Asn Ile Tyr Thr Ile Tyr Gln Ala Glu Asn Arg Asp Lys

```
                595                 600                 605
Ala Tyr Ile Tyr Gly Gly Glu Ile Ser Thr Lys Phe Asn Phe Gly Thr
610                 615                 620

Trp Phe Glu Gln Val Asp Gly Leu Ser Ala Thr Leu Ala Leu Gly Tyr
625                 630                 635                 640

Ser Glu Gly Lys Ser Lys Ser Tyr Ser Gly Asp Lys Tyr Val Asp
            645                 650                 655

Leu Asp Ser Val Ala Pro Met Lys Ala Ile Val Gly Val Ala Trp Asp
                660                 665                 670

Asp Pro Ala Lys Arg Tyr Gly Thr Ala Leu Thr Ala Thr Phe Val Lys
            675                 680                 685

Gly Lys Gln Ala Thr Ala Thr Asn Arg Glu Ser Tyr Ser Asn Ser Gly
690                 695                 700

Ser Ala Ile Thr Asp Ala Ser Ser Asp Tyr Met Arg Val Pro Gly Tyr
705                 710                 715                 720

Gly Met Leu Asp Trp Thr Ala Tyr Trp Gln Val Ala Lys Asn Val Arg
                725                 730                 735

Leu Asn Gly Gly Val Tyr Asn Leu Thr Asp Arg Lys Tyr Trp Asp Tyr
            740                 745                 750

Leu Ser Ser Arg Asn Ile Glu Thr Gly Thr Asn Gln Asp Ala Asn Asp
                755                 760                 765

Lys Ala Leu Ala Val Met Pro Gly Arg Thr Trp Gln Leu Gly Val Asn
770                 775                 780

Val Asp Phe
785

<210> SEQ ID NO 25
<211> LENGTH: 2139
<212> TYPE: DNA
<213> ORGANISM: Klebsiella pneumoniae

<400> SEQUENCE: 25
ttggttcagg atgatcttat gaacgtggct atttctcgaa aacgcccggg gctgctgtat     60
gcccttgcgg tcacactccc cttcaccgcg caagccgaag agacggtggt ggtcactgcc    120
accccgccgg cgtccgccag cgcgccgacg gagggctaca gcgccagcac ctcgctcggg    180
gcgacgaaaa ccgaccagcc gttaatcact accgccagt cggtgtcggt ggtcacccgc     240
cagcagatgg cggatcaggg ggcgaatacc atcagccagg cgctggaata taccccgggg    300
gtctactcca gcttcggcgg cggcgccacc cggttcgacg ccatctccct gcgcggctac    360
cacggcggcg acgtcgataa cctgttcctc gacggcatgc gcctgatgag cgacggcggc    420
agccataacg tactgcaaat cgacccgtgg tttatcgaac gcgtggatgt gatccgcggc    480
ccctcctccg cgctctacgg gcagagcgtg ccgggcggcg tggtcaacct gacttccaaa    540
cgtccgcagt tcagccagca gggccacatc cgcctgaccg gcggcacgca aaataccaaa    600
ggcgcggcct tcgattacac cgacgccatc aatgaccagt gggcatggcg gctgatcggg    660
atgacccgca gcagcgacac gcagtatgac catacccgcg aagagcgcta cgcgatttcg    720
ccttccctgc tgtggcagcc ggacagcgac acctcgctgc tgctgcgcgc ctatctgcaa    780
aaagatcctt ccggcggcta ccacggctct tgccgctgg acggcacccg ctacgcgcac    840
aatggccgta agctctcccc cagcaccaac gaaggcgatc cgggagatgg ctatcagcgc    900
cgccagcaga tctacagcta tgagtttgac caccagttca ccgacgtctg gtcggtctat    960
tccgccggga gctacaccca taccaacgtc tccctcgatc aggtctacca ggtcggctgg   1020
```

-continued

```
atagatgaaa gcgacatgct ggcccgcggc tacagcggtt cgcgcggttc gctggacggc    1080
tggtcaaccg ataaccgcct gcgcgccgat ttcaatacag gcgacctggc gcacaccctg    1140
atcctcggcg ccgaatatca tcgcttccgt aacgacctgt ggaccggcgc cggcggcgcg    1200
gcgcccctta acccgtttag cggctatacc gagcagaccg gacataccgt tacctacagc    1260
gacgacaata tcgccgcta ttaccagacc gggctgtatc tgcaggatga gatggtctgg     1320
aaccgctggc atgtggatgt ttccgcccgc tacgaccgca tcgtttccca gcaggtcagc    1380
gatacccagg ggacctcaaa ccgccgttca gacgaccata tcagcggccg cgcctcgctg    1440
ttgtacgccc tggacaacgg tctgtcgccc tacctgagct acagccaggc gatcactccg    1500
gcgatgctgc cgggcgcgga cggcaaaccg ttgaaaccga ccaccgccga acaggttgaa    1560
gccggcctga agttccagcc gccgggcagc agcgatctct atagcatcgc gatttacgac    1620
ctgacgcaaa aggatgtcgc cactcgcgac ccgaacatcg ccaccgccac ctatattccg    1680
gcgggtaagg tccattccca gggcgttgag ctggaagcgc accaccagat caccccgcag    1740
ctgagtacta tcgcctcgta tacctggaat cgtctgcgtt ccaggacac ccaagacggg     1800 accgacaata acacgccgca gctgaccccg gatcagatgg cctccttctg ggcgcgctat    1860
cagttcccgg cggggatctc cgttggcgcc ggcgtccgct acatcggtaa acagtgggcg    1920
gatgatgcca caccgcgcg gctgccgtcg gtcacgttga tggacgccat gatgcgggcc     1980
gacctcggcg tctggtcgcc aacgctgaaa ggcgcttatg tgcaggttaa cgccaacaat    2040
atcggcgacc gcgagtatat ttccggctgc tatggcaccg gcaactgtta ctggggagca    2100
gagcgcagcg ttatagccac cgtgggctac gatttctga                           2139
```

<210> SEQ ID NO 26
<211> LENGTH: 712
<212> TYPE: PRT
<213> ORGANISM: Klebsiella pneumoniae

<400> SEQUENCE: 26

```
Met Val Gln Asp Asp Leu Met Asn Val Ala Ile Ser Arg Lys Arg Pro
1               5                   10                  15

Gly Leu Leu Tyr Ala Leu Ala Val Thr Leu Pro Phe Thr Ala Gln Ala
            20                  25                  30

Glu Glu Thr Val Val Thr Ala Thr Pro Ala Ser Ala Ser Ala
        35                  40                  45

Pro Thr Glu Gly Tyr Ser Ala Ser Thr Ser Leu Gly Ala Thr Lys Thr
    50                  55                  60

Asp Gln Pro Leu Ile Thr Thr Ala Gln Ser Val Ser Val Thr Arg
65                  70                  75                  80

Gln Gln Met Ala Asp Gln Gly Ala Asn Thr Ile Ser Gln Ala Leu Glu
                85                  90                  95

Tyr Thr Pro Gly Val Tyr Ser Ser Phe Gly Gly Gly Ala Thr Arg Phe
            100                 105                 110

Asp Ala Ile Ser Leu Arg Gly Tyr His Gly Gly Asp Val Asp Asn Leu
        115                 120                 125

Phe Leu Asp Gly Met Arg Leu Met Ser Asp Gly Ser His Asn Val
    130                 135                 140

Leu Gln Ile Asp Pro Trp Phe Ile Glu Arg Val Asp Val Ile Arg Gly
145                 150                 155                 160

Pro Ser Ser Ala Leu Tyr Gly Gln Ser Val Pro Gly Gly Val Val Asn
                165                 170                 175
```

```
Leu Thr Ser Lys Arg Pro Gln Phe Ser Gln Gln Gly His Ile Arg Leu
            180                 185                 190

Thr Gly Gly Thr Gln Asn Thr Lys Gly Ala Ala Phe Asp Tyr Thr Asp
        195                 200                 205

Ala Ile Asn Asp Gln Trp Ala Trp Arg Leu Ile Gly Met Thr Arg Ser
    210                 215                 220

Ser Asp Thr Gln Tyr Asp His Thr Arg Glu Glu Arg Tyr Ala Ile Ser
225                 230                 235                 240

Pro Ser Leu Leu Trp Gln Pro Asp Ser Asp Thr Ser Leu Leu Leu Arg
                245                 250                 255

Ala Tyr Leu Gln Lys Asp Pro Ser Gly Gly Tyr His Gly Ser Leu Pro
            260                 265                 270

Leu Asp Gly Thr Arg Tyr Ala His Asn Gly Arg Lys Leu Ser Pro Ser
        275                 280                 285

Thr Asn Glu Gly Asp Pro Gly Asp Gly Tyr Gln Arg Arg Gln Gln Ile
    290                 295                 300

Tyr Ser Tyr Glu Phe Asp His Gln Phe Thr Asp Val Trp Ser Val Tyr
305                 310                 315                 320

Ser Ala Gly Ser Tyr Thr His Thr Asn Val Ser Leu Asp Gln Val Tyr
                325                 330                 335

Gln Val Gly Trp Ile Asp Glu Ser Asp Met Leu Ala Arg Gly Tyr Ser
            340                 345                 350

Gly Ser Arg Gly Ser Leu Asp Gly Trp Ser Thr Asp Asn Arg Leu Arg
        355                 360                 365

Ala Asp Phe Asn Thr Gly Asp Leu Ala His Thr Leu Ile Leu Gly Ala
    370                 375                 380

Glu Tyr His Arg Phe Arg Asn Asp Leu Trp Thr Gly Ala Gly Gly Ala
385                 390                 395                 400

Ala Pro Leu Asn Pro Phe Ser Gly Tyr Thr Glu Gln Thr Gly His Thr
                405                 410                 415

Val Thr Tyr Ser Asp Asp Asn Asn Arg Arg Tyr Tyr Gln Thr Gly Leu
            420                 425                 430

Tyr Leu Gln Asp Glu Met Val Trp Asn Arg Trp His Val Asp Val Ser
        435                 440                 445

Ala Arg Tyr Asp Arg Ile Val Ser Gln Gln Val Ser Asp Thr Gln Gly
    450                 455                 460

Thr Ser Asn Arg Arg Ser Asp Asp His Ile Ser Gly Arg Ala Ser Leu
465                 470                 475                 480

Leu Tyr Ala Leu Asp Asn Gly Leu Ser Pro Tyr Leu Ser Tyr Ser Gln
                485                 490                 495

Ala Ile Thr Pro Ala Met Leu Pro Gly Ala Asp Gly Lys Pro Leu Lys
            500                 505                 510

Pro Thr Thr Ala Glu Gln Val Glu Ala Gly Leu Lys Phe Gln Pro Pro
        515                 520                 525

Gly Ser Ser Asp Leu Tyr Ser Ile Ala Ile Tyr Asp Leu Thr Gln Lys
    530                 535                 540

Asp Val Ala Thr Arg Asp Pro Asn Ile Ala Thr Ala Tyr Ile Pro
545                 550                 555                 560

Ala Gly Lys Val His Ser Gln Gly Val Glu Leu Glu Ala His His Gln
                565                 570                 575

Ile Thr Pro Gln Leu Ser Thr Ile Ala Ser Tyr Thr Trp Asn Arg Leu
            580                 585                 590
```

```
Arg Phe Gln Asp Thr Gln Asp Gly Thr Asp Asn Asn Thr Pro Gln Leu
            595                 600                 605

Thr Pro Asp Gln Met Ala Ser Phe Trp Ala Arg Tyr Gln Phe Pro Ala
610                 615                 620

Gly Ile Ser Val Gly Ala Gly Val Arg Tyr Ile Gly Lys Gln Trp Ala
625                 630                 635                 640

Asp Asp Ala Asn Thr Ala Arg Leu Pro Ser Val Thr Leu Met Asp Ala
                645                 650                 655

Met Met Arg Ala Asp Leu Gly Val Trp Ser Pro Thr Leu Lys Gly Ala
            660                 665                 670

Tyr Val Gln Val Asn Ala Asn Asn Ile Gly Asp Arg Glu Tyr Ile Ser
        675                 680                 685

Gly Cys Tyr Gly Thr Gly Asn Cys Tyr Trp Gly Ala Glu Arg Ser Val
    690                 695                 700

Ile Ala Thr Val Gly Tyr Asp Phe
705                 710
```

```
<210> SEQ ID NO 27
<211> LENGTH: 1104
<212> TYPE: DNA
<213> ORGANISM: Klebsiella pneumoniae

<400> SEQUENCE: 27
atgaaagtta aagtactgtc cctcctggta ccggctctgc tggtagcagg cgcagcaaat      60
gcggctgaaa tttataacaa agacggcaac aaattagacc tgtacggtaa aattgacggt     120
ctgcactact tctctgacga caagagcgtc gacggcgacc agacctacat gcgtgtaggc     180
gtgaaaggcg aaacccagat caacgaccag ctgaccggtt acggccagtg ggaatacaac     240
gttcaggcga caacactga agctccagc gatcaggcat ggactcgtct ggcattcgca      300
ggcctgaaat ttggcgacgc gggctctttc gactacggtc gtaactacgg cgtagtatac     360
gacgtaacgt cctggaccga cgttctgccg gaattcggcg cgacaccta cggttctgac      420 aacttcctgc agtcccgtgc taacggcgtt gcaacctacc gtaactctga tttcttcggt     480
ctggttgacg gcctgaactt tgctctgcag tatcaggggta aaacggcag cgtcagcggc     540 gaaggcgctc tgtctcctac caacaacggt cgtaccgcct gaaacagaa cggcgacggt     600 tacggtactt tctgacccta tgacatctat gatggcatca cgctggtttt cgcatactct     660
aactccaaac gtcttggcga ccagaacagc aagctggcac tgggtcgtgg cgacaacgct     720
gaaacctaca ccggcggtct gaaatacgat gcgaacaaca tctacctggc cactcagtac     780
acccagacct acaacgcgac ccgcgccggt tccctgggct ttgctaacaa agcgcagaac     840
ttcgaagtgg ttgctcagta ccagttcgac ttcggtctgc gtccgtccgt ggcttacctg     900
cagtctaaag gtaaggatct ggaaggctac ggcgaccagg acatcctgaa atatgttgac     960
gttggcgcga cctactactt caacaaaaac atgtccacct atgttgacta caaaatcaac    1020
ctgctggacg acaacagctt cacccacaac gccggtatct ctaccgacga cgtggttgca    1080
ctgggcctgg tttaccagtt ctaa                                            1104
```

```
<210> SEQ ID NO 28
<211> LENGTH: 367
<212> TYPE: PRT
<213> ORGANISM: Klebsiella pneumoniae

<400> SEQUENCE: 28

Met Lys Val Lys Val Leu Ser Leu Leu Val Pro Ala Leu Leu Val Ala
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Gly | Ala | Ala | Asn | Ala | Ala | Glu | Ile | Tyr | Asn | Lys | Asp | Gly | Asn | Lys | Leu |
|  |  | 20 |  |  |  |  | 25 |  |  |  |  | 30 |  |  |  |
| Asp | Leu | Tyr | Gly | Lys | Ile | Asp | Gly | Leu | His | Tyr | Phe | Ser | Asp | Asp | Lys |
|  |  | 35 |  |  |  |  | 40 |  |  |  |  | 45 |  |  |  |
| Ser | Val | Asp | Gly | Asp | Gln | Thr | Tyr | Met | Arg | Val | Gly | Val | Lys | Gly | Glu |
|  |  | 50 |  |  |  |  | 55 |  |  |  |  | 60 |  |  |  |
| Thr | Gln | Ile | Asn | Asp | Gln | Leu | Thr | Gly | Tyr | Gly | Gln | Trp | Glu | Tyr | Asn |
| 65 |  |  |  |  | 70 |  |  |  |  | 75 |  |  |  |  | 80 |
| Val | Gln | Ala | Asn | Asn | Thr | Glu | Ser | Ser | Asp | Gln | Ala | Trp | Thr | Arg |
|  |  |  |  | 85 |  |  |  |  | 90 |  |  |  |  | 95 |
| Leu | Ala | Phe | Ala | Gly | Leu | Lys | Phe | Gly | Asp | Ala | Gly | Ser | Phe | Asp | Tyr |
|  |  |  | 100 |  |  |  |  | 105 |  |  |  |  | 110 |  |  |
| Gly | Arg | Asn | Tyr | Gly | Val | Val | Tyr | Asp | Val | Thr | Ser | Trp | Thr | Asp | Val |
|  |  |  | 115 |  |  |  |  | 120 |  |  |  |  | 125 |  |  |
| Leu | Pro | Glu | Phe | Gly | Gly | Asp | Thr | Tyr | Gly | Ser | Asp | Asn | Phe | Leu | Gln |
|  |  | 130 |  |  |  |  | 135 |  |  |  |  | 140 |  |  |  |
| Ser | Arg | Ala | Asn | Gly | Val | Ala | Thr | Tyr | Arg | Asn | Ser | Asp | Phe | Phe | Gly |
| 145 |  |  |  |  | 150 |  |  |  |  | 155 |  |  |  |  | 160 |
| Leu | Val | Asp | Gly | Leu | Asn | Phe | Ala | Leu | Gln | Tyr | Gln | Gly | Lys | Asn | Gly |
|  |  |  |  | 165 |  |  |  |  | 170 |  |  |  |  | 175 |  |
| Ser | Val | Ser | Gly | Glu | Gly | Ala | Leu | Ser | Pro | Thr | Asn | Asn | Gly | Arg | Thr |
|  |  |  | 180 |  |  |  |  | 185 |  |  |  |  | 190 |  |  |
| Ala | Leu | Lys | Gln | Asn | Gly | Asp | Gly | Tyr | Gly | Thr | Ser | Leu | Thr | Tyr | Asp |
|  |  |  | 195 |  |  |  |  | 200 |  |  |  |  | 205 |  |  |
| Ile | Tyr | Asp | Gly | Ile | Ser | Ala | Gly | Phe | Ala | Tyr | Ser | Asn | Ser | Lys | Arg |
|  |  | 210 |  |  |  |  | 215 |  |  |  |  | 220 |  |  |  |
| Leu | Gly | Asp | Gln | Asn | Ser | Lys | Leu | Ala | Leu | Gly | Arg | Gly | Asp | Asn | Ala |
| 225 |  |  |  |  | 230 |  |  |  |  | 235 |  |  |  |  | 240 |
| Glu | Thr | Tyr | Thr | Gly | Gly | Leu | Lys | Tyr | Asp | Ala | Asn | Asn | Ile | Tyr | Leu |
|  |  |  |  | 245 |  |  |  |  | 250 |  |  |  |  | 255 |  |
| Ala | Thr | Gln | Tyr | Thr | Gln | Thr | Tyr | Asn | Ala | Thr | Arg | Ala | Gly | Ser | Leu |
|  |  |  | 260 |  |  |  |  | 265 |  |  |  |  | 270 |  |  |
| Gly | Phe | Ala | Asn | Lys | Ala | Gln | Asn | Phe | Glu | Val | Val | Ala | Gln | Tyr | Gln |
|  |  |  | 275 |  |  |  |  | 280 |  |  |  |  | 285 |  |  |
| Phe | Asp | Phe | Gly | Leu | Arg | Pro | Ser | Val | Ala | Tyr | Leu | Gln | Ser | Lys | Gly |
|  |  | 290 |  |  |  |  | 295 |  |  |  |  | 300 |  |  |  |
| Lys | Asp | Leu | Glu | Gly | Tyr | Gly | Asp | Gln | Asp | Ile | Leu | Lys | Tyr | Val | Asp |
| 305 |  |  |  |  | 310 |  |  |  |  | 315 |  |  |  |  | 320 |
| Val | Gly | Ala | Thr | Tyr | Tyr | Phe | Asn | Lys | Asn | Met | Ser | Thr | Tyr | Val | Asp |
|  |  |  |  | 325 |  |  |  |  | 330 |  |  |  |  | 335 |  |
| Tyr | Lys | Ile | Asn | Leu | Leu | Asp | Asp | Asn | Ser | Phe | Thr | His | Asn | Ala | Gly |
|  |  |  | 340 |  |  |  |  | 345 |  |  |  |  | 350 |  |  |
| Ile | Ser | Thr | Asp | Asp | Val | Val | Ala | Leu | Gly | Leu | Val | Tyr | Gln | Phe |
|  |  |  | 355 |  |  |  |  | 360 |  |  |  |  | 365 |  |

<210> SEQ ID NO 29
<211> LENGTH: 1071
<212> TYPE: DNA
<213> ORGANISM: Klebsiella pneumoniae

<400> SEQUENCE: 29

| atgaaaaaga cagctatcgc gattgcagtg gcactggctg gcttcgctac cgtagcgcag | 60 |
| gccgctccga agataacac ctggtatgca ggtggtaaac tgggttggtc ccagtatcac | 120 |

```
gacaccggtt tctacggtaa cggtttccag aacaacaacg gtccgacccg taacgatcag    180
cttggtgctg gtgcgttcgg tggttaccag gttaacccgt acctcggttt cgaaatgggt    240
tatgactggc tgggccgtat ggcatataaa ggcagcgttg acaacggtgc tttcaaagct    300
cagggcgttc agctgaccgc taaactgggt tacccgatca ctgacgatct ggacatctac    360
acccgtctgg gcggcatggt ttggcgcgct gactccaaag caactacgc ttctaccggc    420 gtttcccgta gcgaacacga cactggcgtt tccccagtat ttgctggcgg cgtagagtgg    480
gctgttactc gtgacatcgc tacccgtctg gaataccagt gggttaacaa catcggcgac    540
gcgggcactg tgggtacccg tcctgataac ggcatgctga gcctgggcgt ttcctaccgc    600
ttcggtcagg aagatgctgc accggttgtt gctccggctc cggctccggc tccggaagtg    660
gctaccaagc acttcaccct gaagtctgac gttctgttca acttcaacaa agctaccctg    720
aaaccggaag gtcagcaggc tctggatcag ctgtacactc agctgagcaa catggatccg    780
aaagacggtt ccgctgttgt tctgggctac accgaccgca tcggttccga agcttacaac    840
cagcagctgt ctgagaaacg tgctcagtcc gttgttgact acctggttgc taaaggcatc    900
ccggctggca aaatctccgc tcgcggcatg ggtgaatcca acccggttac tgcaacacc    960 tgtgacaacg tgaaagctcg cgctgccctg atcgattgcc tggctccgga tcgtcgtgta    1020
gagatcgaag ttaaaggcta caagaagtt gtaactcagc cggcggctta a             1071
```

<210> SEQ ID NO 30
<211> LENGTH: 356
<212> TYPE: PRT
<213> ORGANISM: Klebsiella pneumoniae

<400> SEQUENCE: 30

```
Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Gly
            20                  25                  30

Lys Leu Gly Trp Ser Gln Tyr His Asp Thr Gly Phe Tyr Gly Asn Gly
        35                  40                  45

Phe Gln Asn Asn Asn Gly Pro Thr Arg Asn Asp Gln Leu Gly Ala Gly
    50                  55                  60

Ala Phe Gly Gly Tyr Gln Val Asn Pro Tyr Leu Gly Phe Glu Met Gly
65                  70                  75                  80

Tyr Asp Trp Leu Gly Arg Met Ala Tyr Lys Gly Ser Val Asp Asn Gly
                85                  90                  95

Ala Phe Lys Ala Gln Gly Val Gln Leu Thr Ala Lys Leu Gly Tyr Pro
            100                 105                 110

Ile Thr Asp Asp Leu Asp Ile Tyr Thr Arg Leu Gly Gly Met Val Trp
        115                 120                 125

Arg Ala Asp Ser Lys Gly Asn Tyr Ala Ser Thr Gly Val Ser Arg Ser
    130                 135                 140

Glu His Asp Thr Gly Val Ser Pro Val Phe Ala Gly Gly Val Glu Trp
145                 150                 155                 160

Ala Val Thr Arg Asp Ile Ala Thr Arg Leu Glu Tyr Gln Trp Val Asn
                165                 170                 175

Asn Ile Gly Asp Ala Gly Thr Val Gly Thr Arg Pro Asp Asn Gly Met
            180                 185                 190

Leu Ser Leu Gly Val Ser Tyr Arg Phe Gly Gln Glu Asp Ala Ala Pro
        195                 200                 205
```

```
Val Val Ala Pro Ala Pro Ala Pro Glu Val Ala Thr Lys His
        210                 215                 220

Phe Thr Leu Lys Ser Asp Val Leu Phe Asn Phe Asn Lys Ala Thr Leu
225                 230                 235                 240

Lys Pro Glu Gly Gln Gln Ala Leu Asp Gln Leu Tyr Thr Gln Leu Ser
                245                 250                 255

Asn Met Asp Pro Lys Asp Gly Ser Ala Val Val Leu Gly Tyr Thr Asp
                260                 265                 270

Arg Ile Gly Ser Glu Ala Tyr Asn Gln Gln Leu Ser Glu Lys Arg Ala
            275                 280                 285

Gln Ser Val Val Asp Tyr Leu Val Ala Lys Gly Ile Pro Ala Gly Lys
        290                 295                 300

Ile Ser Ala Arg Gly Met Gly Glu Ser Asn Pro Val Thr Gly Asn Thr
305                 310                 315                 320

Cys Asp Asn Val Lys Ala Arg Ala Ala Leu Ile Asp Cys Leu Ala Pro
                325                 330                 335

Asp Arg Arg Val Glu Ile Glu Val Lys Gly Tyr Lys Glu Val Val Thr
                340                 345                 350

Gln Pro Ala Ala
        355
```

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
caacggtgtg gttactgacg                                              20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
tctacgaagt ggccgttttc                                              20

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gatacggagt atgcctttac ggtg                                         24

<210> SEQ ID NO 34
<211> LENGTH: 24
<212> TYPE: DNA
<213> ORGANISM: Artificial Sequence
<220> FEATURE:

-continued

<221> NAME/KEY: source
<223> OTHER INFORMATION: /note="Description of Artificial Sequence: Synthetic primer"

<400> SEQUENCE: 34
tagcctttat caagcggata ctgg         24

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<211> LENGTH: 741
<212> TYPE: PRT
<213> ORGANISM: Klebsiella pneumoniae

<400> SEQUENCE: 41

```
Ala Gln Val Asp Ile Ala Pro Gly Ser Leu Asp Lys Ala Leu Asn Gln
1               5                   10                  15

Tyr Ala Ala His Ser Gly Ile Thr Leu Ser Val Asp Ala Ser Leu Thr
            20                  25                  30

Arg Gly Lys Gln Ser Asn Gly Leu His Gly Asp Tyr Asp Val Glu Ser
        35                  40                  45

Gly Leu Gln Gln Leu Leu Asp Gly Ser Gly Leu Gln Val Lys Pro Leu
    50                  55                  60

Gly Asn Asn Ser Trp Thr Leu Glu Pro Ala Pro Ala Pro Lys Glu Asp
65                  70                  75                  80

Ala Leu Thr Val Val Gly Asp Trp Leu Gly Asp Ala Arg Glu Asn Asp
                85                  90                  95

Val Phe Glu His Ala Gly Ala Arg Asp Val Ile Arg Arg Glu Asp Phe
            100                 105                 110
```

-continued

Ala Lys Thr Gly Ala Thr Thr Met Arg Glu Val Leu Asn Arg Ile Pro
        115                 120                 125

Gly Val Ser Ala Pro Glu Asn Asn Gly Thr Gly Ser His Asp Leu Ala
    130                 135                 140

Met Asn Phe Gly Ile Arg Gly Leu Asn Pro Arg Leu Ala Ser Arg Ser
145                 150                 155                 160

Thr Val Leu Met Asp Gly Ile Pro Val Pro Phe Ala Pro Tyr Gly Gln
                165                 170                 175

Pro Gln Leu Ser Leu Ala Pro Val Ser Leu Gly Asn Met Asp Ala Ile
            180                 185                 190

Asp Val Val Arg Gly Gly Ala Val Arg Tyr Gly Pro Gln Ser Val
        195                 200                 205

Gly Gly Val Val Asn Phe Val Thr Arg Ala Ile Pro Gln Asp Phe Gly
    210                 215                 220

Ile Glu Ala Gly Val Glu Gly Gln Leu Ser Pro Thr Ser Ser Gln Asn
225                 230                 235                 240

Asn Pro Lys Glu Thr His Asn Leu Met Val Gly Gly Thr Ala Asp Asn
                245                 250                 255

Gly Phe Gly Thr Ala Leu Leu Tyr Ser Gly Thr Arg Gly Ser Asp Trp
            260                 265                 270

Arg Glu His Ser Ala Thr Arg Ile Asp Asp Leu Met Leu Lys Ser Lys
        275                 280                 285

Tyr Ala Pro Asn Glu Val His Thr Phe Asn Ser Leu Leu Gln Tyr Tyr
    290                 295                 300

Asp Gly Glu Ala Asp Met Pro Gly Gly Leu Ser Arg Ala Asp Tyr Asp
305                 310                 315                 320

Ala Asp Arg Trp Gln Ser Thr Arg Pro Tyr Asp Arg Phe Trp Gly Arg
                325                 330                 335

Arg Lys Leu Ala Ser Leu Gly Tyr Gln Phe Gln Pro Asp Ser Gln His
            340                 345                 350

Lys Phe Asn Ile Leu Gly Phe Tyr Thr Gln Thr Leu Arg Ser Gly Tyr
        355                 360                 365

Leu Glu Gln Gly Lys Arg Ile Thr Leu Ser Pro Arg Asn Tyr Trp Val
    370                 375                 380

Arg Gly Ile Glu Pro Arg Tyr Ser Gln Ser Phe Met Ile Gly Pro Ser
385                 390                 395                 400

Ala His Glu Val Gly Val Gly Tyr Arg Tyr Val Asn Glu Ser Thr His
                405                 410                 415

Glu Met Arg Tyr Tyr Thr Ala Thr Ser Ser Gly Gln Leu Pro Ser Gly
            420                 425                 430

Ser Ser Pro Tyr Asp Arg Asp Thr Arg Ser Gly Thr Glu Ala His Ala
        435                 440                 445

Trp Tyr Leu Asp Asp Lys Ile Asp Ile Gly Asn Trp Thr Ile Thr Pro
    450                 455                 460

Gly Met Arg Phe Glu His Ile Glu Ser Tyr Gln Asn Asn Ala Ile Lys
465                 470                 475                 480

Gly Thr His Glu Glu Val Ser Tyr Asn Ala Pro Leu Pro Ala Leu Asn
                485                 490                 495

Val Leu Tyr His Leu Thr Asp Ser Trp Asn Leu Tyr Ala Asn Thr Glu
            500                 505                 510

Gly Ser Phe Gly Thr Val Gln Tyr Ser Gln Ile Gly Lys Ala Val Gln
        515                 520                 525

Ser Gly Asn Val Glu Pro Glu Lys Ala Arg Thr Trp Glu Leu Gly Thr

```
                530            535            540
Arg Tyr Asp Asp Gly Ala Leu Thr Ala Glu Met Gly Leu Phe Leu Ile
545                 550                 555                 560

Asn Phe Asn Asn Gln Tyr Asp Ser Asn Gln Thr Asn Asp Thr Val Thr
                565                 570                 575

Ala Arg Gly Lys Thr Arg His Thr Gly Leu Glu Thr Gln Ala Arg Tyr
                580                 585                 590

Asp Leu Gly Thr Leu Thr Pro Thr Leu Asp Asn Val Ser Val Tyr Ala
                595                 600                 605

Ser Tyr Ala Tyr Val Asn Ala Glu Ile Arg Glu Lys Gly Asp Thr Tyr
                610                 615                 620

Gly Asn Gln Val Pro Phe Ser Pro Lys His Lys Gly Thr Leu Gly Val
625                 630                 635                 640

Asp Tyr Lys Pro Gly Asn Trp Thr Phe Asn Leu Asn Ser Asp Phe Gln
                645                 650                 655

Ser Ser Gln Phe Ala Asp Asn Ala Asn Thr Val Lys Glu Ser Ala Asp
                660                 665                 670

Gly Ser Thr Gly Arg Ile Pro Gly Phe Met Leu Trp Gly Ala Arg Val
                675                 680                 685

Ala Tyr Asp Phe Gly Pro Gln Met Ala Asp Leu Asn Leu Ala Phe Gly
                690                 695                 700

Val Lys Asn Ile Phe Asp Gln Asp Tyr Phe Ile Arg Ser Tyr Asp Asp
705                 710                 715                 720

Asn Asn Lys Gly Ile Tyr Ala Gly Gln Pro Arg Thr Leu Tyr Met Gln
                725                 730                 735

Gly Ser Leu Lys Phe
                740

<210> SEQ ID NO 42
<211> LENGTH: 702
<212> TYPE: PRT
<213> ORGANISM: Klebsiella pneumoniae

<400> SEQUENCE: 42

Ala Glu Gln Pro Lys Gln Glu Glu Thr Ile Thr Val Val Ala Ala Pro
1               5                   10                  15

Ala Ala Gln Glu Asn Ala Trp Gly Pro Ala Pro Thr Ile Ala Ala Lys
                20                  25                  30

Arg Ser Ala Thr Ala Thr Lys Thr Asp Thr Pro Ile Glu Lys Thr Pro
                35                  40                  45

Gln Ser Val Ser Val Val Thr Arg His Glu Met Glu Met Arg Gln Pro
                50                  55                  60

Thr Thr Val Lys Glu Ala Leu Ser Tyr Thr Pro Ser Val Phe Ser Thr
65                  70                  75                  80

Arg Gly Ser Ser Thr Thr Tyr Asp Val Val Thr Ile Arg Gly Phe Thr
                85                  90                  95

Thr Ser Thr Thr Val Asn Thr Asn Gln Tyr Leu Asp Gly Met Lys Leu
                100                 105                 110

Gln Gly Asn Asn Tyr Ser Glu Val Ser Met Asp Pro Tyr Phe Leu Glu
                115                 120                 125

Arg Val Glu Val Met Arg Gly Pro Thr Ser Val Leu Tyr Gly Asn Ser
                130                 135                 140

Asn Pro Gly Gly Ile Val Ser Met Val Ser Lys Arg Pro Thr Thr Glu
145                 150                 155                 160
```

-continued

```
Pro Leu Lys Glu Val Gln Phe Lys Met Gly Thr Asp Asn Leu Trp Gln
            165                 170                 175
Thr Gly Phe Asp Phe Ser Asp Ala Ile Asp Asp Ala Gly Val Trp Ser
        180                 185                 190
Tyr Arg Leu Thr Gly Leu Gly Arg Ser Gln Asp Ala Gln Gln Gln Met
    195                 200                 205
Ala Lys Ser Thr Arg Tyr Ala Val Ala Pro Ser Phe Ser Trp Arg Pro
210                 215                 220
Asp Asp Lys Thr Asp Phe Thr Phe Leu Ser Asn Phe Gln Asn Asp Pro
225                 230                 235                 240
Asp Ala Gly Tyr Tyr Gly Trp Leu Pro Arg Glu Gly Thr Val Val Pro
                245                 250                 255
Tyr Tyr Asp Ala Asn Gly Lys Ala His Lys Leu Pro Thr Asp Phe Asn
            260                 265                 270
Glu Gly Glu Ser Asp Asn Lys Ile Ser Arg Arg Gln Lys Met Val Gly
        275                 280                 285
Tyr Ser Phe Ser His Gln Phe Asp Asp Thr Phe Thr Val Arg Gln Asn
    290                 295                 300
Leu Arg Tyr Ala Asp Val His Thr Leu Tyr Arg Ser Val Tyr Gly Asn
305                 310                 315                 320
Gly Tyr Val Ala Pro Gly Tyr Met Asn Arg Ala Tyr Val Arg Ser Asp
                325                 330                 335
Glu His Leu Asn Thr Phe Thr Val Asp Thr Gln Leu Gln Ser Asp Phe
            340                 345                 350
Ala Thr Gly Ala Val Ser His Thr Leu Leu Thr Gly Val Asp Tyr Ser
        355                 360                 365
Arg Met Arg Asn Asp Val Asp Ala Asp Tyr Gly Thr Ala Asp Pro Ile
    370                 375                 380
Ser Met Ser Asn Pro Gln Tyr Gly Asn Pro Asn Ile Gln Val Thr Phe
385                 390                 395                 400
Pro Tyr Ala Val Leu Asn Arg Met Glu Gln Thr Gly Leu Tyr Ala Gln
                405                 410                 415
Asp Gln Met Glu Trp Asp Lys Trp Val Met Thr Leu Gly Gly Arg Tyr
            420                 425                 430
Asp Tyr Ala Thr Thr Ser Thr Leu Thr Arg Ala Thr Asn Ser Leu Ala
        435                 440                 445
Glu Asn His Asp Gln Gln Phe Ser Trp Arg Gly Gly Ile Asn Tyr Leu
    450                 455                 460
Phe Asp Asn Gly Ile Ser Pro Tyr Phe Ser Tyr Ser Glu Ser Phe Glu
465                 470                 475                 480
Pro Val Ser Gly Ser Asn Ser Arg Gly Gln Pro Phe Asp Pro Ser Arg
                485                 490                 495
Gly Lys Gln Tyr Glu Ala Gly Val Lys Tyr Val Pro Lys Asp Met Pro
            500                 505                 510
Val Val Val Thr Ala Ala Val Tyr Gln Leu Thr Lys Asp Lys Asn Leu
        515                 520                 525
Thr Ala Asp Pro Ala Asn Gln Ala Phe Ser Ile Gln Thr Gly Glu Ile
    530                 535                 540
Arg Ser Arg Gly Leu Glu Leu Glu Ala Lys Ala Val Asn Ala Asn
545                 550                 555                 560
Ile Asn Val Thr Ala Ala Tyr Ser Tyr Thr Asp Ala Glu Tyr Thr His
                565                 570                 575
Asp Thr Val Phe Asn Gly Lys Arg Pro Ala Glu Val Pro Arg Asn Met
```

```
                    580                 585                 590
Ala Ser Leu Trp Ala Asp Tyr Thr Phe His Glu Thr Ala Leu Ser Gly
                595                 600                 605

Leu Thr Ile Gly Ala Gly Ala Arg Tyr Ile Gly Ser Thr Val Ser Tyr
            610                 615                 620

Tyr Lys Asn Asp Thr Ser Thr Gly Lys Lys Asn Asp Ala Phe Ser Val
625                 630                 635                 640

Ala Gly Tyr Ala Leu Met Asp Ala Thr Val Lys Tyr Asp Leu Ala Arg
                645                 650                 655

Phe Gly Leu Pro Gly Ser Ser Val Gly Val Asn Val Asn Asn Leu Phe
            660                 665                 670

Asp Arg Glu Tyr Val Ser Ser Cys Tyr Ser Glu Tyr Ala Cys Tyr Trp
        675                 680                 685

Gly Ala Gly Arg Gln Val Val Ala Thr Ala Thr Phe Arg Phe
        690                 695                 700

<210> SEQ ID NO 43
<211> LENGTH: 632
<212> TYPE: PRT
<213> ORGANISM: Klebsiella pneumoniae

<400> SEQUENCE: 43

Asp Val Asn Glu Glu Thr Leu Val Val Thr Ala Ser Ala Thr Glu Gln
1               5                   10                  15

Asn Val Lys Asp Ala Pro Ala Ser Ile Ser Val Ile Thr Gln Gln Asp
                20                  25                  30

Leu Gln Arg Lys Pro Val Gln Asn Leu Lys Asp Val Leu Arg Asp Val
            35                  40                  45

Pro Gly Val Gln Leu Thr Asn Glu Gly Asp Asn Arg Lys Gly Val Ser
        50                  55                  60

Ile Arg Gly Leu Ser Ser Ser Tyr Thr Leu Ile Leu Val Asp Gly Lys
65                  70                  75                  80

Arg Val Asn Ser Arg Asn Ala Val Phe Arg His Asn Asp Phe Asp Leu
                85                  90                  95

Asn Trp Ile Pro Val Asp Ala Ile Glu Arg Ile Glu Val Val Arg Gly
            100                 105                 110

Pro Met Ser Ser Leu Tyr Gly Ser Asp Ala Leu Gly Gly Val Val Asn
        115                 120                 125

Ile Ile Thr Lys Lys Ile Gly Gln Lys Trp Thr Gly Thr Leu Ser Ala
130                 135                 140

Asp Thr Thr Ile Gln Glu His Arg Asp Arg Gly Asp Thr Tyr Asn Gly
145                 150                 155                 160

Gln Phe Phe Thr Ser Gly Pro Leu Ile Asp Gly Val Leu Gly Met Lys
                165                 170                 175

Ala Tyr Gly Ser Leu Ala Lys Arg Ala Lys Asp Asp Pro Gln Ser Ser
            180                 185                 190

Ser Asn Ala Thr Gly Glu Thr Pro Arg Ile Glu Gly Phe Thr Ser Arg
        195                 200                 205

Asp Gly Asn Val Glu Phe Ala Trp Thr Pro Asn Glu Asn His Asp Phe
    210                 215                 220

Thr Ala Gly Tyr Gly Phe Asp Arg Gln Asp Arg Asp Ser Asp Ser Leu
225                 230                 235                 240

Asp Arg Asn Arg Leu Glu Arg Glu Asn Tyr Ser Leu Ser His Asn Gly
                245                 250                 255
```

-continued

Arg Trp Asp Ile Gly Asn Ser Glu Leu Lys Phe Tyr Gly Glu Lys Val
            260                 265                 270

Asp Asn Lys Asn Pro Gly Gln Ser Gly Thr Ile Thr Ser Glu Ser Asn
        275                 280                 285

Ala Ile Asp Gly Lys Tyr Val Leu Pro Leu Gly Met Ile Asn Gln Leu
    290                 295                 300

Val Thr Phe Gly Gly Glu Trp Arg His Asp Lys Leu Lys Asp Pro Val
305                 310                 315                 320

Asn Leu Ser Ser Gly Gln Ser Thr Ser Ala Ser Gln Tyr Ala Leu
                325                 330                 335

Phe Ile Glu Asp Glu Trp Arg Ile Ile Glu Pro Leu Ala Leu Thr Thr
            340                 345                 350

Gly Ile Arg Met Asp Asp His Gln Thr Tyr Gly Asp His Trp Ser Pro
            355                 360                 365

Arg Ala Tyr Leu Val Tyr Asn Ala Thr Asp Thr Val Thr Val Lys Gly
        370                 375                 380

Gly Trp Ala Thr Ala Phe Lys Ala Pro Ser Leu Leu Gln Leu Asn Pro
385                 390                 395                 400

Asp Trp Thr Thr Asn Ser Cys Arg Gly Ser Cys Ser Ile Val Gly Asn
            405                 410                 415

Pro Asp Leu Lys Pro Glu Thr Ser Glu Ser Phe Glu Leu Gly Leu Tyr
            420                 425                 430

Tyr Arg Gly Glu Gly Trp Leu Glu Asn Val Glu Gly Ser Ile Thr
        435                 440                 445

Thr Phe Gln Asn Asn Val Asp Asp Met Ile Asp Val Leu Arg Thr Ser
450                 455                 460

Ser Ala Ser Glu Ala Pro Gly Tyr Pro Asn Phe Val Gly Trp Lys Thr
465                 470                 475                 480

Val Asn Gly Lys Arg Val Pro Ile Phe Arg Tyr Phe Asn Val Asn Lys
            485                 490                 495

Ala Arg Ile Lys Gly Val Glu Thr Glu Val Lys Ile Pro Phe Gly Asp
            500                 505                 510

Glu Trp Lys Leu Thr Val Asn Tyr Thr Tyr Asn Asp Gly Arg Asp Leu
        515                 520                 525

Ser Asn Gly Gly Asp Lys Pro Leu Gln Thr Leu Pro Phe His Thr Ala
530                 535                 540

Asn Gly Thr Leu Asp Trp Lys Pro Leu Asp Asp Trp Ser Phe Tyr Val
545                 550                 555                 560

Thr Ala Asn Tyr Thr Gly Gln Gln Arg Ala Val Ser Ala Thr Gly Lys
            565                 570                 575

Thr Pro Gly Gly Tyr Thr Leu Phe Asp Val Gly Ala Ala Trp Gln Val
            580                 585                 590

Thr Lys Asn Val Lys Leu Arg Ser Gly Val Gln Asn Val Gly Asp Lys
        595                 600                 605

Asp Leu Ser Arg Asp Asp Tyr Ser Tyr Thr Glu Glu Gly Arg Arg Tyr
        610                 615                 620

Phe Met Ala Val Asp Tyr Arg Phe
625                 630

<210> SEQ ID NO 44
<211> LENGTH: 717
<212> TYPE: PRT
<213> ORGANISM: Klebsiella pneumoniae
<220> FEATURE:
<221> NAME/KEY: MOD_RES
<222> LOCATION: (455)..(458)
<223> OTHER INFORMATION: Any amino acid

<400> SEQUENCE: 44

```
Ala Glu Thr Ala Thr Asp Asp Lys Asn Ser Ala Ala Glu Glu Thr Met
1               5                   10                  15

Val Val Thr Ala Ala Glu Gln Asn Leu Gln Ala Pro Gly Val Ser Thr
                20                  25                  30

Ile Thr Ala Asp Glu Ile Arg Lys Arg Pro Ala Arg Asp Val Ser
            35                  40                  45

Glu Ile Ile Arg Thr Met Pro Gly Val Asn Leu Thr Gly Asn Ser Thr
50                  55                  60

Ser Gly Gln Arg Gly Asn Asn Arg Gln Ile Asp Ile Arg Gly Met Gly
65                  70                  75                  80

Pro Glu Asn Thr Leu Ile Leu Ile Asp Gly Lys Pro Val Thr Ser Arg
                85                  90                  95

Asn Ser Val Arg Leu Gly Trp Arg Gly Glu Arg Asp Thr Arg Gly Asp
                100                 105                 110

Thr Ser Trp Val Pro Pro Glu Ile Ile Glu Arg Ile Glu Val Ile Arg
            115                 120                 125

Gly Pro Ala Ala Ala Arg Tyr Gly Asn Gly Ala Ala Gly Gly Val Val
            130                 135                 140

Asn Ile Ile Thr Lys Lys Thr Gly Asp Glu Trp His Gly Ser Trp Asn
145                 150                 155                 160

Thr Tyr Met Asn Ala Pro Glu His Lys Asp Glu Gly Ser Thr Lys Arg
                165                 170                 175

Thr Asn Phe Ser Leu Ser Gly Pro Leu Gly Gly Asp Phe Ser Phe Arg
                180                 185                 190

Leu Phe Gly Asn Leu Asp Lys Thr Gln Ala Asp Ala Trp Asp Ile Asn
            195                 200                 205

Gln Gly His Gln Ser Glu Arg Thr Gly Ile Tyr Ala Asp Thr Leu Pro
210                 215                 220

Ala Gly Arg Glu Gly Val Lys Asn Lys Asn Ile Asp Gly Leu Val Arg
225                 230                 235                 240

Trp Glu Phe Ala Pro Met Gln Ser Leu Glu Phe Glu Ala Gly Tyr Ser
                245                 250                 255

Arg Gln Gly Asn Leu Tyr Ala Gly Asp Thr Gln Asn Thr Asn Ser Asn
                260                 265                 270

Asp Leu Val Lys Glu Asn Tyr Gly Lys Glu Thr Asn Arg Leu Tyr Arg
            275                 280                 285

Asn Thr Tyr Ser Val Thr Trp Asn Gly Ala Trp Asp Asn Gly Val Thr
290                 295                 300

Thr Ser Asn Trp Ala Gln Tyr Glu Arg Thr Arg Asn Ser Arg Lys Gly
305                 310                 315                 320

Glu Gly Leu Ala Gly Gly Thr Glu Gly Ile Phe Asn Ser Asn Gln Phe
                325                 330                 335

Thr Asp Ile Asp Leu Ala Asp Val Met Leu His Ser Glu Val Ser Ile
                340                 345                 350

Pro Phe Asp Tyr Leu Val Asn Gln Asn Leu Thr Leu Gly Ser Glu Trp
            355                 360                 365

Asn Gln Gln Arg Met Lys Asp Asn Ala Ser Asn Thr Gln Ala Leu Ser
370                 375                 380

Gly Gly Gly Ile Pro Gly Tyr Asp Ser Thr Gly Arg Ser Pro Tyr Ser
385                 390                 395                 400
```

Gln Ala Glu Ile Phe Ser Leu Phe Ala Glu Asn Asn Met Glu Leu Thr
                405                 410                 415

Asp Thr Thr Met Leu Thr Pro Ala Leu Arg Phe Asp His His Ser Ile
            420                 425                 430

Val Gly Asn Asn Trp Ser Pro Ser Leu Asn Leu Ser Gln Gly Leu Trp
        435                 440                 445

Asp Asp Phe Thr Leu Lys Xaa Xaa Xaa Xaa Arg Ala Tyr Lys Ala Pro
450                 455                 460

Ser Leu Tyr Gln Thr Asn Pro Asn Tyr Ile Leu Tyr Ser Lys Gly Gln
465                 470                 475                 480

Gly Cys Tyr Ala Ser Lys Asp Gly Cys Tyr Leu Gln Gly Asn Asp Asp
                485                 490                 495

Leu Lys Ala Glu Thr Ser Ile Asn Lys Glu Ile Gly Leu Glu Phe Lys
            500                 505                 510

Arg Asp Gly Trp Leu Ala Gly Val Thr Trp Phe Arg Asn Asp Tyr Arg
        515                 520                 525

Asn Lys Ile Glu Ala Gly Tyr Ala Pro Val Tyr Gln Asn Asn Lys Gly
    530                 535                 540

Thr Asp Leu Tyr Gln Trp Glu Asn Val Pro Lys Ala Val Val Glu Gly
545                 550                 555                 560

Leu Glu Gly Thr Leu Asn Val Pro Val Ser Glu Thr Val Asn Trp Thr
                565                 570                 575

Asn Asn Ile Thr Tyr Met Leu Gln Ser Lys Asn Lys Glu Thr Gly Asp
            580                 585                 590

Arg Leu Ser Ile Ile Pro Glu Tyr Thr Leu Asn Ser Thr Leu Ser Trp
        595                 600                 605

Gln Val Arg Asp Asp Val Ser Leu Gln Ser Thr Phe Thr Trp Tyr Gly
    610                 615                 620

Lys Gln Glu Pro Lys Lys Tyr Asn Tyr Lys Gly Gln Pro Val Thr Gly
625                 630                 635                 640

Ser Glu Lys Asn Glu Val Ser Pro Tyr Ser Ile Leu Gly Leu Ser Ala
                645                 650                 655

Thr Trp Asp Val Thr Lys Tyr Val Ser Leu Thr Gly Gly Val Asp Asn
            660                 665                 670

Val Phe Asp Lys Arg His Trp Arg Ala Gly Asn Ala Gln Thr Thr Gly
        675                 680                 685

Gly Ala Thr Gly Thr Met Tyr Gly Ala Gly Ala Glu Thr Tyr Asn Glu
    690                 695                 700

Ser Gly Arg Thr Trp Tyr Leu Ser Val Asn Thr His Phe
705                 710                 715

<210> SEQ ID NO 45
<211> LENGTH: 592
<212> TYPE: PRT
<213> ORGANISM: Klebsiella pneumoniae
<220> FEATURE:
<221> NAME/KEY: MOD_RES
<222> LOCATION: (118)..(132)
<223> OTHER INFORMATION: Any amino acid

<400> SEQUENCE: 45

Gln Asp Ser Asn Ser Asp Thr Leu Val Val Thr Ala Asn Arg Phe Gln
1               5                   10                  15

Gln Pro Val Asn Thr Val Leu Ala Pro Thr Asp Ile Val Thr Arg Asp
            20                  25                  30

```
Asp Ile Asp Arg Trp Gln Ser Lys Asp Leu Asn Asp Val Met Arg Arg
         35                  40                  45

Leu Pro Gly Val Asp Ile Ala Arg Asn Gly Gly Met Gly Gln Ser Ala
 50                  55                  60

Ser Leu Tyr Val Arg Gly Thr Glu Ala Arg His Val Leu Val Leu Ile
 65                  70                  75                  80

Asp Gly Val Pro Met Ala Arg Pro Gly Ile Ser Asn Gly Val Asp Ile
                 85                  90                  95

Ser Gln Ile Pro Ile Ser Leu Val Gln Arg Val Glu Tyr Ile Arg Gly
            100                 105                 110

Pro Arg Ser Ala Val Xaa Xaa Xaa Xaa Xaa Xaa Xaa Xaa Xaa
            115                 120                 125

Xaa Xaa Xaa Xaa Thr Asp Ala Glu Arg Ser Gln Ile Asn Ala Gly Ala
130                 135                 140

Gly Thr Asn Gly Tyr Gln Ser Tyr Asp Gly Ala Phe Asn Lys Arg Phe
145                 150                 155                 160

Gly Asn Thr Leu Val Thr Ala Ala Gly Ala Tyr Gln Thr Thr Lys Gly
                165                 170                 175

Phe Asn Val Gln Pro Asn Ser Ser Tyr Ser Gly Asp Ser Asp Arg Asp
                180                 185                 190

Gly Tyr Arg Asn Lys Met Leu Trp Gly Gly Val Gln His Gln Phe Asp
            195                 200                 205

Asp Asn Phe Ser Gly Phe Phe Arg Gly Tyr Gly Tyr Ser Ala Asn Ala
    210                 215                 220

Asp Tyr Asp Gln Gly Asn Trp Gly Tyr Ala Gly Gly Asn Asp Glu Asp
225                 230                 235                 240

Gln Ser Tyr Thr Gln Ser Trp Asp Thr Gly Leu His Tyr His Ser Gly
                245                 250                 255

Ile Tyr Ser Ser Gln Leu Ile Ala Asn Tyr Gln Arg Ile Lys Asp Tyr
                260                 265                 270

Asn Tyr Ser Ser Asp Ala Gly Arg Tyr Ala Ala Gly Thr Thr Leu Asp
            275                 280                 285

Asp Met Glu Gln Arg Tyr Ile Gln Trp Gly Asn Asn Val Val Val Gly
290                 295                 300

His Gly Ala Val Ser Gly Val Asp Trp Lys Gln Glu Lys Leu Lys
305                 310                 315                 320

Ser Ser Gly Thr Thr Ser Thr Asp Val Tyr Lys Arg Asp Thr Thr Gly
                325                 330                 335

Leu Tyr Leu Thr Gly Gln Gln Ile Asp Ser Val Thr Leu Glu Ala
                340                 345                 350

Ser Gly Arg Glu Asp His Asp Glu Gln Phe Gly Trp His Gly Thr Trp
            355                 360                 365

Gln Thr Ala Ala Gly Trp Glu Phe Ile Asp Gly Tyr Arg Thr Thr Leu
370                 375                 380

Ser Tyr Gly Thr Gly Phe Leu Ala Pro Ser Leu Gly Gln Gln Tyr Gly
385                 390                 395                 400

Ala Glu Arg Phe Gly Ile Ala Ser Asn Pro Asn Leu Lys Pro Glu Glu
                405                 410                 415

Ser Lys Gln Trp Glu Ala Gly Leu Glu Gly Leu Thr Gly Pro Val Asp
            420                 425                 430

Trp Arg Leu Ser Ala Tyr Arg Tyr Glu Ile Gln Asn Leu Ile Asp Tyr
            435                 440                 445

Asp Asn Asn Ala Tyr Tyr Asn Val Lys Ser Ala Thr Ile Lys Gly Leu
```

|       |       |       | 450   |       |       |       | 455   |       |       |       | 460   |       |       |
|-------|-------|-------|-------|-------|-------|-------|-------|-------|-------|-------|-------|-------|-------|

Glu Trp Thr Gly Asn Ile Thr Thr Gly Pro Val Glu His His Leu Thr
465                 470                 475                 480

Leu Gln Tyr Val Asp Pro Arg Asp Glu Thr Asn Lys Ile Leu Tyr
            485                 490                 495

Arg Arg Ala Lys Gln Gln Val Lys Tyr Glu Leu Asn Gly Gln Val Tyr
                500                 505                 510

Asp Leu Gly Trp Asp Val Thr Tyr His Tyr Ile Gly Lys Arg Tyr Asp
            515                 520                 525

Tyr Asp Tyr Asp Asn Ser Arg Thr Val Asn Met Gly Gly Leu Ser Leu
        530                 535                 540

Trp Asp Val Gly Leu Ser Tyr Pro Val Thr Ser His Leu Thr Val Arg
545                 550                 555                 560

Gly Lys Ile Ala Asn Leu Phe Asp Lys Asp Tyr Glu Thr Val Tyr Gly
                565                 570                 575

Tyr Gln Ser Ala Gly Arg Glu Tyr Thr Leu Ser Gly Ser Tyr Thr Phe
            580                 585                 590

<210> SEQ ID NO 46
<211> LENGTH: 729
<212> TYPE: PRT
<213> ORGANISM: Klebsiella pneumoniae

<400> SEQUENCE: 46

Ala Glu Asn Ser Val Lys Asn Ser Glu Glu Thr Leu Val Val Glu Ala
1               5                   10                  15

Ala Pro Pro Ser Leu Tyr Ser Pro Gly Ala Ser Ala Asp Pro Lys Phe
            20                  25                  30

Asn Lys Pro Leu Val Asp Thr Thr Arg Thr Ile Thr Val Ile Pro Glu
        35                  40                  45

Gln Val Ile Lys Asp Gln Gly Val Thr Asn Leu Thr Asp Ala Leu Lys
    50                  55                  60

Asn Val Pro Gly Val Gly Ala Phe Tyr Ala Gly Glu Asn Gly Ser Ser
65                  70                  75                  80

Thr Thr Gly Asp Ala Ile Phe Met Arg Gly Val Asp Thr Ser Asn Ser
                85                  90                  95

Ile Tyr Val Asp Gly Ile Arg Asp Ile Gly Ser Val Thr Arg Asp Thr
            100                 105                 110

Phe Asn Thr Gln Gln Val Glu Val Ile Lys Gly Pro Ala Gly Thr Asp
        115                 120                 125

Tyr Gly Arg Ser Ala Pro Ser Gly Ser Ile Asn Met Ile Ser Lys Gln
    130                 135                 140

Pro Arg Leu Asp Ser Gly Ile Asp Gly Ser Ala Ser Ile Gly Ser Ala
145                 150                 155                 160

Trp Ser Arg Arg Gly Thr Leu Asp Leu Asn Gln Ala Phe Ser Asp Asn
                165                 170                 175

Ala Ala Phe Arg Leu Asn Leu Met Gly Glu Lys Thr His Asp Ala Gly
            180                 185                 190

Arg Asp Arg Ile Glu Asn Glu Arg Tyr Gly Ile Ala Pro Ser Leu Ala
        195                 200                 205

Phe Gly Leu Asp Thr Pro Thr Arg Leu Tyr Leu Asn Tyr Leu His Val
    210                 215                 220

Arg Gln Asn Asn Thr Pro Asp Gly Gly Ile Pro Thr Val Gly Leu Pro
225                 230                 235                 240

-continued

Gly Tyr Ser Ala Pro Ser Pro Lys Tyr Ala Leu Asn Ser Thr Gly
                245                 250                 255
Lys Val Asp Thr Ser Asn Phe Tyr Gly Thr Asp Ser Tyr Asp Lys
            260                 265                 270
Ser Thr Thr Asp Ser Gly Thr Leu Arg Phe Glu His Asp Leu Thr Glu
            275                 280                 285
Ser Thr Thr Val Arg Asn Thr Arg Trp Ser Arg Val Lys Gln Glu
            290                 295                 300
Tyr Leu Leu Thr Ala Val Met Gly Gly Ala Asn Asn Ile Thr Ala Pro
305                 310                 315                 320
Asp Ile Asn Asp Val Asn Thr Trp Ser Trp Ser Arg Leu Val Asn Thr
                325                 330                 335
Lys Asp Val Ser Asn Arg Ile Leu Thr Asn Gln Thr Asn Ile Thr Ser
                340                 345                 350
Thr Phe Asp Thr Gly Ser Ile Gly His Asp Val Ser Ala Gly Val Glu
            355                 360                 365
Phe Thr Arg Glu Asn Gln Thr Asn Tyr Gly Val Asn Ala Arg Thr Ala
370                 375                 380
Pro Ala Val Asn Leu Tyr His Pro Val Ser Asn Leu Ser Ile Gly Gly
385                 390                 395                 400
Leu Asp Arg Asn Gly Ala Asn Ala Asn Gly Gln Thr Asp Thr Phe Gly
                405                 410                 415
Ile Tyr Ala Phe Asp Thr Leu Thr Leu Thr Glu Arg Ile Glu Ile Asn
                420                 425                 430
Gly Gly Leu Arg Leu Asp Asn Tyr His Thr Lys Tyr Asp Ser Ala Thr
            435                 440                 445
Ala Cys Gly Gly Ser Gly Arg Gly Ala Ile Ala Cys Pro Pro Gly Gln
        450                 455                 460
Ser Thr Gly Ser Pro Val Thr Thr Val Asp Thr Ala Lys Ser Gly Asn
465                 470                 475                 480
Leu Val Asn Trp Lys Ala Gly Ala Leu Tyr Arg Leu Thr Glu Gln Gly
                485                 490                 495
Asn Val Tyr Val Asn Tyr Ala Ile Ser Gln Gln Pro Pro Gly Gly Ser
            500                 505                 510
Ser Phe Ala Leu Ala Ala Ser Gly Ser Gly Asn Ser Ala Asn Arg Thr
    515                 520                 525
Asp Phe Lys Pro Gln Lys Ala Lys Ser Ser Glu Leu Gly Thr Lys Trp
            530                 535                 540
Gln Ile Phe Asp Asn Arg Leu Leu Leu Ser Ala Ala Leu Phe Arg Thr
545                 550                 555                 560
Asp Ile Glu Asn Glu Val Ala Ala Asn Asp Asp Gly Thr Trp Ser Gln
                565                 570                 575
Tyr Gly Lys Lys Arg Val Glu Gly Tyr Glu Leu Ser Ala Thr Gly Asn
            580                 585                 590
Leu Thr Pro Asp Trp Thr Ile Ile Ala Gly Tyr Thr Gln Gln His Ala
        595                 600                 605
Thr Val Thr Glu Gly Gln Asn Val Ala Gln Asp Gly Ser Ser Ala Leu
    610                 615                 620
Ala Tyr Thr Pro Lys His Ala Phe Thr Leu Trp Gln Tyr Gln Ala
625                 630                 635                 640
Thr Ser Asp Leu Ser Val Gly Gly Val Arg Tyr Val Gly Ser Leu
                645                 650                 655
Arg Arg Gly Ser Asp Gly Ala Val Gly Thr Pro Asp His Thr Glu Gly

```
                      660                 665                 670
Tyr Trp Val Ala Asp Ala Lys Leu Gly Tyr Arg Val Asn Ser Asn Leu
                675                 680                 685

Asp Leu Gln Leu Asn Met Tyr Asn Leu Phe Asp Thr Asp Tyr Val Ala
            690                 695                 700

Ser Ile Asn Lys Ser Gly Tyr Arg Tyr His Pro Gly Glu Pro Arg Thr
705                 710                 715                 720

Phe Met Leu Thr Ala Asn Val His Phe
                725
```

<210> SEQ ID NO 47

<400> SEQUENCE: 47

000

<210> SEQ ID NO 48

<400> SEQUENCE: 48

000

<210> SEQ ID NO 49
<211> LENGTH: 707
<212> TYPE: PRT
<213> ORGANISM: Klebsiella pneumoniae

<400> SEQUENCE: 49

```
Ala Gln Ser Asp Glu Asp Ser Ile Ile Val Ser Ala Asn Arg Thr His
1               5                   10                  15

Arg Thr Val Ala Glu Met Ala Gln Thr Thr Trp Val Ile Glu Gly Gln
            20                  25                  30

Glu Ile Glu Gln Gln Val Gln Gly Gly Lys Glu Phe Lys Asp Val Leu
        35                  40                  45

Ala Gln Leu Ile Pro Gly Ile Asp Val Ser Ser Gln Gly Arg Thr Asn
    50                  55                  60

Tyr Gly Met Asn Met Arg Gly Arg Ala Ile Val Val Leu Ile Asp Gly
65                  70                  75                  80

Val Arg Leu Asn Ser Ser Arg Thr Asp Ser Arg Gln Leu Asp Ala Ile
                85                  90                  95

Asp Pro Phe Asn Ile Glu His Ile Glu Val Ile Ser Gly Ala Thr Ser
            100                 105                 110

Leu Tyr Gly Gly Gly Ser Thr Gly Gly Leu Ile Asn Ile Val Thr Lys
        115                 120                 125

Lys Gly Gln Gln Asp Arg Gln Val Asp Leu Glu Val Gly Ser Lys Ser
    130                 135                 140

Gly Phe Ala Asn Ser Asn Asp His Asp Glu Arg Val Ala Ala Ala Val
145                 150                 155                 160

Ser Gly Gly Thr Asp His Ala Ser Gly Arg Leu Ser Val Ala Tyr Gln
                165                 170                 175

Arg Phe Gly Gly Trp Tyr Asp Gly Asn Thr Asp Ala Leu Ile Leu Asp
            180                 185                 190

Asn Thr Gln Thr Gly Leu Gln His Ser Asp Arg Leu Asp Val Met Gly
        195                 200                 205

Thr Gly Thr Ile Glu Ile Asp Asn Asn Arg Gln Leu Gln Leu Val Thr
    210                 215                 220

Gln Tyr Tyr Lys Ser Gln Gly Asp Asp Asp Tyr Gly Leu Trp Leu Gly
```

```
            225                 230                 235                 240
Lys Asn Met Ser Ala Val Thr Ser Gly Gly Lys Ala Tyr Thr Thr Asp
                245                 250                 255

Gly Leu Asn Ser Asp Arg Ile Pro Gly Thr Glu Arg His Leu Ile Ser
                260                 265                 270

Leu Gln Tyr Ser Asp Ala Asp Phe Gly Gln Asn Leu Val Ser Gln
                275                 280                 285

Val Tyr Tyr Arg Asp Glu Ser Leu Thr Phe Tyr Pro Phe Pro Thr Leu
                290                 295                 300

Thr Lys Gly Gln Val Ser Ser Phe Ser Ser Gln Gln Asp Thr Asp
305                 310                 315                 320

Gln Tyr Gly Ala Lys Leu Thr Leu Asn Ser Gln Pro Leu Ala Gly Trp
                325                 330                 335

Asp Leu Thr Trp Gly Leu Asp Ala Asp His Glu Thr Phe Asn Ala Asn
                340                 345                 350

Gln Met Phe Phe Asp Leu Pro Gln Ser Met Ala Ser Gly Gly Leu His
                355                 360                 365

Asn Glu Ser Ile Tyr Thr Thr Gly Arg Tyr Pro Gly Tyr Ser Ile Ser
                370                 375                 380

Asn Val Ala Pro Phe Leu Gln Ser Ser Tyr Asp Leu Asn Asp Ile Phe
385                 390                 395                 400

Thr Val Ser Gly Gly Val Arg Tyr Gln Trp Thr Glu Asn Arg Val Asp
                405                 410                 415

Asp Phe Val Gly Tyr Ala Gln Gln Gln Asp Ile Ala Asn Gly Lys Ala
                420                 425                 430

Arg Ser Ala Asp Ala Ile Lys Gly Gly Lys Thr Asp Tyr Asp Asn Phe
                435                 440                 445

Leu Phe Asn Ala Gly Ile Val Ala His Leu Thr Glu Arg Gln Gln Thr
                450                 455                 460

Trp Phe Asn Phe Ser Gln Gly Val Glu Leu Pro Asp Pro Gly Lys Tyr
465                 470                 475                 480

Tyr Gly Ile Gly Lys Tyr Gly Ala Ala Val Asn Gly His Leu Pro Leu
                485                 490                 495

Ile Ser Ser Val Asn Val Asp Asp Ser Pro Leu Gln Gly Ile Lys Val
                500                 505                 510

Asn Ser Tyr Glu Leu Gly Trp Arg Tyr Thr Gly Asp Asn Leu Arg Thr
                515                 520                 525

Gln Leu Ala Ala Tyr Tyr Ser Thr Ser Asp Lys Thr Ile Val Val Asn
                530                 535                 540

Arg Thr Asp Met Thr Ile Asp Val Gln Ser Asp Lys Arg Arg Ile Tyr
545                 550                 555                 560

Gly Val Glu Gly Ala Val Asp Tyr Phe Ile Pro Asp Ser Asp Trp Ser
                565                 570                 575

Val Gly Gly Asn Phe Asn Val Leu Lys Ser Gln Val Gln Thr Asp Gly
                580                 585                 590

Arg Trp Gln Lys Trp Asp Val Thr Leu Ala Ser Pro Ser Lys Ala Thr
                595                 600                 605

Ala Trp Val Gly Trp Ala Pro Asp Pro Trp Ser Leu Arg Val Gln Ser
                610                 615                 620

Gln Gln Val Phe Asp Leu Ser Asp Ala Ala Gly Asn Lys Leu Glu Gly
625                 630                 635                 640

Tyr Asn Thr Val Asp Phe Ile Gly Ser Tyr Ala Leu Pro Val Gly Lys
                645                 650                 655
```

Leu Thr Phe Ser Ile Glu Asn Leu Leu Asn Glu Asp Tyr Val Thr Ile
        660                 665                 670

Trp Gly Gln Arg Ala Pro Leu Tyr Ser Pro Thr Tyr Gly Ser Ser
        675                 680                 685

Ser Leu Tyr Glu Tyr Lys Gly Arg Gly Arg Thr Phe Gly Leu Asn Tyr
        690                 695                 700

Ala Leu Thr
705

<210> SEQ ID NO 50

<400> SEQUENCE: 50

000

<210> SEQ ID NO 51
<211> LENGTH: 703
<212> TYPE: PRT
<213> ORGANISM: Klebsiella pneumoniae

<400> SEQUENCE: 51

Ala Asp Ala Ala Ala Lys Gln Pro Gly Glu Glu Thr Leu Ile Val
1               5                   10                  15

Glu Ala Asn Glu Thr Ser Asp Phe Lys Ser Gly Gly Asp Leu Val Val
            20                  25                  30

Pro Ala Phe Leu Asp Gly Gln Ile Ala His Gly Gly Arg Leu Gly Met
        35                  40                  45

Leu Gly Glu Gln Lys Ala Met Asp Val Pro Phe Asn Val Ile Gly Tyr
    50                  55                  60

Thr Ser Lys Leu Ile Gln Asp Gln Gln Ala Lys Thr Ile Ala Asp Val
65                  70                  75                  80

Val Ser Asn Asp Ala Gly Val Gln Ala Val Gln Gly Tyr Gly Asn Phe
                85                  90                  95

Ala Glu Thr Tyr Arg Ile Arg Gly Phe Lys Leu Asp Gly Asp Asp Met
            100                 105                 110

Thr Met Gly Gly Leu Ala Gly Val Val Pro Arg Gln Val Met Asp Thr
        115                 120                 125

Gln Met Leu Glu Arg Val Glu Ile Phe Lys Gly Ala Asn Ser Leu Leu
    130                 135                 140

Asn Gly Ala Ala Ser Ser Gly Val Gly Gly Val Ile Tyr Leu Glu Pro
145                 150                 155                 160

Lys Arg Ala Glu Asp Leu Pro Thr Ala Arg Val Gly Val Asp Tyr Thr
                165                 170                 175

Ser Asp Ser Gln Val Gly Gly Thr Leu Asp Leu Gly Arg Arg Phe Gly
            180                 185                 190

Asp Asn Asn Gln Phe Gly Ala Arg Val Asn Leu Val His Arg Glu Gly
        195                 200                 205

Glu Gly Ala Ile Asp Asn Asp Lys Arg Arg Thr Thr Leu Ala Ser Leu
    210                 215                 220

Gly Leu Asp Tyr Arg Gly Asp Arg Phe Arg Ser Ser Leu Asp Phe Gly
225                 230                 235                 240

Tyr Gln Lys Lys Thr Phe His Gly Gly Thr Met Gly Val Asn Ile Ser
                245                 250                 255

Gly Val Asp Phe Val Pro Ala Leu Pro Asp Asn Ser Lys Asn Tyr Ser
            260                 265                 270

```
Gln Lys Trp Gly Tyr Ser Asp Ile Glu Ser Glu Phe Gly Met Ala Lys
            275                 280                 285

Ala Glu Tyr Asp Leu Thr Asp Ser Trp Thr Val Tyr Ser Ala Leu Gly
        290                 295                 300

Gly Gln His Ser His Glu Ile Gly Thr Tyr Ser Ala Pro Lys Leu Leu
305                 310                 315                 320

Asn Lys Asn Gly Asp Ala Thr Val Gly Arg Leu Asp Thr Asn Arg Ile
                325                 330                 335

Ile Asp Ala Ile Ser Gly Met Gly Gly Val Arg Gly Asp Phe Asn Thr
            340                 345                 350

Gly Ala Ile Ser His Thr Val Asn Leu Gly Tyr Ala Ala Gln Val His
        355                 360                 365

Thr Asp Ala Thr Ala Trp Arg Met Ser Ala Arg Asn Pro Thr Thr Asn
370                 375                 380

Ile Tyr Asp Asn His Asp Val Ala Met Pro Asp Asn Ala Tyr Phe Gly
385                 390                 395                 400

Gly Asn Tyr His Asp Pro Leu Val Thr Ser Arg Ser Arg Thr Gln Gly
                405                 410                 415

Trp Leu Leu Ser Asp Thr Leu Gly Phe Phe Asn Asp Lys Val Leu Phe
            420                 425                 430

Thr Ala Ala Arg His Gln Lys Val Val Arg Asn Tyr Ser Asn
                435                 440                 445

Ala Thr Gly Leu Glu Asp Thr Ser Ser Arg Tyr Thr Gln Ser Arg Trp
        450                 455                 460

Met Pro Thr Phe Gly Leu Val Tyr Lys Pro Trp Glu Gln Leu Ser Leu
465                 470                 475                 480

Tyr Ala Asn His Thr Glu Ala Leu Gln Pro Gly Ser Val Ala Pro Thr
                485                 490                 495

Thr Ala Asn Ala Gly Gln Ser Thr Gly Ile Ala His Ser Lys Gln
                500                 505                 510

Asp Glu Val Gly Val Lys Ile Asp Tyr Gly Thr Ile Gly Gly Ser Leu
            515                 520                 525

Ala Leu Phe Glu Ile Lys Lys Pro Asn Ala Ile Ser Asp Thr Ala Gly
530                 535                 540

Asn Tyr Gly Leu Asp Gly Glu Gln Arg Asn Arg Gly Val Glu Met Asn
545                 550                 555                 560

Val Phe Gly Glu Pro Met Leu Gly Leu Arg Leu Asn Ala Ser Thr Val
                565                 570                 575

Trp Leu Asp Ala Lys Gln Thr Lys Thr Ala Glu Gly Ala Thr Asp Gly
            580                 585                 590

Lys Asp Ala Ile Gly Val Ala Asn Phe Tyr Ala Val Leu Gly Ala Glu
                595                 600                 605

Tyr Asp Ile Lys Pro Val Glu Gly Leu Thr Thr Ala Arg Val Asn
610                 615                 620

His Ser Gly Ser Gln Tyr Ala Asp Ala Asn Thr Lys Lys Leu Asp
625                 630                 635                 640

Ser Tyr Thr Thr Leu Asp Leu Gly Leu Arg Tyr Arg Met Arg Leu Asn
                645                 650                 655

Ala Asp Gln Asn Glu Met Ile Trp Arg Val Gly Val Thr Asn Val Thr
            660                 665                 670

Asn Glu Lys Tyr Trp Ser Gly Ile Asp Asp Thr Gly Thr Tyr Leu Phe
        675                 680                 685

Glu Gly Asp Pro Arg Thr Val Arg Val Ser Met Ser Tyr Asp Phe
```

```
                 690                 695                 700

<210> SEQ ID NO 52
<211> LENGTH: 756
<212> TYPE: PRT
<213> ORGANISM: Klebsiella pneumoniae

<400> SEQUENCE: 52

Ala Asp Thr Ser Ala Val Ser Gly Glu Ala Val Asp Thr Ser Glu
1               5                   10                  15

Gln Met Thr Val Thr Ala Pro Ala Pro Val Gln Lys Ala Gly Ser Glu
            20                  25                  30

His Ser Ile Ser Ala Arg Glu Leu Glu Asn Lys Gly Ala Asn Asp Phe
        35                  40                  45

Gly Ser Ile Met Arg Tyr Glu Pro Leu Ile Ser Ala Thr Gly Ala Ser
    50                  55                  60

Gly Gly Ser Gly Asn Gly Lys Ser Gly Phe Asp Arg Gly Gly Tyr Thr
65                  70                  75                  80

Gly Tyr Asn Ile Arg Gly Met Glu Ser Asn Arg Val Gly Ile Asp Val
                85                  90                  95

Asp Gly Ile Ala Gln Pro Asn Ala Thr Gly Arg Gly Tyr Val Gly Arg
            100                 105                 110

Ala Gly Leu Asn Thr Phe Gly Ile Gly Arg Asp Tyr Ile Asp Pro Tyr
        115                 120                 125

Met Tyr Gly Ser Val Asp Ile Gln Ser Gly Ala Thr Ser Thr Glu Thr
130                 135                 140

Ala Asn Ser Ala Ile Gly Gly Asn Val Ser Phe Arg Pro Lys Ser Ala
145                 150                 155                 160

Asp Asp Tyr Leu Arg Pro Gly Lys Thr Ser Ala Phe Gly Tyr Arg Ser
                165                 170                 175

Gly Tyr Asp Ser Ala Asp Arg Ser Trp His Asn Gly Val Thr Val Ala
            180                 185                 190

Gly Gly Asp Glu Phe Leu Arg Gly Ile Leu Val Tyr Ser Arg Arg Asp
        195                 200                 205

Gly Gln Glu Thr Glu Asn Asn Ser Gly Thr Val Asp Ala Tyr Pro Ala
210                 215                 220

Asn Trp His Ser Asp Ala Phe Leu Ala Ser Gly Ile Trp Gln Pro Asn
225                 230                 235                 240

Asp Glu His Lys Leu Thr Ser Thr Phe Asp Tyr Tyr His Lys Thr Asn
                245                 250                 255

His Thr His Tyr Asp Thr Trp Asp Ser Ser Gly Asn Ser Thr Ile Gly
            260                 265                 270

Thr Ala Asn Gln Thr Ser Gln Thr Arg Arg Trp Gly Leu Ser Leu Lys
        275                 280                 285

Asp Asp Trp Thr Pro Met Asn Asp Tyr Leu Asp Ser Val Ser Thr Lys
290                 295                 300

Ile Tyr Tyr Gln His Thr Glu Ala His Asp Trp Tyr Met Pro Asp
305                 310                 315                 320

Ser Val Thr Arg Arg Met Gln Thr Val Asn Ser Asn Tyr Asp Thr Asp
                325                 330                 335

Thr Trp Gly Leu Gln Thr Ala Leu Ala Lys Thr Leu Gly Arg His Asp
            340                 345                 350

Leu Ser Ala Gly Phe Asn Ala Ser Thr Ser Lys Thr Gln Arg Pro Phe
        355                 360                 365
```

```
Ser Gln Ser Pro Ile Pro Ser Val Tyr Ser Glu Ile Met Gln Pro Glu
    370                 375                 380
Ala Asp Ser Arg Ser Tyr Thr Leu Gly Gly Phe Val Gln Asp Lys Ile
385                 390                 395                 400
Asn Phe Asp Leu Asp Ser His Asn Phe Ala Val Ile Pro Gly Val Arg
                405                 410                 415
Val Val His Gln Ser Thr Lys Pro Glu Asn Leu Ser Asp Leu Ala Ala
            420                 425                 430
Asn Ser Ser Val Leu Ser Glu Ser Val Ala Asn Leu Tyr Gly Lys
        435                 440                 445
Asn Ser Asp Thr Gln Val Leu Pro Ser Leu Thr Phe Gln Tyr Asp Leu
    450                 455                 460
Thr Pro Arg Leu Met Thr Tyr Leu Gln Tyr Gln Arg Gly Ala Gln Phe
465                 470                 475                 480
Pro Asn Ala Ser Gln Leu Tyr Gly Ser Trp Asn Leu Gly Ser Ser Tyr
                485                 490                 495
Ala Gly Ser Gln Gln Tyr Ala Leu Ile Gly Asn Thr Asp Leu Lys Thr
            500                 505                 510
Glu Thr Ser Asp Asn Leu Glu Trp Gly Leu Lys Gly Glu Val Thr Glu
        515                 520                 525
Gly Ile Thr Leu Arg Thr Ala Leu Phe Tyr Asn Ser Tyr Lys Asn Phe
    530                 535                 540
Ile Ala Tyr Thr Arg Tyr Thr Arg Ala Asn Asn Pro Gly Gln Phe Thr
545                 550                 555                 560
Asn Val Pro Ser Asn Ile Tyr Thr Ile Tyr Gln Ala Glu Asn Arg Asp
                565                 570                 575
Lys Ala Tyr Ile Tyr Gly Gly Glu Ile Ser Thr Lys Phe Asn Phe Gly
            580                 585                 590
Thr Trp Phe Glu Gln Val Asp Gly Leu Ser Ala Thr Leu Ala Leu Gly
        595                 600                 605
Tyr Ser Glu Gly Lys Ser Lys Ser Ser Tyr Ser Gly Asp Lys Tyr Val
    610                 615                 620
Asp Leu Asp Ser Val Ala Pro Met Lys Ala Ile Val Gly Val Ala Trp
625                 630                 635                 640
Asp Asp Pro Ala Lys Arg Tyr Gly Thr Ala Leu Thr Ala Thr Phe Val
                645                 650                 655
Lys Gly Lys Gln Ala Thr Ala Thr Asn Arg Glu Ser Tyr Ser Asn Ser
            660                 665                 670
Gly Ser Ala Ile Thr Asp Ala Ser Ser Asp Tyr Met Arg Val Pro Gly
        675                 680                 685
Tyr Gly Met Leu Asp Trp Thr Ala Tyr Trp Gln Val Ala Lys Asn Val
    690                 695                 700
Arg Leu Asn Gly Gly Val Tyr Asn Leu Thr Asp Arg Lys Tyr Trp Asp
705                 710                 715                 720
Tyr Leu Ser Ser Arg Asn Ile Glu Thr Gly Thr Asn Gln Asp Ala Asn
                725                 730                 735
Asp Lys Ala Leu Ala Val Met Pro Gly Arg Thr Trp Gln Leu Gly Val
            740                 745                 750
Asn Val Asp Phe
        755

<210> SEQ ID NO 53
<211> LENGTH: 680
<212> TYPE: PRT
```

<213> ORGANISM: Klebsiella pneumoniae

<400> SEQUENCE: 53

```
Glu Glu Thr Val Val Thr Ala Thr Pro Ala Ser Ala Ser Ala
1               5                   10                  15

Pro Thr Glu Gly Tyr Ser Ala Ser Thr Ser Leu Gly Ala Thr Lys Thr
            20                  25                  30

Asp Gln Pro Leu Ile Thr Thr Ala Gln Ser Val Ser Val Thr Arg
        35                  40                  45

Gln Gln Met Ala Asp Gln Gly Ala Asn Thr Ile Ser Gln Ala Leu Glu
    50                  55                  60

Tyr Thr Pro Gly Val Tyr Ser Ser Phe Gly Gly Ala Thr Arg Phe
65                  70                  75                  80

Asp Ala Ile Ser Leu Arg Gly Tyr His Gly Asp Val Asp Asn Leu
                85                  90                  95

Phe Leu Asp Gly Met Arg Leu Met Ser Asp Gly Gly Ser His Asn Val
                100                 105                 110

Leu Gln Ile Asp Pro Trp Phe Ile Glu Arg Val Asp Val Ile Arg Gly
            115                 120                 125

Pro Ser Ser Ala Leu Tyr Gly Gln Ser Val Pro Gly Gly Val Val Asn
130                 135                 140

Leu Thr Ser Lys Arg Pro Gln Phe Ser Gln Gln Gly His Ile Arg Leu
145                 150                 155                 160

Thr Gly Gly Thr Gln Asn Thr Lys Gly Ala Ala Phe Asp Tyr Thr Asp
                165                 170                 175

Ala Ile Asn Asp Gln Trp Ala Trp Arg Leu Ile Gly Met Thr Arg Ser
            180                 185                 190

Ser Asp Thr Gln Tyr Asp His Thr Arg Glu Glu Arg Tyr Ala Ile Ser
        195                 200                 205

Pro Ser Leu Leu Trp Gln Pro Asp Ser Asp Thr Ser Leu Leu Leu Arg
210                 215                 220

Ala Tyr Leu Gln Lys Asp Pro Ser Gly Gly Tyr His Gly Ser Leu Pro
225                 230                 235                 240

Leu Asp Gly Thr Arg Tyr Ala His Asn Gly Arg Lys Leu Ser Pro Ser
                245                 250                 255

Thr Asn Glu Gly Asp Pro Gly Asp Gly Tyr Gln Arg Arg Gln Gln Ile
            260                 265                 270

Tyr Ser Tyr Glu Phe Asp His Gln Phe Thr Asp Val Trp Ser Val Tyr
        275                 280                 285

Ser Ala Gly Ser Tyr Thr His Thr Asn Val Ser Leu Asp Gln Val Tyr
    290                 295                 300

Gln Val Gly Trp Ile Asp Glu Ser Asp Met Leu Ala Arg Gly Tyr Ser
305                 310                 315                 320

Gly Ser Arg Gly Ser Leu Asp Gly Trp Ser Thr Asp Asn Arg Leu Arg
                325                 330                 335

Ala Asp Phe Asn Thr Gly Asp Leu Ala His Thr Leu Ile Leu Gly Ala
            340                 345                 350

Glu Tyr His Arg Phe Arg Asn Asp Leu Trp Thr Gly Ala Gly Gly Ala
        355                 360                 365

Ala Pro Leu Asn Pro Phe Ser Gly Tyr Thr Glu Gln Thr Gly His Thr
    370                 375                 380

Val Thr Tyr Ser Asp Asp Asn Asn Arg Arg Tyr Tyr Gln Thr Gly Leu
385                 390                 395                 400
```

```
Tyr Leu Gln Asp Glu Met Val Trp Asn Arg Trp His Val Asp Val Ser
            405                 410                 415

Ala Arg Tyr Asp Arg Ile Val Ser Gln Gln Val Ser Asp Thr Gln Gly
        420                 425                 430

Thr Ser Asn Arg Arg Ser Asp Asp His Ile Ser Gly Arg Ala Ser Leu
    435                 440                 445

Leu Tyr Ala Leu Asp Asn Gly Leu Ser Pro Tyr Leu Ser Tyr Ser Gln
450                 455                 460

Ala Ile Thr Pro Ala Met Leu Pro Gly Ala Asp Gly Lys Pro Leu Lys
465                 470                 475                 480

Pro Thr Thr Ala Glu Gln Val Glu Ala Gly Leu Lys Phe Gln Pro Pro
                485                 490                 495

Gly Ser Ser Asp Leu Tyr Ser Ile Ala Ile Tyr Asp Leu Thr Gln Lys
            500                 505                 510

Asp Val Ala Thr Arg Asp Pro Asn Ile Ala Thr Ala Thr Tyr Ile Pro
        515                 520                 525

Ala Gly Lys Val His Ser Gln Gly Val Glu Leu Glu Ala His His Gln
    530                 535                 540

Ile Thr Pro Gln Leu Ser Thr Ile Ala Ser Tyr Thr Trp Asn Arg Leu
545                 550                 555                 560

Arg Phe Gln Asp Thr Gln Asp Gly Thr Asp Asn Asn Thr Pro Gln Leu
                565                 570                 575

Thr Pro Asp Gln Met Ala Ser Phe Trp Ala Arg Tyr Gln Phe Pro Ala
            580                 585                 590

Gly Ile Ser Val Gly Ala Gly Val Arg Tyr Ile Gly Lys Gln Trp Ala
        595                 600                 605

Asp Asp Ala Asn Thr Ala Arg Leu Pro Ser Val Thr Leu Met Asp Ala
    610                 615                 620

Met Met Arg Ala Asp Leu Gly Val Trp Ser Pro Thr Leu Lys Gly Ala
625                 630                 635                 640

Tyr Val Gln Val Asn Ala Asn Asn Ile Gly Asp Arg Glu Tyr Ile Ser
                645                 650                 655

Gly Cys Tyr Gly Thr Gly Asn Cys Tyr Trp Gly Ala Glu Arg Ser Val
            660                 665                 670

Ile Ala Thr Val Gly Tyr Asp Phe
        675                 680

<210> SEQ ID NO 54
<211> LENGTH: 346
<212> TYPE: PRT
<213> ORGANISM: Klebsiella pneumoniae

<400> SEQUENCE: 54

Ala Glu Ile Tyr Asn Lys Asp Gly Asn Lys Leu Asp Leu Tyr Gly Lys
1               5                   10                  15

Ile Asp Gly Leu His Tyr Phe Ser Asp Lys Ser Val Asp Gly Asp
            20                  25                  30

Gln Thr Tyr Met Arg Val Gly Val Lys Gly Glu Thr Gln Ile Asn Asp
        35                  40                  45

Gln Leu Thr Gly Tyr Gly Gln Trp Glu Tyr Asn Val Gln Ala Asn Asn
    50                  55                  60

Thr Glu Ser Ser Ser Asp Gln Ala Trp Thr Arg Leu Ala Phe Ala Gly
65                  70                  75                  80

Leu Lys Phe Gly Asp Ala Gly Ser Phe Asp Tyr Gly Arg Asn Tyr Gly
                85                  90                  95
```

```
Val Val Tyr Asp Val Thr Ser Trp Thr Asp Val Leu Pro Glu Phe Gly
            100                 105                 110

Gly Asp Thr Tyr Gly Ser Asp Asn Phe Leu Gln Ser Arg Ala Asn Gly
        115                 120                 125

Val Ala Thr Tyr Arg Asn Ser Asp Phe Phe Gly Leu Val Asp Gly Leu
    130                 135                 140

Asn Phe Ala Leu Gln Tyr Gln Gly Lys Asn Gly Ser Val Ser Gly Glu
145                 150                 155                 160

Gly Ala Leu Ser Pro Thr Asn Asn Gly Arg Thr Ala Leu Lys Gln Asn
                165                 170                 175

Gly Asp Gly Tyr Gly Thr Ser Leu Thr Tyr Asp Ile Tyr Asp Gly Ile
            180                 185                 190

Ser Ala Gly Phe Ala Tyr Ser Asn Ser Lys Arg Leu Gly Asp Gln Asn
        195                 200                 205

Ser Lys Leu Ala Leu Gly Arg Gly Asp Asn Ala Glu Thr Tyr Thr Gly
    210                 215                 220

Gly Leu Lys Tyr Asp Ala Asn Asn Ile Tyr Leu Ala Thr Gln Tyr Thr
225                 230                 235                 240

Gln Thr Tyr Asn Ala Thr Arg Ala Gly Ser Leu Gly Phe Ala Asn Lys
                245                 250                 255

Ala Gln Asn Phe Glu Val Val Ala Gln Tyr Gln Phe Asp Phe Gly Leu
            260                 265                 270

Arg Pro Ser Val Ala Tyr Leu Gln Ser Lys Gly Lys Asp Leu Glu Gly
        275                 280                 285

Tyr Gly Asp Gln Asp Ile Leu Lys Tyr Val Asp Val Gly Ala Thr Tyr
    290                 295                 300

Tyr Phe Asn Lys Asn Met Ser Thr Tyr Val Asp Tyr Lys Ile Asn Leu
305                 310                 315                 320

Leu Asp Asp Asn Ser Phe Thr His Asn Ala Gly Ile Ser Thr Asp Asp
                325                 330                 335

Val Val Ala Leu Gly Leu Val Tyr Gln Phe
            340                 345

<210> SEQ ID NO 55
<211> LENGTH: 335
<212> TYPE: PRT
<213> ORGANISM: Klebsiella pneumoniae

<400> SEQUENCE: 55

Ala Pro Lys Asp Asn Thr Trp Tyr Ala Gly Gly Lys Leu Gly Trp Ser
1               5                   10                  15

Gln Tyr His Asp Thr Gly Phe Tyr Gly Asn Gly Phe Gln Asn Asn Asn
                20                  25                  30

Gly Pro Thr Arg Asn Asp Gln Leu Gly Ala Gly Ala Phe Gly Gly Tyr
            35                  40                  45

Gln Val Asn Pro Tyr Leu Gly Phe Glu Met Gly Tyr Asp Trp Leu Gly
        50                  55                  60

Arg Met Ala Tyr Lys Gly Ser Val Asp Asn Gly Ala Phe Lys Ala Gln
65                  70                  75                  80

Gly Val Gln Leu Thr Ala Lys Leu Gly Tyr Pro Ile Thr Asp Asp Leu
                85                  90                  95

Asp Ile Tyr Thr Arg Leu Gly Gly Met Val Trp Arg Ala Asp Ser Lys
            100                 105                 110

Gly Asn Tyr Ala Ser Thr Gly Val Ser Arg Ser Glu His Asp Thr Gly
```

```
            115                 120                 125
Val Ser Pro Val Phe Ala Gly Gly Val Glu Trp Ala Val Thr Arg Asp
    130                 135                 140

Ile Ala Thr Arg Leu Glu Tyr Gln Trp Val Asn Asn Ile Gly Asp Ala
145                 150                 155                 160

Gly Thr Val Gly Thr Arg Pro Asp Asn Gly Met Leu Ser Leu Gly Val
                165                 170                 175

Ser Tyr Arg Phe Gly Gln Glu Asp Ala Ala Pro Val Val Ala Pro Ala
            180                 185                 190

Pro Ala Pro Ala Pro Glu Val Ala Thr Lys His Phe Thr Leu Lys Ser
        195                 200                 205

Asp Val Leu Phe Asn Phe Asn Lys Ala Thr Leu Lys Pro Glu Gly Gln
    210                 215                 220

Gln Ala Leu Asp Gln Leu Tyr Thr Gln Leu Ser Asn Met Asp Pro Lys
225                 230                 235                 240

Asp Gly Ser Ala Val Val Leu Gly Tyr Thr Asp Arg Ile Gly Ser Glu
                245                 250                 255

Ala Tyr Asn Gln Gln Leu Ser Glu Lys Arg Ala Gln Ser Val Val Asp
            260                 265                 270

Tyr Leu Val Ala Lys Gly Ile Pro Ala Gly Lys Ile Ser Ala Arg Gly
        275                 280                 285

Met Gly Glu Ser Asn Pro Val Thr Gly Asn Thr Cys Asp Asn Val Lys
    290                 295                 300

Ala Arg Ala Ala Leu Ile Asp Cys Leu Ala Pro Asp Arg Arg Val Glu
305                 310                 315                 320

Ile Glu Val Lys Gly Tyr Lys Glu Val Val Thr Gln Pro Ala Ala
                325                 330                 335

<210> SEQ ID NO 56
<211> LENGTH: 1983
<212> TYPE: DNA
<213> ORGANISM: Escherichia coli

<400> SEQUENCE: 56
atgagaggat cgcatcacca tcaccatcac ggatctggct ctggatctgg tatcgaggga      60
aggcctgtcg atgatgatgg cgaaacgatg gttgtcactg catcttccgt gaacaaaaac     120
cttaaagatg ctcccgccag tatcagcgtc attacccagg aagacctgca gcgaaaaccg     180
gtacagaatc tgaaggatgt cctcaaagaa gtgcctggcg tacaactgac gaacgaaggg     240
gataaccgta agggcgtaag tattcgtggt ctggacagca gctacaccct gattcttgtc     300
gacggtaaac gcgttaactc ccgcaatgcc gtcttccgcc acaatgattt cgatctgaac     360
tggatcccgg tcgattccat cgaacgtatt gaagtggttc gtggcccgat gtcgtcgctg     420
tacggttccg atgcgctcgg cggtgtagtg aatatcatca ccaaaaaaat cggtcagaaa     480
tggtcgggca ccgttaccgt cgataccacc gttcaggaac atcgcgatcg cggtgatacc     540
tataacggtc aattctttac cagcggacca ttaattgacg gcgtgctggg aatgaaagct     600
tacggcagcc tggcaaaacg tgaaaaggat gacccgcaaa actcaacgac caccgatacc     660
ggagaaacgc cgcgtattga aggattctcc agccgcgacg gcaatgtcga atttgcctgg     720
acaccgaatc aaaatcacga tttttactgc cggatacggtt cgaccgtca ggatcgtgat     780 tccgactcgc tggacaaaaa ccgcctggaa cgccagaact actccgtcag ccataatggg     840
cgttgggatt acggcaccag cgaactgaaa tactacggtg agaaagtcga gaacaaaaac     900
```

-continued

```
cctggcaaca gcagcccgat aacttccgaa agcaatacgg tcgacggcaa atacacgttg      960
ccgctgacgg cgattaatca gtttctcacg gttggcggtg aatggcgtca cgacaaactt     1020
agcgatgcgg tgaacctgac cggggggaacc agctccaaaa cgtctgccag ccagtacgcg     1080
ctgtttgtgg aagatgaatg gcggatcttc gagccgctgg cgctgacgac cggcgtgcgt     1140
atggacgatc acgaaaccta cggtgaacac tggagtccgc gtgcctacct ggtttataac     1200
gccaccgaca ccgtaacggt gaaagggggc tgggcgacgg catttaaagc cccttctctg     1260
ttgcaactta gccctgactg gacgagcaat tcctgccgtg gcgcatgtaa gattgtgggt     1320
agcccggatc tgaaaccaga aaccagcgaa agttgggagc tggggcttta ctacatgggt     1380
gaagaaggct ggctggaagg ggttgaatcc agcgttaccg ttttccgtaa cgatgtgaaa     1440
gatcgtatca gcattagccg tacgtctgac gtcaatgctg caccgggcta ccaaaacttt     1500
gtcggttttg agacgggcgc taacggacgg cgcataccgg tatttagcta ctacaacgtt     1560
aacaaagctc gtattcaggg cgtggaaacc gaactgaaaa ttccgttcaa cgatgaatgg     1620
aaactgtcga tcaactacac ctacaacgat ggtcgtgatg tcagcaacgg cgaaaacaaa     1680
ccgctatccg atctgccgtt ccatactgct aacggtacgc tggactggaa accgctggcg     1740
ctggaagact ggtcattcta tgtttctggt cactataccg gcagaaacg cgccgacagc     1800 gcgacggcta aaacaccggg cggttatacc atctggaata ccggcgcggc ctggcaggtg     1860
actaaagacg tcaaactgcg cgcaggcgtg ctgaaccttg cgacaagga tctcagtcgt     1920 gacgactaca gctataacga agacggacgt cgttacttta tggcagtgga ttatcgcttc     1980
tga                                                                  1983
```

<210> SEQ ID NO 57
<211> LENGTH: 660
<212> TYPE: PRT
<213> ORGANISM: Escherichia coli

<400> SEQUENCE: 57

```
Met Arg Gly Ser His His His His His His Gly Ser Gly Ser Gly Ser
1               5                   10                  15

Gly Ile Glu Gly Arg Pro Val Asp Asp Gly Glu Thr Met Val Val
            20                  25                  30

Thr Ala Ser Ser Val Glu Gln Asn Leu Lys Asp Ala Pro Ala Ser Ile
        35                  40                  45

Ser Val Ile Thr Gln Glu Asp Leu Gln Arg Lys Pro Val Gln Asn Leu
    50                  55                  60

Lys Asp Val Leu Lys Glu Val Pro Gly Val Gln Leu Thr Asn Glu Gly
65                  70                  75                  80

Asp Asn Arg Lys Gly Val Ser Ile Arg Gly Leu Asp Ser Ser Tyr Thr
                85                  90                  95

Leu Ile Leu Val Asp Gly Lys Arg Val Asn Ser Arg Asn Ala Val Phe
            100                 105                 110

Arg His Asn Asp Phe Asp Leu Asn Trp Ile Pro Val Asp Ser Ile Glu
        115                 120                 125

Arg Ile Glu Val Val Arg Gly Pro Met Ser Ser Leu Tyr Gly Ser Asp
    130                 135                 140

Ala Leu Gly Gly Val Val Asn Ile Ile Thr Lys Lys Ile Gly Gln Lys
145                 150                 155                 160

Trp Ser Gly Thr Val Thr Val Asp Thr Thr Val Gln Glu His Arg Asp
                165                 170                 175
```

```
Arg Gly Asp Thr Tyr Asn Gly Gln Phe Phe Thr Ser Gly Pro Leu Ile
            180                 185                 190

Asp Gly Val Leu Gly Met Lys Ala Tyr Gly Ser Leu Ala Lys Arg Glu
        195                 200                 205

Lys Asp Asp Pro Gln Asn Ser Thr Thr Asp Thr Gly Glu Thr Pro
210                 215                 220

Arg Ile Glu Gly Phe Ser Ser Arg Asp Gly Asn Val Glu Phe Ala Trp
225                 230                 235                 240

Thr Pro Asn Gln Asn His Asp Phe Thr Ala Gly Tyr Gly Phe Asp Arg
                245                 250                 255

Gln Asp Arg Asp Ser Asp Ser Leu Asp Lys Asn Arg Leu Glu Arg Gln
        260                 265                 270

Asn Tyr Ser Val Ser His Asn Gly Arg Trp Asp Tyr Gly Thr Ser Glu
            275                 280                 285

Leu Lys Tyr Tyr Gly Glu Lys Val Glu Asn Lys Asn Pro Gly Asn Ser
        290                 295                 300

Ser Pro Ile Thr Ser Glu Ser Asn Thr Val Asp Gly Lys Tyr Thr Leu
305                 310                 315                 320

Pro Leu Thr Ala Ile Asn Gln Phe Leu Thr Val Gly Gly Glu Trp Arg
                325                 330                 335

His Asp Lys Leu Ser Asp Ala Val Asn Leu Thr Gly Gly Thr Ser Ser
            340                 345                 350

Lys Thr Ser Ala Ser Gln Tyr Ala Leu Phe Val Glu Asp Glu Trp Arg
        355                 360                 365

Ile Phe Glu Pro Leu Ala Leu Thr Thr Gly Val Arg Met Asp Asp His
    370                 375                 380

Glu Thr Tyr Gly Glu His Trp Ser Pro Arg Ala Tyr Leu Val Tyr Asn
385                 390                 395                 400

Ala Thr Asp Thr Val Thr Val Lys Gly Gly Trp Ala Thr Ala Phe Lys
                405                 410                 415

Ala Pro Ser Leu Leu Gln Leu Ser Pro Asp Trp Thr Ser Asn Ser Cys
            420                 425                 430

Arg Gly Ala Cys Lys Ile Val Gly Ser Pro Asp Leu Lys Pro Glu Thr
        435                 440                 445

Ser Glu Ser Trp Glu Leu Gly Leu Tyr Tyr Met Gly Glu Glu Gly Trp
    450                 455                 460

Leu Glu Gly Val Glu Ser Ser Val Thr Val Phe Arg Asn Asp Val Lys
465                 470                 475                 480

Asp Arg Ile Ser Ile Ser Arg Thr Ser Asp Val Asn Ala Ala Pro Gly
                485                 490                 495

Tyr Gln Asn Phe Val Gly Phe Glu Thr Gly Ala Asn Gly Arg Arg Ile
            500                 505                 510

Pro Val Phe Ser Tyr Tyr Asn Val Asn Lys Ala Arg Ile Gln Gly Val
        515                 520                 525

Glu Thr Glu Leu Lys Ile Pro Phe Asn Asp Glu Trp Lys Leu Ser Ile
    530                 535                 540

Asn Tyr Thr Tyr Asn Asp Gly Arg Asp Val Ser Asn Gly Glu Asn Lys
545                 550                 555                 560

Pro Leu Ser Asp Leu Pro Phe His Thr Ala Asn Gly Thr Leu Asp Trp
                565                 570                 575

Lys Pro Leu Ala Leu Glu Asp Trp Ser Phe Tyr Val Ser Gly His Tyr
            580                 585                 590

Thr Gly Gln Lys Arg Ala Asp Ser Ala Thr Ala Lys Thr Pro Gly Gly
```

```
                  595                 600                 605

Tyr Thr Ile Trp Asn Thr Gly Ala Ala Trp Gln Val Thr Lys Asp Val
            610                 615                 620

Lys Leu Arg Ala Gly Val Leu Asn Leu Gly Asp Lys Asp Leu Ser Arg
625                 630                 635                 640

Asp Asp Tyr Ser Tyr Asn Glu Asp Gly Arg Arg Tyr Phe Met Ala Val
                645                 650                 655

Asp Tyr Arg Phe
            660

<210> SEQ ID NO 58
<211> LENGTH: 638
<212> TYPE: PRT
<213> ORGANISM: Escherichia coli

<400> SEQUENCE: 58

Val Asp Asp Gly Glu Thr Met Val Val Thr Ala Ser Ser Val Glu
1               5                  10                  15

Gln Asn Leu Lys Asp Ala Pro Ala Ser Ile Ser Val Ile Thr Gln Glu
            20                  25                  30

Asp Leu Gln Arg Lys Pro Val Gln Asn Leu Lys Asp Val Leu Lys Glu
        35                  40                  45

Val Pro Gly Val Gln Leu Thr Asn Glu Gly Asp Asn Arg Lys Gly Val
    50                  55                  60

Ser Ile Arg Gly Leu Asp Ser Ser Tyr Thr Leu Ile Leu Val Asp Gly
65                  70                  75                  80

Lys Arg Val Asn Ser Arg Asn Ala Val Phe Arg His Asn Asp Phe Asp
                85                  90                  95

Leu Asn Trp Ile Pro Val Asp Ser Ile Glu Arg Ile Glu Val Val Arg
            100                 105                 110

Gly Pro Met Ser Ser Leu Tyr Gly Ser Asp Ala Leu Gly Gly Val Val
        115                 120                 125

Asn Ile Ile Thr Lys Lys Ile Gly Gln Lys Trp Ser Gly Thr Val Thr
    130                 135                 140

Val Asp Thr Thr Val Gln Glu His Arg Asp Arg Gly Asp Thr Tyr Asn
145                 150                 155                 160

Gly Gln Phe Phe Thr Ser Gly Pro Leu Ile Asp Gly Val Leu Gly Met
                165                 170                 175

Lys Ala Tyr Gly Ser Leu Ala Lys Arg Glu Lys Asp Asp Pro Gln Asn
            180                 185                 190

Ser Thr Thr Thr Asp Thr Gly Glu Thr Pro Arg Ile Glu Gly Phe Ser
        195                 200                 205

Ser Arg Asp Gly Asn Val Glu Phe Ala Trp Thr Pro Asn Gln Asn His
    210                 215                 220

Asp Phe Thr Ala Gly Tyr Gly Phe Asp Arg Gln Asp Arg Asp Ser Asp
225                 230                 235                 240

Ser Leu Asp Lys Asn Arg Leu Glu Arg Gln Asn Tyr Ser Val Ser His
                245                 250                 255

Asn Gly Arg Trp Asp Tyr Gly Thr Ser Glu Leu Lys Tyr Tyr Gly Glu
            260                 265                 270

Lys Val Glu Asn Lys Asn Pro Gly Asn Ser Ser Pro Ile Thr Ser Glu
        275                 280                 285

Ser Asn Thr Val Asp Gly Lys Tyr Thr Leu Pro Leu Thr Ala Ile Asn
    290                 295                 300
```

Gln Phe Leu Thr Val Gly Gly Glu Trp Arg His Asp Lys Leu Ser Asp
305                 310                 315                 320

Ala Val Asn Leu Thr Gly Gly Thr Ser Ser Lys Thr Ser Ala Ser Gln
            325                 330                 335

Tyr Ala Leu Phe Val Glu Asp Glu Trp Arg Ile Phe Glu Pro Leu Ala
        340                 345                 350

Leu Thr Thr Gly Val Arg Met Asp Asp His Glu Thr Tyr Gly Glu His
    355                 360                 365

Trp Ser Pro Arg Ala Tyr Leu Val Tyr Asn Ala Thr Asp Thr Val Thr
370                 375                 380

Val Lys Gly Gly Trp Ala Thr Ala Phe Lys Ala Pro Ser Leu Leu Gln
385                 390                 395                 400

Leu Ser Pro Asp Trp Thr Ser Asn Ser Cys Arg Gly Ala Cys Lys Ile
            405                 410                 415

Val Gly Ser Pro Asp Leu Lys Pro Glu Thr Ser Glu Ser Trp Glu Leu
        420                 425                 430

Gly Leu Tyr Tyr Met Gly Glu Glu Gly Trp Leu Glu Gly Val Glu Ser
    435                 440                 445

Ser Val Thr Val Phe Arg Asn Asp Val Lys Asp Arg Ile Ser Ile Ser
450                 455                 460

Arg Thr Ser Asp Val Asn Ala Ala Pro Gly Tyr Gln Asn Phe Val Gly
465                 470                 475                 480

Phe Glu Thr Gly Ala Asn Gly Arg Arg Ile Pro Val Phe Ser Tyr Tyr
            485                 490                 495

Asn Val Asn Lys Ala Arg Ile Gln Gly Val Glu Thr Glu Leu Lys Ile
        500                 505                 510

Pro Phe Asn Asp Glu Trp Lys Leu Ser Ile Asn Tyr Thr Tyr Asn Asp
    515                 520                 525

Gly Arg Asp Val Ser Asn Gly Glu Asn Lys Pro Leu Ser Asp Leu Pro
530                 535                 540

Phe His Thr Ala Asn Gly Thr Leu Asp Trp Lys Pro Leu Ala Leu Glu
545                 550                 555                 560

Asp Trp Ser Phe Tyr Val Ser Gly His Tyr Thr Gly Gln Lys Arg Ala
            565                 570                 575

Asp Ser Ala Thr Ala Lys Thr Pro Gly Gly Tyr Thr Ile Trp Asn Thr
        580                 585                 590

Gly Ala Ala Trp Gln Val Thr Lys Asp Val Lys Leu Arg Ala Gly Val
    595                 600                 605

Leu Asn Leu Gly Asp Lys Asp Leu Ser Arg Asp Tyr Ser Tyr Asn
610                 615                 620

Glu Asp Gly Arg Arg Tyr Phe Met Ala Val Asp Tyr Arg Phe
625                 630                 635

<210> SEQ ID NO 59
<211> LENGTH: 2241
<212> TYPE: DNA
<213> ORGANISM: Escherichia coli

<400> SEQUENCE: 59
atgagaggat cgcatcacca tcaccatcac ggatctggct ctggatctgg tatcgaggga      60
aggcctcaag agccgaccga tactcctgtt tcacatgacg ataccattgt cgttaccgcc     120
gccgagcaga acttgcaggc gcctggcgtt tcgaccatta ccgcagatga atccgcaaa      180 aacccggttg cccgcgatgt atcggagatc attcgtacca tgcctggcgt taacctgacc     240

```
ggtaactcca ccagtggtca gcgtggtaat aaccgccaga ttgatattcg cggcatgggt    300
ccggaaaaca cgctgatttt gattgacggc aagccggtaa gcagccgtaa ctctgtgcgt    360
cagggctggc gtggcgagcg cgatacccgt ggtgatacct cctgggtgcc gcctgaaatg    420
attgaacgta ttgaagttct gcgtggtccg cagctgcgc gttatggcaa cggcgcggcg     480
ggcggcgtgg ttaacatcat taccaaaaaa ggcagcggtg agtggcacgg ctcctgggat    540
gcttatttca atgcgccaga acataaagag gaaggtgcca ccaaacgcac caacttcagc    600
ctgaccggtc cgctgggcga cgaattcagc ttccgcttgt atggcaacct cgacaaaacc    660
caggctgacg cgtgggatat caaccagggc catcagtccg cgcgtgccgg aacgtatgcc    720
acgacgttac cagccgggcg cgaaggggtg atcaacaaag atattaatgg cgtggtgcgc    780
tgggacttcg cgcctctgca gtcactcgaa ctggaagcgg gctacagccg ccagggtaac    840
ctgtatgcgg gtgatacgca gaacaccaac tctgacgctt acactcgatc gaaatatggc    900
gatgaaacca accgcctgta tcgccagaac tactcgctga cctggaacgg tggctgggat    960
aacggcgtga ccaccagcaa ctgggtgcag tacgaacaca cccgtaactc gcgtattccg   1020
gaaggtctgg cgggcggtac cgaagggaaa tttaacgaaa aagcggcaca ggattttgta   1080
gatatcgatc ttgatgacgt gatgctgcac agcgaagtta acctgccgat tgatttcctc   1140
gtaaaccaaa cgctgacgct gggtacagag tggaatcagc aacggatgaa ggacttaagt   1200
tccaacaccc aggcgctgac cgggacgaat accggcggtg ctattgatgg tgtgagtgcc   1260
accgaccgta gcccgtattc aaaagcagaa attttctcgc tgtttgccga aaacaatatg   1320
gagctgactg acagcaccat cgtaacgccg gggctgcgtt tcgatcatca cagtattgtc   1380
ggcaataact ggagcccggc gctgaacata tcgcaaggtt aggcgatga cttcacgctg    1440
aaaatgggca tcgcccgcgc ctataaagcg ccgagcctgt accagactaa cccaaactac   1500
attctctaca gtaaaggtca gggctgctat gccagcgcgg gcggctgcta tctgcaaggt   1560
aatgatgacc tgaaagcaga aaccagcatc aacaaggaga ttggtctgga gttcaaacgc   1620
gacggttggc tggcgggcgt gacctggttc cgtaacgatt atcgcaataa gattgaagcg   1680
ggctatgtgg ctgtagggca aaacgcagtc ggcaccgatc tctatcagtg ggataacgta   1740
ccgaaagcgg tggttgaagg tctggaagga tcgttaaacg taccggttag cgaaacggtg   1800
atgtggacca ataacatcac ttatatgctg aagagtgaaa acaaaaccac gggcgaccgt   1860
ttgtcgatca tcccggagta tacgttgaac tcaacgctga gctggcaggc acgggaagat   1920
ttgtcgatgc aaacgacctt cacctggtac ggcaaacagc agccgaagaa gtacaactat   1980
aaaggtcagc cagcggttgg accggaaacc aaagaaatca gtccgtacag cattgttggc   2040
ctgagcgcga cctgggatgt gacgaagaat gtcagtctga ccggcggcgt ggacaacctg   2100
ttcgacaaac gtttgtggcg tgcgggtaat gcccagacca cggcgatct ggcaggggcc    2160
aactatatcg ccggtgccgg tgcgtatacc tataacgagc cgggacgtac gtggtatatg   2220
agcattaata ctcacttctg a                                             2241
```

<210> SEQ ID NO 60
<211> LENGTH: 746
<212> TYPE: PRT
<213> ORGANISM: Escherichia coli

<400> SEQUENCE: 60

Met Arg Gly Ser His His His His His His Gly Ser Gly Ser Gly Ser
1               5                   10                  15

-continued

```
Gly Ile Glu Gly Arg Pro Gln Glu Pro Thr Asp Thr Pro Val Ser His
        20                  25                  30

Asp Asp Thr Ile Val Val Thr Ala Ala Glu Gln Asn Leu Gln Ala Pro
            35                  40                  45

Gly Val Ser Thr Ile Thr Ala Asp Glu Ile Arg Lys Asn Pro Val Ala
    50                  55                  60

Arg Asp Val Ser Glu Ile Ile Arg Thr Met Pro Gly Val Asn Leu Thr
65                  70                  75                  80

Gly Asn Ser Thr Ser Gly Gln Arg Gly Asn Asn Arg Gln Ile Asp Ile
                85                  90                  95

Arg Gly Met Gly Pro Glu Asn Thr Leu Ile Leu Ile Asp Gly Lys Pro
            100                 105                 110

Val Ser Ser Arg Asn Ser Val Arg Gln Gly Trp Arg Gly Glu Arg Asp
        115                 120                 125

Thr Arg Gly Asp Thr Ser Trp Val Pro Pro Glu Met Ile Glu Arg Ile
    130                 135                 140

Glu Val Leu Arg Gly Pro Ala Ala Ala Arg Tyr Gly Asn Gly Ala Ala
145                 150                 155                 160

Gly Gly Val Val Asn Ile Ile Thr Lys Lys Gly Ser Gly Glu Trp His
                165                 170                 175

Gly Ser Trp Asp Ala Tyr Phe Asn Ala Pro Glu His Lys Glu Glu Gly
            180                 185                 190

Ala Thr Lys Arg Thr Asn Phe Ser Leu Thr Gly Pro Leu Gly Asp Glu
        195                 200                 205

Phe Ser Phe Arg Leu Tyr Gly Asn Leu Asp Lys Thr Gln Ala Asp Ala
    210                 215                 220

Trp Asp Ile Asn Gln Gly His Gln Ser Ala Arg Ala Gly Thr Tyr Ala
225                 230                 235                 240

Thr Thr Leu Pro Ala Gly Arg Glu Gly Val Ile Asn Lys Asp Ile Asn
                245                 250                 255

Gly Val Val Arg Trp Asp Phe Ala Pro Leu Gln Ser Leu Glu Leu Glu
            260                 265                 270

Ala Gly Tyr Ser Arg Gln Gly Asn Leu Tyr Ala Gly Asp Thr Gln Asn
        275                 280                 285

Thr Asn Ser Asp Ala Tyr Thr Arg Ser Lys Tyr Gly Asp Glu Thr Asn
    290                 295                 300

Arg Leu Tyr Arg Gln Asn Tyr Ser Leu Thr Trp Asn Gly Gly Trp Asp
305                 310                 315                 320

Asn Gly Val Thr Thr Ser Asn Trp Val Gln Tyr Glu His Thr Arg Asn
                325                 330                 335

Ser Arg Ile Pro Glu Gly Leu Ala Gly Gly Thr Glu Gly Lys Phe Asn
            340                 345                 350

Glu Lys Ala Ala Gln Asp Phe Val Asp Ile Asp Leu Asp Asp Val Met
        355                 360                 365

Leu His Ser Glu Val Asn Leu Pro Ile Asp Phe Leu Val Asn Gln Thr
    370                 375                 380

Leu Thr Leu Gly Thr Glu Trp Asn Gln Gln Arg Met Lys Asp Leu Ser
385                 390                 395                 400

Ser Asn Thr Gln Ala Leu Thr Gly Thr Asn Thr Gly Gly Ala Ile Asp
                405                 410                 415

Gly Val Ser Ala Thr Asp Arg Ser Pro Tyr Ser Lys Ala Glu Ile Phe
            420                 425                 430

Ser Leu Phe Ala Glu Asn Asn Met Glu Leu Thr Asp Ser Thr Ile Val
```

435                 440                 445
Thr Pro Gly Leu Arg Phe Asp His His Ser Ile Val Gly Asn Asn Trp
    450                 455                 460

Ser Pro Ala Leu Asn Ile Ser Gln Gly Leu Gly Asp Asp Phe Thr Leu
465                 470                 475                 480

Lys Met Gly Ile Ala Arg Ala Tyr Lys Ala Pro Ser Leu Tyr Gln Thr
                485                 490                 495

Asn Pro Asn Tyr Ile Leu Tyr Ser Lys Gly Gln Gly Cys Tyr Ala Ser
            500                 505                 510

Ala Gly Gly Cys Tyr Leu Gln Gly Asn Asp Asp Leu Lys Ala Glu Thr
        515                 520                 525

Ser Ile Asn Lys Glu Ile Gly Leu Glu Phe Lys Arg Asp Gly Trp Leu
    530                 535                 540

Ala Gly Val Thr Trp Phe Arg Asn Asp Tyr Arg Asn Lys Ile Glu Ala
545                 550                 555                 560

Gly Tyr Val Ala Val Gly Gln Asn Ala Val Gly Thr Asp Leu Tyr Gln
                565                 570                 575

Trp Asp Asn Val Pro Lys Ala Val Val Glu Gly Leu Glu Gly Ser Leu
            580                 585                 590

Asn Val Pro Val Ser Glu Thr Val Met Trp Thr Asn Asn Ile Thr Tyr
        595                 600                 605

Met Leu Lys Ser Glu Asn Lys Thr Thr Gly Asp Arg Leu Ser Ile Ile
    610                 615                 620

Pro Glu Tyr Thr Leu Asn Ser Thr Leu Ser Trp Gln Ala Arg Glu Asp
625                 630                 635                 640

Leu Ser Met Gln Thr Thr Phe Thr Trp Tyr Gly Lys Gln Gln Pro Lys
                645                 650                 655

Lys Tyr Asn Tyr Lys Gly Gln Pro Ala Val Gly Pro Glu Thr Lys Glu
            660                 665                 670

Ile Ser Pro Tyr Ser Ile Val Gly Leu Ser Ala Thr Trp Asp Val Thr
        675                 680                 685

Lys Asn Val Ser Leu Thr Gly Gly Val Asp Asn Leu Phe Asp Lys Arg
    690                 695                 700

Leu Trp Arg Ala Gly Asn Ala Gln Thr Thr Gly Asp Leu Ala Gly Ala
705                 710                 715                 720

Asn Tyr Ile Ala Gly Ala Gly Ala Tyr Thr Tyr Asn Glu Pro Gly Arg
                725                 730                 735

Thr Trp Tyr Met Ser Ile Asn Thr His Phe
            740                 745

<210> SEQ ID NO 61
<211> LENGTH: 724
<212> TYPE: PRT
<213> ORGANISM: Escherichia coli

<400> SEQUENCE: 61

Gln Glu Pro Thr Asp Thr Pro Val Ser His Asp Asp Thr Ile Val Val
1               5                   10                  15

Thr Ala Ala Glu Gln Asn Leu Gln Ala Pro Gly Val Ser Thr Ile Thr
                20                  25                  30

Ala Asp Glu Ile Arg Lys Asn Pro Val Ala Arg Asp Val Ser Glu Ile
            35                  40                  45

Ile Arg Thr Met Pro Gly Val Asn Leu Thr Gly Asn Ser Thr Ser Gly
        50                  55                  60

```
Gln Arg Gly Asn Asn Arg Gln Ile Asp Ile Arg Gly Met Gly Pro Glu
 65                  70                  75                  80

Asn Thr Leu Ile Leu Ile Asp Gly Lys Pro Val Ser Ser Arg Asn Ser
             85                  90                  95

Val Arg Gln Gly Trp Arg Gly Glu Arg Asp Thr Arg Gly Asp Thr Ser
            100                 105                 110

Trp Val Pro Pro Glu Met Ile Glu Arg Ile Glu Val Leu Arg Gly Pro
            115                 120                 125

Ala Ala Ala Arg Tyr Gly Asn Gly Ala Ala Gly Val Val Asn Ile
        130                 135                 140

Ile Thr Lys Lys Gly Ser Gly Glu Trp His Gly Ser Trp Asp Ala Tyr
145                 150                 155                 160

Phe Asn Ala Pro Glu His Lys Glu Glu Gly Ala Thr Lys Arg Thr Asn
                165                 170                 175

Phe Ser Leu Thr Gly Pro Leu Gly Asp Glu Phe Ser Phe Arg Leu Tyr
            180                 185                 190

Gly Asn Leu Asp Lys Thr Gln Ala Asp Ala Trp Asp Ile Asn Gln Gly
            195                 200                 205

His Gln Ser Ala Arg Ala Gly Thr Tyr Ala Thr Thr Leu Pro Ala Gly
        210                 215                 220

Arg Glu Gly Val Ile Asn Lys Asp Ile Asn Gly Val Val Arg Trp Asp
225                 230                 235                 240

Phe Ala Pro Leu Gln Ser Leu Glu Leu Glu Ala Gly Tyr Ser Arg Gln
                245                 250                 255

Gly Asn Leu Tyr Ala Gly Asp Thr Gln Asn Thr Asn Ser Asp Ala Tyr
            260                 265                 270

Thr Arg Ser Lys Tyr Gly Asp Glu Thr Asn Arg Leu Tyr Arg Gln Asn
            275                 280                 285

Tyr Ser Leu Thr Trp Asn Gly Trp Asp Asn Gly Val Thr Thr Ser
        290                 295                 300

Asn Trp Val Gln Tyr Glu His Thr Arg Asn Ser Arg Ile Pro Glu Gly
305                 310                 315                 320

Leu Ala Gly Gly Thr Glu Gly Lys Phe Asn Glu Lys Ala Ala Gln Asp
                325                 330                 335

Phe Val Asp Ile Asp Leu Asp Asp Val Met Leu His Ser Glu Val Asn
            340                 345                 350

Leu Pro Ile Asp Phe Leu Val Asn Gln Thr Leu Thr Leu Gly Thr Glu
            355                 360                 365

Trp Asn Gln Gln Arg Met Lys Asp Leu Ser Ser Asn Thr Gln Ala Leu
370                 375                 380

Thr Gly Thr Asn Thr Gly Gly Ala Ile Asp Gly Val Ser Ala Thr Asp
385                 390                 395                 400

Arg Ser Pro Tyr Ser Lys Ala Glu Ile Phe Ser Leu Phe Ala Glu Asn
                405                 410                 415

Asn Met Glu Leu Thr Asp Ser Thr Ile Val Thr Pro Gly Leu Arg Phe
            420                 425                 430

Asp His His Ser Ile Val Gly Asn Asn Trp Ser Pro Ala Leu Asn Ile
        435                 440                 445

Ser Gln Gly Leu Gly Asp Asp Phe Thr Leu Lys Met Gly Ile Ala Arg
        450                 455                 460

Ala Tyr Lys Ala Pro Ser Leu Tyr Gln Thr Asn Pro Asn Tyr Ile Leu
465                 470                 475                 480

Tyr Ser Lys Gly Gln Gly Cys Tyr Ala Ser Ala Gly Gly Cys Tyr Leu
```

|  | 485 |  |  |  | 490 |  |  |  | 495 |  |  |
|---|---|---|---|---|---|---|---|---|---|---|---|

Gln Gly Asn Asp Asp Leu Lys Ala Glu Thr Ser Ile Asn Lys Glu Ile
            500                 505                 510

Gly Leu Glu Phe Lys Arg Asp Gly Trp Leu Ala Gly Val Thr Trp Phe
            515                 520                 525

Arg Asn Asp Tyr Arg Asn Lys Ile Glu Ala Gly Tyr Val Ala Val Gly
        530                 535                 540

Gln Asn Ala Val Gly Thr Asp Leu Tyr Gln Trp Asp Asn Val Pro Lys
545                 550                 555                 560

Ala Val Val Glu Gly Leu Glu Gly Ser Leu Asn Val Pro Val Ser Glu
                565                 570                 575

Thr Val Met Trp Thr Asn Asn Ile Thr Tyr Met Leu Lys Ser Glu Asn
            580                 585                 590

Lys Thr Thr Gly Asp Arg Leu Ser Ile Ile Pro Glu Tyr Thr Leu Asn
            595                 600                 605

Ser Thr Leu Ser Trp Gln Ala Arg Glu Asp Leu Ser Met Gln Thr Thr
        610                 615                 620

Phe Thr Trp Tyr Gly Lys Gln Gln Pro Lys Lys Tyr Asn Tyr Lys Gly
625                 630                 635                 640

Gln Pro Ala Val Gly Pro Glu Thr Lys Glu Ile Ser Pro Tyr Ser Ile
                645                 650                 655

Val Gly Leu Ser Ala Thr Trp Asp Val Thr Lys Asn Val Ser Leu Thr
            660                 665                 670

Gly Gly Val Asp Asn Leu Phe Asp Lys Arg Leu Trp Arg Ala Gly Asn
            675                 680                 685

Ala Gln Thr Thr Gly Asp Leu Ala Gly Ala Asn Tyr Ile Ala Gly Ala
        690                 695                 700

Gly Ala Tyr Thr Tyr Asn Glu Pro Gly Arg Thr Trp Tyr Met Ser Ile
705                 710                 715                 720

Asn Thr His Phe

<210> SEQ ID NO 62
<211> LENGTH: 2193
<212> TYPE: DNA
<213> ORGANISM: Escherichia coli

<400> SEQUENCE: 62
atgagaggat cgcatcacca tcaccatcac ggatctggct ctggatctgg tatcgaggga      60
aggcctcagc aaaacgatga taatgagatc atagtgtctg ccagccgcag caatcgaact     120
gtagcggaga tggcgcaaac cacctgggtt atcgaaaatg ccgaactgga gcagcagatt     180
cagggcggta aagagctgaa agacgcactg gctcagttaa tccccggcct tgatgtcagc     240
agccagagcc gaaccaacta cggtatgaac atgcgtggcc gcccgctggt tgtcctgatt     300
gacggtgtgc gcctcaactc ttcacgttcc gacagccgac aactggactc tgtcgatcct     360
tttaatatcg accatattga agtgatctcc ggcgcgacgg ccctgtacgg tggcgggagt     420
accggagggt tgatcaacat cgtgaccaaa aaggccagcc ggaaaccat gatggagttt       480 gaggctggca caaaaagtgg ctttaacagc agtaaagatc acgatgagcg cattgccggt     540
gctgtctccg gcggaaatga ccatatctcc ggacgtcttt ccgtggcata tcagaaattt     600
ggcggctggt tgacggtaa cggcgatgcc accctgcttg ataacaccca gaccggcctg     660
cagcactcca atcggctgga catcatggga accggtacgc tgaacatcga tgaatcccgg     720
cagcttcaac tgataacgca gtactataaa agtcaggggg acgacaatta cgggcttaat      780

```
ctcgggaaag gcttttccgc catcagcggg agcagcacac catacgtcag taagggctg    840
aattctgacc gcattcccgg cactgagcgg catttgatca gcctgcagta ctctgacagt    900
gatttcctga gacaggaact ggtcggtcag gtttactacc gcgatgagtc gttgcggttc    960
tacccgttcc cgacggtaaa tgcgaataaa caggcgacgg ctttctcctc gtcacagcag    1020
gataccgacc agtacggcat gaaactgact ctgaacagcc aacttatgga cggctggcaa    1080
atcacctggg ggctggatgc tgagcatgag cgctttacct ccaaccagat gttcttcgat    1140
ctggctcagg caagtgcttc cggagggctg aacaaccata agatttacac caccgggcgc    1200
tatccgtcat atgacatcac caatctggcg gccttcctgc aatccagcta tgacattaat    1260
gatatttta ccgttagcgg tggcgtacgc tatcagtata ctgagaacag ggtagatgat    1320
ttcatcgact acacgcagca acagaagatt gctgccggga aggcgatatc tgccgacgcc    1380
attcctggtg gttcggtaga ttacgataac tttctgttca atgctggtct gctgatgcac    1440
atcaccgaac gtcagcaggc atggttcaat ttttcccagg gggtggcatt gccggatccg    1500
gggaaatatt atggtcgcgg catctatggt gcagcagtga acggccatct tcccctgaca    1560
aagagcgtga acgtcagcga cagtaagctg gaaggcgtga aagtcgattc ttatgaactg    1620
ggctggcgct ttaccggtga caacctgcgg actcaaatcg cggcatatta ctcgctttcc    1680
aataagagcg tggaaaggaa taaagatctg accatcagtg tgaaggacga caggcgccgt    1740
atttacggcg tggaaggtgc ggtggactac ctgatcccgg atactgactg gagtaccggt    1800
gtgaacttca atgtgctgaa aaccgagtcg aaagtgaacg gtcaatggca aaaatatgac    1860
gtgaaggaat caagtccatc gaaagcgaca gcttacatta actgggcgcc ggaaccgtgg    1920
agtctgcgtg tacagagcac cacttctttc gacgtaagcg atgcagaggg taacgatatt    1980
aatggttaca ctaccgtcga ttttatcagt agttggcagc ttccggtggg aacactcagc    2040
ttcagcgttg agaacctctt cgaccgtgac tataccactg tctggggaca gcgtgcacct    2100
ctgtactaca gcccgggtta cggccctgct tcactgtacg actacaaagg ccggggccga    2160
acctttggtc tgaactactc agtgctgttc tga                                 2193
```

<210> SEQ ID NO 63
<211> LENGTH: 730
<212> TYPE: PRT
<213> ORGANISM: Escherichia coli

<400> SEQUENCE: 63

Met Arg Gly Ser His His His His His Gly Ser Gly Ser Gly Ser
1               5                   10                  15

Gly Ile Glu Gly Arg Pro Gln Gln Asn Asp Asp Asn Glu Ile Ile Val
            20                  25                  30

Ser Ala Ser Arg Ser Asn Arg Thr Val Ala Glu Met Ala Gln Thr Thr
        35                  40                  45

Trp Val Ile Glu Asn Ala Glu Leu Glu Gln Gln Ile Gln Gly Gly Lys
    50                  55                  60

Glu Leu Lys Asp Ala Leu Ala Gln Leu Ile Pro Gly Leu Asp Val Ser
65                  70                  75                  80

Ser Gln Ser Arg Thr Asn Tyr Gly Met Asn Met Arg Gly Arg Pro Leu
                85                  90                  95

Val Val Leu Ile Asp Gly Val Arg Leu Asn Ser Ser Arg Ser Asp Ser
            100                 105                 110

Arg Gln Leu Asp Ser Val Asp Pro Phe Asn Ile Asp His Ile Glu Val

```
            115                 120                 125
Ile Ser Gly Ala Thr Ala Leu Tyr Gly Gly Ser Thr Gly Gly Leu
            130                 135                 140
Ile Asn Ile Val Thr Lys Lys Gly Gln Pro Glu Thr Met Met Glu Phe
145                 150                 155                 160
Glu Ala Gly Thr Lys Ser Gly Phe Asn Ser Ser Lys Asp His Asp Glu
                165                 170                 175
Arg Ile Ala Gly Ala Val Ser Gly Gly Asn Asp His Ile Ser Gly Arg
                180                 185                 190
Leu Ser Val Ala Tyr Gln Lys Phe Gly Gly Trp Phe Asp Gly Asn Gly
                195                 200                 205
Asp Ala Thr Leu Leu Asp Asn Thr Gln Thr Gly Leu Gln His Ser Asn
            210                 215                 220
Arg Leu Asp Ile Met Gly Thr Gly Thr Leu Asn Ile Asp Glu Ser Arg
225                 230                 235                 240
Gln Leu Gln Leu Ile Thr Gln Tyr Tyr Lys Ser Gln Gly Asp Asp Asn
                245                 250                 255
Tyr Gly Leu Asn Leu Gly Lys Gly Phe Ser Ala Ile Ser Gly Ser Ser
                260                 265                 270
Thr Pro Tyr Val Ser Lys Gly Leu Asn Ser Asp Arg Ile Pro Gly Thr
                275                 280                 285
Glu Arg His Leu Ile Ser Leu Gln Tyr Ser Asp Ser Asp Phe Leu Arg
                290                 295                 300
Gln Glu Leu Val Gly Gln Val Tyr Tyr Arg Asp Glu Ser Leu Arg Phe
305                 310                 315                 320
Tyr Pro Phe Pro Thr Val Asn Ala Asn Lys Gln Ala Thr Ala Phe Ser
                325                 330                 335
Ser Ser Gln Gln Asp Thr Asp Gln Tyr Gly Met Lys Leu Thr Leu Asn
                340                 345                 350
Ser Gln Leu Met Asp Gly Trp Gln Ile Thr Trp Gly Leu Asp Ala Glu
                355                 360                 365
His Glu Arg Phe Thr Ser Asn Gln Met Phe Asp Leu Ala Gln Ala
                370                 375                 380
Ser Ala Ser Gly Gly Leu Asn Asn His Lys Ile Tyr Thr Thr Gly Arg
385                 390                 395                 400
Tyr Pro Ser Tyr Asp Ile Thr Asn Leu Ala Ala Phe Leu Gln Ser Ser
                405                 410                 415
Tyr Asp Ile Asn Asp Ile Phe Thr Val Ser Gly Gly Val Arg Tyr Gln
                420                 425                 430
Tyr Thr Glu Asn Arg Val Asp Asp Phe Ile Asp Tyr Thr Gln Gln Gln
                435                 440                 445
Lys Ile Ala Ala Gly Lys Ala Ile Ser Ala Asp Ala Ile Pro Gly Gly
                450                 455                 460
Ser Val Asp Tyr Asp Asn Phe Leu Phe Asn Ala Gly Leu Leu Met His
465                 470                 475                 480
Ile Thr Glu Arg Gln Gln Ala Trp Phe Asn Phe Ser Gln Gly Val Ala
                485                 490                 495
Leu Pro Asp Pro Gly Lys Tyr Tyr Gly Arg Gly Ile Tyr Gly Ala Ala
                500                 505                 510
Val Asn Gly His Leu Pro Leu Thr Lys Ser Val Asn Val Ser Asp Ser
                515                 520                 525
Lys Leu Glu Gly Val Lys Val Asp Ser Tyr Glu Leu Gly Trp Arg Phe
                530                 535                 540
```

-continued

```
Thr Gly Asp Asn Leu Arg Thr Gln Ile Ala Ala Tyr Tyr Ser Leu Ser
545                 550                 555                 560

Asn Lys Ser Val Glu Arg Asn Lys Asp Leu Thr Ile Ser Val Lys Asp
            565                 570                 575

Asp Arg Arg Ile Tyr Gly Val Glu Gly Ala Val Asp Tyr Leu Ile
        580                 585                 590

Pro Asp Thr Asp Trp Ser Thr Gly Val Asn Phe Asn Val Leu Lys Thr
        595                 600                 605

Glu Ser Lys Val Asn Gly Gln Trp Gln Lys Tyr Asp Val Lys Glu Ser
        610                 615                 620

Ser Pro Ser Lys Ala Thr Ala Tyr Ile Asn Trp Ala Pro Glu Pro Trp
625                 630                 635                 640

Ser Leu Arg Val Gln Ser Thr Ser Phe Asp Val Ser Asp Ala Glu
            645                 650                 655

Gly Asn Asp Ile Asn Gly Tyr Thr Thr Val Asp Phe Ile Ser Ser Trp
            660                 665                 670

Gln Leu Pro Val Gly Thr Leu Ser Phe Ser Val Glu Asn Leu Phe Asp
            675                 680                 685

Arg Asp Tyr Thr Thr Val Trp Gly Gln Arg Ala Pro Leu Tyr Tyr Ser
690                 695                 700

Pro Gly Tyr Gly Pro Ala Ser Leu Tyr Asp Tyr Lys Gly Arg Gly Arg
705                 710                 715                 720

Thr Phe Gly Leu Asn Tyr Ser Val Leu Phe
            725                 730

<210> SEQ ID NO 64
<211> LENGTH: 708
<212> TYPE: PRT
<213> ORGANISM: Escherichia coli

<400> SEQUENCE: 64

Gln Gln Asn Asp Asp Asn Glu Ile Ile Val Ser Ala Ser Arg Ser Asn
1               5                   10                  15

Arg Thr Val Ala Glu Met Ala Gln Thr Thr Trp Val Ile Glu Asn Ala
            20                  25                  30

Glu Leu Glu Gln Gln Ile Gln Gly Gly Lys Glu Leu Lys Asp Ala Leu
        35                  40                  45

Ala Gln Leu Ile Pro Gly Leu Asp Val Ser Ser Gln Ser Arg Thr Asn
    50                  55                  60

Tyr Gly Met Asn Met Arg Gly Arg Pro Leu Val Val Leu Ile Asp Gly
65              70                  75                  80

Val Arg Leu Asn Ser Ser Arg Ser Asp Ser Arg Gln Leu Asp Ser Val
            85                  90                  95

Asp Pro Phe Asn Ile Asp His Ile Glu Val Ile Ser Gly Ala Thr Ala
        100                 105                 110

Leu Tyr Gly Gly Gly Ser Thr Gly Gly Leu Ile Asn Ile Val Thr Lys
    115                 120                 125

Lys Gly Gln Pro Glu Thr Met Met Glu Phe Glu Ala Gly Thr Lys Ser
130                 135                 140

Gly Phe Asn Ser Ser Lys Asp His Asp Glu Arg Ile Ala Gly Ala Val
145                 150                 155                 160

Ser Gly Gly Asn Asp His Ile Ser Gly Arg Leu Ser Val Ala Tyr Gln
            165                 170                 175

Lys Phe Gly Gly Trp Phe Asp Gly Asn Gly Asp Ala Thr Leu Leu Asp
        180                 185                 190
```

```
Asn Thr Gln Thr Gly Leu Gln His Ser Asn Arg Leu Asp Ile Met Gly
            195                 200                 205

Thr Gly Thr Leu Asn Ile Asp Glu Ser Arg Gln Leu Gln Leu Ile Thr
210                 215                 220

Gln Tyr Tyr Lys Ser Gln Gly Asp Asp Asn Tyr Gly Leu Asn Leu Gly
225                 230                 235                 240

Lys Gly Phe Ser Ala Ile Ser Gly Ser Thr Pro Tyr Val Ser Lys
                245                 250                 255

Gly Leu Asn Ser Asp Arg Ile Pro Gly Thr Glu Arg His Leu Ile Ser
                260                 265                 270

Leu Gln Tyr Ser Asp Ser Asp Phe Leu Arg Gln Glu Leu Val Gly Gln
            275                 280                 285

Val Tyr Tyr Arg Asp Glu Ser Leu Arg Phe Tyr Pro Phe Pro Thr Val
290                 295                 300

Asn Ala Asn Lys Gln Ala Thr Ala Phe Ser Ser Gln Gln Asp Thr
305                 310                 315                 320

Asp Gln Tyr Gly Met Lys Leu Thr Leu Asn Ser Gln Leu Met Asp Gly
                325                 330                 335

Trp Gln Ile Thr Trp Gly Leu Asp Ala Glu His Glu Arg Phe Thr Ser
                340                 345                 350

Asn Gln Met Phe Phe Asp Leu Ala Gln Ala Ser Ala Ser Gly Gly Leu
            355                 360                 365

Asn Asn His Lys Ile Tyr Thr Thr Gly Arg Tyr Pro Ser Tyr Asp Ile
            370                 375                 380

Thr Asn Leu Ala Ala Phe Leu Gln Ser Ser Tyr Asp Ile Asn Asp Ile
385                 390                 395                 400

Phe Thr Val Ser Gly Gly Val Arg Tyr Gln Tyr Thr Glu Asn Arg Val
                405                 410                 415

Asp Asp Phe Ile Asp Tyr Thr Gln Gln Gln Lys Ile Ala Ala Gly Lys
                420                 425                 430

Ala Ile Ser Ala Asp Ala Ile Pro Gly Gly Ser Val Asp Tyr Asp Asn
            435                 440                 445

Phe Leu Phe Asn Ala Gly Leu Leu Met His Ile Thr Glu Arg Gln Gln
450                 455                 460

Ala Trp Phe Asn Phe Ser Gln Gly Val Ala Leu Pro Asp Pro Gly Lys
465                 470                 475                 480

Tyr Tyr Gly Arg Gly Ile Tyr Gly Ala Ala Val Asn Gly His Leu Pro
                485                 490                 495

Leu Thr Lys Ser Val Asn Val Ser Ser Lys Leu Glu Gly Val Lys
                500                 505                 510

Val Asp Ser Tyr Glu Leu Gly Trp Arg Phe Thr Gly Asp Asn Leu Arg
            515                 520                 525

Thr Gln Ile Ala Ala Tyr Tyr Ser Leu Ser Asn Lys Ser Val Glu Arg
530                 535                 540

Asn Lys Asp Leu Thr Ile Ser Val Lys Asp Arg Arg Arg Ile Tyr
545                 550                 555                 560

Gly Val Glu Gly Ala Val Asp Tyr Leu Ile Pro Asp Thr Asp Trp Ser
                565                 570                 575

Thr Gly Val Asn Phe Asn Val Leu Lys Thr Glu Ser Lys Val Asn Gly
            580                 585                 590

Gln Trp Gln Lys Tyr Asp Val Lys Glu Ser Ser Pro Ser Lys Ala Thr
            595                 600                 605
```

-continued

```
Ala Tyr Ile Asn Trp Ala Pro Glu Pro Trp Ser Leu Arg Val Gln Ser
    610             615                 620

Thr Thr Ser Phe Asp Val Ser Asp Ala Glu Gly Asn Asp Ile Asn Gly
625             630                 635                 640

Tyr Thr Thr Val Asp Phe Ile Ser Ser Trp Gln Leu Pro Val Gly Thr
                645                 650                 655

Leu Ser Phe Ser Val Glu Asn Leu Phe Asp Arg Asp Tyr Thr Thr Val
                660             665                 670

Trp Gly Gln Arg Ala Pro Leu Tyr Tyr Ser Pro Gly Tyr Gly Pro Ala
        675                 680                 685

Ser Leu Tyr Asp Tyr Lys Gly Arg Gly Arg Thr Phe Gly Leu Asn Tyr
    690                 695                 700

Ser Val Leu Phe
705
```

PROTEINS AND IMMUNIZING COMPOSITIONS CONTAINING KLEBSIELLA PROTEINS AND METHODS OF USE

CROSS-REFERENCE TO RELATED APPLICATIONS

This application is continuation of U.S. application Ser. No. 15/741,574, filed Jan. 3, 2018, now U.S. Pat. No. 11,000,582, and which is a § 371 U.S. National Stage of International Application No. PCT/US16/41614, filed Jul. 8, 2016, which claims the benefit of U.S. Provisional Application Ser. No. 62/190,947, filed Jul. 10, 2015, disclosures of which are incorporated by reference herein in their entireties.

SEQUENCE LISTING

This application contains a Sequence Listing electronically submitted via EFS-Web to the United States Patent and Trademark Office as an ASCII text file entitled "29300470201_SequenceListing_ST25.txt" having a size of 229 kilobytes and created on Sep. 22, 2016. The information contained in the Sequence Listing is incorporated by reference herein.

BACKGROUND

Bacterial infections now account for some 1.7 million cases of hospital-acquired infections yearly in the United States (4.5 per 100 admissions), with an overall mortality rate in the range of 20% to 60% or 99,000 deaths directly associated with a hospital acquired infection. The economic impact due to such infections is estimated to cost between 5 billion to 10 billion dollars annually in the United States.

Gram negative bacterial infections and their sequelae are frequently lethal. It is estimated that over 700,000 patients become susceptible to bacterial infections each year in the United States alone. Of these, 160,000 actually develop septicemia, resulting in 50,000 deaths annually. The majority of these are hospital-acquired infections due to such gram negative bacilli as *E. coli* (most common pathogen isolated from patients with gram negative sepsis), followed in frequency by *Klebsiella pneumoniae* and *Pseudomonas aeruginosa*.

Infections caused by gram negative bacteria, including Enterobacteriaceae, continue to be a significant concern in both human healthcare and animal agricultural settings. Bacteria in the family Enterobacteriaceae are a large heterogeneous group whose natural habitat is the intestinal tract of both humans and animals. The family includes many genera and is subdivided into eight tribes including: Escherichieae, Edwardsielleae, Salmonelleae, Citrobactereae, Klebsielleae, Proteeae, Yersineae, and Erwineae. Many species of the Enterobacteriaceae family are often opportunistic pathogens with clinically relevant significance including *Escherichia* spp., *Klebsiella* spp., *Enterobacter* spp., *Proteus* spp., *Providencia* spp., *Serratia* spp., *Citrobacter* spp., *Morganella* spp., *Shigella* spp., and *Salmonella* spp., are among the top twenty organisms responsible for causing infection. When clinically important diseases do occur they are often caused by *E. coli*, but others can infect and cause debilitating disease. In most cases the bacteria become pathogenic when they reach tissues outside of their normal intestinal environment when normal host defenses are inadequate. This is particularly seen today in the young or elderly; often in terminal stages of a primary infection due to immunological incompetence or immunosuppression; allowing the organism to reach the blood stream to cause sepsis resulting in death or secondary sequelae.

*Klebsiella* species are rod shaped gram negative, facultative anaerobic bacteria belonging to the family Enterobacteriaceae. Today, 7 species are known with demonstrated similarities in DNA homology: *Klebsiella pneumoniae*, *Klebsiella ozaenae*, *Klebsiella rhinoscleromatis*, *Klebsiella oxytoca*, *Klebsiella planticola*, *Klebsiella terrigena*, and *Klebsiella ornithinolytica*. *Klebsiella* are ubiquitous in nature. They are often found in a variety of environments such as soil, vegetation, water, and the intestinal tract of humans and animals. In both humans and animals *Klebsiella* may colonize the skin or hide, pharynx or gastrointestinal tract, and are often regarded as normal flora in many parts of the colon and the intestinal tract. *Klebsiella pneumoniae* and *Klebsiella oxytoca* are the two most clinically relevant species in both animal and human populations.

The pathogenicity of *Klebsiella* can be attributed to multiple virulence factors including production of a heat-stable enterotoxin, capsular polysaccharides (CPS), lipopolysaccharides, adhesins (type 1 and 3 pili, KPF-28 fimbria, CF29K and aggregative adhesin), and iron acquisition systems (Podschun et al., Clin. Microbiol. Rev. 11(4): 589-603. 1998; Yu et al., Emerg. Inf. Dis. 13:986-993, 2007).

*Klebsiella* in animals are an important cause of metritis and infertility in horses, mastitis in bovine species, hematogenous osteomyelitis originating in pulmonary lesions in cattle, accumulation of pus in the pyothorax in horses, bronchopneumonia in both cats and dogs and a sequelae of secondary infections often following immunosuppression resulting from drug therapy, malnutrition, stress, endocrine diseases and other infections including canine parvovirus and feline immunodeficiency virus infection.

Today agriculture is critical for human welfare as it contributes to food, one major necessity for global survival. A number of factors adversely affect the stability and health of animal populations, by far one of the most important is infectious diseases which can cause widespread death in adult and/or young animals. Bacterial infections in production animals may severely affect all aspects of animal health resulting in tremendous economic losses to all sectors. Today zoonotic and emerging infectious diseases pose a threat to human health. At least 61 percent of all human pathogens are transmissible between animals and humans. Zoonosis make up 75 percent of emerging infectious diseases. The increase in infectious diseases in production animals and zoonotic diseases is primarily due to agricultural intensification, particularly in cattle (beef and dairy), swine, and poultry sectors.

In humans the interactions of *Klebsiella* range from opportunistic pathogens (mainly in hospitalized patients and community acquired infections) to asymptomatic carriage that frequent the intestinal tract and less frequently the nasopharynx. As nosocomial infections, *Klebsiella* are mostly associated with infections of urinary and respiratory tracts as well as wound and soft tissue infections that can lead to fatal septicemia. The spectrum of clinical syndromes includes bacteremia, pneumonia, urinary tract infection (UTI), thrombophlebitis, upper respiratory tract infection, cholecystitis, wound infection, osteomyelitis, endogenous endophthalmitis, endophthalmitis; endocarditis, and meningitis. It is estimated that *Klebsiella* account for 8% of endemic hospital infection and 3-7% of epidemic outbreaks (Stamm et al., Comparison of endemic and epidemic nosocomial infections, pp 9-13. In R. E. Dixon (ed.), Nosocomial infections. Yorke Medical Books, Atlanta, GA 1981). *Kleb-*

*siella* cause as many as 14% of cases of primary bacteremia, second only to *E. coli* as a cause of gram-negative sepsis. *Klebsiella* has been isolated from bronchial alveolar lavage samples of 21% of patients with cystic fibrosis (Lyczak et al. *Clinical microbiology reviews* 15.2 (2002): 194-222).

*K. rhinoscleroma* and *K. ozaenae* are less common and rarely induce clinical infection. *K. rhinoscleroma* can induce a chronic inflammatory process involving the nasopharynx, while *K. ozaenae* induces a chronic atrophic rhinitis characterized by necrosis of the nasal mucosa and mucopurulent nasal discharge.

*K. oxytoca* has been implicated in neonatal bacteremia among premature infants and in neonatal intensive care units.

The emergence of *K. pneumoniae* producing carbapenemases has become a global health concern with serious clinical significance in both animal and human health sectors. *K. pneumoniae* carbapenemases (KPCs) have been shown to confer resistance to multiple antimicrobial agents, including nearly all β-lactams, fluoroquinolones, and aminoglycosides. Carbapenems are a class of β-lactam antibiotics with a broad spectrum of antibacterial activity used to treat infections caused by Gram-negative bacteria such as *E. coli* and *K. pneumoniae* that produce extended-spectrum β-lactamases. Carbapenemases are enzymes produced by *K. pneumoniae* that are capable of inactivating Carbapenems and sometimes other classes of β-lactam. Carbapenemases are found in bacteria belonging to the family of Enterobacteriaceae, *Pseudomonas* spp, and *Acinetobacter* spp. This resistant mechanism limits the number of agents available for the treatment of *K. pneumoniae*.

In human populations *K. pneumoniae* infections are common in hospitals where they cause pneumonia (characterized by emission of bloody sputum) and urinary tract infections in catheterized patients. In fact, *K. pneumoniae* is second only to *E. coli* as a urinary tract pathogen. It accounts for 6 to 17 percent of all nosocomial urinary tract infection (UTI). *Klebsiella* infections are encountered far more often now than in the past, and this increased occurrence may be due to the bacterium's antibiotic resistance properties. *Klebsiella* species may contain resistance plasmids (R-plasmids) which confer resistance to such antibiotics as Ampicillin and Carbenicillin (Wu et al., Clin Microbial Infect, 11: 893-897. 2005). To make matters worse, the R-plasmids can be transferred to other enteric bacteria not necessarily of the same species. Hospital outbreaks of multidrug-resistant *Klebsiella* spp. are often caused by a new type of strain, an ESBL producer (extended spectrum beta lactamase). The incidence of ESBL-producing strains among clinical *Klebsiella* isolates has been steadily increasing over the past several years. Frequencies of up to 40% have been reported in certain regions. To treat *K. pneumoniae* infections, there are few antibiotics available like Cefepime, Polymyxin B, Carbapenem, Meropenem and Imipenem (Parchuri et al., Heart lung, 5: 360-363. 2005; Ueda et al., Antimicrob Agents Chemother, 49: 4185-4196. 2005; Sanchez et al. Emerg Infect Dis 19.1 (2013): 133-6).

An alternative to the use of antibiotics for controlling *K. pneumoniae* is to attempt immunological control through vaccination. Effective vaccines against *Klebsiella* would greatly alleviate the significant global morbidity and mortality caused by these bacteria. Safe and effective vaccines against *Klebsiella* have been attempted with limited success. A number of bacterial constituents have been evaluated as potential vaccine development strategies, and include adhesions and fimbriae, capsular polysaccharides, lipopolysaccharides (LPS), and outer membrane proteins. Anti-capsular polysaccharide antibodies were found to provide a high degree of protection against corresponding capsular serotypes (Cryz et al., J Infect Dis, 150: 817-822. 1984; Cryz et al J Clin Microbiol, 23: 687-690. 1986). A 24-valent *Klebsiella* capsular polysaccharide vaccine was evaluated in Phase 1 trials that indicated the vaccine was safe (Cryz et al., Infect Immun, 50: 225-230. 1985). Further evaluation of the vaccine revealed a problem faced by anticapsular vaccination was the variability of capsular antigens in the natural *Klebsiella* populations. The selection of vaccine serotypes in the 24-valent vaccine was based on the most prevalent serotypes derived from bacteremic patients found in Europe and the United States. However, the serotypes included in the vaccine represented only 29% of strains found in other geographical areas, and since these serotypes were not included resulted in lack of efficacy. In addition, it has been shown that active immunization with LPS-containing vaccines can result in the induction of adverse toxic reactions, which are caused by the endotoxin content (Yadav et al., Folia Microbiologica, 50: 83-86. 2005). Other vaccine candidates have been evaluated for controlling *Klebsiella* infections utilizing cytotoxin toxoids, hepta- or mono-valent bacterial extracts (Libon et al., Vaccine, 20: 2174-2180. 2002) and/or outer membrane proteins such as OmpA (Jeannin et al., Vaccine 20, Suppl. 4: A23-A27. 2002).

In mammals, it has been shown that the response to tissue injury or bacterial infection results in an acute inflammatory response. This response increases capillary permeability and phagocytic infiltration resulting in the clinical signs recognized as inflammation; swelling, fever, pain and redness. If left uncontrolled, this may lead to death. The activation of humoral factors and the release of cytokines mediate systemic events collectively known as the acute phase protein response which results in a cascade of physiological and biochemical events. The duration of this response is directly related to the severity of the injury and magnitude of the systemic infection. It has been well-documented that during bacterial sepsis, major surgery, burns and other bodily trauma there is an alteration in the concentration of a number of metal ions in serum such as, iron, copper, and zinc. For instance, during the acute phase of an infection there is a decrease in plasma levels of iron and zinc and an increase in copper. The alteration of these trace metal ions in serum may directly affect the severity or progression of any bacterial infection.

Metal ions such as iron have been shown to be an essential nutrient for most organisms due to its role in electron transport. Since iron has very low solubility at neutral pH, it must be kept in solution by association with specialized protein carriers such as transferrin in blood, lactoferrin in secretory fluids, ovotransferrin in albumin, and ferritin within cells. It has been recognized that the concentration of free iron normally present in mammalian hosts is not enough to support the growth of bacteria. Hence, the low availability of iron within host species is one of the first barriers to infection that microorganisms must overcome, and it is not surprising that bacteria have developed strategies for obtaining iron from their hosts.

One of the most studied bacterial systems for iron acquisition is that of siderophores, low molecular weight iron ligands that are able to compete with host protein carriers for ferric iron binding (Miethke et al., Microbiol Mol Rev, 71(3): 413-451. 2007). The chelated iron is actively transported into the bacterial periplasm when the siderophore interacts with specific receptor proteins on the cell surface. The energy required for this activity appears to be dependent on the proteins TonB, ExbB, and ExbD (Miethke et al., Microbiol Mol Rev, 71(3): 413-451. 2007). Once the iron has reached the periplasm, it is transported into the cytoplasm via an ATP binding cassette (ABC) transport system (Budzikiewicz et al., Siderophore from bacteria and from fungi. In: Iron uptake and homeostasis in Microorganisms. 1$^{st}$ ed. Caister Academic Press. Chapter 1, 2010. Once the siderophore-iron complex has entered the cytoplasm, the iron is unloaded and the siderophore is either recycled or degraded.

Most *Klebsiella* strains possess the genes encoding the siderophore receptor proteins FepA, IroN, CirA, FhuA, and FhuE (Williams et al., FEMS Microbiol Lett. 44: 407-412. 1987). A recent study evaluating the effects of single, double, and triple mutants of the fepA, IroN, and CirA proteins to study the specificity of the receptors (Rabsch et al., Infect Immun. 12: 6953-6961 2003). The results suggested that these receptors are not entirely specific; most can utilize the iron from various siderophores and several siderophores can be used by any of the three proteins. In addition, several of the siderophore receptor proteins (iron-regulated proteins) use siderophores produced by other species of bacteria or fungi, a mechanism of iron acquisition referred to as "siderophore piracy" (Jurkevitch et al., Appl Environ Microbiol 58: 119. 1992). The multitude and redundancy of iron uptake systems in *Klebsiella* underscores the importance that the bacteria give to obtaining iron under various conditions. There is considerable evidence that iron acquisition is an important facet of *Klebsiella* pathogenesis (Brisse et al., Prokaryotes, 6: 159-196. 2006).

Currently there are no prophylactic *Klebsiella* vaccines on the market or, according to publicly available information, in active preclinical or clinical development.

SUMMARY OF THE APPLICATION

Provided herein are compositions. In one embodiment, a composition includes at least two isolated proteins having molecular weights of 82 kDa, 78 kDa, 72 kDa, or 68 kDa. The proteins are isolatable from a *Klebsiella pneumoniae* when incubated in media comprising an iron chelator and not isolatable when grown in the media without the iron chelator. The composition protects an animal against infection with *K. pneumoniae*. In one embodiment, the animal is a mouse, a dairy cow, or a human. In one embodiment, at least one of the proteins includes an amino acid sequence that is structurally similar to, or has 100% identity with, SEQ ID NO:41, SEQ ID NO:42, SEQ ID NO:43, or SEQ ID NO:44.

In one embodiment, a composition includes at least two isolated proteins that are structurally similar to, or have 100% identity with, a protein selected from SEQ ID NO:41, SEQ ID NO:42, SEQ ID NO:43, and SEQ ID NO:44.

In one embodiment, a composition includes at least two proteins that are structurally similar to, or have 100% identity with, a protein selected from SEQ ID NO:41, SEQ ID NO:58, SEQ ID NO:61, and SEQ ID NO:64.

In one embodiment, a composition also includes one or two proteins having molecular weights of 35 kDa and 33 kDa that are also isolatable from a *Klebsiella pneumoniae*. In one embodiment, a composition also includes a protein having an amino acid sequence that is structurally similar to, or has 100% identity with, SEQ ID NO:45, SEQ ID NO:46, SEQ ID NO:49, SEQ ID NO:51, SEQ ID NO:52, SEQ ID NO:53, SEQ ID NO:58, SEQ ID NO:61, or SEQ ID NO:64. In one embodiment, the composition also includes an 87 kDa protein isolatable from a *K. pneumoniae* when incubated in media comprising an iron chelator. In one embodiment, a composition also includes a pharmaceutically acceptable carrier. In one embodiment, a composition also includes an adjuvant.

Also provided herein are methods. In one embodiment, a method includes administering to a subject an amount of the composition described herein effective to induce the subject to produce antibody that specifically binds to at least one protein of the composition. In one embodiment, a method includes administering an effective amount of the composition described herein to a subject having or at risk of having an infection caused by a gram negative microbe. In one embodiment, a method includes administering an effective amount of a composition described herein to a subject having or at risk of having an infection caused by a gram negative microbe. In one embodiment, a method includes administering an effective amount of a composition described herein to a subject colonized by a gram negative microbe. The gram negative microbe can be selected from *K. pneumoniae, K. oxytoca, E. coli, Enterobacter* spp., *Serratia* spp., *Proteus* spp., *Citrobacter* spp., or a combination thereof.

In one embodiment, a method is for treating a condition in a subject, and includes administering an effective amount of the composition described herein to a subject in need thereof. In one embodiment, he subject has or at risk of having an infection caused by a *Klebsiella* spp. In one embodiment, the condition is caused by *K. pneumoniae, K. oxytoca, E. coli, Enterobacter* spp., *Serratia* spp., *Proteus* spp., *Citrobacter* spp., or a combination thereof. In different embodiments, the condition can include mastitis, high somatic cell counts in a subject's milk, low milk production. or a combination thereof.

In one embodiment, the subject is a mammal, such as a human or a bovine. In one embodiment, the *Klebsiella* spp. is *K. pneumonia* or *K. oxytoca*. In one embodiment, at least 700 micrograms (μg) and no greater than 1,200 μg of protein is administered.

Also provided herein are kits. In one embodiment, a kit includes in separate containers, an isolated protein of a composition described herein, and a reagent that detects an antibody that specifically binds the protein. In one embodiment, a kit includes in separate containers, an antibody that specifically binds an isolated protein of a composition described herein, and a second reagent that specifically binds the protein.

Further provided herein is an isolated whole cell that includes a a protein of a composition described herein, and isolated antibody that specifically binds to the whole cell.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 7-21. Amino acid sequences of proteins encoded by *Klebsiella pneumoniae* 1571 and an example of a nucleotide sequence encoding the corresponding protein.

FIGS. 36-38. Amino acid sequences encoded by *E. coli* strain CFT073 and an example of a nucleotide sequence encoding the corresponding protein.

DETAILED DESCRIPTION OF ILLUSTRATIVE EMBODIMENTS

Proteins

Provided herein are proteins and compositions including proteins. As used herein, "protein" refers broadly to a polymer of two or more amino acids linked by peptide bonds. Thus, for example, the terms peptide, oligopeptide, protein, and enzyme are included within the definition of protein. This term also includes post-expression modifications of the protein, such as glycosylations, acetylations, phosphorylations, and the like. The term protein does not connote a specific length of a polymer of amino acids. A protein may be isolatable directly from a natural source, or can be prepared with the aid of recombinant, enzymatic, or chemical techniques. In the case of a protein that is naturally occurring, such a protein is typically isolated.

An "isolated" protein is one that has been removed from its natural environment. For instance, an isolated protein is a protein that has been removed from the cytoplasm or from the membrane of a cell, and many of the proteins, nucleic acids, and other cellular material of its natural environment are no longer present.

(MALDI-TOF MS, also referred to herein as MALDI), or by determining the molecular weight of a deduced protein sequence (see Table 1). Unless indicated otherwise, molecular weight refers to molecular weight as determined by resolving a protein using an SDS polyacrylamide gel having a stacking gel of about 4% and a resolving gel of about 10% under reducing and denaturing conditions. In one embodiment, the molecular weight of a protein identified by SDS-PAGE includes molecular weights of 1, 2, 3, 4, or 5 kDa above and below the stated value. In one embodiment, the molecular weight of a protein identified by SDS-PAGE includes molecular weights of 1, 2, 3, 4, or 5 kDa above and below the stated value.

TABLE 1

Comparison of molecular weights of proteins.

The Comparison of Molecular Weights in Kilodaltons (kDa) of the Vaccine Composition of *Klebsiella pneumonia* 1571 as Examined by SDS-PAGE and MALD-TOF

| Protein Analysis | Isolate ID | Light top band | FepA | FecA | FhuA | CirA | OmpC | OmpA |
|---|---|---|---|---|---|---|---|---|
| SDS-PAGE | 1571 | 87 | 82 | 78 | 72 | 68 | 35 | 33 |
| MALDI-TOF | 1571 | Not analyzed | 82 | 83 | 81 | 71 | 40 | 38 |
| Predicted MW based on AA Sequence of full length protein | 1571 | Not analyzed | 82.2 | 82.7 | 81.3 | 71 | 40 | 38 |

Figure 4:
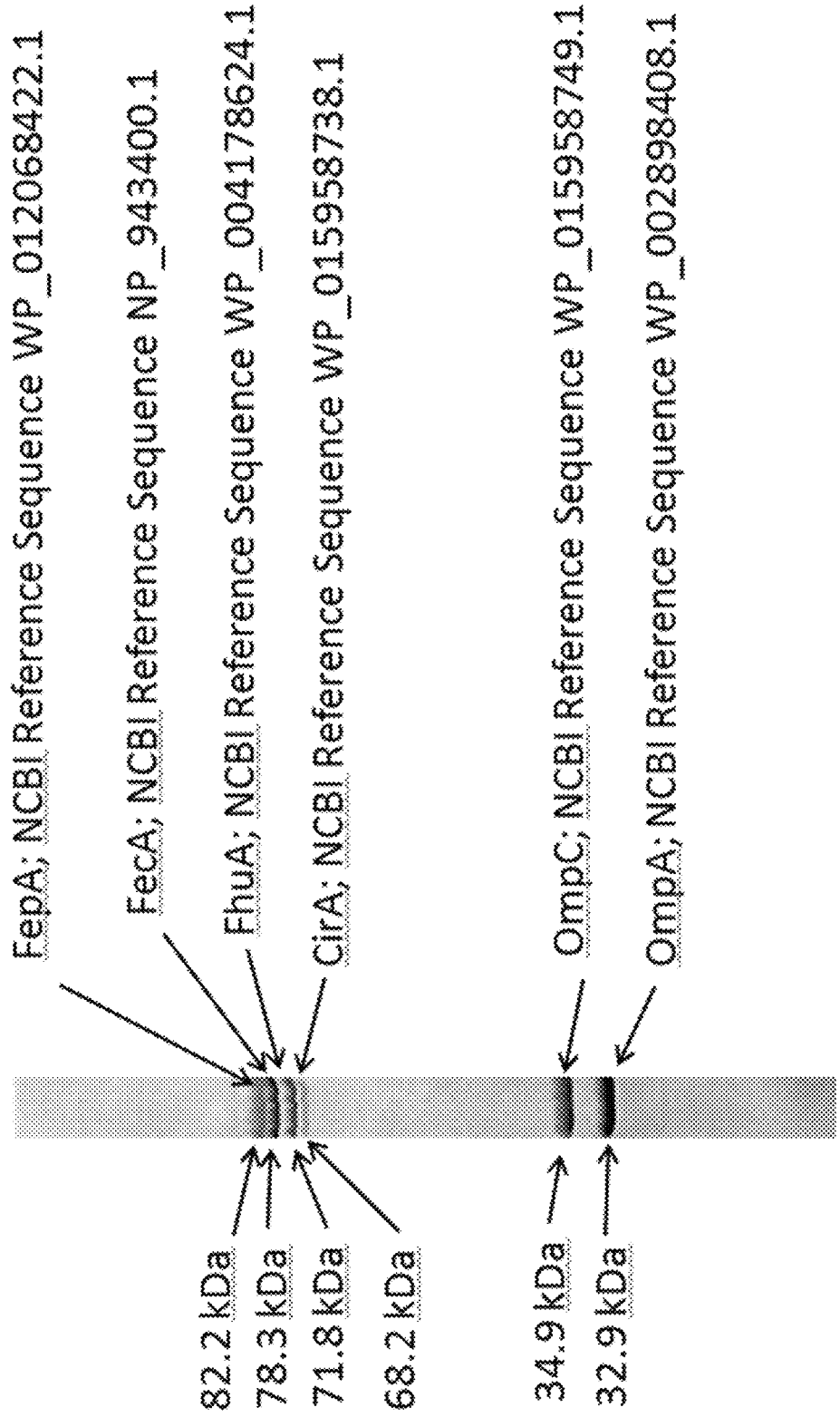
FIG. 4. *Klebsiella pneumoniae* 1571 LC/MS/MS. *Klebsiella pneumoniae* 1571 isolate showing siderophore receptor proteins CirA, FecA, FepA and FhuA, along with porin proteins OmpC and OmpA identified by LC/MS/MS.

Table 1. Protein Analysis: The molecular weights of the metal regulated proteins and porins of *Klebsiella pneumonia* were analyzed by single dimension SDS-PAGE, MALDI-TOF-MS, and the predicted molecular weight based on amino acid sequence.
Note:
there were 7 bands visualized in the SDS-PAFE Gel. The top band was light, and not analyzed by MALDI-TOF (FIG. 4). The other six bands have SDS-PAGE MW of 82, 78, 72, 68, 35 and 33 kDa. Six of the seven bands in the SDS-PAGE gel were excised and examined by MALDI-TOF-MS.

A protein characterized as "isolatable" from a particular source is a protein that, under appropriate conditions, is produced by the identified source, although the protein may be obtained from alternate sources using, for example, recombinant, chemical, or enzymatic techniques well known to those skilled in the art. Thus, characterizing a protein as "isolatable" from a particular source does not imply any specific source from which the protein must be obtained or any particular conditions or processes under which the protein must be obtained.

A "purified" protein is one that is at least 60% free, at least 75% free, or at least 90% free from other components with which it is naturally associated. Proteins that are produced outside the organism in which they naturally occur, e.g., through chemical or recombinant means, are considered to be isolated and purified by definition, since they were never present in a natural environment.

A protein described herein can be characterized by molecular weight, amino acid sequence, nucleic acid that encodes the protein, immunological activity, or any combination of two or more such characteristics. The molecular weight of a protein, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Molecular weights of proteins described herein were determined by gel electrophoresis, by matrix assisted laser desorption/ionization time-of-flight spectrometry A protein of the present invention may be a metal-regulated protein. As used herein, a "metal-regulated protein" is a protein that is natively expressed by a microbe at a greater level when the microbe is grown in low metal conditions compared to growth of the same microbe in high metal conditions. Examples of metal-regulated proteins include siderophore receptor proteins. Low metal and high metal conditions are described herein. For instance, one class of metal-regulated protein produced by *Klebsiella* spp. is not expressed at detectable levels during growth of the microbe in high metal conditions but is expressed at detectable levels during growth in low metal conditions.

Examples of metal-regulated proteins isolatable from *K. pneumoniae* after growth in low iron conditions have molecular weights of between 100 kDa and 60 kDa, such as 97 kDa to 66 kDa. Specific examples of metal-regulated proteins isolatable from *K. pneumoniae* after growth in low iron conditions include proteins of 87 kDa, 82 kDa, 78 kDa, 72 kDa, and 68 kDa as determined by SDS-PAGE (Table 1). Examples of the proteins having molecular weights of 82 kDa, 78 kDa, 72 kDa, and 68 kDa, and nucleotide sequences encoding the proteins, are shown in FIGS. 7-10.

Other metal regulated proteins expected to be expressed by and isolatable from *K. pneumoniae* and expected to play a role in acquisition of metals include proteins having molecular weights of 83 kDa, 78 kDa, 78.4 kDa, 76.2 kDa, 74.7 kDa, and 66.2 kDa, where the molecular weight is determined from the deduced amino acid sequence. Examples of these proteins, and nucleotide sequences encoding the proteins, are shown in FIGS. 11, 12, 15, and 17-19. Additional examples of metal-regulated proteins include recombinantly-produced versions of proteins described herein. A recombinantly-produced protein may include the entire amino acid sequence translatable from an mRNA transcript. Alternatively, a recombinantly-produced metal-regulated protein can include a fragment of the entire translatable amino acid sequence. For example, a recombinantly-produced metal-regulated protein may lack a cleavable sequence at either end of the protein—e.g., a cleavable signal sequence at the amino terminus of the protein.

Other metal regulated proteins include the proteins shown at SEQ ID NO:58, SEQ ID NO:61, and SEQ ID NO:64 (FIGS. 36-38). Thus, a metal-regulated protein can be a protein that includes the amino acid sequence depicted in, for example, SEQ ID NO:41, SEQ ID NO:42, SEQ ID NO:43, SEQ ID NO:44, SEQ ID NO:45, SEQ ID NO:46, SEQ ID NO:49, SEQ ID NO:51, SEQ ID NO:52, SEQ ID NO:53, SEQ ID NO:58, SEQ ID NO:61, or SEQ ID NO:64.

Other metal regulated proteins expected to be expressed by and isolatable from *K. pneumoniae* and expected to play a role in acquisition of metals include proteins that include the amino acid sequences depicted in SEQ ID NO:14, SEQ ID NO:16, and SEQ ID NO:20.

Also provided herein are proteins that are not metal-regulated. Such proteins are expressed in the presence of a metal ion such as, for example, in the presence of ferric chloride, and also expressed when grown in low iron conditions. Examples of such proteins include porins. Examples of such proteins isolatable from *Klebsiella* spp., including *K. pneumoniae*, have molecular weights of between 26 kDa and 45 kDa. In one embodiment, non-metal regulated proteins produced by *Klebsiella* spp. are 35 kDa and 33 kDa as determined by SDS-PAGE. Examples of these proteins, and nucleotide sequences encoding the proteins, are shown in FIGS. 20 and 21.

Thus, a protein that is not metal-regulated can be a protein that includes the amino acid sequence depicted in, for example, SEQ ID NO:54, and SEQ ID NO:55 (FIGS. 20 and 21).

Whether a protein is a metal-regulated protein or not can be determined by methods useful for comparing the presence of proteins, including, for example, gel filtration, gel electrophoresis including sodium dodecyl sulfate-polyacrylamide gel electrophoresis (SDS-PAGE), capillary electrophoresis, mass spectrometry, and liquid chromatography including HPLC. Separate cultures of a microbe are grown under high metal conditions and under low metal conditions, proteins of the present invention are isolated as described herein, and the proteins present in each culture are resolved and compared. Typically, an equal amount of proteins from each culture is used. Preferably, the proteins are resolved using an SDS polyacrylamide gel having a stacking gel of about 4% and a resolving gel of about 10% under reducing and denaturing conditions. For instance, 30 micrograms (µg) of total protein from each culture may be used and loaded into wells of a gel. After running the gel and staining the proteins with Coomasie Brilliant Blue, the two lanes can be compared. When determining whether a protein is or is not expressed at a detectable level, 30 µg of total protein from a culture is resolved on an SDS-PAGE gel and stained with Coomasie Brilliant Blue using methods known in the art. A protein that can be visualized by eye is considered to be expressed at a detectable level, while a protein that cannot be visualized by eye is considered to not be expressed at a detectable level.

Alternatively, whether a protein is metal-regulated or not can be determined using microarray-based gene expression analysis. Separate cultures of a microbe are grown under high metal conditions and under low metal conditions, RNA is extracted from cells of each culture, and differences in RNA expression in cells grown in high metal conditions versus RNA expression in cells grown in low metal conditions are detected and compared. For example, labeled cDNA can be prepared from 8-10 µg of bacterial RNA using known and routine methods. The labeled cDNA can be applied to a microarray of the *K. pneumoniae* genome. Such microarrays are commercially available and gene expression using such arrays is routine.

Proteins described herein may have immunological activity. "Immunological activity" refers to the ability of a protein to elicit an immunological response in an animal. An immunological response to a protein is the development in an animal of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in an animal that prevents or inhibits infection by *Klebsiella* spp., for instance, *K. pneumoniae* or *K. oxytoca*. Whether a protein has protective immunological activity can be determined by methods known in the art such as, for example, methods described in Examples 11-14. For example, a protein described herein, or combination of proteins described herein, protects an animal against challenge with a *Klebsiella* spp. A protein of the present invention may have seroactive activity. "Seroactive activity" refers to the ability of a candidate protein to react with antibody present in convalescent serum from an animal infected with a *Klebsiella* spp., for instance, *K. pneumoniae* or *K. oxytoca*. In some aspects, the convalescent serum may be from an animal infected with *K. pneumoniae* or *K. oxytoca*. Proteins of the present invention may have immunoregulatory activity. "Immunoregulatory activity" refers to the ability of a protein to act in a nonspecific manner to enhance an immune response to a particular antigen. Methods for determining whether a protein has immunoregulatory activity are known in the art.

A protein described herein can have the characteristics of a reference protein. The characteristics can include, for example, molecular weight, amino acid sequence, activity, or any combination thereof. The reference protein can be one expressed by a gram negative microbe, such as a member of the family Enterobacteriacea, preferably, *Klebsiella* spp., more preferably, *K. pneumoniae*. An example of a *K. pneumoniae* strain is *K. pneumoniae* 1571.

A protein described herein can have an amino acid sequence that is structurally similar, as described below, to the amino acid sequence of SEQ ID NO:41, SEQ ID NO:42, SEQ ID NO:43, SEQ ID NO:44, SEQ ID NO:45, SEQ ID NO:46, SEQ ID NO:49, SEQ ID NO:50, SEQ ID NO:51, SEQ ID NO:52, SEQ ID NO:53, SEQ ID NO:54, SEQ ID NO:55, SEQ ID NO:58, SEQ ID NO:61, or SEQ ID NO:64. In one embodiment, a protein described herein can include a region of amino acids that is structurally similar, as described below, to the amino acid sequence of SEQ ID NO:14, SEQ ID NO:16, or SEQ ID NO:20.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

Protein Sequence Similarity and Protein Sequence Identity

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein or any known metal-regulated protein, as appropriate. A candidate protein is the protein being compared to the reference protein. A candidate protein can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison WI). Alternatively, proteins may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a protein containing deletions or additions of one or more contiguous or noncontiguous amino acids that do not eliminate a functional activity—such as, for example, immunological activity—of the protein are also contemplated.

Thus, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

As described in Example 9 and shown in Table 3, the metal regulated proteins described herein are conserved. Table 3 shows high levels of percent identity of different proteins present in *K. pneumoniae, E. coli,* and *Enterobacter.* A person of ordinary skill can easily align the amino acid sequences of a metal regulated protein that is expressed by different microbes using readily available algorithms, for instance CLUSTALW, and identify amino acids and regions that are conserved and amino acids and regions that are variable across the metal regulated proteins. A person of ordinary skill in the art can deduce from such data regions of the protein in which substitutions, particularly conservative substitutions, may be permitted without unduly affecting activity of the modified polypeptide.

Consequently, a protein described herein can include certain variants including, for example, homologous proteins that originate—biologically or recombinantly—from microbial species or strains other than the microbial species or strain from which the polypeptide was originally isolated and/or identified.

A protein as described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of proteins on nickel columns. Such gene modification techniques and suitable additional sequences are well known in the molecular biology arts.

A "modification" of a protein as described herein includes a protein (or an analog thereof such as, e.g., a fragment thereof) that is chemically or enzymatically derivatized at one or more constituent amino acid. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified proteins as described herein may retain the biological activity—such as, for example, immunological activity—of the unmodified protein or may exhibit a reduced or increased biological activity compared to the unmodified protein.

A protein as described herein (including a biologically active analog thereof and/or a modification thereof) can include a native (naturally occurring), a recombinant, a chemically synthesized, or an enzymatically synthesized protein. For example, a protein as described herein may be prepared by isolating the protein from a natural source or may be prepared recombinantly by conventional methods including, for example, preparation as fusion proteins in bacteria or other host cells.

A protein expressed by a reference microbe can be obtained by growing the reference microbe under low metal conditions as described herein and the subsequent isolation of a protein by the processes disclosed herein. Alternatively, a protein expressed by a reference microbe can be obtained by identifying coding regions expressed at higher levels when the microbe is grown in low metal conditions—e.g., metal-regulated. A metal-regulated coding region can be cloned and expressed, and the expressed metal-regulated protein may be identified by the processes described herein. A candidate protein can be isolatable from a microbe or identified from a microbe, preferably a gram negative microbe, more preferably, a member of the family Enterobacteriaceae, such as *Klebsiella* spp. such as, for example, *K. pneumoniae*, or *K. oxytoca*. A candidate protein may also be produced using enzymatic or chemical techniques.

Polynucleotide Sequence Similarity and Polynucleotide Sequence Identity

Proteins as described herein also may be identified in terms of the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence that encodes a protein or SEQ ID NO:41, 42, 43, 44, 45, 46, 49, 51, 52, 53, 54, 55, 58, 61, or 64) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes the appropriate nucleotide sequence selected from, for example, the appropriate portion of SEQ ID NO:1, 3, 5, 7, 9, 11, 13, 15, 17, 19, 21, 23, 25, 27, or 29, that encodes a protein without the signal sequence. For example, two polynucleotide sequences can be compared using the Blastn program of the BLAST 2 search algorithm, as described by Tatiana et al., *FEMS Microbiol Lett.*, 1999; 174: 247-250, and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

This disclosure also provides whole cell preparations of a microbe, where the microbe expresses one or more of the proteins as described herein. The microbe can express the proteins naturally, or can be engineered to express one or more of the proteins described herein recombinantly. The cells present in a whole cell preparation may be inactivated such that the cells cannot replicate but the immunological activity of the proteins as described herein expressed by the microbe is maintained. Typically, the cells may be killed by exposure to agents such as glutaraldehyde, formalin, or formaldehyde.

Compositions

A composition as described herein may include at least one protein described herein, or a number of proteins that is an integer greater than one (e.g., at least two, at least three, at least four). Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein in the section headed "Protein sequence similarity and protein sequence identity." In one embodiment, a composition that includes the proteins described herein is a subset of proteins expressed by a microbe, such as a *K. pneumoniae*, under low metal conditions, such as low iron conditions, and is a combination of proteins does not naturally exist.

A recombinantly-produced protein may be expressed from a vector that permits expression of the protein when the vector is introduced into an appropriate host cell. A host cell may be constructed to produce one or more recombinantly-produced proteins as described herein and, therefore, can include one more vectors that include at least one polynucleotide that encodes a protein as described herein. Thus, each vector can include one or more polynucleotides as described herein—i.e., a polynucleotide that encodes a protein as described herein.

Certain compositions such as, for example, those including recombinantly-produced proteins, can include a maximum number of proteins. In some embodiments, the maximum number of proteins can refer to the maximum total number of proteins. Certain compositions can include, for example, no more than 50 proteins such as, for example, no more than 40 proteins, no more than 30 proteins, no more than 25 proteins, no more than 20 proteins, no more than 15 proteins, no more than 10 proteins, no more than nine proteins, no more than eight proteins, no more than seven proteins, no more than six proteins, no more than five proteins, no more than four proteins, no more than three proteins, no more than two proteins, or no more than one protein. In other embodiments, a maximum number of recombinantly-produced proteins may be specified in a similar manner. In still other embodiments, a maximum number of nonrecombinantly-produced proteins may be specified in a similar manner.

A composition can include proteins isolatable from one microbe, or can be isolatable from a combination of two or more microbes. For instance, a composition can include proteins isolatable from two or more *Klebsiella* spp., or from a *Klebsiella* spp. and a different microbe that is not a member of the genus *Klebsiella*.

In certain embodiments, a composition can include a whole cell preparation in which the whole cell expresses one or more of the proteins as described herein. In some of these embodiments, the whole cell can be a *Klebsiella* spp., in other embodiments, the whole cell is one genetically engineered to express one or more of the proteins. In some embodiments, a composition can include whole cell preparations from two, three, four, five, or six strains.

In one embodiment, a composition includes polypeptides expressed by a *Klebsiella* spp. during growth in low iron and at least one, at least two, at least three, or more recombinantly produced proteins. For instance, the *Klebsiella* spp. can be engineered to express at least one recombinant protein, or a composition isolated from a *Klebsiella* spp. can be supplemented with a least one recombinant protein expressed by a second cell. In one embodiment, such a composition is not naturally occurring.

Specific examples of compositions include, but are not limited to, the following. In one embodiment, a composition includes at least two metal regulated proteins having molecular weights selected from 82 kDa, 78 kDa, 72 kDa, and 68 kDa as determined by SDS-PAGE. For instance, a composition can include proteins having molecular weights of 82 kDa, 78 kDa, 72 kDa, and 68 kDa; 82 kDa, 78 kDa, and 72 kDa; 82 kDa, 78 kDa, and 68 kDa; 82 kDa, 72 kDa, and 68 kDa; 78 kDa, 72 kDa, and 68 kDa; 82 kDa and 78 kDa; 82 kDa and 68 kDa; or 72 kDa and 68 kDa. Optionally, a composition includes one or two proteins that are not metal regulated, where the proteins have molecular weights of 35 kDa and 33 kDa as determined by SDS-PAGE. Optionally, a composition includes a metal regulated protein having a molecular weight of 87 kDa as determined by SDS-PAGE. Optionally, a composition includes at least one metal regulated proteins expected to be expressed by and isolatable from *K. pneumoniae*, such as a protein having a molecular weight of 83 kDa, 78 kDa, 78.4 kDa, 76.2 kDa, 74.7 kDa, or 66.2 kDa, where the molecular weight is determined from the deduced amino acid sequence. Thus, in one embodiment a composition includes two, three, or four metal regulated proteins having molecular weights of 82 kDa, 78 kDa, 72 kDa, and 68 kDa, two proteins that are not metal regulated and have molecular weights of 35 kDa and 33 kDa, and a metal regulated protein having a molecular weight of 87 kDa.

In one embodiment, a composition includes at least two proteins that are structurally similar to proteins selected from SEQ ID NO:41, SEQ ID NO:42, SEQ ID NO:43, and SEQ ID NO:44. For instance, a composition can include proteins that are structurally similar to SEQ ID NO:41, SEQ ID NO:42, SEQ ID NO:43, and SEQ ID NO:44; SEQ ID NO:41, SEQ ID NO:42, and SEQ ID NO:43; SEQ ID NO:41, SEQ ID NO:42, and SEQ ID NO:44; SEQ ID NO:41, SEQ ID NO:43, and SEQ ID NO:44; SEQ ID NO:42, SEQ ID NO:43, and SEQ ID NO:44; SEQ ID NO:41, SEQ ID NO:42; SEQ ID NO:41, and SEQ ID NO:44; SEQ ID NO:43, and SEQ ID NO:44. Optionally, a composition includes an additional two proteins that are structurally similar to SEQ ID NO:54 and SEQ ID NO:55. Optionally, a composition includes at least one protein that is structurally similar to a protein selected from SEQ ID NO:45, SEQ ID NO:46, SEQ ID NO:49, SEQ ID NO:51, SEQ ID NO:52, SEQ ID NO:53, SEQ ID NO:58, SEQ ID NO:61, and SEQ ID NO:64. Optionally, a composition includes at least one protein that is structurally similar to a protein that includes a region of amino acids that is structurally similar to the amino acid sequence of SEQ ID NO:14, SEQ ID NO:16, or SEQ ID NO:20.

In one embodiment, a composition includes at least two proteins that are structurally similar to proteins selected from SEQ ID NO:41, SEQ ID NO:58, SEQ ID NO:61, and SEQ ID NO:64. For instance, a composition can include proteins that are structurally similar to SEQ ID NO:41, SEQ ID NO:58, SEQ ID NO:61, and SEQ ID NO:64; SEQ ID NO:41, SEQ ID NO:58, and SEQ ID NO:61; SEQ ID NO:41, SEQ ID NO:58, and SEQ ID NO:64; SEQ ID NO:41, SEQ ID NO:61, and SEQ ID NO:64; SEQ ID NO:58, SEQ ID NO:61, and SEQ ID NO:64; SEQ ID NO:41 and SEQ ID NO:58; SEQ ID NO:41 and SEQ ID NO:64; or SEQ ID NO:61, and SEQ ID NO:64. Optionally, a composition includes an additional two proteins that are structurally similar to SEQ ID NO:54 and SEQ ID NO:55. Optionally, a composition includes at least one protein that is structurally similar to a protein selected from SEQ ID NO:42, SEQ ID NO:43, and SEQ ID NO:44, SEQ ID NO:45, SEQ ID NO:46, SEQ ID NO:49, SEQ ID NO:51, SEQ ID NO:52, and SEQ ID NO:53. Optionally, a composition includes at least one protein that is structurally similar to a protein that includes a region of amino acids that is structurally similar to the amino acid sequence of SEQ ID NO:14, SEQ ID NO:16, or SEQ ID NO:20.

Optionally, a protein as described herein can be covalently bound or conjugated to a carrier protein to improve the immunological properties of the protein. Useful carrier proteins are known in the art. The chemical coupling of proteins as described herein can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-ma-leimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (see, for instance, Harlow and Lane, Antibodies, A Laboratory Manual, generally and Chapter 5, Cold Spring Harbor Laboratory, Cold Spring Harbor, New York, NY (1988)).

A composition described herein can include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site.

The concentration of LPS can be determined using routine methods known in the art. Such methods typically include measurement of dye binding by LPS (see, for instance, Keler and Nowotny, *Analyt. Biochem.*, 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, NY (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX- ATE (Sigma Chemical Co., St. Louis, MO; see Sigma Technical Bulletin No. 210), and PYROTELL (Associates of Cape Cod, Inc., East Falmouth, MA). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, MD, Catalog No. 235503), and Associates of Cape Cod, Inc., (Catalog No. E0005). In general, when a composition of the present invention is prepared by isolating polypeptides from a microbe by a method as described herein (e.g., a method that includes disrupting and solubilizing the cells, and collecting the insoluble polypeptides), the amount of LPS in a composition of the present invention is less than the amount of LPS present in a mixture of same amount of the same microbe that has been disrupted under the same conditions but not solubilized. Typically, the level of LPS in a composition described herein is decreased by, in increasing order of preference, at least 50%, at least 60%, at least 70%, at least 80%, at least 90%, at least 95%, or at least 99% relative to the level of LPS in a composition prepared by disrupting, but not solubilizing, the same microbe. In one embodiment, the level of LPS in a composition described herein is decreased by greater than 90%, greater than 95%, or greater than 99% compared to the level of LPS in a composition prepared by disrupting, but not solubilizing, the same microbe.

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in Emery and Straub (WO 01/37810 (2001)), and Emery et al., (WO 96/01620 (1996)). Implants can be produced at sizes small enough to be administered by aerosol or spray. Implants also can include nanospheres and microspheres.

A composition as described herein may be administered in an amount sufficient to treat certain conditions as described herein. The amount of proteins or whole cells present in a composition as described herein can vary. For instance, the dosage of proteins can be between 0.01 micrograms (μg) and 300 mg, typically between 0.1 mg and 10 mg. In one embodiment, the dosage of proteins may be at least 700 μg, at least 900 μg, or at least 1,000 μg. In one embodiment, the dosage may be no greater than 1,800 μg, no greater than 1,600 μg, no greater than 1,400 μg, or no greater than 1,200 μg. When the composition is a whole cell preparation, the cells can be present at a concentration of, for instance, $10^2$ bacteria/ml, $10^3$ bacteria/ml, $10^4$ bacteria/ml, $10^5$ bacteria/ml, $10^6$ bacteria/ml, $10^7$ bacteria/ml, $10^8$ bacteria/ml, or $10^9$ bacteria/ml. For an injectable composition (e.g. subcutaneous, intramuscular, etc.) the proteins may be present in the composition in an amount such that the total volume of the composition administered is 0.5 ml to 5.0 ml, typically 1.0 to 2.0 ml. When the composition is a whole cell preparation, the cells are preferably present in the composition in an amount that the total volume of the composition administered is 0.5 ml to 5.0 ml, typically 1.0 to 2.0 ml. The amount administered may vary depending on various factors including, but not limited to, the specific proteins chosen, the weight, physical condition and age of the animal, and the route of administration. Thus, the absolute weight of the protein included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al., (U.S. Pat. No. 6,027,736).

The formulations may be conveniently presented in unit dosage form and may be prepared by methods well known in the art of pharmacy. Methods of preparing a composition with a pharmaceutically acceptable carrier include the step of bringing the active compound (e.g., a protein or whole cell as described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyl dioctadecyl ammonium bromide (DDA), avridine, aluminum hydroxide, oils, saponins, alpha-tocopherol, polysaccharides, emulsified paraffins (including, for instance, those available from under the tradename EMULSIGEN from MVP Laboratories, Ralston, Nebraska), ISA-70, RIBI and other substances known in the art. It is expected that proteins as described herein will have immunoregulatory activity and that such proteins may be used as adjuvants that directly act as T cell and/or B cell activators or act on specific cell types that enhance the synthesis of various cytokines or activate intracellular signaling pathways. Such proteins are expected to augment the immune response to increase the protective index of the existing composition.

In another embodiment, a composition as described herein including a pharmaceutically acceptable carrier can include a biological response modifier, such as, for example, IL-2, IL-4 and/or IL-6, TNF, IFN-α, IFN-γ, and other cytokines that effect immune cells. An immunizing composition can also include other components known in the art such as an antibiotic, a preservative, an anti-oxidant, or a chelating agent.

Methods of Making

The present invention also provides methods for obtaining the proteins described herein. The proteins and whole cells of the present invention may be isolatable from a member of the family Enterobacteriaceae. Microbes useful for obtaining proteins of the present invention and making whole cell preparations are commercially available from a depository such as American Type Culture Collection (ATCC). In addition, such microbes are readily obtainable by techniques routine and known to the art. The microbes may be derived from an infected animal as a field isolate, and used to obtain proteins and/or whole cell preparations of the present invention, or stored for future use, for example, in a frozen repository at −20° C. to −95° C., or −40° C. to −50° C., in bacteriological media containing 20% glycerol, and other like media.

When a protein of the present invention is to be obtained from a microbe, the microbe can be incubated under low metal conditions. As used herein, the phrase "low metal conditions" refers to an environment, typically bacteriological media, which contains amounts of a free metal that cause a microbe to express metal-regulated proteins at a detectable level. As used herein, the phrase "high metal conditions" refers to an environment that contains amounts of a free metal that cause a microbe to either not express one or more of the metal-regulated proteins described herein at a detectable level, or to express such a protein at a decreased level compared to expression of the metal-regulated protein under low metal conditions. In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

Low metal conditions are generally the result of the addition of a metal chelating compound to a bacteriological medium, the use of a bacteriological medium that contains low amounts of a metal, or the combination thereof. High metal conditions are generally present when a chelator is not present in the medium, a metal is added to the medium, or the combination thereof. Examples of metal chelators include natural and synthetic compounds. Examples of natural compounds include plant phenolic compounds, such as flavonoids. Examples of flavonoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis (2-pyridylmethyl)-ethylene diamine.

Examples of synthetic iron chelators include 2,2'-dipyridyl (also referred to in the art as ∀,∀'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. An example of a general divalent cation chelator is CHELEX resin. Preferably, 2,2'-dipyridyl is used for the chelation of iron. Typically, 2,2'-dipyridyl is added to the media at a concentration of at least 0.0025 micrograms/milliliter (µg/ml), at least 0.25 µg/ml, at least 25 µg/ml, at least 50 µg/ml, or higher amounts depending on the growth characteristics of the microbe.

It is expected that a *Klebsiella* spp. with a mutation in a fur gene will result in the constitutive expression of many, if not all, of the metal regulated proteins of the present invention. The production of a fur mutation in a *Klebsiella* spp. can be produced using routine methods including, for instance, transposon, chemical, or site-directed mutagenesis useful for generating gene knock-out mutations in gram negative bacteria.

The medium used to incubate the microbe and the volume of media used to incubate the microbe can vary. When a microbe is being evaluated for the ability to produce one or more of the proteins described herein, the microbe can be grown in a suitable volume, for instance, 10 milliliters to 1 liter of medium. When a microbe is being grown to obtain proteins for use in, for instance, administration to animals, the microbe may be grown in a fermenter to allow the isolation of larger amounts of proteins. Methods for growing microbes in a fermenter are routine and known to the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C.

In some aspects of the invention, a microbe may be harvested after growth. Harvesting includes concentrating the microbe into a smaller volume and suspending in a medium different than the growth medium. Methods for concentrating a microbe are routine and known in the art, and include, for example, filtration or centrifugation. Typically, the concentrated microbe is suspended in an appropriate buffer. An example of a buffer that can be used contains Tris-base (7.3 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted.

When the microbe is to be used as a whole cell preparation, the harvested cells may be processed using routine and known methods to inactivate the cells. Alternatively, when a microbe is to be used to prepare proteins described herein, the microbe may be disrupted using chemical, physical, or mechanical methods routine and known to the art, including, for example, boiling, French press, sonication, digestion of peptidoglycan (for instance, by digestion with lysozyme), or homogenization. An example of a suitable device useful for homogenization is a model C500-B AVESTIN homogenizer, (Avestin Inc, Ottawa Canada). As used herein, "disruption" refers to the breaking up of the cell. Disruption of a microbe can be measured by methods that are routine and known to the art, including, for instance, changes in optical density. Typically, when the percent transmittance of a 1:100 dilution of a microbe is 40%-60% prior to disruption, the percent transmittance is increased to 80% (increase of 20%-40%)

following disruption. When physical or mechanical methods are used, the temperature during disruption is typically kept low, preferably at 4° C., to further minimize proteolytic degradation. When chemical methods are used the temperature may be increased to optimize for the cell disruption. A combination of chemical, physical, and mechanical methods may also be used to solubilize the cell wall of microbe. As used herein, the term "solubilize" refers to dissolving cellular materials (e.g., proteins, nucleic acids, carbohydrates) into the aqueous phase of the buffer in which the microbe was disrupted, and the formation of aggregates of insoluble cellular materials. Without intending to be limited by theory, the conditions for solubilization are believed to result in the aggregation of proteins of the present invention into insoluble aggregates that are large enough to allow easy isolation by, for instance, centrifugation.

The insoluble aggregates that include one or more of the proteins of the present invention may be isolated by methods that are routine and known to the art. In one embodiment, the insoluble aggregates are isolated by ultrafiltration. In one embodiment, the insoluble aggregates are isolated by centrifugation. Typically, centrifugation of proteins, such as membrane proteins, can be accomplished by centrifugal forces of 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of continuous flow centrifuges, for instance T-1 Sharples (Alfa Laval Separations, Warminster, PA), which can be used with a flow rate of 250 ml/minute at 17 psi at a centrifugal force of 46,000×g to 60,000×g. Other large scale centrifuges can be used, such as the tubular bowl, chamber, and disc configurations. Such centrifuges are routinely used and known in the art, and are commercially available from such manufactures as Pennwalt, Westfalia and Alpha Laval.

The final harvested proteins are washed and/or dialyzed against an appropriate buffer using methods known in the art, for instance diafiltration, precipitation, hydrophobic chromatography, ion-exchange chromatography, or affinity chromatography, or ultrafiltration and washing the proteins, for instance, in alcohol, by diafiltration. After isolation, the proteins are suspended in buffer and stored at low temperature, for instance, −20° C. or below.

In those aspects of the present invention where a whole cell preparation is to be made, after growth a microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated protein of the invention may be prepared recombinantly. When prepared recombinantly, a polynucleotide encoding the protein may be identified and cloned into an appropriate expression host. The recombinant expression host may be grown in an appropriate medium, disrupted, and the proteins isolated as described above. Alternatively, when a recombinant protein forms inclusion bodies routine methods can be used to isolate and purify the recombinant protein. For instance, inclusion bodies can be extracted from the expression host and the protein present in the inclusion bodies solubilized above.

Methods of Use

Also provided are methods of using the compositions described herein. The methods include administering to an animal an effective amount of a composition described herein. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, dogs or cats), members of the family Cervidae (including, for instance, deer, elk, moose, caribou and reindeer), or human.

In some aspects, the methods may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some aspects of the present invention annual boosters will not be necessary, as an animal will be challenged in the field by exposure to microbes expressing proteins present in the compositions having epitopes that are identical to or structurally related to epitopes present on proteins of the composition administered to the animal.

In one aspect, the invention is directed to methods for making antibodies, for instance by inducing the production of antibody in an animal, or by recombinant techniques. The antibody produced includes antibody that specifically binds at least one protein present in the composition. In this aspect of the invention, an "effective amount" is an amount effective to result in the production of antibody in the animal. Methods for determining whether an animal has produced antibodies that specifically bind proteins present in a composition of the present invention can be determined as described herein. The present invention further includes antibody that specifically bind to a protein of the present invention, and compositions including such antibodies.

The method may be used to produce antibody that specifically binds proteins expressed by a microbe other than the microbe from which the proteins of the composition were isolated. As used herein, an antibody that can "specifically bind" a protein is an antibody that interacts with the epitope of the antigen that induced the synthesis of the antibody, or interacts with a structurally related epitope. At least some of the proteins present in the compositions of the present invention typically include epitopes that are conserved in the proteins of different species and different genera of microbes. Accordingly, antibody produced using a composition derived from one microbe is expected to bind to proteins expressed by other microbes and provide broad spectrum protection against gram negative organisms. Examples of gram negative microbes to which the antibody may specifically bind are members of the family Vibrionaceae (including, for instance, *Vibrio cholerae*), *Campylobacter* spp. (including, for instance, *C. jejuni*), members of the family Enterobacteriaceae (including, for instance, *Klebsiella* spp., *E. coli*, *Shigella* spp., *Salmonella* spp., *Proteus* spp., *Serratia* spp., and *Yersinia* spp.), members of the family Pasteurellaceae, preferably *Pasturella* spp. (including, for instance, *P. multocida* and *P. haemolytica*), and members of the family Pseudomonadaceae, preferably *Pseudomonas* spp., (including, for instance, *Pseudomonas aeruginosa*). Examples of *Klebsiella* spp. include *K. pneu-*

*moniae* and *K. oxytoca*. Examples of *Salmonella* spp. include *Salmonella enterica* serovars., Bredeney, Dublin, Agona, Blockley, Enteriditis, Typhimurium, Hadar, Heidelberg, Montevideo, Muenster, Newport senftenberg, *Salmonella cholerasuis*, and *S. typhi*. Examples of strains of *E. coli* include, for example, *E. coli* serotypes O1a, O2a, O78, and O157, different O:H serotypes including 0104, 0111, 026, 0113, 091, hemolytic strains of enterotoxigenic *E. coli* such as K88$^+$, F4$^+$, F18ab$^+$, and F18ac$^+$, and uropathogenic strains of *E. coli*. Therefore, antibody produced using a composition of proteins described herein may be used to identify and characterize proteins independent of the origin, source, and/or manner of obtaining the protein.

The present invention is also directed to the use of such antibody to target a microbe expressing a protein of the present invention or a protein having an epitope structurally related to an epitope present on a protein of the present invention. A compound can be covalently bound to an antibody, where the compound can be, for instance, a toxin. Likewise, such compounds can be covalently bound to a bacterial siderophore to target the microbe. The chemical coupling or conjugation of an antibody of the present invention, or a fragment thereof (such as a Fab fragment), can be carried out using known and routine methods.

In one aspect the invention is also directed to treating an infection in an animal, including a human, caused by a gram negative microbe. As used herein, the term "infection" refers to the presence of a gram negative microbe in an animal's body, which may or may not be clinically apparent. Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of the composition of the present invention to an animal having, or at risk of having, an infection caused by a gram negative microbe, and determining whether the number of microbes causing the infection has decreased. The gram negative microbe may be, for instance, a member of the family Vibrionaceae (including, for instance, *Vibrio cholerae*), *Campylobacter* spp. (including, for instance, *C. jejuni*), a member of the family Enterobacteriaceae (including, for instance, *Klebsiella* spp., *E. coli, Shigella* spp., *Salmonella* spp., *Proteus* spp., *Serratia* spp., *Yersinia* spp., *Enterobacter* spp. and *Citrobacter* spp.), a member of the family Pasteurellaceae, preferably *Pasturella* spp. (including, for instance, *P. multocida* and *P. haemolytica*), or a member of the family Pseudomonadaceae. In one embodiment, the animal has, or is at risk of having, an infection caused by *K. pneumoniae* or *K. oxytoca*. In this aspect of the invention, an "effective amount" is an amount effective to reduce the number of the specified microbes in an animal or reduce the likelihood that the animal experiences a clinically-evident infection compared to an animal to which the composition is not administered. Methods for determining whether an infection is caused by a gram negative microbe, such as *K. pneumoniae* or *K. oxytoca*, are routine and known in the art, as are methods for determining whether the infection has decreased.

In another aspect, the present invention is directed to methods for treating one or more symptoms or clinical signs of certain conditions in an animal that may be caused by infection by a gram negative microbe. The method includes administering an effective amount of a composition of the present invention to an animal having or at risk of having a condition, or exhibiting symptoms and/or clinical signs of a condition, and determining whether at least one symptom and/or clinical sign of the condition is changed, preferably, reduced. The gram negative microbe may be, for instance, a member of the family Vibrionaceae (including, for instance, *Vibrio cholerae*), *Campylobacter* spp. (including, for instance, *C. jejuni*), a member of the family Enterobacteriaceae (including, for instance, *Klebsiella* spp., *E. coli, Shigella* spp., *Salmonella* spp., *Proteus* spp., *Serratia* spp., and *Yersinia* spp.), a member of the family Pasteurellaceae, preferably *Pasturella* spp. (including, for instance, *P. multocida* and *P. haemolytica*), or a member of the family Pseudomonadaceae. In one embodiment, the animal has a condition caused by *K. pneumoniae* or *K. oxytoca*. In one embodiment, the animal has a condition caused by a uropathogenic *E. coli*. Examples of symptoms and/or clinical signs caused by a gram negative microbial infection are known to the person skilled in the art.

Treatment of symptoms and/or clinical signs associated with conditions caused by a gram negative infection can be prophylactic or, alternatively, can be initiated after the development of a condition described herein. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Treatment initiated after the development of a condition may result in decreasing the severity of the symptoms or signs of one of the conditions, or completely removing the symptoms or signs. In this aspect of the invention, an "effective amount" is an amount effective to prevent the manifestation of symptoms or signs of a disease, decrease the severity of the symptoms or signs of a disease, and/or completely remove the symptoms or signs. The successful treatment of a gram negative microbial infection in an animal is disclosed in Examples 11-19, which demonstrates the protection against disease caused by *K. pneumoniae* in a mouse model by administering a composition described herein. This mouse model is a commonly accepted model for the study of disease caused by *K. pneumoniae*.

In one embodiment, the condition is mastitis in a milk producing animal, such as a cow. The method includes administering an effective amount of a composition described herein to a milk producing animal having or at risk of having mastitis, and determining whether at least one symptom or sign of mastitis is reduced. Mastitis refers to inflammation of the mammary gland. Physical, chemical and usually bacteriological changes in the milk and pathological changes in the glandular tissue characterize it. These glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. In many cases the diagnosis of subclinical infections has come to depend largely on indirect tests which depend on the leukocyte content of the milk or somatic cell count (SCC). The most common organisms that infect the udder are coliform bacteria, such as, *K. pneumoniae*, *K. oxytoca*, *E. coli*, *Enterobacter* spp., *Serratia* spp., *Proteus* spp., and *Citrobacter* spp. Other organisms that cause mastitis less frequently include *Pseudomonas* spp., *Brucella* spp., *Corynebacterium* spp., *Mycoplasma* spp., and *Pasteurella* spp.

In another embodiment, the condition is a high somatic cell count (SSC) in an animal's milk, such as a cow. The method includes administering an effective amount of a composition described herein to a milk producing animal having or at risk of having high somatic cell counts, and determining whether the somatic cell count in milk obtained from the animal contains reduced somatic cell counts compared to milk obtained from the animal before receiving the composition. In another embodiment, provided herein is a method for reducing somatic cell counts in an animal's milk. Somatic cells include leucocytes of the animal, and are typically present at low levels in normal milk. High levels of somatic cells in milk, for instance, greater than 200,000 cells per milliliter of milk. High levels of somatic cells in milk may be indicative of infection (mastitis), but may also be unassociated with infection. SCC is monitored, typically by milk processing plants, using methods that are routine to the art. The SCC is reduced to less than 750,000 cells/ml, less than 400,000 cells/ml, or less than 200,000 cells/ml.

In another embodiment, the condition is treating low milk production by a milk producing animal, such as a cow. The method includes administering an effective amount of the composition of the present invention to a milk producing animal having or at risk of having a low milk production, and determining whether milk production by the animal is increased compared to milk production by the animal before receiving the composition. Another embodiment is directed to a method for increasing milk production in a milk producing animal, such as a cow. The method includes administering a composition described herein to a milk producing animal, and determining whether milk production by the animal is increased compared to milk production by the animal before receiving the composition. The milk production by a milk producing animal after administration of composition described herein is increased by at least 0.1%, at least 0.5%, at least 1%, or at least 3%. Milk production by a cow is can be determined before administration and 2 weeks, 8 weeks, or 16 weeks after administration of the composition.

The present invention also provides methods for decreasing colonization by gram negative microbes, for instance blocking the attachment sites of gram negative microbes, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioles, alveoli), digestive system (for instance, mouth, salivary glands, esophagus, liver, stomach, large and small intestine), excretory system (for instance, kidney, ureter, bladder, and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like. In one embodiment, the gram negative microbe is *K. pneumoniae* or *K. oxytoca*.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a subcolonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition of the present invention to an animal colonized by, or at risk of being colonized by, a gram negative microbe. In this aspect of the invention, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to other animals of the same or different species.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24):10029-33; Daugherty et al., Nucleic Acids Res., 1991, 19(9): 2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a protein of the present invention or a protein having an epitope structurally related to an epitope present on a protein of the present invention.

Animal models, in particular mouse models, are available for experimentally evaluating the compositions of the present invention. These mouse models (e.g., Meno and Amako, 1991, Microbiol. Immuniol., 35(10):841-848; Vered et al., 2014, BMC Genomics, 15:865; Kurupati et al., Clinical Vaccine Immunol., 18(1):82-88; Lundberg et al., 2013, Human Vaccines Immunotherapeutics, 9(3):497-505; and Toky et al., 2003, Folia Microbiol (Praha), 48(5):665-669) are commonly accepted models for the study of disease caused by members of the genus *Klebsiella*, and *K. pneumoniae* in particular. In those cases where a member of the genus *Klebsiella* causes disease in an animal, for instance a cow, the natural host can be used to experimentally evaluate the compositions described herein.

However, protection in a mouse model is not the only way to assess whether a composition can confer protection to an animal against infection by a *Klebsiella* spp. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in conferring protection against infection such as, for example, complement fixation, opsonization, neutralization, and/or agglutination. Moreover, some subclasses of antibodies are better than others at specific functions; for example, for complement fixation the following hierarchy exists for human IgG subclasses: IgG3>IgG1>IgG2>IgG4).

Antibody immunological functions can be studied in a variety of ways. For instance, Western blots are used to identify antigen-specific binding based on size of separated proteins, while the standard enzyme-linked immunosorbant assay (ELISA) is used to produce quantitative information about antibody titers within serum. Antibody surface binding studies are used to determine whether antibody in serum are able to recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against microbial infection. However, one skilled in the art further recognizes that a lack of antibody binding in an assay such as, for example, a Western blot, ELISA, or surface binding assay does not mean that the assayed antigen fails to provide immunological activity against microbial infection.

Antibodies can mediate bacterial death by blocking the acquisition of nutrients (e.g iron) or initiating complement-mediated membrane perforation that leads to osmotic lysis. Bactericidal antibodies can be assayed by mixing serum with live cultures and measuring for the presence of viable bacteria under appropriate conditions known to those skilled in the art. Techniques such as opsonophagocytosis assays (OPA), in which antibody and complement-bound bacteria are combined with human or mouse phagocytes to determine levels of bacterial killing, are useful for studying antibody function. A similar oxidative burst assay can be used to assess the level of reactive oxygen species (ROS) by fresh human or mouse neutrophils following interaction with antibody and complement-bound bacteria.

In some cases, one can determine that a candidate protein possesses cell-mediated immunological activity and, therefore, the candidate protein may exhibit immunological activity in the absence of inducing the production of antibodies. Cytotoxic or CD8 T cells primarily kill infected cells directly through various effector mechanisms, while helper CD4 T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated CD4+ T cell, a memory CD8+ T cell, etc. In addition, cytokines and other products of T cells can be studied by isolating the T cells from lymphoid tissue and restimulating them with cognate antigen. Following antigen stimulation the T cells produce cytokines that may be visualized by, for example, intracellular cytokine staining coupled with flow cytometry, or collecting the cell supernatants and using Luminex bead technology to measure 15-25 cytokines simultaneously.

Thus, in addition to mouse models, those of ordinary skill in the art recognize that immunological activity commensurate with the methods described herein may correlate with any one or more of the following: Western blot data showing that serum from animals exposed to a microbial pathogen contains antibody that specifically binds to a candidate protein, cell surface binding assays demonstrating that antibody that specifically binds to a candidate protein specifically binds to a microbial pathogen, opsonophagocytosis data, and cytokine induction.

Another aspect of the present invention provides methods for detecting antibody that specifically binds proteins described herein. These methods are useful in, for instance, detecting whether an animal has antibody that specifically binds proteins described herein, and diagnosing whether an animal may have a condition caused by a microbe expressing proteins described herein, or expressing proteins that share epitopes with the proteins described herein. Such diagnostic systems may be in kit form. The methods include contacting an antibody with a preparation that includes a protein described herein to result in a mixture. The antibody may be present in a biological sample, for instance, blood, milk, or colostrum. The method further includes incubating the mixture under conditions to allow the antibody to specifically bind the protein to form a protein:antibody complex. As used herein, the term "protein:antibody complex" refers to the complex that results when an antibody specifically binds to a protein. The preparation that includes the proteins described herein may also include reagents, for instance a buffer, that provide conditions appropriate for the formation of the protein:antibody complex. The protein:antibody complex is then detected. The detection of antibodies is known in the art and can include, for instance, immunofluorescence or peroxidase. The methods for detecting the presence of antibodies that specifically bind to proteins described herein can be used in various formats that have been used to detect antibody, including radioimmunoassay and enzyme-linked immunosorbent assay.

Kits

The present invention also provides a kit for detecting antibody that specifically binds a protein described herein. The antibody detected may be obtained from an animal suspected to have an infection caused by a gram negative microbe, such as *K. pneumoniae* or *K. oxytoca*. In another embodiment, the present invention provides a kit for detecting a protein described herein.

The kit includes at least one of the proteins described herein (e.g., one, at least two, at least three, etc.), or an antibody described herein in a suitable packaging material in an amount sufficient for at least one assay. Optionally, other reagents such as buffers and solutions needed to practice the invention are also included. For instance, a kit may also include a reagent to permit detection of an antibody that specifically binds to a protein described herein, such as a detectably labeled secondary antibody designed to specifically bind to an antibody obtained from an animal. Instructions for use of the packaged proteins are also typically included. As used herein, the phrase "packaging material" refers to one or more physical structures used to house the contents of the kit. The packaging material is constructed by well known methods, generally to provide a sterile, contaminant-free environment. The packaging material may have a label which indicates that the proteins can be used for detecting antibody that specifically binds proteins of the present invention. In addition, the packaging material contains instructions indicating how the materials within the kit are employed to detect the antibody. As used herein, the term "package" refers to a container such as glass, plastic, paper, foil, and the like, capable of holding within fixed limits the proteins, and other reagents, for instance a secondary antibody. Thus, for example, a package can be a microtiter plate well to which microgram quantities of proteins have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like The present invention is illustrated by the following examples. It is to be understood that the particular examples, materials, amounts, and procedures are to be interpreted broadly in accordance with the scope and spirit of the invention as set forth herein.

Example 1

Isolation of Clinical Isolates of *Klebsiella Pneumonia, Klebsiella Oxytoca* and *Enterobacter*

Isolates of *Klebsiella pneumonia, Klebsiella oxytoca* and *Enterobacter* were isolated from infected udders of cows on commercial dairy herds showing clinical signs of Coliform mastitis as diagnosed by the attending veterinarian (i.e. presence of abnormal milk; watery consistency, clots, blood, garget, pus, swelling of the udder and bacterial culture identification of milk samples). Master seed stocks of the *Klebsiella pneumonia, Klebsiella oxytoca* and *Enterobacter* were prepared by inoculating each of the isolates into 5000 ml of Tryptic Soy Broth (Difco Laboratories, Detroit, MI) containing 30 micrograms per milliliter (μg/ml) of 2,2-dipyridyl (Sigma-Aldrich St. Louis, MO). The cultures were grown while stirring at 200 rpm for 6 hours at 37° C. The bacteria were collected by centrifugation at 10,000×g. The bacterial pellets from each isolate was resuspended into 500 ml Tryptic Soy Broth containing 20% glycerol, and sterilely dispensed into 2 ml cryogenic vials (1 ml per vial) and stored at −90° C. Each isolate was given an identification number designating it as a master seed. For example; seventeen *Klebsiella pneumonia* isolates were identified and designated as 1101, 1437, 1438, 1439, 1440, 1563, 1565, 1566, 1567, 1569, 1570, 1571, 1572, 1573, 1574, 1575, and 1576. *Klebsiella oxytoca* was designated as 1564 and *Enterobacter* was designated as 1568. The Bovine master seed number for *Klebsiella pneumoniae* was designated as 1571, the bovine master seed number for *Klebsiella oxytoca* was 1564, and the bovine master seed number for *Enterobacter* was 1568. The master seed number for a human isolate of *Klebsiella pneumoniae* was prepared and designated LM21 (also referred to herein as 1748). A human UTI *E. coli* isolate used as a reference strain designated as CFT073. The master seeds of each isolate were expanded into working seeds that was then used for the production of metal regulated proteins. A small laboratory scale process was developed to examine initial metal-regulated protein expression of multiple *Kleb-*

*siella* isolates whereas a large-scale production process was developed involving fermentation, bacterial harvest, disruption, solubilization, concentration, diafiltration, and isolation of final vaccine antigens. Both the small and large scaled-up process for metal-regulated protein expression produced identical protein profiles when examined by single dimension SDS-PAGE.

Example 2

Identification and Differentiation of *Klebsiella Pneumoniae* from *Klebsiella Oxytoca* by Polymerase Chain Reaction (PCR)

Figure 1:
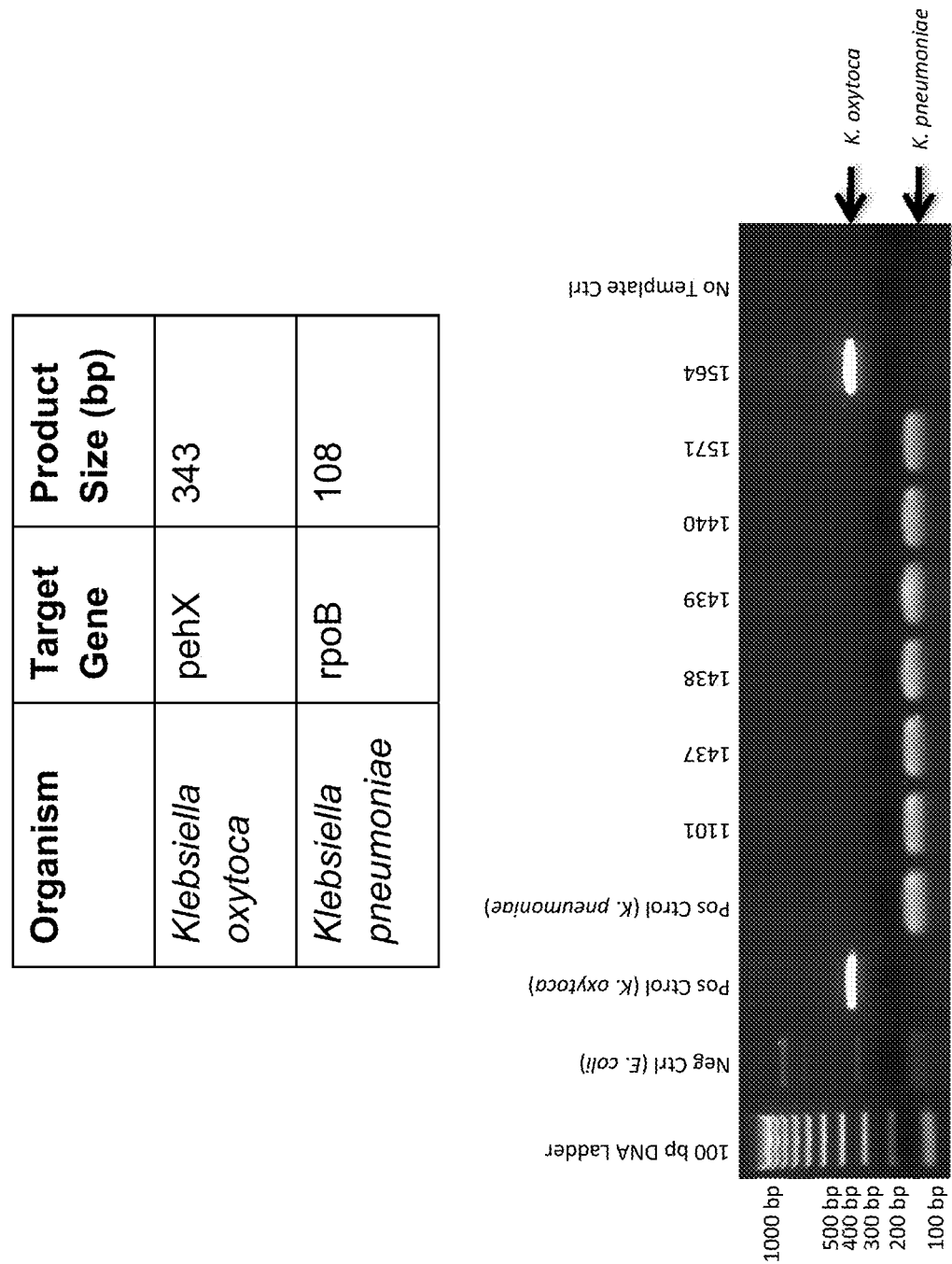
FIG. 1. *Klebsiella* multiplex PCR for identity confirmation of *Klebsiella pneumoniae*, *Klebsiella oxytoca* and *Escherichia coli*.

To differentiate *Klebsiella pneumoniae* 1571 from *Klebsiella oxytoca* 1564 isolates from both human and bovine species exhibiting clinical signs of disease, a multiplex polymerase chain reaction (PCR) was used with species specific primers as described by Chander et al. (2011, Intern J Appl Res Vet Med. 9:138-142). The position of bands on an agarose gel, 108 bp for *Klebsiella pneumoniae* 1571 and 343 bp for *K. oxytoca* 1564 confirmed strain identity (FIG. 1).

Primers and PCR Amplification: Working seeds of Example 1 were plated on blood agar in duplicate. The plates were incubated at 35-40° C. for 18-24 hours. After incubation the plates were visually examined and determined to be pure. A single, well isolated colony from one of the duplicate pure culture plates was suspended in 100 μL sterile water. The suspension was boiled for 10 minutes to lyse the cells, and allowed to cool at room temperature. The suspension was then centrifuged for 2 minutes at 13,000 rpm in a table top microcentrifuge. The supernatant containing the DNA Template was transferred to a new, sterile microcentrifuge tube and stored at −20° C. until use.

Species specific primers were used for the amplification of *K. pneumoniae* and *K. oxytoca* in a single reaction mixture (Table 2). Positive controls of *K. oxytoca* and *K. pneumoniae* were included in the assay. A no-primer negative control of *Escherichia coli* was also included. PCR reactions were set up using a Qiagen Multiplex PCR Kit according to the manufacturer's instructions. The reaction mixture consisted of: 25 μL 2× Qiagen Multiplex PCR Master Mix of each primer (forward and reverse); 5 μL 10× Primer Mix; 15 μL RNase-free water; 5 μL crude DNA template; and 50 μL total volume. The reaction conditions for PCR were as follows: initial denaturation at 95° C. for 15 minutes; 30 cycles of denaturation at 94° C. for 30 seconds; annealing at 55° C. for 1.5 minutes; and extension at 72° C. for 1.5 minutes.

TABLE 2

Sequences of primers used to identify and distinguish *Klebsiella pneumoniae* and *Klebsiella oxytoca*.

| Target Organism | Sequence (5'-3') | Product Size (bp) |
|---|---|---|
| *Klebsiella pneumoniae* | CAA CGG TGT GGT TAC TGA CG (SEQ ID NO: 31) TCT ACG AAG TGG CCG TTT TC (SEQ ID NO: 32) | 108 |
| *Klebsiella oxytoca* | GAT ACG GAG TAT GCC TTT ACG GTG (SEQ ID NO: 33) TAGCCTTTATCAAGCGGA TACTGG (SEQ ID NO: 34) | 343 |

The PCR products were visualized by electrophoresis on a 1% agarose gel (prestained with ethidium bromide) in 0.5× Tris/Boric Acid/EDTA (TBE) and UV trans-illumination. A 100 bp DNA ladder was used as molecular weight markers (FIG. 1).

Example 3

Process for Screening Metal Regulated Protein Expression of Multiple Isolates Grown Under Conditions of Metal Ion Restriction The screening of metal regulated proteins as well as the immunizing compositions used in the following examples were prepared using the proteins derived from *Klebsiella pneumoniae* originating from bovine species having clinical signs of disease.

Figure 2:
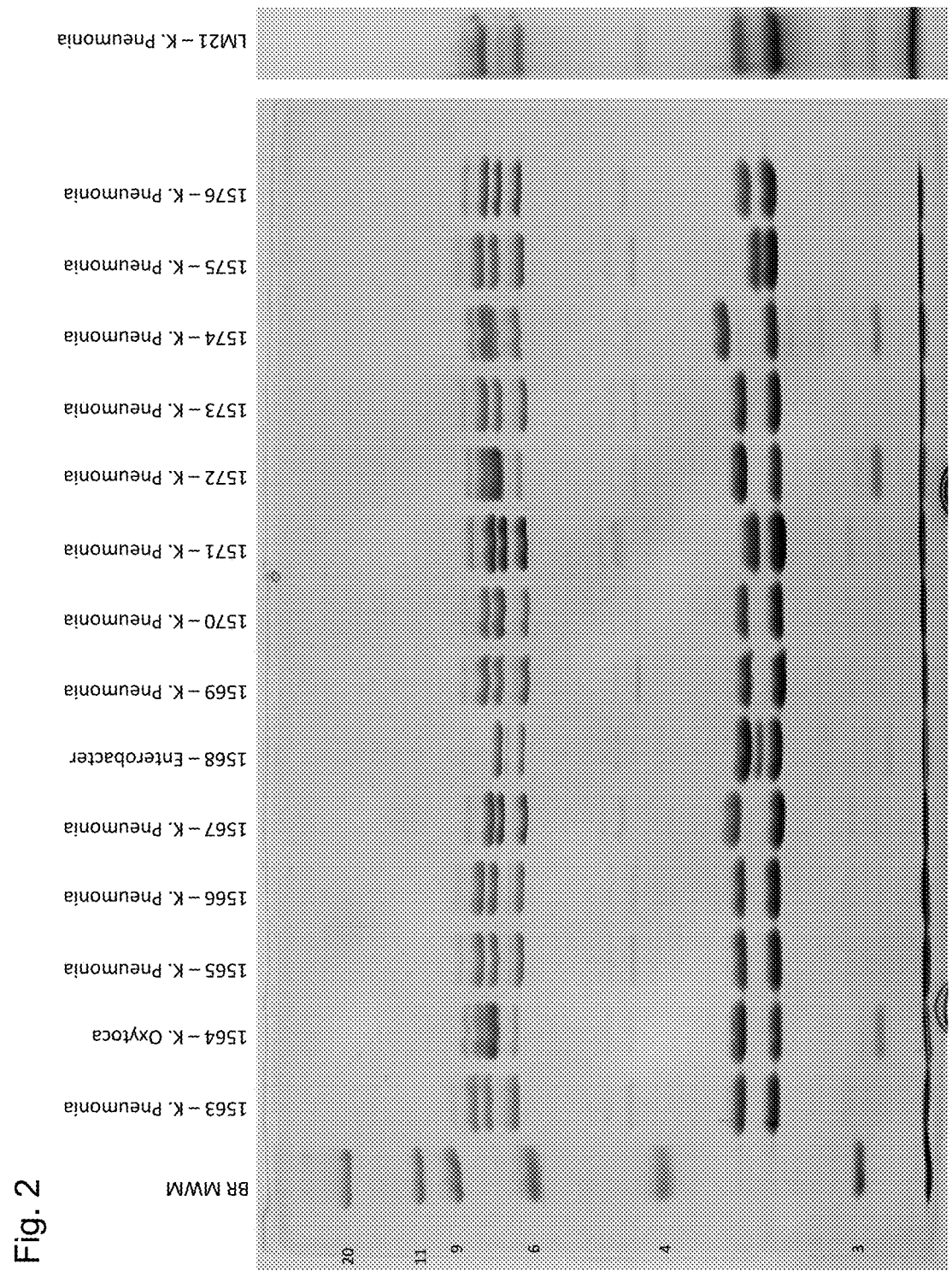
FIG. 2. Electrophoretic profile of bovine field isolates of *Klebsiella pneumonia*, *Klebsiella oxytoca*, and *Enterobacter* isolated from cows with mastitis and *Klebsiella pneumonia* human isolate LM21 showing the conservation of metal regulated protein profiles.

Multiple field isolates of *K. pneumoniae* 1563, 1565, 1566, 1567, 1569, 1570, 1571, 1572, 1573, 1574, 1575, and 1576 and single isolates of *K. oxytoca* 1564 and *Enterobacter* 1568 were collected from multiple Dairy herds showing clinical signs of mastitis. The human isolate of *K. pneumoniae* LM21 was also screened for metal regulated proteins. Each isolate was grown under conditions of iron restriction and the outer membrane profiles of proteins expressed under iron restriction was examined by SDS-PAGE (FIG. 2). Briefly, each of the isolates to be examined was inoculated into TSB containing 300 μM 2,2-diprydyl and incubated at 37° C. Following incubation for 12 hours, the cultures were subcultured (1:100) into 500 ml of iron-limiting media and incubated at 37° C. After 8 hours each culture was centrifuged at 10,000×g for 20 minutes, resuspended in 40 ml of osmotic shock buffer (7.3 g/l Tris Base; 1.86 g/l EDTA, pH 8.9, and disrupted by sonication, to yield a suspension. The suspensions were centrifuged at 32,000×g for 12 minutes to clarify or remove large cellular debris. The supernatants were collected and solubilized by the addition of 4% sodium lauroyl sarcosinate at 4° C. for 24 hours. The detergent-insoluble outer membrane protein-enriched fractions were collected by centrifugation at 32,000×g for 2.5 hours at 4° C. The protein pellets were resuspended in 200 μl Tris-buffer (pH 7.2).

The protein-enriched extracts derived from each isolate were size-fractionated on SDS-PAGE gels using a 4% stacking gel and 10% resolving gel. Samples for electrophoresis were prepared by combining 10 μl of sample with 30 μl of SDS reducing sample buffer (62.5 mM Tris-HCL pH 6.8, 20% glycerol, 2% SDS, 5% β-mercaptoethanol) and boiled for 4 minutes. Samples were electrophoresed at 18 mA constant current for 5 hours at 4° C. using a Protein II xi cell power supply (BioRad Laboratories, Richmond, CA, model 1000/500). The electrophoretic profiles comparing proteins derived from multiple isolates of *K. pneumonia, K. oxytoca Enterobacter* of bovine and human origin are shown in FIG. 2.

The SDS-PAGE patterns of the protein-enriched extracts showed a high degree of conservatism among all isolates examined, with the molecular weights ranging for the metal regulated proteins from 97 kDa to 66 kDa and non-metal regulated proteins, e.g., porins, ranging from 35 kDa to 33 kDa (Table 1). The electrophoretic profiles were analyzed using the Phoretix 1D Pro Gel Software (Total Lab; United Kingdom) to evaluate banding patterns and molecular weight calibration between each strain.

Example 4

Analysis of Metal-Regulated Proteins Under Iron Replete and Iron Deplete by Single Dimension SDS-PAGE To obtain a better perspective of the up-regulation of metal-regulated proteins of *Klebsiella pneumoniae* 1571, the isolate was grown in iron replete and iron deplete media conditions. Briefly, the organism was grown from a frozen master seed stock, previously prepared by sub-culturing into two separate 500 ml bottles. One bottle contained of 200 ml of sterile TSB containing 300 µM 2,2-diprydyl (Sigma-Aldrich St. Louis, MO) while the second bottle contained 200 ml of Tryptic Soy broth containing 200 µM ferric chloride (Sigma-Aldrich St. Louis, MO). Cultures were incubated for 12 hours with continuous stirring at 200 rpm at 37° C. Following the 12 hour incubation period, the cultures were sub-cultured (1:100) into 500 ml of either the iron-replete and/or the iron-deplete media and incubated at 37° C. for 8 hours. After 8 hours each culture was centrifuged at 10,000×g for 20 minutes, and resuspended in 40 ml of osmotic shock buffer (7.3 g/l Tris Base; 1.86 g/l EDTA), pH 8.9. The suspensions were centrifuged at 32,000×g for 12 minutes to clarify or remove large cellular debris. The supernatants were collected and solubilized by the addition of 4% sodium lauroyl sarcosinate at 4° C. for 24 hours. The detergent-insoluble outer membrane protein-enriched fractions were collected by centrifugation at 32,000×g for 2.5 hours at 4° C. The protein pellets were resuspended in 200 µl Tris-buffer (pH 7.2).

Figure 3:
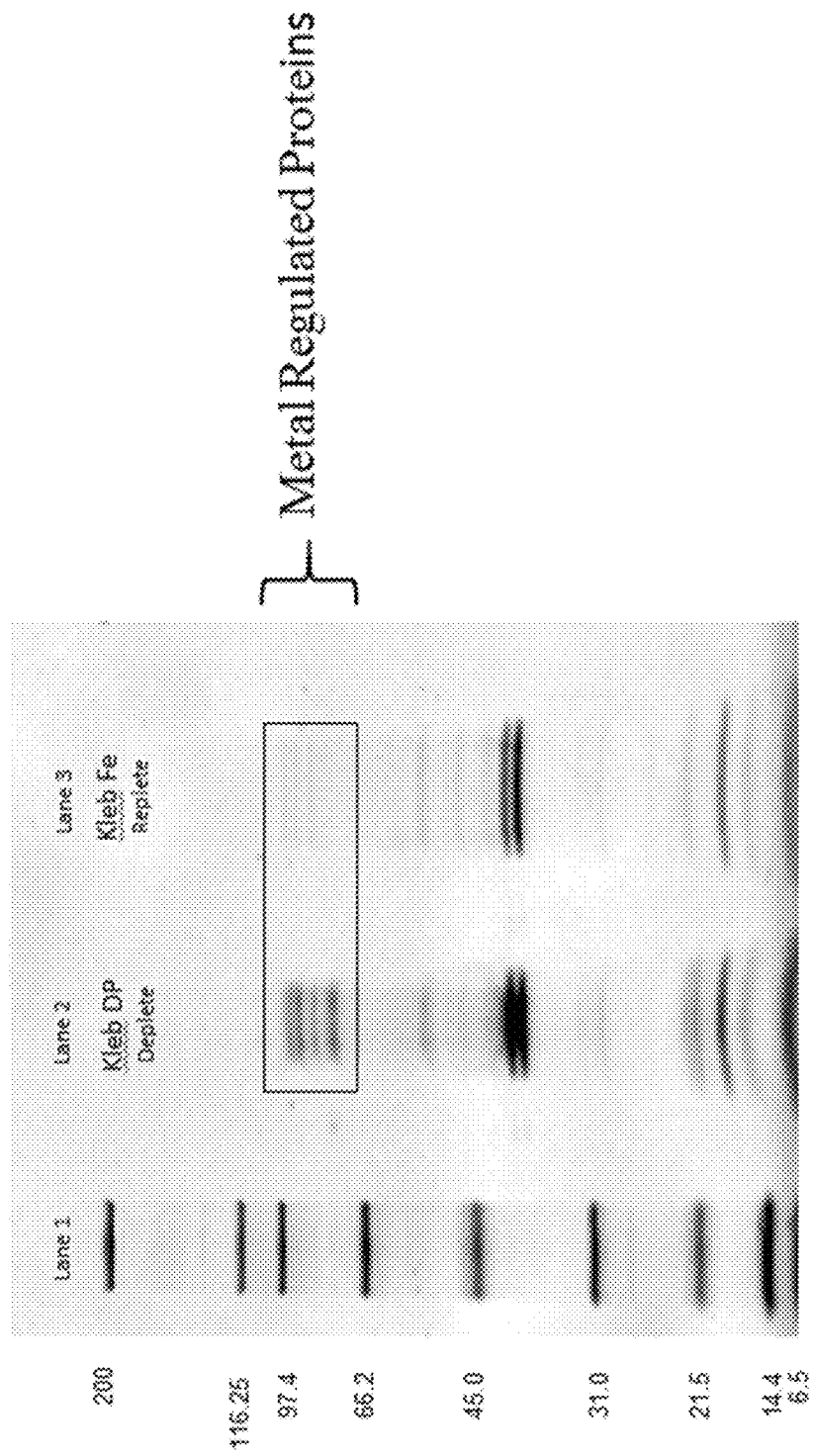
FIG. 3. Difference in outer membrane protein profiles comparing iron-replete and iron-deplete growth conditions of *Klebsiella pneumoniae* 1571 showing the expression of metal regulated proteins in the iron-replete condition as examined by SDS-PAGE. Lane 1, molecular weight marker; lane 2, iron deplete; lane 3, iron replete.

The protein-enriched extracts derived from each isolate were size-fractionated on SDS-PAGE gels using a 4% stacking gel and 10% resolving gel. Samples for electrophoresis were prepared by combining 10 µl of sample with 30 µl of SDS reducing sample buffer (62.5 mM Tris-HCL pH 6.8, 20% glycerol, 2% SDS, 5% β-mercaptoethanol) and boiled for 4 minutes. Samples were electrophoresed at 18 mA constant current for 5 hours at 4° C. using a Protein II xi cell power supply (BioRad Laboratories, Richmond, CA, model 1000/500). The electrophoretic profile comparing protein profiles derived from the *K. pneumonia*, grown under iron-replete and iron-deplete growth conditions are shown in FIG. 3.

Example 5

Large Scale Process for the Manufacture of Metal-Regulated Proteins

Fermentation

A cryogenic vial of the working seed (1 ml at $10^9$ CFU/ml) was used to inoculate 500 ml of 37° C. tryptic soy broth (TSB) without dextrose (Bacto) containing 34 micrograms/liter 2,2-dipyridyl (Sigma), 2.5 grams/liter yeast extract (Bacto) and glycerol (3% vol/vol). The culture was incubated at 37° C. for 16 hours while agitating at 160 rpm, and then divided between two 1.5 L bottles of the above media. This second culture was allowed to grow for an additional 2.5 hours at 37° C. This culture was used to inoculate a 400 L DCI-Biolafitte SIP fermentor, (DCI, St. Cloud, MN) charged with 300 liters of the above-described media with the addition of Mazu DF 204 defoamer (150 ml). The parameters of the fermentation were as follows: dissolved oxygen (DO) was maintained at 60%+/−20% by increasing agitation to 500 rev/minute sparged with 17-120 liters of air/minute, 0-60 liters of air/minute and 5 pounds per square inch (psi) back pressure. The pH was held constant between 6.9 and 7.2 by automatic titration with 50% NaOH and 25% H3PO4. The temperature was maintained at 37° C. The fermentation was allowed to continue growth for 5.5 hours at which point the fermentation was terminated by lowing the temperature of the fermentor to 15° C. and lowering pH to 5.0 with 25% H3PO4 (optical density 15 at 540 nanometers at a 1:20 dilution). The culture was sterilely transferred to a 200-liter tank (LEE Process Systems and Equipment model 2000LDBT) in preparation for harvest.

Harvest

The bacterial fermentation was concentrated and washed using a Pall Filtron Tangential Flow Maxisette-25 (Pall Filtron Corporation, Northboro, MA) equipped with four 30 ft² Alpha 0.1 um open channel filters (Pall Filtron, catalog No. PSM10C52) connected to a Waukesha Model 130 U2 feed pump (Waukesha Cherry-Burrell, Delevan, WI) The original culture volume of 300 liters was reduced to 60 liters using a filter inlet pressure of 30-40 psi and a retentate pressure of 2-15 psi. The bacterial retentate was then washed using 200 liters of a sodium acetate tryhidrate solution pH 5.0 which was composed of 2.72 grams/liter sodium acetate tryhidrate. The 60 liters of bacterial retentate was then washed with 100 liters of osmotic shock buffer (OMS) containing 14.52 grams/liter Tris-base and 1.86 grams/liter EDTA adjusted to a pH of 8.6. The EDTA in the OMS served to assist removal of much of LPS from the cell wall, while the elevated pH prevented much of the proteolytic degradation after freezing and disruption. Protease inhibitors may be used instead of, or in addition to, an elevated pH. The retentate was then concentrated down to 40 liters to help remove any contaminating exogenous proteins, 200 more liters of the above OMS was then added to wash all bacteria through the filters into the harvest tank. The retentate was mixed thoroughly while in the 200-liter tank using a bottom mount magnetically driven mixer. The retentate was sterilely dispensed (5 liters) into gamma irradiated 5 liter Invitro™ containers and placed into a −20° C. freezer for storage. Freezing the bacterial pellet served to weaken the cell wall structure making downstream disruption more efficient. The pellet mass was calculated by centrifuging 1 ml sample of the fermented culture and final harvest. Pre-weighted 1ml conical tubes were centrifuged at 13,000 rpms for 10 minutes in a Microfuge 18. The supernatant was poured off and the pellet was re-suspended in sterile water. This mixture was again centrifuged at 13,000 rpms for 5 minutes before it was once again decanted. This washed pellet was placed in a 125° C. oven for 75 minutes before being weighed and extrapolated to determine harvest volume pellet mass. The fermentation process yielded a dry pellet mass of 2.3 kilograms.

Alternative methods for bacterial harvest can be used. Bacterial harvest may be performed by the use of hollow fiber filter methods. Bacterial culture is harvested using filter cartridges ranging in size from 0.2 µM to 5 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Disruption (Homogenization)

Frozen bacterial cell slurry in OMS were thawed at 4° C. (2.3 kg of pellet mass). The liquid culture suspension from each container was aseptically aspirated into a 200 liter process tank (Model 200LDBT) with a bottom mounted mixer (Lightnin Mixer Model MBI610H55) containing 13 liters OMS pH 8.5. The volume of OMS was determined by calculating the homogenizing volume by multiplying the pellet mass by 30.8 L/Kg and taking the homogenizing volume and subtracting the volume of bacteria from the fermentation harvest. The bulk bacterial suspension was chilled to 4° C. with continuous mixing for 18 hours at 18 Hz at which time it was disrupted by homogenization. Briefly, the 200 liter tank containing the bacterial suspension was connected to an AVESTIN Model EF-0500B Homogenizer (Avestin, Rosemont, IL). A second 200 liter process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 60 psi via a Waukesha model 30U2 pump (Waukesha) through the homogenizer (500 Liters/hour) and back to the tank of origin, while the homogenizer pressure was adjusted to 11,000-30,000 psi. Prior to the first pass, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The number of passes through the homogenizer was standardized for different organisms based on the integrity of the cell wall and variation in the degree of disruption, which had a direct correlation in the efficiency of solubilization and quality of end product. For example, the disruption of *Salmonella* passed two times through the homogenizer gave a final percent transmittance between 78-83% T at a 1:100 dilution. *E. coli* having the same pellet mass and starting OD gave a % T of 80-86% (at a 1:100 dilution) after the second pass. It has been observed that bacteria differ in their cell wall integrity and vary in their capacity of disruption under identical condition. This variation can affect the degree and efficiency of solubilization and recovery of metal regulated proteins. In general, cells were passed through the homogenizer until the transmittance of at least 80% was reached after a minimum of two passes.

After homogenization, sodium lauroyl sarcosinate (HAMPTOSYL L-30, Chem/Serv) was aseptically added to the homogenized bacterial suspension for solubilization. The amount of sarcosine (30%) added equaled 0.083 times the solubilizing volume, in liters, (solubilizing volume was determined by multiplying the fermentation dry pellet mass by 34.7 L/Kg). The tank was removed from the homogenizer and placed in a 2-7° C. cooler and mixed at 18 Hz for 12-96 hours. This time period was helpful to complete solubilization. It was discovered that increasing the solubilization time in OMS at an elevated pH (8.0-8.5) that metal regulated proteins aggregated together forming large insoluble aggregates that were easily removed by centrifugation. The optimal OD after solubilization was usually between 25-30% T at 540 nm. 12-24 hours prior to protein harvest 0.15% of formalin was added to the final solubilizing volume as a preservative.

Protein Harvest

The aggregated metal regulated proteins within the solubilized process fluid were collected by centrifugation using T-1 Sharples, (Alfa Laval Seperations, Warminster, PA). Briefly, the tank of solubilized homogenate was fed into twelve Sharples with a feed rate of 200 ml/minute at 11 psi at a centrifugal speed of 30,000 rpm. The effluent was collected into a second 200 liter process tank through a closed sterile loop allowing for multiple passes through the centrifuges while maintaining a closed system. The temperature during centrifugation was kept at 4° C. The solubilized homogenate was passed up to 12 times across the centrifuges with a feed rate of 150 ml/minute at 21 psi at a centrifugal speed of 50,000 rpm. Protein was collected after the first pass and discarded, at which point the solubilized fluid was concentrated to ⅓ of its original volume. This decrease in volume shortened the process time for passes 2-12. Briefly, the solubilized homogenate tank was connected to a Pall Filtron AT25 Holder, equipped with three 30.1 ft$^2$ screen-channel series Omega 10 kd Maxisette filters (Pall Filtron) connected to a Waukesha Model 130U2 feed pump for concentration. After concentration, centrifugation was continued until the process was completed. Protein was collected after each pass. The protein was collected, resuspended and dispensed into two 8 Liter containers containing Tris-buffer pH 8.5 containing 0.3% formalin (Sigma) as preservative. The containers were placed into a mixer Model Turbula T10B (M.O. Industries, Wippany, New Jersey) and mixed until the protein was re-suspended in the buffer solution.

Diafiltration

The protein suspension was washed by diafiltration at 4° C. to remove any contaminating sarcosine that may have been bound to the protein. The two containers of protein were aspirated into a 200 Liter tank containing 40 ml TBW/g protein harvested of Tris-Buffer pH 8.5 containing 0.3% formalin equipped with a bottom mount Lightnin mixer, Model MBI610H55 mixing at 20 Hz. The process tank was placed in a 33° C. incubator for a minimum of 12 hours for protein inactivation. The process tank was sterilely connected to a MILLIPORE PELLICON Tangential Flow Filter assembly (Millipore Corporation, Bedford, MA), equipped with two 26.9 ft$^2$ screen-channel series Omega 10K Centrasette filter (Pall Filtron) connected to a Waukesha Model 30U2 feed pump. The solution was concentrated down to approximately 35 liters and was re-suspended with 200 liters of Tris-buffer, pH 7.4, containing 0.1% formalin solution. The solution was again concentrated down to approximately 35 liters and re-suspended again with 200 liters of a Tris-buffer, pH 7.4, containing 0.1% formalin solution. The solution was then concentrated down to approximately 35 liters and re-suspended with 80 liters of Tris-buffer, pH 7.4, containing 0.1% formalin solution. The solution was then concentrated by filtration to a target volume of 6.5 times the protein pellet mass. The protein concentrate was aseptically dispensed into sterile 20 liter Nalgene containers and placed into a 33° C. incubator for 12-24 hours for the final antigen inactivation.

This process produced a composition containing metal regulated proteins with a decrease in the amount of LPS and very little to no sarcosine residue. The protein was examined by SDS-PAGE for purity and banding profile, and also examined for bacterial contamination, residual sarcosine and LPS. The banding profile of the finished product showed consistent patterns as examined by electrophoresis. The composition was tested for sarcosine by the use of a modified agar gel diffusion test in which sheep red blood cells (5%) were incorporated into an agar base (1.5%). Wells were cut into the agar and samples of the finished product along with control samples of known concentrations of sarcosine at 0.05, 0.1, 0.2, 0.3, 0.4, 0.5 1.0 and 2.0% were placed into the wells. The gel was incubated at 25° C. for 24 hours and the degree of hemolysis was determined compared to the controls. The process removes the level of detectable sarcosine below 0.05%, which at this concentration showed minimal hemolysis in control samples. The concentration of LPS was examined by a *Limulus* amebocyte lysate (LAL) test available under the tradename PYROTELL (Associates of Cape Cod, Inc., East Falmouth, MA).

After cell lysis by freezing and homogenization, protein may be harvested by hollow fiber methods. Bacterial lysate is filtered to separate whole cells and large debris from small particulates and soluble protein. This may be accomplished using a range of sizes of hollow fiber cartridges from 0.2 µM to 5 kDa; preferably with a 0.65 µM nominal pore size. In this manner, whole unlysed cells and large debris are retained and possibly concentrated by the filter while protein and small particulates of interest are passed through the filter and collected. Additionally, it may be desirable to wash the retentate from 1-20× with buffer to increase the harvest of proteins of interest.

Subsequent to the primary harvest above, bacterial membranes of the small particulates are solubilized with sarcosine as described above, followed by further fractionation or protein harvest and wash by hollow fiber methods. This serves three functions: the removal of undesired cytosolic proteins, the removal of undesired membrane components including LPS and the hydrophobic aggregation of desired metal-regulated prottein and porin proteins into higher molecular weight forms. After the solubilizing step, the solution is filtered using hollow fiber cartridges ranging in size from 0.2 µM to 5 kDa; preferably with a Laboratory and/or Pilot Scale Ultrafiltration Cartridge (for example, (UFP-750-E-6A) size 6A Ultrafiltration Hollow Fiber Cartridge (63.5 cm L); Polysulfone membrane, optionally having a 750 000 NMWC pore size, GE Healthcare Pittsburgh, PA). This step can also include concentration (2-20×) and diafiltration wash steps (1×-20×) with buffer and ethanol to enhance the removal of undesired protein, membraneous components, DNA and sarcosine and thus increase the purity of the harvested metal-regulated proteins and porin proteins.

An example of the proteins present in the composition prepared as described above is shown in FIG. 4. Five higher molecular weight proteins (four of which are identified in FIG. 4 as FepA, FecA, FhuA, and CirA, and one migrating above the band identified as FepA) and two lower molecular weight bands identified in FIG. 4 as OmpC and OmpA) were observed after resolving the proteins on an SDS-PAGE gel.

Example 6

Characterization of Metal Regulated Proteins of *Klebsiella Pneumoniae* Isolate 1571

The proteins of the composition prepared as described in Example 5 from the *K. pneumoniae* strain 1571 were characterized using MALDI-TOF MS. These methods were also used for the *K. oxytoca* and *Enterobacter* isolates The proteins of the composition prepared as described in Example 5 from the *K. pneumoniae* strain 1571 was characterized using matrix assisted laser desorption/ionization time-of-flight spectrometry (MALDI-TOF MS). A portion of the composition was resolved using a sodium dodecyl sulfate-polyacrylamide gel. After the proteins of a composition had been resolved, the gel was stained with either coomasie brilliant blue or silver to visualize the proteins. This method was also used to characterize compositions obtained from *K. oxytoca* and *Enterobacter* isolates Materials and Methods Excision and washing. After resolving proteins using SDS-PAGE and staining to visualize the proteins, the gel was washed for 10 minutes with water twice. Each protein band of interest was excised by cutting as close to the protein band as possible to reduce the amount of gel present in the sample. Six gel fragments were prepared using the six bands identified in FIG. 4 as FepA, FecA, FhuA, CirA, OmpC, and OmpA.

Each gel slice was cut into 1×1 mm cubes and placed in 1.5 ml tube. The gel pieces were washed with water for 15 minutes. All the solvent volumes used in the wash steps were approximately equal to twice the volume of the gel slice. The gel slice was next washed with water/acetonitrile (1:1) for 15 minutes. When the proteins had been stained with silver, the water/acetonitrile mixture was removed, the gel pieces dried in a SPEEDVAC (ThermoSavant, Holbrook, NY) and then reduced and alkylated as described below. When the gel pieces were not silver-stained, the water/acetonitrile mixture was removed, and acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for 15 minutes, the liquid removed, and the gel pieces dried in a SPEEDVAC.

Reduction and alkylation. The dried gel pieces were rehydrated in 10 mM DTT and 100 mM $NH_4HCO_3$, and incubated for 45 minutes at 56° C. After allowing the tubes to cool to room temperature, the liquid was removed and the same volume of a mixture of 55 mM iodoacetamide and 100 mM $NH_4HCO_3$ was immediately added. This was incubated for 30 minutes at room temperature in the dark. The liquid was removed, acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for15 minutes, the liquid removed, and the gel pieces dried in a SPEEDVAC. If the gel was stained with coomasie blue, and residual coomassie still remained, the wash with 100 mM $NH_4HCO_3$/acetonitrile was repeated.

In-gel digestion. Gel pieces were completely dried down in a SPEEDVAC. The pieces were rehydrated in digestion buffer (50 mM $NH_4HCO_3$, 5 mM $CaCl_2$, 12.5 nanograms per microliter (ng/µl) trypsin) at 4° C. Enough buffer was added to cover the gel pieces, and more was added as needed. The gel pieces were incubated on ice for 45 minutes, and the supernatant removed and replaced with 5-2 µl of same buffer without trypsin. This was incubated at 37° C. overnight in an air incubator.

Extraction of peptides. A sufficient volume of 25 mM $NH_4HCO_3$ was added to cover gel pieces, and incubated for 15 minutes (typically in a bath sonicator). The same volume of acetonitrile was added and incubated for 15 minutes (in a bath sonicator if possible), and the supernatant was recovered. The extraction was repeated twice, using 5% formic acid instead of $NH_4HCO_3$. A sufficient volume of 5% formic acid was added to cover gel pieces, and incubated for 15 minutes (typically in a bath sonicator). The same volume of acetonitrile was added and incubated for 15 minutes (typically in a bath sonicator), and the supernatant was recovered. The extracts were pooled, and 10 mM DTT was added to a final concentration of 1 mM DTT. The sample was dried in a SPEEDVAC to a final volume of approximately 5 µl.

Desalting of peptides. The samples were desalted using a ZIPTIP pipette tips (C18, Millipore, Billerica, MA) as suggested by the manufacturer. Briefly, a sample was reconstituted in reconstitution solution (5:95 acetonitrile:H₂O, 0.1%-0.5% trifluoroacetic acid), centrifuged, and the pH checked to verify that it was less than 3. A ZIPTIP was hydrated by aspirating 10 µl of solution 1 (50:50 acetonitrile:H₂O, 0.1% trifluoroacetic acid) and discarding the aspirated aliquots. This was followed by aspirating 10 µl of solution 2 (0.1% trifluoroacetic acid in deionized H₂O) and discarding the aspirated aliquots. The sample was loaded into the tip by aspirating 10 µl of the sample slowly into the tip, expelling it into the sample tube, and repeating this 5 to 6 times. Ten microliters of solution 2 was aspirated into the tip, the solution discarded by expelling, and this process was repeated 5-7 times to wash. The peptides were eluted by aspirating 2.5 µl of ice cold solution 3 (60:40, acetonitrile:H₂O, 0.1% trifluoroacetic acid), expelling, and then re-aspirating the same aliquot in and out of the tip 3 times. After the solution has been expelled from the tip, the tube was capped and stored on ice.

Mass spectrometric peptide mapping. The peptides were suspended in 10 µL to 30 µL of 5% formic acid, and analyzed by MALDI-TOF MS (Bruker Daltonics Inc., Billerica, MA). The mass spectrum of the peptide fragments was determined as suggested by the manufacturer. Briefly, a sample containing the peptides resulting from a tryptic digest were mixed with matrix cyano-4-hydroxycinnamic acid, transferred to a target, and allowed to dry. The dried sample was placed in the mass spectrometer, irradiated, and the time of flight of each ion detected and used to determine a peptide mass fingerprint for each protein present in the composition. Known polypeptides were used to standardize the machine.

Data analysis. The experimentally observed masses for the peptides in each mass spectrum were compared to the expected masses of proteins using the Peptide Mass Fingerprint search method of the MASCOT search engine (Matrix Science Ltd., London, UK, and www.matrixscience.com, see Perkins et al., 1999, Electrophoresis 20, 3551-3567). The search parameters included: database, NCBInr; taxonomy, bacteria (eubacteria); type of search, peptide mass fingerprint; enzyme, trypsin; fixed modifications, carbamidomethyl (C) or none; variable modifications, oxidation (M), carbamidomethyl (C), the combination, or none; mass values, monoisotopic; protein mass, unrestricted; peptide mass tolerance, between ±100 ppm and ±300 ppm or 450 ppm, or ±1 Da; peptide charge state, Mr; max missed cleavages, 0 or 1; number of queries, 25.

SDS-PAGE analysis of the polypeptides indicated that, under the SDS-PAGE conditions used, proteins migrated at 82 kDa, 78 kDa, 72 kDa, 68 kDa, 35 kDa and 33 kDa as determined by SDS-PAGE (Table 1). An additional protein was a light band and migrated at 87 kDa. MALDI analysis and predicted molecular weight based on amino acid sequence showed there was good agreement between the molecular weights of the proteins as estimated using SDS-PAGE and using MALDI (Table 1). The proteins in FIG. 4 were identified by MALDI. These analyses resulted in protein sequences that represent the best protein match for each peptide mass fingerprint. The best protein match for the band labeled FepA was NCBI Reference Sequence WP_012068422.1; the best protein match for the band labeled FecA was NCBI Reference Sequence NP_943400.1; best protein match for the band labeled FhuA was NCBI Reference Sequence WP_004178624.1; best protein match for the band labeled CirA was NCBI Reference Sequence WP_015958738.1; best protein match for the band labeled OmpC was NCBI Reference Sequence WP_015958749.1; and the best protein match for the band labeled OmpA was NCBI Reference Sequence WP_002898408.1.

Genomic Sequencing

Genomic DNA was isolated from the *Klebsiella pneumoniae* 1571 isolate using the CHARGESWITCH gDNA Mini Bacteria Kit (Life Technologies, Carlsbad, CA, product number: CS11301). Prior to extraction of the genomic DNA, a fresh culture of the isolate was grown on Trypticase Soy Agar II with 5% Sheep Blood (Becton, Dickinson and Company, Franklin Lakes, NJ, product code: 221261) overnight at 37° C. The procedure followed the manufacturer protocol. The final yield was 33.7 µg of genomic DNA, which was stored at −20° C. until sequencing. The genomic DNA was submitted to ACGT, Inc. for sequencing (Wheeling, IL).

Identifying Target Genes

After receiving the complete genomic sequence of the isolate, tblastn alignments were performed with the National Center for Biotechnology Information (NCBI) database to identify the possible genes of interest. The first analysis of the *Klebsiella pneumoniae* 1571 genomic sequence used the results of the data analysis of the six bands by MALDI. This analysis resulted in the identification of the following proteins encoded by genes present in the *Klebsiella pneumoniae* 1571 genomic sequence: FepA, FecA, FhuA, CirA, OmpC, and OmpA. These proteins, and the genes encoding them, are disclosed at FIGS. 10, 7, 8, 9, 20, and 21, respectively. Another analysis of the complete genomic sequence was based on Ton B dependent homologs within the sequence. The algorithm parameters were Matrix: BLOSUM62 and Gap Costs: Existence: 11 Extension: 1. A blastx search was used to identify the proteins translated by the homologous genes found with the tblastn alignment. The algorithm parameters were Matrix: BLOSUM62 and Gap Costs: Existence: 11 Extension: 1. Pairwise sequence alignments of the identified homologues of metal regulated polypeptides. The algorithm parameters were Matrix: BLOSUM62, Gap Open: 14, Gap Extend: 4, Alternative Matches: 1.

To identify possible homologues to other metal regulated proteins BtuB, YbiL, YncD, IroN, IutA, FitA, FcuA, Ferric Enterbactin Colicin B/D receptor and FoxA a "tblastn" alignment was performed against the sequenced genome of the *Klebsiella pneumoniae* isolate. Nine possible homologues were identified by looking at the sequences with highest identities respectively within the genome, and are disclosed at FIGS. 11-19. A partial nucleotide sequence and predicted amino acid sequence of three of the possible homologues were identified (YncD, IroN, and FitA, FIGS. 13, 14, and 16, respectively).

Example 7

Hyper-Immunization of Holstein Steers and Preparation of Polyclonal Antibody

Two Holstein Steers at four months of age were vaccinated subcutaneously three times at 28 day intervals using the *Klebsiella pneumoniae* 1571 composition as described in Examples 5 and 6. The immunizing composition included polypeptides having molecular weights of 87 kDa, 82 kDa, 78 kDa, 72 kDa, 68 kDa, 35 kDa, and 33 kDa as determined by SDS-PAGE. The proteins were emulsified into a single vaccine formulation. Briefly, 320 mg antigen (metal-regulated proteins and porins) was mixed into 355 ml of physiological saline. The antigen solution was emulsified into 80 ml of EMULSIGEN to give a final dose of 1500 µg total protein at a 22.5% EMULSIGEN concentration in a 2 ml injectable volume. Twenty eight days after the third vaccination 2.0 liters of blood from each steer was pooled and allowed to clot at 4° C. for 24 hours. The serum was separated from whole blood by centrifugation at 3000×g for 30 minutes. The serum; 800 ml was again centrifuged at 10,000×g for 30 minutes to remove any contaminating cell debris and then aliquoted into 25 ml volumes in sterile 50 ml conical tubes (Fisher Scientific) and frozen at −80° C. until use. Twenty five milliters of hyperimmunized serum was purified using standard ammonium sulfate precipitation. Briefly, exogenous serum proteins were removed first prior to antibody precipitation by adding 0.5 volumes of saturated ammonium sulfate pH 7.2. The solution was stirred at 100 rpm for 24 hours at 4° C. The solution was again centrifuged at 3000×g for 30 minutes. The supernatant was collected and precipitated again by adding enough saturated ammonium sulfate to bring the final concentration to 55% saturation. The solution was stirred at 100 rpm for 24 hours at 4° C. The precipitate was centrifuged at 3000×g for 30 minutes. The final pellet from each sample was resuspended into 2 ml PBS pH 7.2. The precipitated antibodies were then dialyzed using a 50,000 molecular cut off dialysis tubing (Pierce, Rockford Ill.) for 30 hours against three 1 liter changes of phosphate-buffered saline to remove ammonium sulfate. The first two liter changes were preserved with 0.02% sodium azide. The final 1 liter buffer change contained no preservative. The dialysate was collected and centrifuged again to remove any remaining debris at 3000×g for 30 minutes. The antibody solution was stored at 4° C. for less than 48 hours prior to use. Each sample was plated on blood agar to verify sterility.

Example 8

Cross-Reactivity of the *Klebsiella Pneumoniae* 1571 Metal-Regulated Proteins with Other Strains of *Klebsiella, E. Coli* and *Enterobacter*

The hyperimmunized serum produced against the purified metal-regulated proteins of *Klebsiella pneumoniae* 1571 of Example 7 was examined for its cross-reactivity to bacteria from different genera and species. Metal-regulated proteins from Example 3 (*Klebsiella* 1564, 1569, 1571, LM21, *Enterobacter* 1568, and *E. coli* O157) were subjected to electrophoresis followed by western blot analysis with the *Klebsiella pneumoniae* 1571 hyperimmunized serum as described in Example 7. Metal-regulated proteins from *E. coli* O157 were also prepared as described in Example 3 and examined.

Figure 5A:
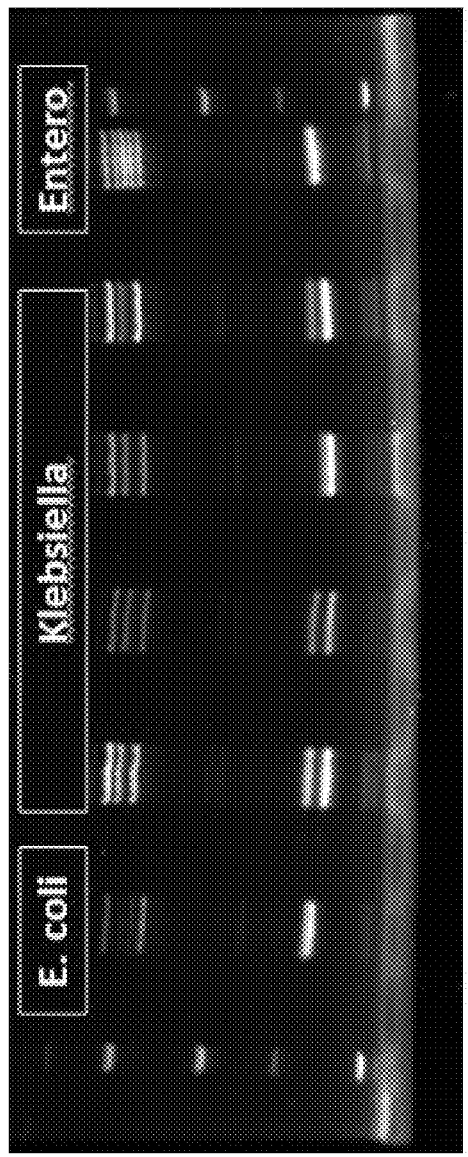
FIG. 5. Electrophoretic profile (FIG. 5A) and western Blot (FIG. 5B) of different genera and species of *E. coli*, *K. pneumoniae*, *K. oxytoca*, *Enterobacter* and *K. pneumoniae* LM21 showing the variation and cross-reactivity of metal regulated protein profiles. Hyperimmunized sera derived from *Klebsiella pneumonia* 1571 was used for the western blot.
Figure 5B:
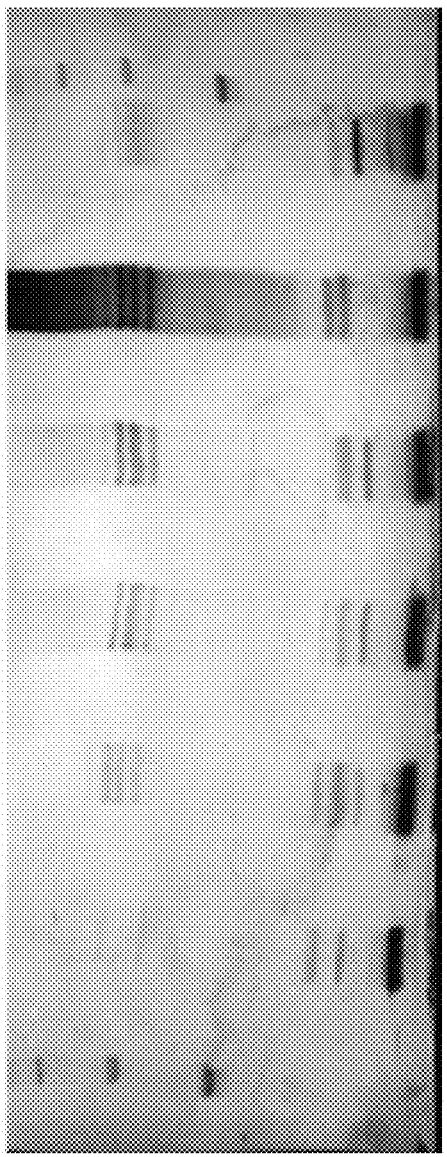

The purified metal-regulated proteins of *E. coli* O157, *Klebsiella* of bovine and human origin, and *Enterobacter* were subjected to electrophoresis followed by western blot analysis with the hyperimmunized serum of *Klebsiella pneumoniae* 1571 as described in Example 7. Briefly, the outer membrane preps were size-fractionated on an SDS-PAGE gel using a 4% stacking gel and 7.5% resolving gel. A 10 µl sample was combined with 10 µl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, CA). Band migration was visualized using broad range kaleidoscope standards (BioRad) to aid in the electro-blot transfer while biotinylated broad range standards were used as molecular weight references on the blot (see FIGS. 5A and 5B). For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the polyclonal hyperimmunized sera collected from the immunized steers as described in example 7. The primary antibody was diluted 1/50 in TBS containing 1% fish gelatin, 0.05% TWEEN 20 and 0.2% sodium azide (Antibody Buffer). The membrane was incubated with the primary antibody solution overnight on a shaker at room temperature. The membrane was then washed two times in TBS containing 0.05% TWEEN 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1× AP color development Buffer (BioRad) for 30 min. at 37° C. on a shaker. The resulting Western immunoblot was documented using a BioRad GS-800 Densitometer (see FIGS. 5A and 5B).

Western blot analysis revealed that the positive antisera prepared against the purified metal-regulated proteins of example 5 reacted intensely with multiple metal-regulated proteins of *E. coli* O157 (lane 2) *K. oxytoca* (lane 3), *K. pneumoniae* 1569 (lane 4) *K. pneumoniae* LM21 (lane 5), *Klebsiella pneumoniae* 1571 (lane 6) and *Enterobacter* 1568 (lane 7). These results show that the metal-regulated proteins of *Klebsiella pneumoniae* have a high degree of antigenic homology to different strains of *Klebsiella* and different genera and species of bacteria.

Example 9

Sequence Identity of Metal-Regulated Proteins

To further substantiate the homology of various metal-regulated proteins of the *Klebsiella pneumoniae* 1571 to other *Klebsiella, E. coli* and *Enterobacter* isolates, the amino acid sequence identity of multiple peptides (CirA, FcuA, FecA, FhuA, and IutA) was examined to determine the percent homology. Isolates were also selected based on specific disease conditions, such as mastitis in bovine species and septicemia, pneumonia, neonatal sepsis, liver abscesses, urinary tract infections, cerebrospinal infections and ETEC diarrhea in humans. Protein sequences were analyzed using the default settings of NCBI's protein BLAST (blastp). Matches with e-values equal to zero and query coverage >95% were considered for the homology. Table 3 shows the metal-regulated proteins that are shared between *Klebsiella pneumoniae* 1571 and other isolates of *Klebsiella, E. coli*, and *Enterobacter* that induced different disease conditions in both agricultural animals and humans. Not all isolates contain every iron regulated protein examined, but as can be seen from Table 3 most metal-regulated proteins approach 99-100% identity across the *Klebsiella* strains. In addition, most of the metal-regulated proteins found in the *Klebsiella pneumoniae* 1571 vaccine strain show significant identity of greater than 60% and up to 99% compared to other isolates of *E. coli* and *Enterobacter*. Considering that individual metal-regulated proteins are composed of more than 600 amino acids, and that the immune response recognizes epitopes that range from 5-20 amino acids, it clearly demonstrates that these proteins are excellent target antigens. Thus, a vaccine prepared using metal-regulated proteins would be expected to provide a broadly protective vaccine directed against multible gram negative pathogens responsible for a broad spectrum of disease conditions in both human and animal populations.

TABLE 3

Percent identity of the amino acid sequence for siderophore receptors proteins in *Klebsiella*, *Escherichia*, and *Enterobacter* genera and strains.

| Strain | Isolate ID | Disease | CirA | FcuA | FecA | FhuA | IutA |
|---|---|---|---|---|---|---|---|
| *Klebsiella pneumoniae* 1571 | | Mastitis (bovine) | 100 | 100 | 100 | 100 | 100 |
| *Klebsiella pneumoniae* KPN6 (KPNIH2) | 1087441 | septicemia | 100 | 99 | 99 | 99 | 99 |
| *Klebsiella pneumoniae* VA360 | 1236102 | neonatal sepsis | 100 | 99 | 99 | 99 | 99 |
| *Klebsiella pneumoniae* MP14 | 1341693 | pneumonia | 100 | 99 | | 99 | 99 |
| *Klebsiella pneumoniae* ST258-K28BO | 1185420 | pneumonia | 100 | 99 | 99 | 99 | 99 |
| *Klebsiella pneumoniae* JHCK1 | 1236101 | neonatal sepsis | 100 | 99 | 99 | 99 | 99 |
| *Klebsiella pneumoniae* CG43 | 1244085 | liver abscess | | 99 | 99 | 99 | 99 |
| *Klebsiella pneumoniae* ATCC BAA-2146 | 1263871 | urinary tract infection | 100 | 99 | | 99 | 99 |
| *Enterobacter cloacae* EC_38VIM1 | 1334630 | septicemia | 81 | 69 | 99 | 83 | 70 |
| *Enterobacter cloacae* UCICRE 11 | 1329855 | unknown | 36 | 69 | 99 | 83 | 71 |
| *Enterobacter cloacae* UCICRE 3 | 1329852 | unknown | 36 | 69 | 99 | 83 | 70 |
| *Enterobacter cloacae* ATCC 13047 | 716541 | cerebrospinal infection | 81 | 69 | | 61 | 71 |
| *Escherichia coli* EC958 O25b:H4-ST131 | 941322 | urinary tract infection | 81 | 27 | 99 | 60 | 73 |
| *Escherichia coli* CFT073 | 199310 | urinary tract infection | 36 | 27 | | 60 | 73 |
| *Escherichia coli* H10407 | 316401 | ETEC diarrhea | 81 | | 99 | 61 | |
| *Escherichia coli* ECC-1470 | 758831 | Mastitis (bovine) | 81 | | 99 | 61 | |

Percent identity is indicated by color intensity and the actual percentage. A blank cell indicates the gene is not encoded by that strain. Protein sequences were analyzed using the default settings of NCBI's protein BLAST (blastp). Matches with e-values equal to zero and query coverage >95% were considered for the homology. Bacterial isolates were also selected based on their clinical manifestation of disease to include mastitis in bovine and septicemia, pneumonia, neonatal sepsis, liver abscesses, urinary tract infections, cerebrospinal infections and ETEC diarrhea in humans.

Example 10

Serial Passage of *Klebsiella Pneumoniae* 1571 in Mice to Enhance Virulence

To enhance virulence *Klebsiella pneumoniae* 1571 was serially passaged in the new host species, mouse. Briefly, using the culture as described above of example 1 two mice were subcutaneously injected with either 0.1 or 0.2 ml at $1.0 \times 10^9$ CFU/ml of the isolate. Twenty four hours post inoculation mice were morbid but did not die. Mice were euthanized by cervical dislocation and each liver was cultured using a flamed loop and plated onto Blood agar. Plates were incubated at 37° C. for 24 hours. A number of colonies from the 0.2 dose had grown on the Blood agar plates indicating the isolates had gone systemic. These colonies were streaked for isolation and again passed through mice using the same regiment. The final mouse passage resulted in all mice dying at 24 hours post challenge, clearly demonstrating that the isolate adapted to grow in the new host species by the enhancement of virulence with death as the outcome parameter. The isolate was sub-cultured from the final liver isolation and expanded into a frozen challenge seed. Briefly a single colony from the Blood plate was sub-cultured into 20 ml of TSB containing 32 gm TSB, 5 gm yeast extract, and 2,2-dipyridyl at 25 µg/liter. The culture was allowed to stir at 200 rpm for 2 hours at which point was sub-cultured in the same media that was pre-warmed to 37° C. After the 2 hour time period 10 ml of the culture was transferred to 100 ml of pre-warmed TSB as described above except the concentration of 2,2-dipyridyl was 25 µg/l. This culture was allowed to grow until they reached an OD 1.0 at 540 nm at which point was centrifuged at 8000 rpm for 10 minutes and re-suspended into 90 ml cold TSB as described above; except it contained 20% glycerol. One ml aliquots of the bacterial suspension was dispensed into 2 ml cryovials; labeled and stored at −90° C. until use.

Example 11

Preparation of the Immunizing Compositions Derived from *Klebsiella Pneumoniae* 1571

The proteins made from *Klebsiella pneumoniae* 1571 as described in Example 5 were used to prepare a composition for administration to mice to determine the efficacy of the vaccine against a live virulent homologous and heterologous challenge. Eighty female CF-1 mice obtained from Harlan Breeding Laboratories (Indianapolis, IN) weighing 16-22 grams were equally distributed into four groups (20 mice/group), two vaccinate groups and two placebo groups. Mice were housed in polycarbonate mouse cages (Ancore Corporation, Bellmore, NY). Four cages were used for each treatment group (5 mice/cage) to minimize the number of mice for each cage. Groups were designated as 1-4. Group 1 was designated as the *Klebsiella* Placebo, group 2 was designated as the *E. coli* Placebo while groups 3 and 4 were both vaccinated with the *Klebsiella pneumoniae* 1571 composition of Example 5. The vaccine composition contained the proteins illustrated in FIG. 4.

Example 12

Mouse Vaccination

The stock vaccine was prepared by emulsifying the aqueous protein suspension (1000 µg total protein/ml) into the commercial adjuvant, EMULSIGEN, (MVP Laboratories, Ralston, Nebraska) to give and adjuvant concentration of 22.5% vol/vol. A mouse dose was administered to give a final dose of 100 µg total protein in a 0.1 ml injectable volume. A placebo was prepared by replacing the antigen with physiological saline in the above formulation and emulsifying the suspension into EMULSIGEN to give and adjuvant concentration of 22.5%. Food and water were supplied ad libitum to all mice. Mice were vaccinated subcutaneously two times at 21 day intervals with the placebo and/or the *Klebsiella pneumoniae* vaccine.

Example 13

Preparation of Challenge Organisms

The *Klebsiella pneumoniae* isolate 1571 as described in Example 10 was used for the homologous challenge of groups 1 and 3 while mice in groups 2 and 4 were challenged with *E. coli* CFT073 (heterologous challenge). Briefly, the challenge isolates from frozen stocks was streaked onto blood agar plates and incubated at 37° C. for 18 hours. A single colony from either the *Klebsiella* plate or the *E. coli* plate was sub-cultured into one of two 50 ml bottles of Tryptic Soy Broth (Difco) containing 25 μg/ml 2,2' dipyridyl. The cultures were incubated at 37° C. for 6 hours while rotating at 200 rpm until an OD of 0.95-1.0 at 540 nm was reached at which point was centrifuged at 10,000×g for 10 minutes at 4° C. to pellet the bacteria. The bacterial pellet was washed twice by centrifugation in physiological saline at 4° C. The final pellet was resuspended back to 100 ml in physiological saline and used for challenge. Just prior to challenge, 1 ml of the above bacterial suspension was serially diluted ten-fold to enumerate the number of CFU/mouse dose.

Example 14

Challenge

Mice were challenged 28 days post second vaccination. Mice in groups 1 and 3 were challenged intraperitoneally with $5.7 \times 10^7$ CFU of *Klebsiella pneumoniae* 1571 in a 0.1 ml volume, while mice in groups 2 and 4 were challenged intraperitoneally with $1.3 \times 10^7$ CFU of *E. coli* CFT073 in a 0.1 ml volume. Mice were monitored daily for mortality for 10 days post-challenge.

Figure 6:
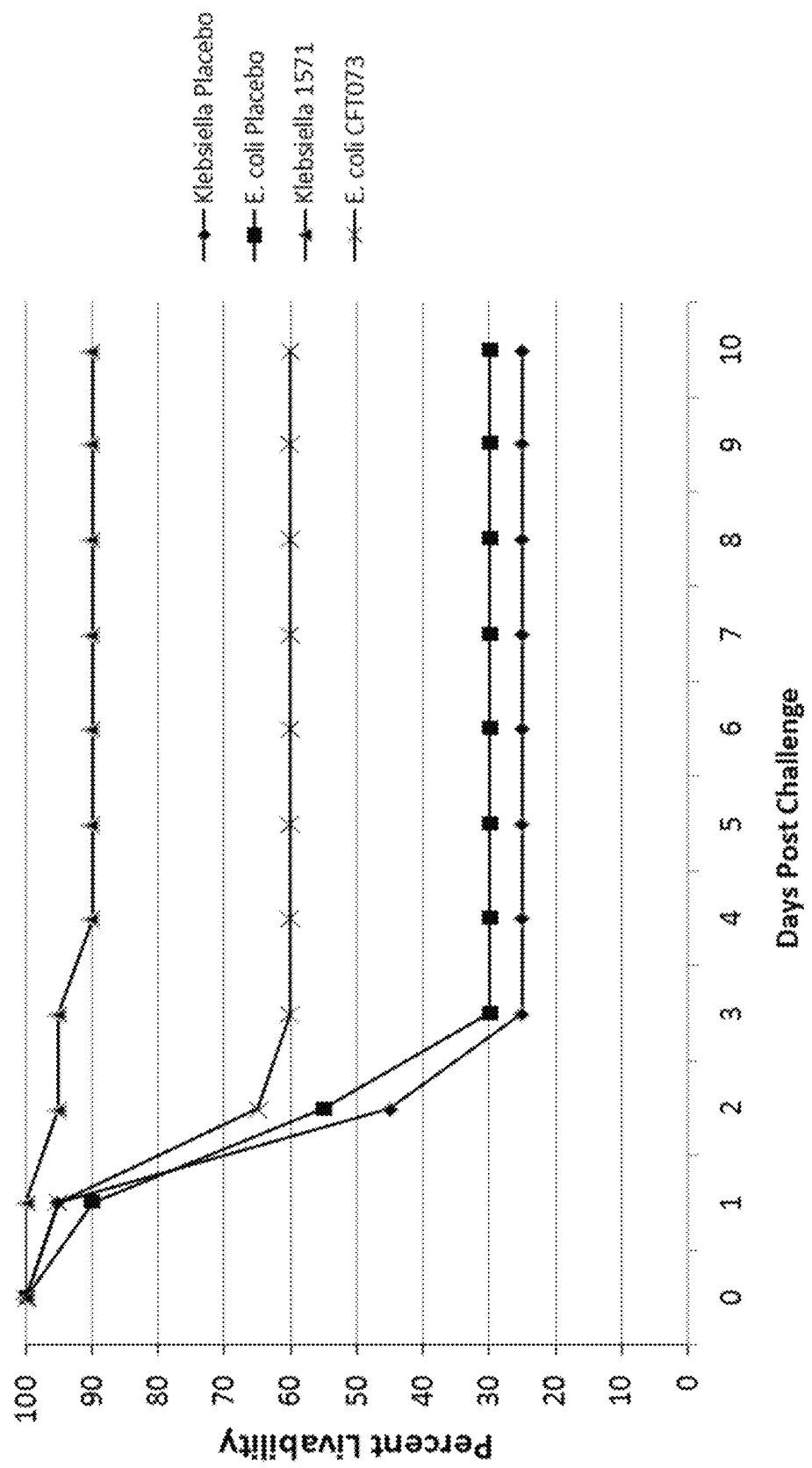
FIG. 6. Cross-protection of *Klebsiella pneumoniae* 1571 vaccine against a homologous and heterologous challenge in mice.

When comparing mortality in challenged mice in groups 1 and 3 (homologous challenge), vaccinated mice of group 3 showed a high degree of protection (90% livability) in contrast to its placebo control showing only 25% survival. In comparison, mice vaccinated with the *Klebsiella* 1571 composition and challenged with *E. coli* CFT073 (heterologous challenge) showed a significant degree of protection at 60% livability in contrast to its placebo control having only 30% livability at the dose of the vaccine given. It is expected that immunizing with a higher dose of antigen, e.g., 150 ug-200 ug, there would be a higher degree of protection. The results clearly demonstrate that the *Klebsiella pneumoniae* 1571 composition has the capability of protecting against another genera of bacteria FIG. 6.

Example 15

Construction of Expression Clones and Purification of Recombinant Metal-Regulated Proteins The amino acid sequences for the metal-regulated proteins FecA (from *Klebsiella pneumoniae* strain 1571) (SEQ ID NO:41 where the fourth amino acid is N), and CirA, FepA and IutA (from *E. coli* strain CFT073) (FIGS. 36-38) were submitted to GENEART (Life Technologies, Carlsbad, CA) for assembly. The GENEOPTIMIZER (Life Technologies) software was used to reverse translate the protein sequences into DNA for optimized gene synthesis. The sequences were cloned into the pQE30Xa expression vector (Qiagen, Valencia, CA), which adds an N-terminal 6× Histidine tag, and the vector was used to transform the XL-1 blue *E. coli* strain. Recombinant metal-regulated proteins were expressed and purified using standard methods. Frozen bacterial stocks (100 ul) were used to inoculate 20 ml of Luria-Bertani Broth with 100 ug/ml Ampicillin for plasmid maintenance, and the culture was grown at 37° C. in a shaking incubator (250 rpm). After 16 hours the culture was diluted 1:50 into 1 L of Luria-Bertani Broth with 100 ug/ml Ampicillin, grown to an optical density (600 nm) of 0.6, and then induced with 1 mM IPTG for 4 hours. Bacterial pellets were harvested by centrifugation at 4,000×g for 20 minutes at 4° C., washed in phosphate buffered saline, and then resuspended in 20 mM Tris buffer with 100 ug/ml lysozyme. The cells were then disrupted by sonication at 50% duty cycle and 5 output (Branson Sonifier, Danbury, CT) for 8 minutes on ice. The lysate was subjected to centrifugation for 10 min at 40,000×g at 4° C. to remove insoluble material. The soluble supernatants were processed by immobilized metal affinity chromatography (HisTrap FF 5 ml, GE Healthcare) to purify the Histidine-tagged recombinant protein, and then anion exchange chromatography to increase the purity and remove endotoxin. Protein concentration was estimated using the BCA method (Pierce) and protein purity was measured at greater than 70 percent by SDS-PAGE densitometry. Endotoxin was verified to be below 40 EU/mg proteins using the Kinetic-Turbidimetric Test for Bacterial Endotoxins using *Limulus* amoebocyte lysate. These results are summarized in Table 4.

TABLE 4

Results from purification of recombinant metal-regulated proteins.

| Protein | Protein concentration (mg/mL) | Purity (%) | Endotoxin Level (EU/mg) | Final Buffer |
|---|---|---|---|---|
| FecA | 1.9 | 85% | <10 | 50 mM Tris, 1 mM EDTA, 800 mM Urea, 51 mM n-OG |
| CirA | 16.7 | 70% | 38.6 | 20 mM Tris, 300 mM Urea, 0.5% ZWITTERGENT |
| FepA | 13.1 | 91% | 5 | 50 mM Tris, 300 mM Urea, 51 mM n-OG |
| IutA | 2.1 | 88% | 19 | 50 mM Tris, 300 mM Urea, 51 mM n-OG |

Example 16

Vaccine-Mediated Protection in a Mouse Sepsis Model Evaluating Multiple Vaccine Formulations A mouse sepsis model was chosen to evaluate the following vaccine compositions; *Klebsiella pneumoniae* bovine strain 1571, extracted metal-regulated proteins of *Klebsiella pneumoniae* human strain LM21 (prepared as described in Example 5), and a formulation containing four recombinant metal-regulated proteins FecA, CirA, FepA and IutA (prepared as described in Example 15). Eighty female CF-1 mice weighing 16-22 grams were purchased from Charles River Laboratory (Wilmington, MA) and randomly divided into 6 groups (15 mice per group except group 1, which contained 10 mice). Groups were designated as 1-6. Group 1, 2, and 3 were designated as controls. Group 1 was the naïve control (non-vaccinated/challenged), Group 2 was the adjuvant control having 50% incomplete Freunds adjuvant, 10 μg CpG and 2.5 monophosphoryl lipid A (MPLA) (vaccinated/challenged), and Group 3 was the adjuvant control having 50% incomplete Freunds adjuvant (vaccinated/challenged). Groups 4, 5, and 6 were vaccinated with their respective vaccine formulations that correlated to their appropriate adjuvant control groups (Table 5). Mice were housed in polycarbonate mouse cages (Ancore Corporation, Bellmore, NY). Three cages were used for each treatment group (5 mice/cage) to minimize the number of mice for each cage. All mice were allowed to acclimate one week prior to the first vaccination. The individual vaccine formulations were evaluated for their ability to protect against death in a mouse sepsis model using *Klebsiella pneumonia* 1571 as the challenge organism (Example 10).

TABLE 5

Experimental Design.

| Groups | Mice | Vaccine | Antigen (ug) | Adjuvant | Vaccine Volume (ul) | # Vaccines | Vaccine Route |
|---|---|---|---|---|---|---|---|
| 1 | 10 | Naïve | None | None | N/A | N/A | N/A |
| 2 | 15 | Placebo-1 | None | 50% IFA + 10 μg CpG + 2.5 μg MPLA | 100 | 3 | SC |
| 3 | 15 | Placebo-2 | None | 50% IFA | 100 | 3 | SC |
| 4 | 15 | 1571 Vaccine | 100 μg | 50% IFA | 100 | 3 | SC |
| 5 | 15 | 1748 Vaccine | 100 μg | 50% IFA | 100 | 3 | SC |
| 6 | 15 | Recombinant FecA, CirA, FepA and IutA | 20 μg each | 50% IFA + 10μg CpG + 2.5 μg MPLA | 100 | 3 | SC |

Example 17

Vaccine Preparation and Vaccination

For vaccine preparation, 100 micrograms of the protein extracts derived from each of the *Klebsiella* strains 1571 and LM21 or 20 micrograms of each recombinant protein in phosphate buffered saline was formulated with their appropriate test adjuvant (see Table 5). Mice were immunized three times subcutaneously in the subscapular girdle with 0.1 ml of the appropriate vaccine at 14 day intervals. All mice were challenged 42 days post the second vaccination.

Example 18

Preparation of Challenge Organism

The *Klebsiella pneumoniae* 1571 bacterial challenge isolate was prepared from a frozen stock described in Example 10. Briefly, the challenge isolate from the frozen stock was streaked onto a blood agar plate and incubated at 37° C. for 18 hours. A single colony was sub-cultured into 100 ml of Tryptic Soy Broth (Difco) containing 25 μg/ml 2,2' dipyridyl. The cultures were incubated at 37° C. for 6 hours while rotating at 200 rpm until an OD of 0.95-1.0 at 540 nm was reached at which point was centrifuged at 10,000×g for 10 minutes at 4° C. to pellet the bacteria. The bacterial pellet was washed once by centrifugation in physiological saline at 4° C. The final pellet was resuspended back to 100 ml in physiological saline and used for challenge. All mice were challenged intraperitoneally with 8.5×10⁷ colony forming units of *Klebsiella pneumoniae* 1571 in a 0.1 ml volume. Just prior to challenge, 1 ml of the above bacterial suspension was serially diluted ten-fold to enumerate the number of CFU/mouse dose.

Example 19

Challenge Results

Figure 22:
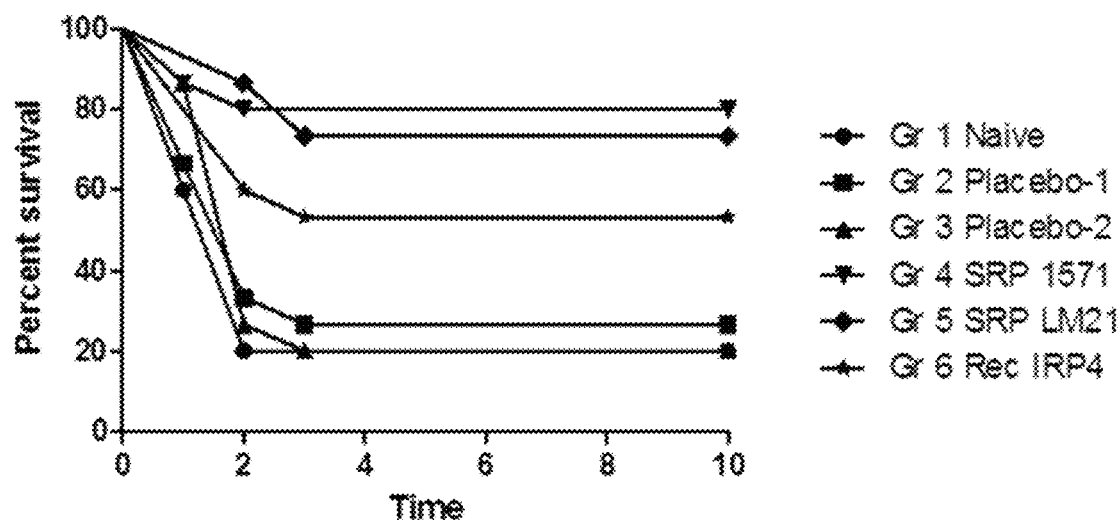
FIG. 22. Survival of mice after challenge with *Klebsiella pneumoniae* 1571.

Of the naïve and placebo controls, eighty percent (80%) of the naïve mice of Group 1 died following challenge compared to 73% death in mice of Group 2 and 80% death in mice of Group-3 (Table 6). These results demonstrate that the adjuvant alone did not provide protection against the challenge indicating there was no non-specific immunity induced by the adjuvant. By comparison, only three mice died (80% survival) of Group 4 using the vaccine composition derived from *Klebsiella* 1571 (homologous to the challenge) (Table 6, FIG. 22). In comparison, only four mice died (74% survival) of Group 5 using the vaccine composition derived from *Klebsiella* 1748 (heterologous to the challenge) (Table 6, FIG. 22). These results clearly demonstrate that the vaccine composition prepared from *Klebsiella pneumonia* 1571 can provide protective immunity against a homologous and heterologous challenge or protection against multiple strains of *Klebsiella*.

In comparison, the vaccine composition of the recombinant proteins that were initially identified by MALDI and then cloned, expressed, and purified from *E. coli* including FecA, CirA, FepA and IutA also induced a significant degree of protection against the challenge. Fifty three percent (53%) of the mice vaccinated with the recombinant proteins (tested at a single dose of 20 μg of each protein) survived the challenge. It is expected that a higher concentration (e.g., a microgram dose) of the recombinant proteins would result in equivalent protection as compared to the extracted protein groups. In addition, the amount of endotoxin in this composition was less than 100 EU per dose. Taking this into consideration one could state that the LPS did not provide protection based on the presence of somatic antigens, since the somatic antigens that may contaminate the vaccine composition were derived from *E. coli* and not *Klebsiella*. Based on this information and the heterologous nature of the challenge strain, one can conclude that the degree of protection was due to the recombinant proteins in the vaccine composition.

TABLE 6

Total Mortality and Percent Livability following *Klebsiella* 1571 Challenge

| Treatments Groups 1-6 | Mortality - Days Post Challenge | | | | | | | | | | Total Mortality | Percent Mortality (%) |
|---|---|---|---|---|---|---|---|---|---|---|---|---|
| | 1 | 2 | 3 | 4 | 5 | 6 | 7 | 8 | 9 | 10 | | |
| 1) Naïve Control | 4 | 4 | 0 | 0 | 0 | 0 | 0 | 0 | 0 | 0 | 8 | 80 |
| 2) Placebo-I Adjuvanted | 5 | 5 | 1 | 0 | 0 | 0 | 0 | 0 | 0 | 0 | 11 | 73 |

TABLE 6-continued

Total Mortality and Percent Livability following *Klebsiella* 1571 Challenge

| Treatments | Mortality - Days Post Challenge | | | | | | | | | | Total | Percent |
|---|---|---|---|---|---|---|---|---|---|---|---|---|
| Groups 1-6 | 1 | 2 | 3 | 4 | 5 | 6 | 7 | 8 | 9 | 10 | Mortality | Mortality (%) |
| 3 Placebo-2 Adjuvanted | 2 | 9 | 1 | 0 | 0 | 0 | 0 | 0 | 0 | 0 | 12 | 80 |
| 4) 1571 Vaccine | 2 | 1 | 0 | 0 | 0 | 0 | 0 | 0 | 0 | 0 | 3 | 20 |
| 5) LM21 vaccine | 0 | 2 | 2 | 0 | 0 | 0 | 0 | 0 | 0 | 0 | 4 | 26 |
| 6) Recombinant FecA, CirA, FepA and IutA (IRP4) | 0 | 6 | 1 | 0 | 0 | 0 | 0 | 0 | 0 | 0 | 7 | 47 |

Example 20

The Efficacy of Metal-Regulated Proteins Derived from *Klebsiella Pneumonia* 1571 Against an Intramammary Challenge in Holstein Heifers Mastitis is the inflammation of the mammary gland and udder tissue, and is a major endemic disease of dairy cattle. It usually occurs as an immune response to bacterial invasion of the teat canal by variety of bacterial species such as *Klebsiella*. In this experimental study a subunit vaccine including metal-regulated proteins derived from *Klebsiella pneumonia* 1571 was used to evaluate the efficacy against a live intermammary challenge in Holstein heifers. The study parameters used for establishing vaccine efficacy between vaccinated and non-vaccinated placebo controls of this experimental study were 1) quantitative clearance following intramammary challenge, 2) somatic cell count, 3) serological response to vaccination, 4) quality of milk, 5) rectal temperature and 6) udder inflammation post challenge.

Example 21

Vaccine Preparation

The vaccine composition made from *Klebsiella pneumoniae* 1571 as described in Example 5 included polypeptides having molecular weights of 87 kDa, 82 kDa, 78 kDa, 72 kDa, 68 kDa, 35 kDa, and 33 kDa as determined by SDS-PAGE. The immunizing composition derived from strain 1571 was used to prepare the experimental vaccine by emulsifying the extracted protein suspension (600 µg total protein per milliliter) into a commercial adjuvant (EMULSIGEN, MVP Laboratories, Ralston Nebr.) using an IKA Process Pilot 2000/4—DR (IKA, Cincinnati, Ohio) to give a final dose of 1,200 µg total protein in a 2.0 ml injectable volume with an adjuvant concentration of 22.5% vol/vol. A placebo vaccine was prepared by substituting physiological saline for the aqueous protein suspension in the above protocol.

Example 22

Experimental Design and Herd Vaccination

Eight Holstein heifers at approximately 60-days pre-calving were randomly allocated to two groups consisting of 4 heifers per group. Heifers were identified by ear tags and left to co-mingle with approximately 500 cows on a large commercial dairy. Heifers in group-1 served as placebo controls while heifers in group-2 were vaccinated with the *Klebsiella pneumonia* 1571 vaccine composition of Example 21. Heifers were vaccinated subcutaneously in the upper right shoulder two times at 21 day intervals with 2 ml of the placebo and/or the *Klebsiella pneumoniae* 1571 vaccine. Heifers were fed twice daily a total mixed ration appropriate for their stage of production. All heifers had as libitum access to water during the study.

Blood was taken at the time of first vaccination, the second vaccination, and again two weeks post second vaccination. All blood was collected in sterile 13×75 millimeter (mm) VACUTAINER collection tubes, brand SST No. 369783, (Becton Dickinson, Franklin Lakes, N.J.). After clotting, the blood tubes were centrifuged at 800×g for 30 minutes and frozen at −80° C. until analysis. At approximately thirty days post-calving heifers were transported to a separate facility for intramammary challenge.

Example 23

Selection of Nalidixic Acid Resistance in *Klebsiella Pneumonia* 1571

The *Klebsiella pneumoniae* 1571 isolate of Example 1 was made Nalidixic Acid resistant. Inducing resistance to a known antibiotic in the challenge strain aids in differentiation of the challenge strain from other *Klebsiella* strains that may contaminate challenged samples due to its prevalence in the environment. To induce antibiotic resistance the *Klebsiella* 1571 strain was grown in increasing concentrations of Nalidixic Acid. Briefly, two 1.0 liter stock solutions of TSB containing 35 gm Tryptic Soy, 5 gm yeast extract, and 2,2-dipyridyl at 25 µg was prepared and autoclaved for 30 minutes and then cooled to 4° C. Nalidixic acid was added to one of the 1 liter TSB stock solutions by membrane filtration through a 0.2 u filter to a final concentration of 150 µg/ml. The TSB now containing 150 µg Nalidixic acid was diluted in 20 ml stocks (50 ml Conical tubes) solution using the TSB without Nalidixic as the diluent to obtain the following concentrations; 0 (no Nalidixic acid), 25 µg/ml, 50 µg/ml, 75 µg/ml, 100 µg/ml, and non-diluted 150 µg.

The *Klebsiella* 1571 isolate of Example 1 was removed from frozen storage, plated onto Blood agar, and incubated at 37° C. for 24 hours at which point a single colony was picked and aseptically inoculated into one of the non-Nalidixic Acid TSB tubes and incubated for 3 hours at 37° C. while stirring at 200 rpm. At three hours post inoculation 2 ml of the culture was transferred into 20 ml of the 25 µg Nalidixic Acid tube that was pre-warmed to 37° C. The culture was allowed to grow at 37° C. while rapidly stirring at 200 rpm for 3 hours. This process was repeated two times and then transferred to the next concentration of Nalidixic Acid. If growth did not occur, the process was repeated in the previous concentration and then transferred to the next increasing concentration. This was done for each concentration until growth was established at the highest concentration of Nalidixic Acid. Once growth was established at the 150 μg/ml level, the culture was then plated onto EMB containing 150 μg/ml Nalidixic Acid. A single colony of the isolate was selected and transferred into 100 ml TSB containing 150 μg/ml Nalidixic acid (media as described above). The culture was allowed to grow at 37° C. for 4.5 hours or until an OD of 1.0 at 540 nm was achieved. The culture was then centrifuged at 8000 rpm for 20 minutes at which point the supernatant was discarded and the pellet re-suspended in 90 ml of TSB media as described above but containing 20% glycerol and 25 ug/ml 2,2-dipyridyl. One ml aliquots of the bacterial suspension was dispensed into 2 ml cryovials and stored at −90° C. until use.

Example 24

Intramammary Challenge with *Klebsiella Pneumonia* 1571

Prior to challenge milk samples from all four quarters of each heifer were collected and bacteriological analysis was conducted to determine that no quarter was infected. On the day of challenge the Nalidixic acid resistant strain of *Klebsiella* 1571 from the frozen stock of Example 23 was diluted in Phosphate Buffered Saline (PBS) pH 7.2 to a previously determined level to yield a challenge dose of 100 Colony Forming Units (CFU) in a 1.0 ml volume. Using a teat cannula all heifers were challenged in one quarter through the teat canal of each udder. The challenged dose was then squeezed up the teat and into the udder by hand. Heifers were monitored at each milking for their rectal temperature, quality of milk, and differences in inflammation of the udder. In addition, a milk sample was collected from the challenged quarter of each heifer for the determination of somatic cell count and enumeration of the challenge organism. Heifers were milked twice daily for 7 days post challenge at which point the study was terminated.

Results

Serological Response to Vaccination

The serological response to vaccination was monitored by ELISA. Each serum sample was run individually using the *Klebsiella Pneumonia* 1571 antigen as the capture molecule. Briefly, 96-well plates were coated with a 1:1,000 dilution of turkey sera from turkeys that had been hyperimmunized with the *Klebsiella Pneumonia* 1571 antigen. After coating, the plates were blocked with PVA/PBS and antigen from *Klebsiella* 1571 antigen was added to the wells and incubated. The antigen was then removed, plates washed, and a 1:1,000 dilution of the bovine sera to be evaluated was added to the plate in duplicate. Sera were removed and the plate was washed. Sheep anti-bovine conjugate was added to the plate at a 1:20,000 dilution and incubated. Conjugate was removed from the plate. The plate was washed, and substrate was added for color development which was subsequently read with a spectrophotometer. For S/P calculations, average signal from the negative control sera was subtracted from all OD values. For samples being evaluated, the average OD of the sample was divided by the average positive control sample OD.

Figure 23:
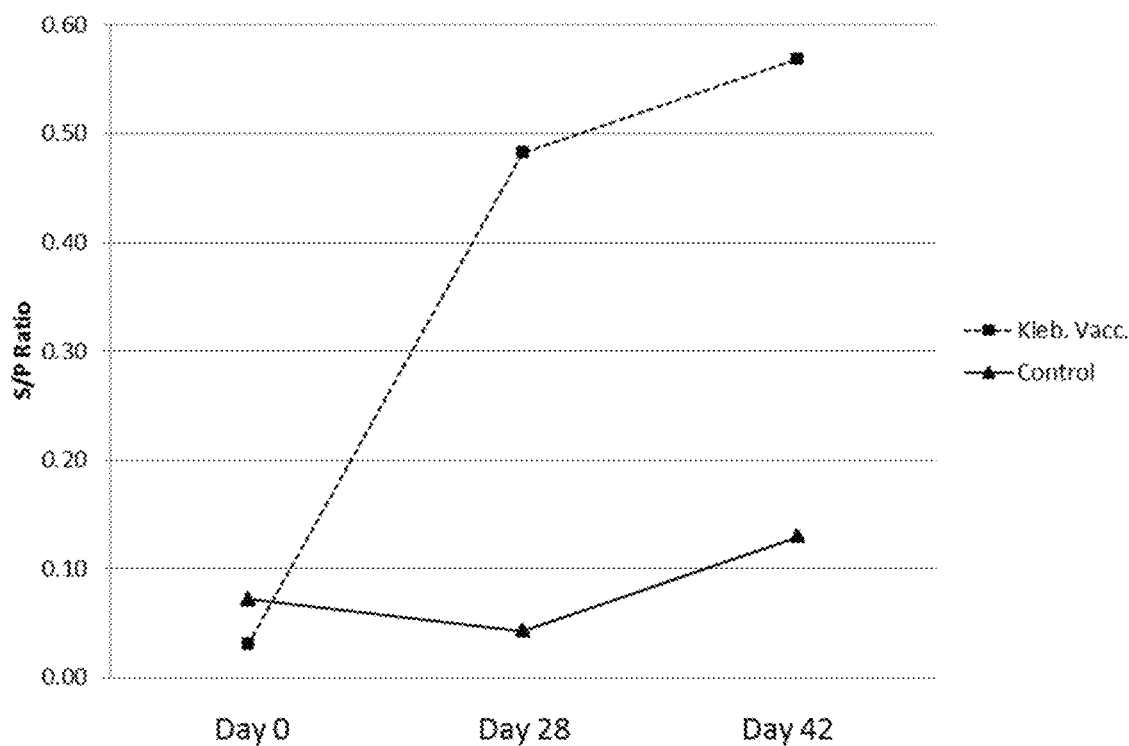
FIG. 23. Serological response of Heifers vaccinated with *Klebsiella pneumoniae* 1571 vaccine measured by ELISA.

FIG. 23 shows the serological response of heifers vaccinated with the *Klebsiella Pneumonia* 1571 vaccine composition. All heifers vaccinated showed an antibody response 21 days after the first vaccination in contrast to the placebo controls. This was followed by an anamnestic response with an increase in antibody 21 day after the second vaccination.

Figure 24:
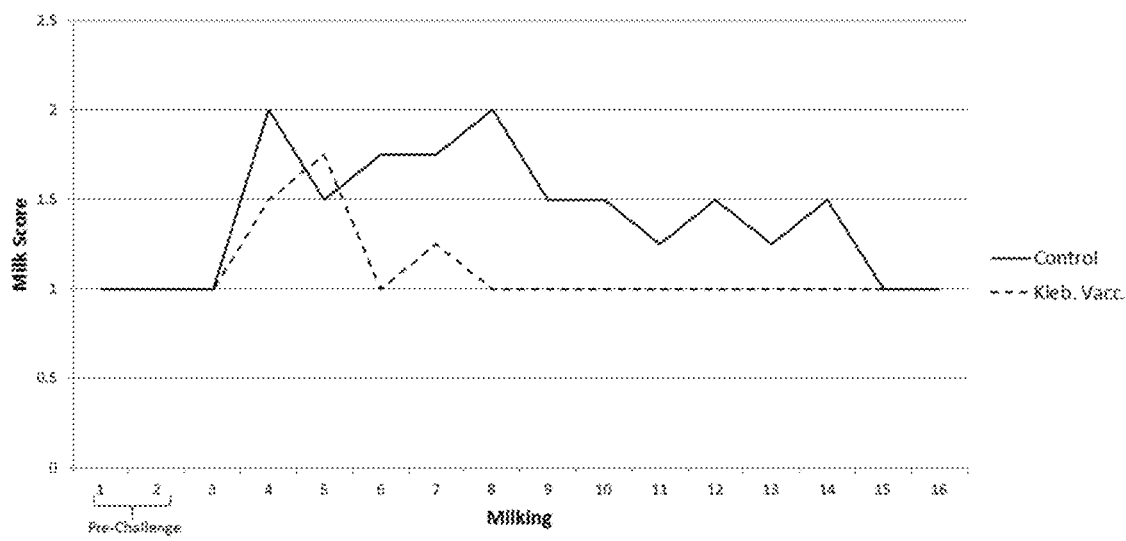
FIG. 24. Milk score of heifers vaccinated with *Klebsiella pneumoniae* 1571 vaccine versus controls following challenge with *K. pneumoniae*. Cumulative milk score after challenge with *Klebsiella pneumoniae* 1571. Difference in cumulative milk score between *Klebsiella pneumoniae* 1571 vaccinates and controls after challenge with *K. pneumoniae*.

Mastitis caused by *Klebsiella pneumonia* in the dairy industry is often responsible for a loss in milk quality often seen as abnormal milk. For example, cows with mastitis can often have milk that includes flakes, small slugs, large clots, or has a stringy watery consistency. These characteristics are indicative of clinical mastitis. FIG. 24 shows the milk score for each heifer over a period of 16 days. A score of 1 is normal, 2 refers to the presence of flakes, 3 refers to the presence of small slugs, 4 refers to the presence of large slugs or clots, and 5 refers to a consistency that is stringy or watery. The results illustrate that vaccinating with the *Klebsiella pneumonia* 1571 composition improved the overall quantitative measure of milk quality. Vaccination statistically improved milk quality over the non-vaccinated controls (p=0.042). This is a direct correlation to a decrease in Mastitis, as all four non-vaccinated controls developed clinical mastitis following challenge while only two of the vaccinated heifers met the definition of mastitis. The presence of mastitis was significantly reduced in vaccinates versus controls (p=0.046).

Figure 25:
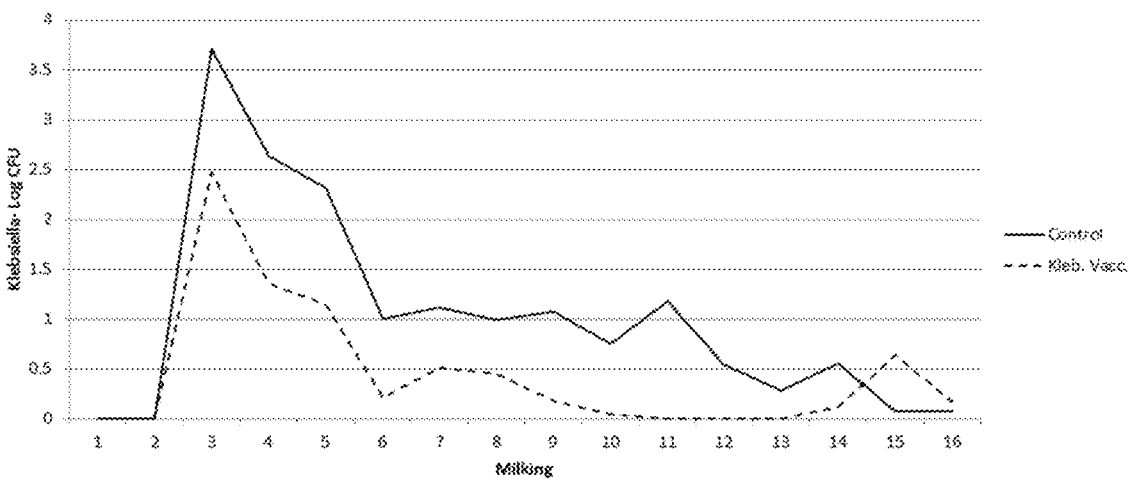
FIG. 25. Difference in quantitative clearance of *Klebsiella pneumoniae* 1571 between vaccinates and controls after homologous challenge.

At 30-days post calving heifers were intramammarily challenged through the teat canal with a 100 CFU of *Klebsiella pneumonia* 1571. Heifers were milked twice daily for 7 consecutive days post challenge. Milk samples from the challenged quarters was collected and frozen at −90° C. until enumerated. FIG. 25 shows the difference in the prevalence of the challenge organism in milk samples between vaccinates and the placebo controls for 2 samplings pre-challenge, and 14 consecutive samplings post challenge (i.e., two samplings per day for 7 consecutive days). There was a significant decrease in the amount of *Klebsiella* being shed in the milk derived from the infected udder of vaccinated heifers compared to controls. Averaged across the study period, the vaccinated heifers had only 15 positive *Klebsiella* milk samples out of 56 sampled or 27%. In contrast; the number of positive *Klebsiella* milk samples in the placebo controls was 64% or 36 positive out of 56 sampled.

Example 25

Evaluation of a Vaccine Composition Derived from *Klebsiella Pneumoniae* in a Chronically Infected Dairy Herd A commercial dairy herd having a history of chronic mastitis attributable to *Klebsiella pneumonia* was chosen for the evaluation of a vaccine composition as described in Example 5. The criterion for establishing vaccine efficacy of this experimental study was based on an estimated prevented fraction with a 95% confidence interval of the following: 1) reduction of the prevalence and incidence of clinical mastitis caused by *Klebsiella pneumoniae* among *Klebsiella* vaccinates compared to placebo controls, 2) reduction of the prevalence and incidence of coliform mastitis among *Klebsiella* vaccinates compared to placebo controls, 3) improvement (i.e., a decrease) in somatic cell count among *Klebsiella* vaccinates compared to placebo controls and 4) improvement (i.e., an increase) in milk production among *Klebsiella* vaccinates and placebo controls.

Example 26

Vaccine Preparation

The vaccine composition made from *Klebsiella pneumoniae* 1571 as described in Example 5 included polypeptides having molecular weights of 87 kDa, 82 kDa, 78 kDa, 72 kDa, 68 kDa, 35 kDa, and 33 kDa as determined by SDS-PAGE. The immunizing composition derived from strain 1571 was used to prepare the experimental vaccine by emulsifying the extracted protein suspension (600 µg total protein per milliliter) into a commercial adjuvant (EMULSIGEN, MVP Laboratories, Ralston Nebr.) using an IKA Process Pilot 2000/4—DR (IKA, Cincinnati, Ohio) to give a final dose of 1,200 µg total protein in a 2.0 ml injectable volume with an adjuvant concentration of 22.5% vol/vol. A placebo vaccine was prepared by substituting physiological saline for the aqueous protein suspension in the above protocol.

Example 27

Experimental Design and Herd Vaccination

The study was conducted as a confirmatory, randomized, blinded, and placebo-controlled efficacy study of controlling *Klebsiella pneumoniae*. A total of 569 head of Holstein or jersey cows and heifers were enrolled in the study. The cows were housed in a single free-stall barn except when they were in their dry period. During the dry period, they were moved to a designated dry-cow barn. Heifers were in a heifer barn until close to calving at which point they were moved to the free-stall barn to join the milking herd. Cows were randomized to receive either the *Klebsiella pneumoniae* 1571 vaccine, or the placebo vaccine containing adjuvant only. Cows and heifers were injected subcutaneously with 2 ml on the day of enrollment, with a second dose administered 3 weeks later. With the exception of cows close to dry-off and cows close to calving, a whole-herd vaccination regimen was done to initiate the study followed by a booster dose 3 weeks later. A dry-cow protocol was set up to vaccinate all cows and heifers with 2 doses of vaccine, 3-4 weeks apart, once they achieved 217 days carrying calf (DCC). The experimental design is summarized in Table 7.

Ninety-six (96) well polystyrene plates were coated with *Klebsiella pneumoniae* 1571 polypeptides as the target antigens. The polypeptides had molecular weights of 87 kDa, 82 kDa, 78 kDa, 72 kDa, 68 kDa, 35 kDa, and 33 kDa as determined by SDS-PAGE. Each serum sample was diluted 4-fold from 1:400 to 1:409,600 and tested in duplicate. Each test plate contained two wells of a target dilution (1:400) of the known positive control sera (hyper-immunized sera of Example 7). These positive control wells served purposes of 1) internal plate control to ensure a valid test and 2) a means of calculating sera titers. Titer was defined as the point at which a sample's dilution curve intercepted 50% of the mean OD value of the positive control wells on the plate. Computer software was used to determine the intercept point to generate and report a calculated titer value for each serum sample tested on the plate.

Figure 26:
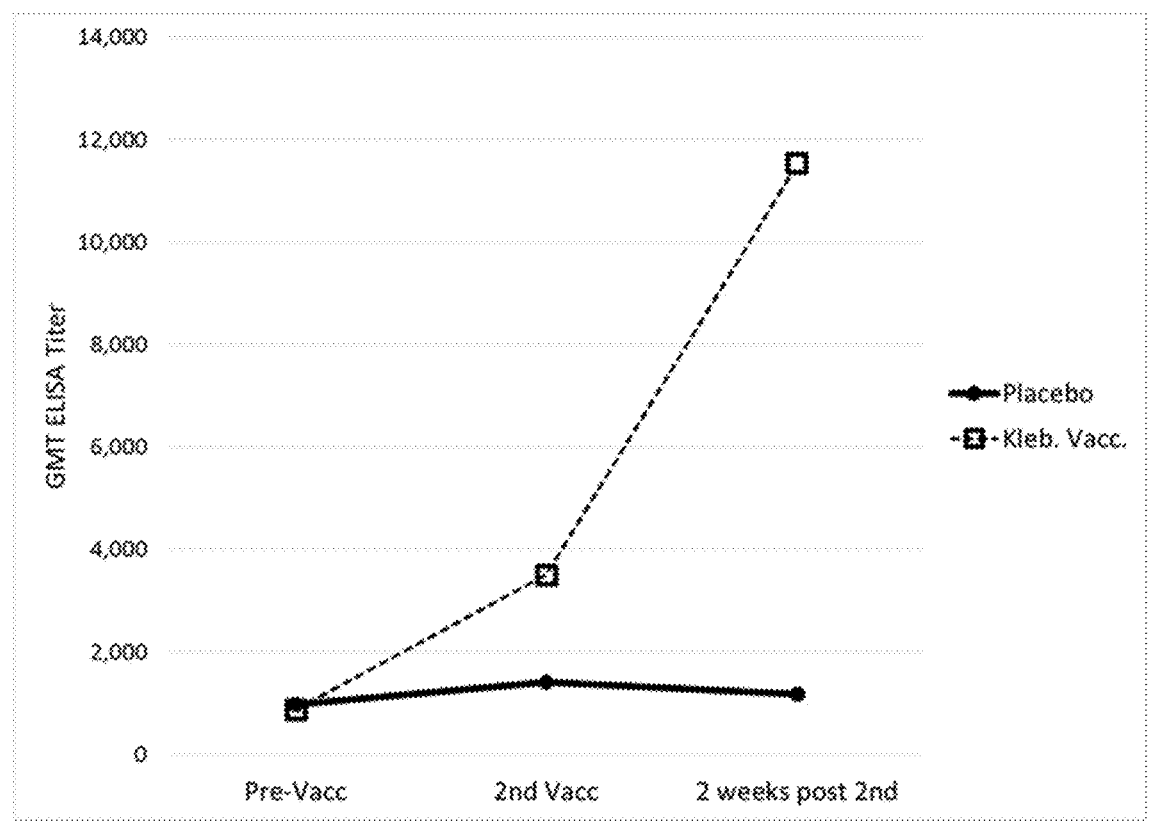
FIG. 26. ELISA serological response of cows vaccinated with the *Klebsiella pneumoniae* 1571 vaccine compared to placebo control cows.

Antibodies against the vaccine polypeptides was detectable in the *Klebsiella pneumoniae* 1571 vaccinates following one dose of vaccine and significantly increased after the second dose (FIG. 26). It is interesting to note that this dairy was chronically infected with *Klebsiella pneumoniae* resulting in continuous mortality through natural exposure. However this exposure did not induce immunity to metal-regulated proteins even though these proteins would have been expressed on the surface of the bacteria under natural field conditions and during infection. It was not until the cows were vaccinated with a vaccine composition of metal-regulated proteins prepared that an adaptive immune response was generated these target immunogens. This can be seen in FIG. 26, where the non-vaccinated animals show no antibody response even though they are continuously exposed to *Klebsiella pneumonia*, in contrast to those that have been vaccinated or primed to recognize the target immunogens in the vaccine composition.

The sera from Example 25 were analyzed by Western Blot to determine what proteins from the vaccine formulation were recognized. Western analysis was done using the WES

TABLE 7

Summary of Animals in the Study

| | | | Month of Study | | | | | | | | | | |
|---|---|---|---|---|---|---|---|---|---|---|---|---|---|
| | | Initiation | 1 | 2 | 3 | 4 | 5 | 6 | 7 | 8 | 9 | 10 | Total |
| A | Controls | 165 | 47 | 15 | 7 | 4 | 5 | 6 | 10 | 5 | 10 | 7 | 281 |
| B | Vaccinates | 160 | 51 | 18 | 7 | 4 | 8 | 6 | 9 | 6 | 10 | 9 | 288 |
| C | Controls | | −4 | 0 | −3 | −3 | −4 | −8 | −10 | −5 | −6 | −4 | −47 |
| D | Vaccinates | | −2 | −1 | −6 | −9 | −3 | −11 | −8 | −2 | −5 | −1 | −48 |
| E | Controls | 165 | 208 | 223 | 227 | 228 | 229 | 227 | 227 | 227 | 231 | 234 | |
| F | Vaccinates | 160 | 209 | 226 | 227 | 222 | 227 | 222 | 223 | 227 | 232 | 240 | |

Table shows the number of animals enrolled and removed each month by treatment group. Rows A & B show original cows vaccinated and additional cows/heifers enrolled each month. Rows C & D shows the number of cows that died or were culled each month. Rows E & F show the total number of animals in the study each month (i.e., number of animals from the previous month minus animals removed each month, plus new animals enrolled each month).

Results

The serological response of each cow to vaccination was measured by an enzyme-linked immunosorbent assay (ELISA). Twenty cows from each group were randomly selected to assess the serological response following vaccination to the *Klebsiella pneumonia* 1571 composition compared to the placebo controls. Cows were bled and their serum harvested at the time of first vaccination, time of second vaccination, and two weeks after their second vaccination. Sera was frozen and stored until analysis by an enzyme-linked immunosorbent assay (ELISA).

Figure 27:
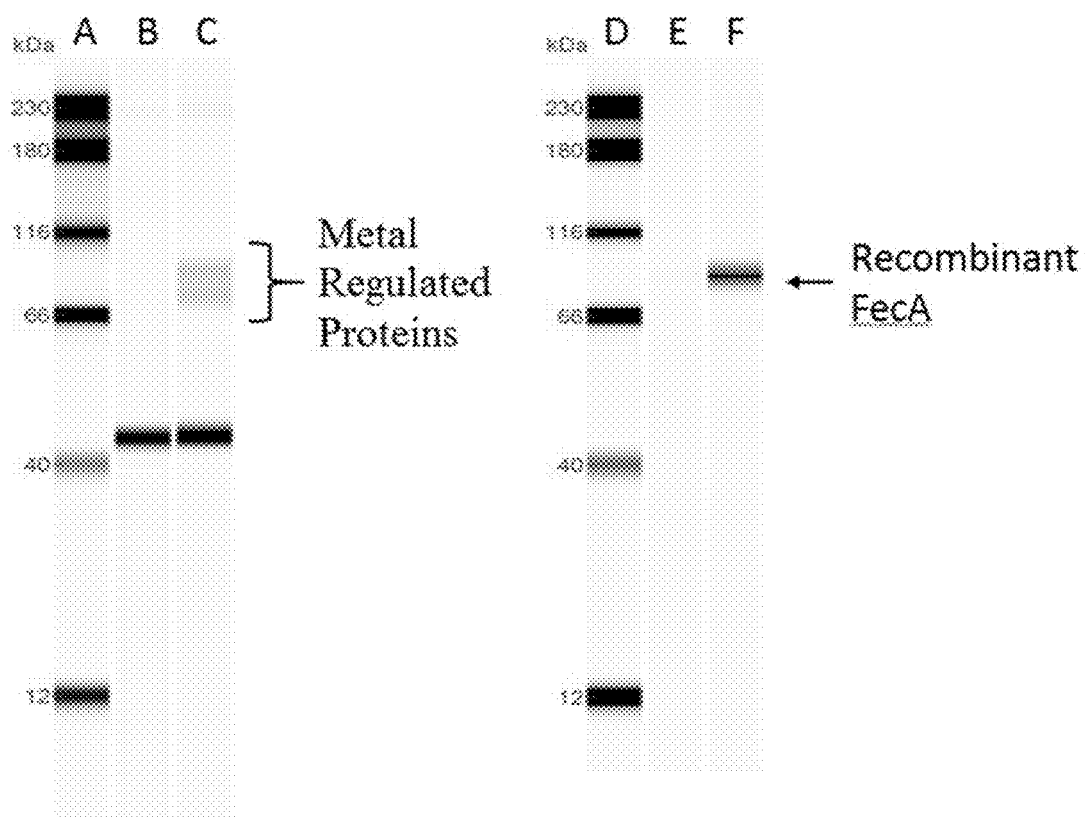
FIG. 27. Western blot using Protein Simple Capillary Electrophoresis System. Sample A, Molecular Weight Marker; Sample B, *Klebsiella pneumonia* 1571 vaccine antigen blotted with placebo sera; Sample C, *Klebsiella pneumonia* 1571 vaccine antigen blotted with sera from *Klebsiella pneumoniae* 1571 vaccinated cows; Sample D, Molecular Weight Marker; Sample E, recombinant FecA blotted with placebo sera; Sample F, recombinant FecA blotted with sera from *Klebsiella pneumoniae* 1571 vaccinated cows.

Capillary Electrophoresis system (Protein Simple, San Jose, CA). Sera from cows vaccinated with the purified polypeptides reacted with the metal regulated proteins in the vaccine composition, whereas sera from cows vaccinated with placebo did not. In addition, cows vaccinated with the purified polypeptides reacted with the recombinant protein FecA, but the sera from placebo vaccinated cows did not (FIG. 27). These data confirm that the vaccine contained the metal-regulated protein FecA. Also, these data confirm that natural infections with *Klebsiella pneumoniae* fail to induce a strong immune response to these proteins.

Cows from Example 27 were milked three times per day and monitored for clinical signs of mastitis such as swollen udders, milk color change, flaky or clumpy milk, etc. In addition, a daily list of cows with a drop in milk production from normal levels was provided to the herdsmen by the farm manager as an extra alert to check for mastitis. If a cow was suspected of having mastitis, two duplicate, but independent milk samples were aseptically collected according to the recommended practices of the National Mastitis Council in case the first sample was contaminated (isolation of >2 organisms) the second sample can be tested.

Milk samples were submitted to the Veterinary Diagnostic Laboratory to determine the causative agent for the mastitis event. Aerobic culture was completed by plating 10 µl on blood and MacConkey agar plates to determine presence and identification of mastitis pathogens including *Klebsiella* spp., and other coliforms including *E. coli* spp, *Enterobacter* spp., *Citrobacter* spp., and *Serratia* spp. Bacterial identification procedures were performed by the state diagnostic laboratory with confirmation of bacterial identification by MALDI-TOF for all isolates. Mastitis events occurring 2 or more weeks after the second vaccination were considered eligible events for the study.

There were 53 cases of clinical mastitis that were confirmed to be due to coliforms and 20 cases of *Klebsiella* mastitis in the cows at 1-90 days in milk for this study. This incidence was sufficient to judge vaccine efficacy.

Figure 28:
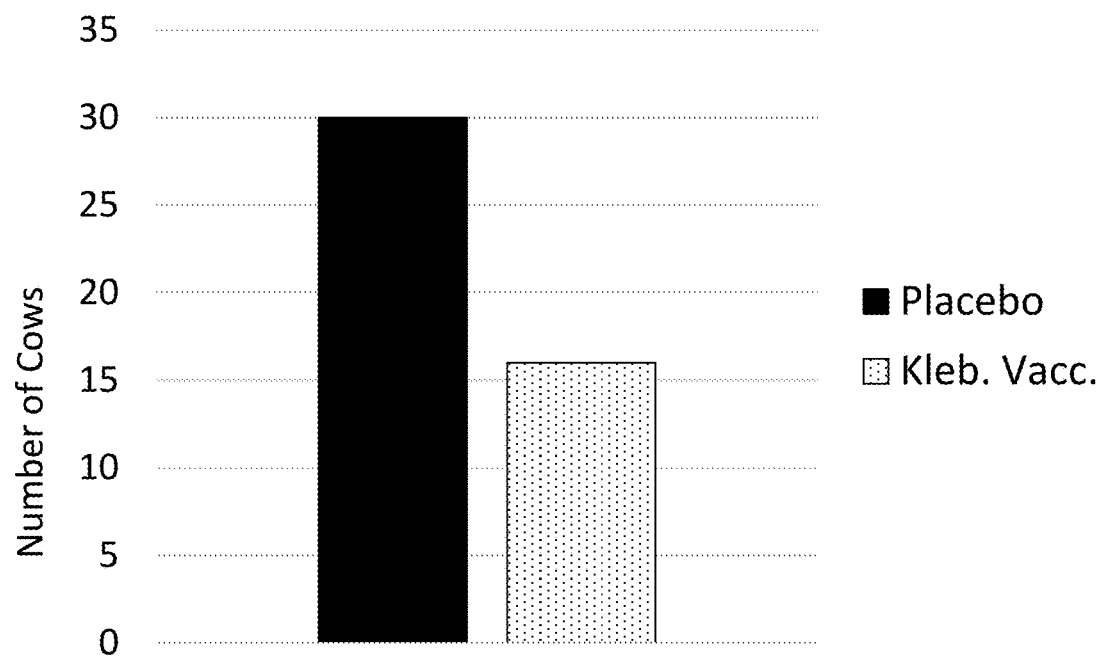
FIG. 28. Prevalence of coliform mastitis following vaccination with *Klebsiella pneumoniae* 1571 vaccine. Graph showing the number of cows 1-90 days in milk with clinical coliform mastitis in the placebo vaccinated group vs. the *Klebsiella pneumoniae* 1571 vaccinated group. Data provides a Prevented Fraction of 0.4667 (95% CI: 0.0494 to 0.7008); P=0.0305.

There were 46 cows that had coliform mastitis during their first 90 days in milk. The coliforms identified by culture of clinically-affected cows include *E. coli, Klebsiella, Enterobacter, Serratia* and *Citrobacter*. Thirty (30) of these cows were in the placebo group (out of 225), and 16 cows were in the *Klebsiella Pneumoniae* 1571 vaccine group (out of 225). The 47% reduction in the prevalence of coliform mastitis in the vaccinated cows was statistically significant (p=0.0305) (FIG. 28).

Figure 29:
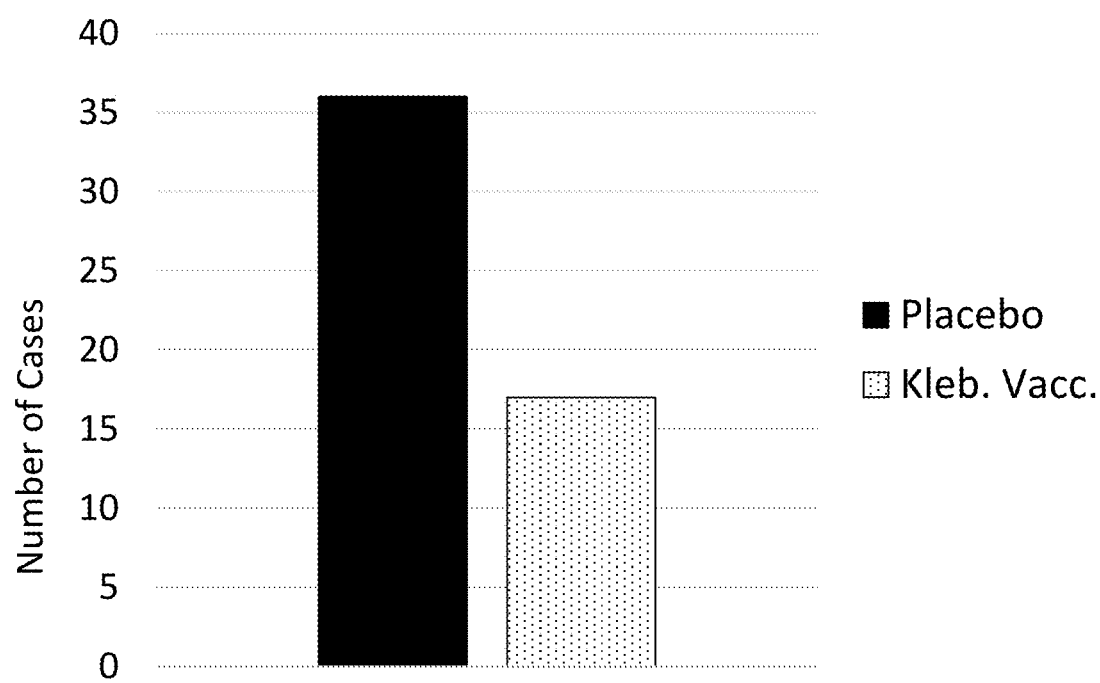
FIG. 29. Incidence of coliform mastitis following vaccination with *Klebsiella pneumoniae* 1571 vaccine. Graph showing the incidence of clinical coliform mastitis in the placebo vaccinated group vs. the *Klebsiella pneumoniae* 1571 vaccinated group. Data provides a Prevented Fraction of 0.5478 (95% CI: 0.1953 to 0.7549); P=0.0057.

There were 53 separate cases of coliform mastitis from cows 1-90 days in milk. Thirty-six (36) of these incidents were from cows in the placebo group, and 17 were from cows in the *Klebsiella Pneumoniae* 1571 vaccine group. The 55% reduction in the incidence of clinical mastitis in vaccinated cows was highly statistically significant (p=0.0057) (FIG. 29).

Figure 30:
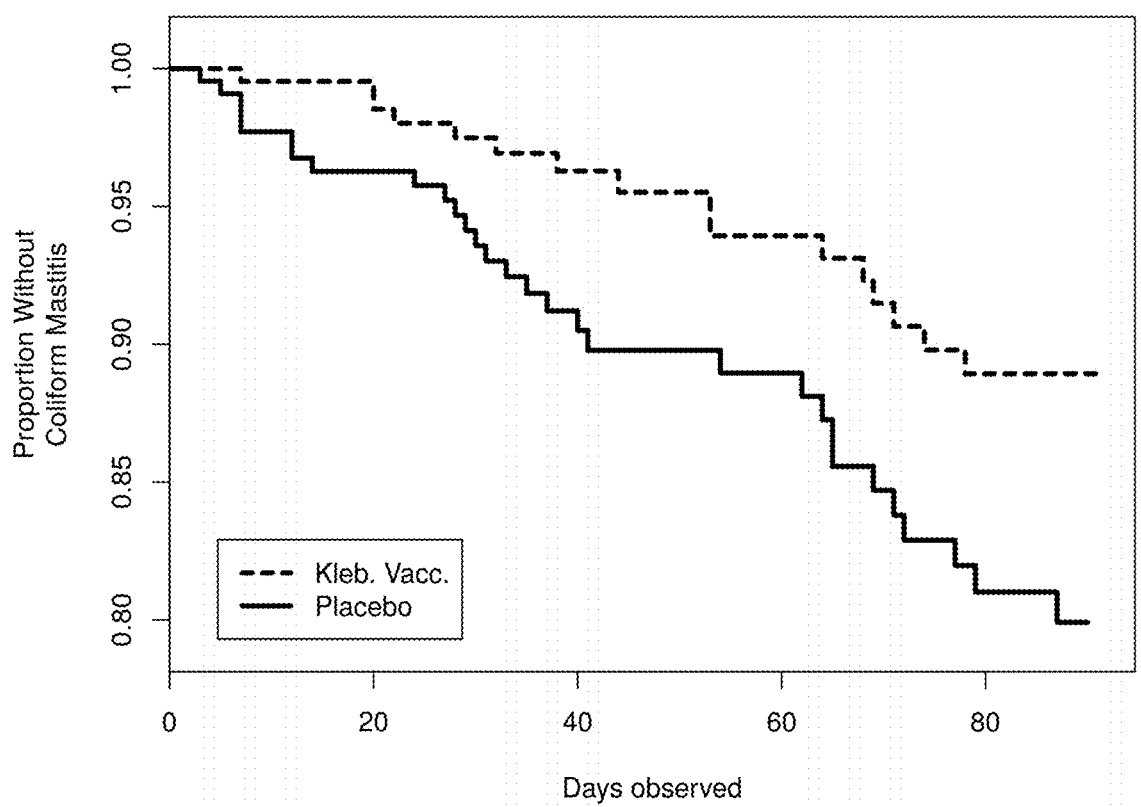
FIG. 30. Graph showings the proportion of cows without coliform mastitis over time. The estimate of the hazard ratio for mastitis caused by coliforms is 0.494 with a 95% confidence interval from 0.269 to 0.906. This suggests an approximately 50.6% decrease in the risk of mastitis from all coliform mastitis causing organisms and agrees with the significant p-value generated (p=0.02278). Each line represents the proportion of individuals that have not yet contracted Coliform mastitis. Each time the line drop represents an observed mastitis event.

With proper vaccine protection, the expectation of a dairy farm would be to see a high proportion of cows without coliform mastitis. FIG. 30 shows the proportion of cows without coliform mastitis over time and demonstrates cows in the Placebo group dropped at a faster rate (i.e., more cows with coliform mastitis) than the cows in the *Klebsiella Pneumoniae* 1571 vaccine group (p=0.02278).

The most common organism causing the coliform mastitis was *Klebsiella*, followed by *E. coli*. It was surprising to see this much coliform mastitis in a herd where cows were being vaccinated 4 times per lactation with a commercially available J5 vaccine. Bedding the cattle on dried manure solids may partly explain the high incidence. However, even in the face of the high challenge, cows vaccinated with the *Klebsiella pneumoniae* 1571 vaccine had significant protection versus cows vaccinated with placebo (FIGS. 28 and 29).

Another major problem with mastitis in the dairy industry are recurrent infections. While the actual costs of a single mastitis episode vary with cattle and milk prices, the economic losses from treatment costs, replacement costs and decreased saleable milk can be devastating. One study conducted in 1991 put the cost of one mastitis episode at $107/cow (Hoblet et al., 1991, J. Am Vet Med. Assoc., 199:190-196). These costs are of course amplified when there are recurrent infections in a single cow. In this study, recurrent infections occurred more often in the placebo group than in the *Klebsiella pneumoniae* 1571 vaccine group which can be seen in Table 8. Note how 9 cows in the placebo group had recurrent mastitis events with 5 cows having 3 or 4 recurrent infections. In comparison, only 4 cows in the vaccinated group had a single recurrence of mastitis during the monitoring period.

TABLE 8

Number of cows with coliform mastitis during the first 90 Days In Milk that repeated with subsequent cases of coliform mastitis during the remainder of their lactation.

| | Total coliform mastitis cows | Number of cows with recurrent coliform mastitis | | | |
|---|---|---|---|---|---|
| | | 1 recurrence | 2 recurrences | 3 recurrences | 4 recurrences |
| Placebo | 30 | 2 | 2 | 4 | 1 |
| Kleb. Vacc. | 16 | 4 | 0 | 0 | 0 |

Figure 31:
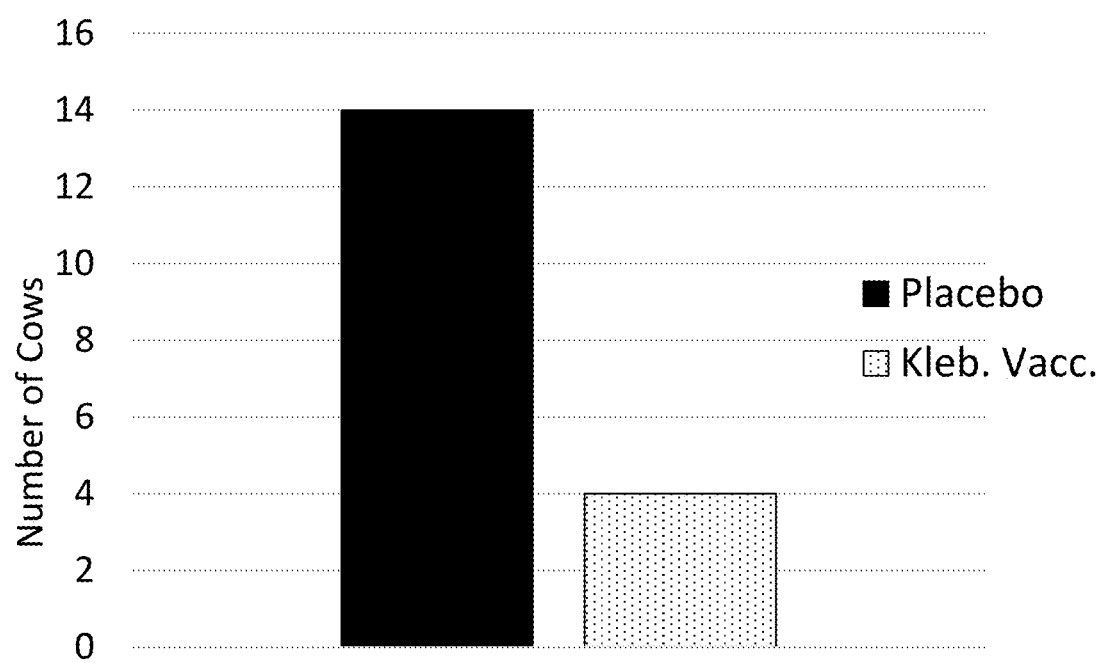
FIG. 31. Prevalence of *Klebsiella* mastitis following vaccination with *Klebsiella pneumoniae* 1571 vaccine. Graph showing the number of cows 1-90 days in milk with clinical *Klebsiella* mastitis in the placebo vaccinated group vs. the *Klebsiella pneumoniae* 1571 vaccinated group.

*Klebsiella* mastitis was the largest coliform problem in this herd. There were 18 cows that had *Klebsiella* mastitis during their first 90 days in milk. Fourteen (14) of these cows were in the placebo group (out of 225), and 4 cows were in the *Klebsiella Pneumoniae* 1571 vaccine group (out of 225) (FIG. 31). The 71% reduction in the prevalence of *Klebsiella* mastitis in the vaccinated group was highly statistically significant (p=0.0171;). As mentioned previously, the experience of the ISU Dairy is that 60-80% of cows with *Klebsiella* mastitis leave the herd within that lactation. With only 4 cows diagnosed with clinical *Klebsiella* mastitis in the *Klebsiella Pneumoniae* 1571 vaccine group versus 14 cows in the placebo group, a predicted 6-8 more cows will be culled or die prior to the end of their lactation in the placebo group than the vaccinated group. Vaccination with the *Klebsiella Pneumoniae* 1571 vaccine reduces costs of mastitis episodes, including reducing culling.

Figure 33:
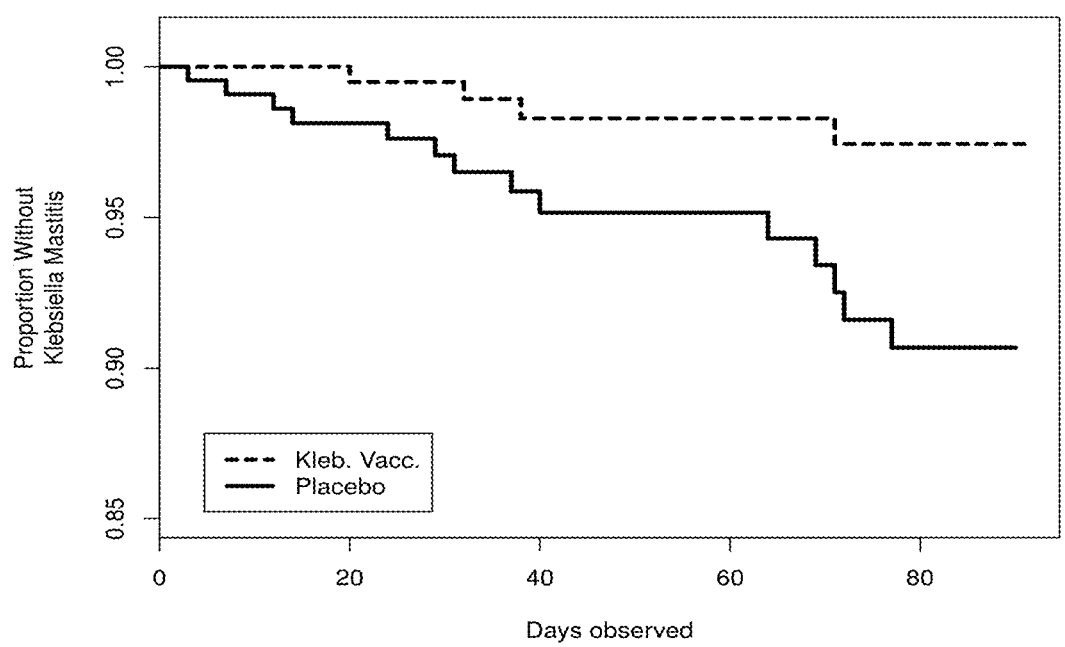
FIG. 33. Graph showing the proportion of cows without *Klebsiella* mastitis over time. The estimate of the hazard ratio for this *Klebsiella* data set is 0.272 with a 95% confidence interval from 0.089 to 0.825. This suggests an approximately 72.8% decrease in the risk of mastitis from *Klebsiella*, and agrees with the significant p-value generated (p=0.0215). Each line represents the proportion of individuals that have not yet contracted a qualifying mastitis. Each time the line drop represents an observed mastitis event.

With proper vaccine protection, the expectation of a dairy farm would be to see a high proportion of cows without *Klebsiella* mastitis. FIG. 33 shows the proportion of cows without *Klebsiella* mastitis over time and demonstrates cows in the Placebo group dropped at a faster rate (i.e., more cows with *Klebsiella* mastitis) than the cows in the *Klebsiella Pneumoniae* 1571 vaccine group (p=0.0215).

Figure 32:
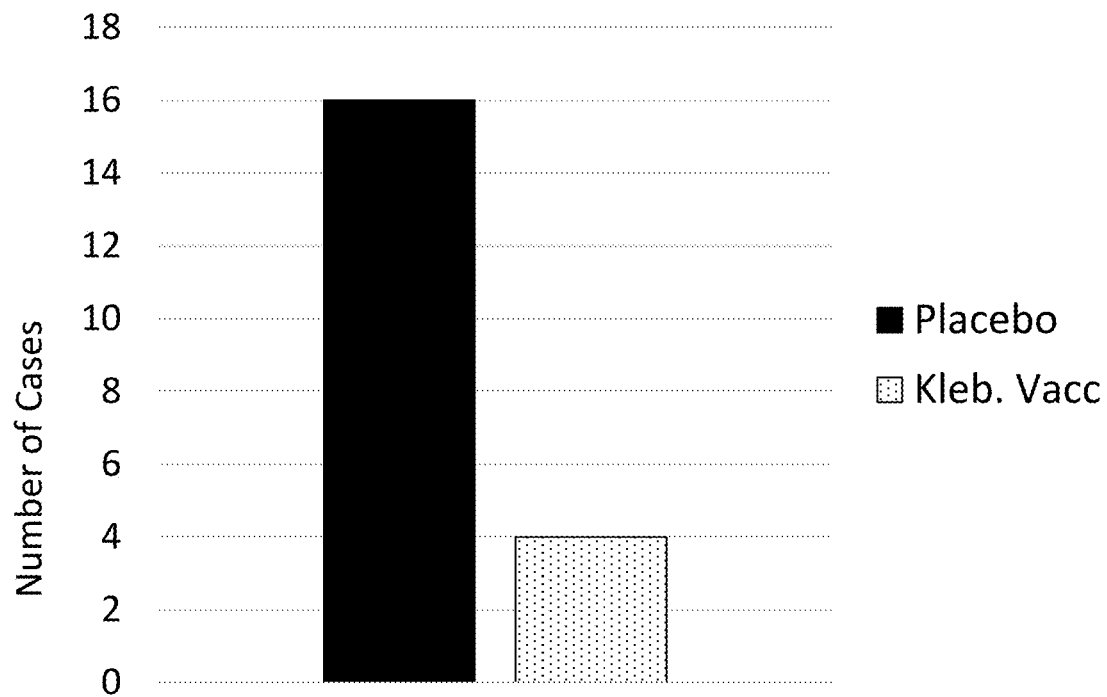
FIG. 32. Incidence of *Klebsiella* mastitis following vaccination with *Klebsiella pneumoniae* 1571 vaccine. Graph shows the number of cases of clinical *Klebsiella* mastitis from cows 1-90 days in milk in the placebo vaccinated group vs. the *Klebsiella pneumoniae* 1571 vaccinated group.

There were 20 separate cases of *Klebsiella* mastitis from cows 1-90 days in milk. Sixteen (16) of these incidents were from cows in the placebo group, where *Klebsiella* mastitis recurred in 2 cows during this short observation period. Only 4 cases of *Klebsiella* mastitis were observed in cows from the *Klebsiella Pneumoniae* 1571 vaccine vaccinated group and none of these animals had a recurrence during the observation period (FIG. 32). The 75% reduction of in the incidence of *Klebsiella* mastitis in the vaccinated cows was highly statistically significant (p=0.0056).

The cows were milked three times a day throughout the study and the pounds of milk produced was electronically recorded via software at the dairy. The cows were tested on approximately a monthly basis by the Dairy Herd Improvement Association (DHIA) and the somatic cell count in the milk for each cow was determined and recorded in Dairy Comp software.

The amount of milk produced by a cow can be a useful indicator of overall health. It is well known in the dairy industry that clinical mastitis reduces milk production in affected cows (Grohn, et. al., 2004, J. Dairy Sci., 87:3358-

Figure 34:
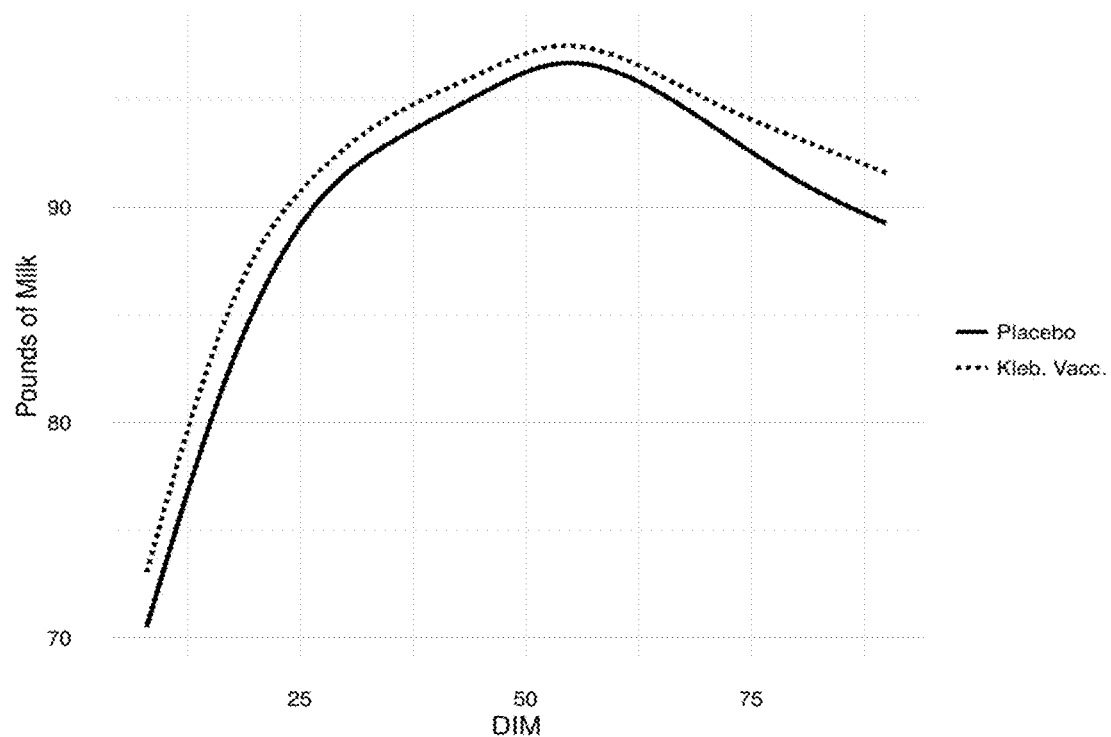
FIG. 34. Plot of daily milk production (pounds of milk per cow) beginning at 8 days in milk (saleable milk) to 90 days in milk.

3374; Pinzon-Sanchez et al., 2011, J. Dairy Sci., 94:1873-1892). In the present study, the *Klebsiella Pneumoniae* 1571 vaccinated cows averaged 2.0 pounds more milk per day than the placebo cows during the first 90 DIM. Over the 90 day period this amounts to a predicted 180 pounds of extra milk per cow, during a time when cows are expected to be in peak lactation. Typically, in the dairy industry each pound of milk increase at the time of peak milk yields an additional 200-250 pounds of milk in a typical 305 day lactation. Therefore, with a 2 pound increase in vaccinated cows at peak milk, this is predicted to yield an additional 400-500 pounds of milk in a typical 305 day lactation. A graph of the average pounds of milk produced per cow in this study up to 90 DIM is shown in FIG. 34.

Figure 35:
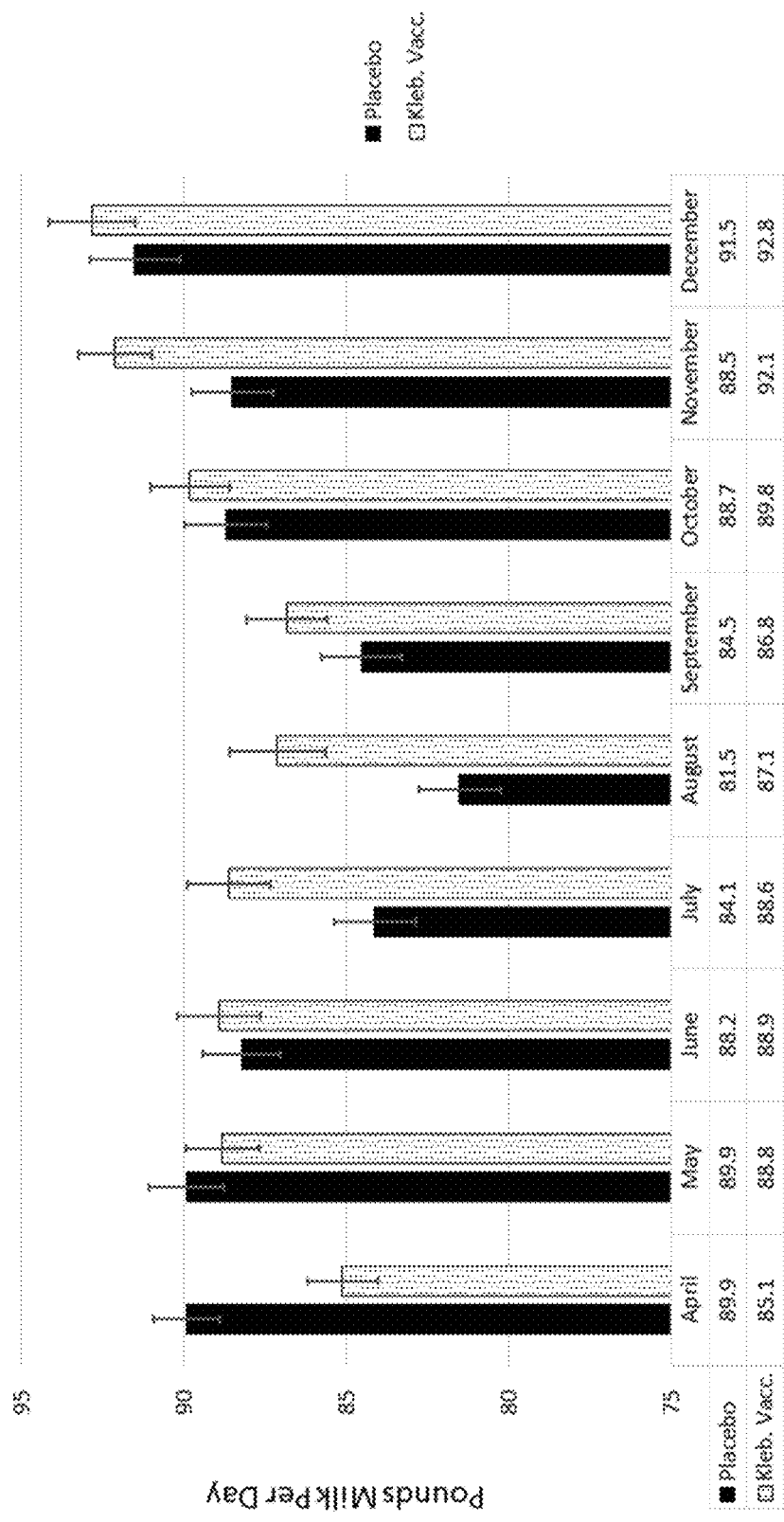
FIG. 35. Average daily milk production per cow from cows vaccinated with *Klebsiella pneumoniae* 1571 vaccine vs. placebo by month of the study. Error bars show 95% confidence interval.

The statistically significant increase in milk production by the *Klebsiella Pneumoniae* 1571 vaccinated cows (P=0.0000) is difficult to explain based solely on the differences in clinical mastitis between the two groups. A more detailed analysis of milk production differences by month (FIG. 35) shows the greatest differences in the summer months. Interestingly, summer conditions provide ideal conditions for coliforms to survive in manure and are associated with increased coliform infections.

Somatic cell counts (SCC) are routinely used to monitor milk quality and typically increase during clinical mastitis. In addition to clinical mastitis that was analyzed in this study, SCC is also a good indicator of sub-clinical mastitis. As mentioned in the milk results, it is surprising to see such a large increase in milk production from clinical mastitis alone. Therefore, SCC was used as an independent indicator of mammary health in the study animals. In this study, somatic cell counts were reduced in the *Klebsiella pneumoniae* 1571 vaccinated cows compared to placebo cows. The data can be analyzed categorically, and numerically. Categorically, the dairy industry uses a threshold of >200,000 cells/ml as an indication of mastitis, even if sub-clinical. Milk from cows vaccinated with placebo were above 200,000 SCC/ml 25.4% of the time, while milk from cows vaccinated with the *Klebsiella pneumoniae* 1571 vaccine were above this level only 11.7% of the time. The 54% reduction in the prevalence of clinically-significant SCC in *Klebsiella pneumoniae* 1571 vaccine group was highly statistically significant (P=0.0000). Quantitative comparison of SCC between groups shows an overall reduction of SCC in vaccinates of 42% which was also highly significant (P=0.0000; Appendix C). The reduction in SCC among vaccinated cows is consistent with the decreased clinical mastitis and provides insight to explain the increased milk production which may be attributable to not only clinical coliform mastitis, but also sub-clinical coliform mastitis.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:
   an isolated protein comprising an amino acid sequence that has at least 80% identity with SEQ ID NO:41 and an isolated protein comprising an amino acid sequence that has at least 80% identity with SEQ ID NO:43;
   an effective amount of an adjuvant; and
   a pharmaceutically acceptable carrier.

2. The composition of claim 1 further comprising a protein comprising an amino acid sequence that has at least 80% identity with SEQ ID NO:45, SEQ ID NO:46, SEQ ID NO:49, SEQ ID NO:51, SEQ ID NO:52, SEQ ID NO:53, SEQ ID NO:58, SEQ ID NO:61, or SEQ ID NO:64.

3. A method comprising:
   administering to a mammalian subject an amount of the composition of claim 1 effective to induce the subject to produce an antibody that specifically binds to at least one protein of the composition.

4. The method of claim 3, wherein the mammalian subject is a bovine subject or a human subject.

5. The method of claim 3, wherein the bovine subject is a dairy cow.

* * * * *